US008518411B2

(12) United States Patent
Oppermann et al.

(10) Patent No.: US 8,518,411 B2
(45) Date of Patent: *Aug. 27, 2013

(54) MODIFIED TGF-β SUPERFAMILY PROTEIN

(75) Inventors: Hermann Oppermann, Medway, MA (US); Mei-Sheng Tai, Shrewsbury, MA (US); John McCartney, Holliston, MA (US)

(73) Assignee: Stryker Corporation, Kalamazoo, MI (US)

(*) Notice: Subject to any disclaimer, the term of this patent is extended or adjusted under 35 U.S.C. 154(b) by 1580 days.

This patent is subject to a terminal disclaimer.

(21) Appl. No.: 11/715,679

(22) Filed: Mar. 7, 2007

(65) Prior Publication Data

US 2012/0122778 A1 May 17, 2012

Related U.S. Application Data

(63) Continuation of application No. 10/816,768, filed on Apr. 2, 2004, now abandoned, which is a continuation of application No. 09/375,333, filed on Aug. 16, 1999, now abandoned.

(60) Provisional application No. 60/103,418, filed on Oct. 7, 1998.

(51) Int. Cl.
*A61K 38/18* (2006.01)
*C07K 14/495* (2006.01)

(52) U.S. Cl.
USPC ........................................ 424/198.1; 530/399

(58) Field of Classification Search
None
See application file for complete search history.

(56) References Cited

U.S. PATENT DOCUMENTS

| 5,011,691 | A |   | 4/1991  | Oppermann et al. |         |
|-----------|---|---|---------|------------------|---------|
| 5,266,683 | A | * | 11/1993 | Oppermann et al. | 530/326 |
| 5,399,677 | A |   | 3/1995  | Wolfman et al.   |         |
| 5,658,882 | A |   | 8/1997  | Celeste et al.   |         |
| 5,674,292 | A |   | 10/1997 | Tucker et al.    |         |
| 5,756,308 | A |   | 5/1998  | Wolfman et al.   |         |
| 5,770,444 | A |   | 6/1998  | Lee et al.       |         |
| 5,800,811 | A |   | 9/1998  | Hall et al.      |         |
| 5,801,014 | A |   | 9/1998  | Lee et al.       |         |
| 5,804,416 | A |   | 9/1998  | Wolfman et al.   |         |
| 5,807,713 | A |   | 9/1998  | Hötten et al.    |         |
| 5,840,325 | A |   | 11/1998 | Kuberasampath et al. |     |
| 6,352,972 | B1|   | 3/2002  | Nimni et al.     |         |
| 6,677,432 | B1| * | 1/2004  | Oppermann et al. | 530/350 |

FOREIGN PATENT DOCUMENTS

| DE | 195 11 243 A | 1/1996  |
| EP | 0150 572 A   | 8/1985  |
| EP | 0433225      | 6/1991  |
| EP | 0626451 A2   | 11/1994 |
| EP | 0676 474 A   | 10/1995 |
| JP | 11-510054    | 9/1999  |
| WO | WO 89/03886  | 5/1989  |
| WO | WO 91/05565  | 5/1991  |
| WO | WO 91/05802  | 5/1991  |
| WO | WO 92/00318  | 1/1992  |
| WO | WO 92/15323  | 9/1992  |
| WO | WO 93/09229  | 5/1993  |
| WO | WO 96/39430  | 12/1996 |
| WO | WO 97/05241  | 2/1997  |

OTHER PUBLICATIONS

Brunner, et al., Site-directed mutagenesis of cysteine residues in the pro region of the transforming growth factor β1 precursor, *J. Biol. Chem.*, 264, pp. 13660-13664 (1989).
Han, et al., Refolding of a recombinant collagecollage-targeted TGF-β2 fusion protein expressed in *Escherichia coli*, Protein Expression and Purification 11, pp. 169-178 1997.
Hilvert, et al., Chemical synthesis of proteins, Chem. Biol., 1, pp. 201-203 (1994).
Lipscomb, et al., Context-dependent protein stabilization by methionine-to-leucine substitution shown in T4 lysozyme, *Protein Sci.*, 7, pp. 765-773 (1998).
Liu, et al., Peptide segment ligation strategy without use of protecting groups, *Proc. Natl. Acad. Sci. USA*, 91, pp. 6584-6588 (1994).
Miranda, et al., Accelerated chemical synthesis of peptides and small proteins, *Proc. Natl. Acad. Sci. USA*, 96, pp. 1181-1186 (1999).
Muir, et al., Expressed protein ligation: A general method for protein engineering, *Proc. Natl. Acad. Sci. USA*, 95, pp. 6705-6710 (1998).
Nikolova, et al.,Semirational design of active tumor suppressor p53 DNA binding domain with enhanced stability, *Proc. Natl. Acad. Sci. USA* 95, pp. 14675-14680 (1998).
Smith, et al., Automatic generation of primary sequence patterns from sets of related proteins, *Proc. Natl. Acad. Sci. USA*, 87, pp. 118-122 (1990).
Wallace, et al., Peptide ligation and semisynthesis, *Curr. Opin. Biotechnol.*, 6, pp. 403-410 (1995).
Wang, et al., Recombinant human bone morphogenetic protein induces bone formation, *Proc. Natl. Acad. Sci. USA*, 87, pp. 2220-2224 (1990).
Andrews et al., "Inhibition of proliferation and induction of differentiation of pluripotent human embryonal carcinoma cells by osteogenic protein-1 (or bone morphogenetic protein-7)," Laboratory Investigation, 71:243-251 (1994).
Rutherford et al., "A new biological approach to vital pulp therapy," Crit. Rev. Oral Biol. Med., 6:218-229 (1995).
Terheyden et al., "Recombinant human osteogenic protein 1 in the rat mandibular augmentation model: differences in morphology of the newly formed bone are dependent on the type of carrier," Mund Kiefer Gesichtschir., 1:272-275 (1997).
Maliakal et al., "Osteogenic protein-1 (BMP-7) inhibits cell proliferation and stimulates the expression of markers characteristic of osteoblast phenotype in rat osteosarcoma (17/2.8) cells," Growth Factors, 11:227-234 (1994).

* cited by examiner

*Primary Examiner* — Ruixiang Li
(74) *Attorney, Agent, or Firm* — Ropes & Gray LLP; James F. Haley, Jr.; Karen Mangasarian

(57) ABSTRACT

The invention provides modified TGF-β family proteins having altered biological or biochemical properties, and methods for making them. Specific modified protein constructs include TGF-β family member proteins that have N-terminal truncations, "latent" proteins, fusion proteins and heterodimers.

14 Claims, 26 Drawing Sheets

FIG. 4

| | | |
|---|---|---|
| OP-1 | CC|A - - PTQLNAI SVLYFDDS- SNVI LKKYRNMVVRA|CGC|H |
| BMP-5 | CC|A - - PTKLNAI SVLYFDDS- SNVI LKKYRNMVVRS|CGC|H |
| BMP-6 | CC|A - - PTKLNAI SVLYFDDN- SNVI LKKYRNMVVRA|CGC|H |
| OP-2 | CC|A - - PTKLSATSVLYYDSS- NNVI LRKHRNMVVKA|CGC|H |
| OP-3 | CC|V - - PTELSAI SLLYYDRN- NNVI LRRERNMVVQA|CGC|H |
| 60A | CC|A - - PTRLGALPVLYHLND- ENVNLKKYRNMI VKS|CGC|H |
| Vg-1 | CC|V - - PTKMSPI SMLFYDNN- DNVVLRHYENMAVDE|CGC|R |
| UNIVIN | CC|A - - PTKLSGI SMLYFDNN- ENVVLRQYEDMVVEA|CGC|R |
| BMP-2 | CC|V - - PTELSAI SMLYLDEN- EKVVLKNYQDMVVEG|CGC|R |
| BMP-4 | CC|V - - PTELSAI SMLYLDEY- DKVVLKNYQEMVVEG|CGC|R |
| GDF-5 | CC|V - - PTRLSPI SI LFI DSA- NNVVYKQYEDMVVES|CGC|R |
| GDF-6 | CC|V - - PTKLTPI SI LYI DAG- NNVVYKQYEDMVVES|CGC|R |
| GDF-7 | CC|V - - PARLSPI SI LYI DAA- NNVVYKQYEDMVVEA|CGC|R |
| CDMP-2 | CC|V - - PTKLTPI SI LYI DAG- NNVVYNEYEEMVVES|CGC|R |
| dpp | CC|V - - PTQLDSVAMLYLNDQ- STVVLKNYQEMTVVG|CGC|R |
| BMP-9 | CC|V - - PTKLSPI SVLYKDDMGVPTLKYHYEGMSVAE|CGC|R |
| DORSALIN | CC|V - - PTKLDAI SI LYKDDAGVPTLI YNYEGMKVAE|CGC|R |
| BMP-10 | CC|V - - PTKLEPI SI LYLDKG- VVTYKFKYEGMAVSE|CGC|R |
| GDF-3 | V|C|V - - PTKLSPI SMLYQDSD- KNVI LRHYEDMVVDE|CGC|G |
| GDF-1 | CC|V - - PERLSPI SVLFFDNE- DNVVLRHYEDMVVDE|CGC|R |
| SCREW | CC|V - - PTVLGAI TI LRYLNE- DI I DLTKYQKAVAKE|CGC|H |
| BMP-3 | CC|V - - PEKMSSLSI LFFDEN- KNVVLKVYPNMTVES|CAC|R |
| NODAL | CC|A - - PVKTKPLSMLYVDN- - GRVLLEHHKDMI VEE|CGC|L |
| TGF-å2 | CC|V - - SQDLEPLTI LYYI G- - KTPKI EQLSNMI VKS|CKC|S |
| TGF-å3 | CC|V - - PQDLEPLTI LYYVG- - RTPKVEQLSNMVVKS|CKC|S |
| TGF-å4 | CC|V - - PQTLDPLPI I YYVG- - RNVRVEQLSNMVVRA|CKC|S |
| TGF-å1 | CC|V - - PQALEPLPI VYYVG- - RKPKVEQLSNMI VRS|CKC|S |
| TGF-å5 | CC|V - - PDVLEPLPI I YYVG- - RTAKVEQLSNMVVRS|CNC|S |
| GDF-9 | S|C|V - - PGKYSPLSVLTI EPD- GSI AYKEYEDMI ATR|CTC|R |
| Inhibinå | CC|A ALPGTMRPLHVRTTSDGGYSFKYETVPNLLTQH|CAC|I |
| InhibinßA | CC|V - - PTKLRPMSMLYYDDG- QNI I KKDI QNMI VEE|CGC|S |
| InhibinßB | CC|I - - PTKLSTMSMLYFDDE- YNI VKRDVPNMI VEE|CGC|A |
| InhibinßC | CC|V - - PTARRPLSLLYYDRD- SNI VKTDI PDMVVEA|CGC|S |
| MIS | CC|V - - PTATAGKLLI SLSE- - ERI SAHHVPNMVATE|CGC|R |
| GDNF | CC|R - - PI AFDDD- - LSFLD- - DNLVYHI LRKHSAKR|CGC|I |
| BMP-11 | CC|T - - PTKMSPI NMLYFNDK- QQI I YGKI PGMVVDR|CGC|S |
| GDF-9 | S|C|V - - PGKYSPLSVLTI EPD- GSI AYKEYEDMI ATR|CTC|R |

```
TGF-ß SUBGROUP +---------------+----------+----------------+---------+--------+
       TGF-ß1: |C|C V R Q L Y I D|F R K D L|G W K - W I H E P K|G Y H A N F|C L G P C|
       TGF-ß2: |C|C L R P L Y I D|F K R D L|G W K - W I H E P K|G Y N A N F|C A G A C|
       TGF-ß3: |C|C V R P L Y I D|F R Q D L|G W K - W V H E P K|G Y Y A N F|C S G P C|
       TGF-ß4: |C|C V R P L Y I D|F R K D L|Q W K - W I H E P K|G Y M A N F|C M G P C|
       TGF-ß5: |C|C V K P L Y I N|F R K D L|G W K - W I H E P K|G Y E A N Y|C L G N C|
      PATTERN: |C|C V R P L Y I D|F R n D L|G W K - W I H E P K|G Y X A N F|C X G j C|
Vg/dpp SUBGROUP+---------------+----------+----------------+---------+--------+
          dpp: |C|R R H S L Y V D|F S - D V|G W D D W I V A P L|G Y D A Y Y|C H G K C|
         Vg-1: |C|K K R H L Y V E|F K - D V|G W Q N W V I A P Q|G Y M A N Y|C Y G E C|
        Vgr-1: |C|K K H E L Y V S|F Q - D L|G W Q D W I I A P K|G Y A A N Y|C D G E C|
          60A: |C|Q M Q T L Y I D|F K - D L|G W H D W I I A P E|G Y G A F Y|C S G E C|
       BMP-2A: |C|K R H P L Y V D|F S - D V|G W N D W I V A P P|G Y H A F Y|C H G E C|
     DORSALIN: |C|R R T S L H V N|F K - E I|G W D S W I I A P K|D Y E A F E|C K G G C|
   BMP-2B/BMP-4: |C|R R H S L Y V D|F S - D V|G W N D W I V A P P|G Y Q A F Y|C H G D C|
        BMP-3: |C|A R R Y L Y V D|F A - D I|G W S E W I I S P K|S F D A Y Y|C S G A C|
        BMP-5: |C|K K H E L K V S|F R - D L|G W Q D W I I A P E|G Y A A F Y|C D G E C|
        BMP-6: |C|R K H E L Y V S|F Q - D L|G W Q D W I I A P K|G Y A A N Y|C D G E C|
     OP-1/BMP-7: |C|K K H E L Y V S|F R - D L|G W Q D W I I A P E|G Y A A Y Y|C E G E C|
         OP-2: |C|R R H E L Y V S|F Q - D L|G W L D W V I A P Q|G Y S A Y Y|C E G E C|
         OP-3: |C|R R H E L Y V S|F R - D L|G W L D S V I A P Q|G Y S A Y Y|C A G E C|
      PATTERN: |C|n n r r L Y V r|F r - D c|G W r D W I I A P p|G Y X A d Y|C r G k C|
GDF SUBGROUP-+---------------+----------+----------------+---------+--------+
        GDF-1: |C|R T R R L H V S|F R - E V|G W H R W V I A P R|G F L A N F|C Q G T C|
        GDF-3: |C|H R H Q L F I N|F Q - D L|G W H K W V I A P K|G F M A N Y|C H G E C|
        GDF-9: |C|E L H D F R L S|F S - Q L|K W D N W I V A P H|R Y N P R Y|C K G D C|
      PATTERN: |C|r X r r f X c r|F r - r c|X W r r W a a A P r|X d X j r d|C r G r C|
INHIBIN SUBGROUP---------------+----------+----------------+---------+--------+
     INHIBIN∝: |C|H R V A L N I S|F Q - E L|G W E R W I V Y P P|S F I F H Y|C H G G C|
    INHIBIN ßA: |C|C K K Q F F V S|F K - D I|G W N D W I I A P S|G Y H A N Y|C E G E C|
    INHIBIN ßB: |C|C R Q Q F F I D|F R - L I|G W N D W I I A P T|G Y Y G N Y|C E G S C|
      PATTERN: |C|X n X X f X a r|F P - X c|G W m r W I a X P j|j d X X r Y|C r G X C|
              +-+---------------+----------+----------------+---------+--------+
              |1|           10  |     20   |           30   |         |        |
              | |    BETA    | HELIX |  LOOP     |   BETA   |  RING   |
              |K|_____FINGER 1_____|KNOT_A_|
```

*FIG. 5A*

```
TGF-ß SUBGROUP----------------------------------------------------------------+-+-+
     TGF-ß1: |P Y I W S - - - - - - - L D T|Q Y S K V L A L Y N Q H N|P - - G A S A A P|C|C|
     TGF-ß2: |P Y L W S - - - - - - - S D T|Q H S R V L S L Y N T I N|P - - E A S A S P|C|C|
     TGF-ß3: |P Y L R S - - - - - - - A D T|T H S T V L G L Y N T L N|P - - E A S A S P|C|C|
     TGF-ß4: |P Y I W S - - - - - - - A D T|Q Y T K V L A L Y N Q H N|P - - G A S A A P|C|C|
     TGF-ß5: |P Y I W S - - - - - - - M D T|Q Y S K V L S L Y N Q N N|P - - G A S I S P|C|C|
    PATTERN: |P Y c W S - - - - - - - X D T|Q e S n V L j L Y N r X N|P - - X A S A j P|C|C|
Vg/dpp SUBGROUP---------------------------------------------------------------+-+-+
        dpp: |P F P L A D H F - - - - N S T|N H A V V Q T L V N N M N|P - - G K V P K A|C|C|
       Vg-1: |P Y P L T E I L - - - - N G S|N H A I L Q T L V H S I E|P - - E D I P L P|C|C|
      Vgr-1: |S F P L N A H M - - - - N A T|N H A I V Q T L V H L M N|P - - E Y V P K P|C|C|
        60A: |N F P L N A H M - - - - N A T|N H A I V Q T L V H L L E|P - - K K V P K P|C|C|
     BMP-2A: |P F P L A D H L - - - - N S T|N H A I V Q T L V N S V N|- - - S K I P K A|C|C|
    DORSALIN:|F F P L T D N V - - - - T P T|K H A I V Q T L V H L Q N|P - - K K A S K A|C|C|
BMP-2B/BMP-4:|P F P L A D H L - - - - N S T|N H A I V Q T L V N S V N|- - - S S I P K A|C|C|
      BMP-3: |Q F P M P K S L - - - - K P S|N H A T I Q S L V R A V G|V V - P G I P E P|C|C|
      BMP-5: |S F P L N A H M - - - - N A T|N H A I V Q T L V H L M F|P - - D H V P K P|C|C|
      BMP-6: |S F P L N A H M - - - - N A T|N H A I V Q T L V H L M N|P - - E Y V P K P|C|C|
   OP-1/BMP-7:|A F P L N S Y M - - - - N A T|N H A I V Q T L V H F I N|P - - E T V P K P|C|C|
       OP-2: |S F P L D S C M - - - - N A T|N H A I L Q S L V H L M K|P - - N A V P K A|C|C|
       OP-3: |I Y P L N S C M - - - - N S T|N H A T M Q A L V H L M K|P - - D I I P K V|C|C|
    PATTERN: |X F P L X X X b - - - - N j T|N H A I a Q T L V r X c r|z z - r X a P K j|C|C|
GDF SUBGROUP-----------------------------------------------------------------+-+-+
      GDF-1: |A L P E T L R G P G G P P A L|N H A V L R A L M H A A A|P T - P G A G S P|C|C|
      GDF-3: |P F S M T T Y L - - - - N S S|N Y A F M Q A L M H M A D|- - - P K V P K A|V|C|
      GDF-9: |P R A V R H R Y - - - - G S P|V H T M V Q N I I Y E K L|D - - P S V P R P|S|C|
    PATTERN: |j X j X r X X X z z z z X j X|X e j f c p X c c e X X X|z z - P X X j r j|X|C|
INHIBIN SUBGROUP-------------------------------------------------------------+-+-+
   INHIBIN α:|G L H I P P N L S L - - P V P|G A P P T P A Q P Y S L -|- - - L P G A Q P|C|C|
   INHIBIN ßA:|P S H I A G T S G S - - S L S|F H S T V I N H Y R M R G|H S P F A N L K S|C|C|
   INHIBIN ßB:|P A Y L A G V P G S - - A S S|F H T A V V N Q Y R M R G|L N - P G T V N S|C|C|
    PATTERN: |j X e c j j X X j X - - j X j|X X j j X X X r X X X X z|z z z X j X X r j|C|C|
             +-----------------------------+-----------------------+-----------------+-+-+
             |        40         50|       60      |      70       | | |
             |                     |      HELIX    |               | | |
             |_____HEEL_____|               |I|K|
```

FIG. 5B

```
TGF-ß SUBGROUP---------------+---------------+---------------+-----+-+
     TGF-ß1: V - - P Q A L E P L P I V Y Y V G - - R K P K V E Q L S N M I V R S C K C S
     TGF-ß2: V - - S Q D L E P L T I L Y Y I G - - K T P K I E Q L S N M I V K S C K C S
     TGF-ß3: V - - P Q D L E P L T I L Y Y V G - - R T P K V E Q L S N M V V K S C K C S
     TGF-ß4: V - - P Q T L D P L P I I Y Y V G - - R N V R V E Q L S N M V V R A C K C S
     TGF-ß5: V - - P D V L E P L P I I Y Y V G - - R T A K V E Q L S N M V V R S C N C S
    PATTERN: V - - P Q X L E P L j I c Y Y V G - - R r j K V E Q L S N M a V n S C K C S
Vg/dpp SUBGROUP--------------+---------------+---------------+-----+-+
        dpp: V - - P T Q L D S V A M L Y L N D Q - S T V V L K N Y Q E M T V V G C G C R
       Vg-1: V - - P T K M S P I S M L F Y D N N - D N V V L R H Y E N M A V D E C G C R
      Vgr-1: A - - P T K L N A I S V L Y F D D N - S N V I L K K Y R N M V V R A C G C H
        60A: A - - P T R L G A L P V L Y H L N D - E N V N L K K Y R N M I V K S C G C H
      BMP-2A: V - - P T E L S A I S M L Y L D E N - E K V V L K N Y Q D M V V E G C G C R
    DORSALIN: V - - P T K L D A I S I L Y K D D A G V P T L I Y N Y E G M K V A E C G C R
  BMP-2B/BMP-4: V - - P T E L S A I S M L Y L D E Y - D K V V L K N Y Q E M V V E G C G C R
      BMP-3: V - - P E K M S S L S I L F F D E N - K N V V L K V Y P N M T V E S C A C R
      BMP-5: A - - P T K L N A I S V L Y F D D S - S N V I L K K Y R N M V V R S C G C H
      BMP-6: A - - P T K L N A I S V L Y F D D N - S N V I L K K Y R N M V V R A C G C H
    OP-1/BMP-7: A - - P T Q L N A I S V L Y F D D S - S N V I L K K Y R N M V V R A C G C H
       OP-2: A - - P T K L S A T S V L Y Y D S S - N N V I L R K H R N M V V K A C G C H
       OP-3: V - - P T E L S A I S L L Y Y D R N - N N V I L R R E R N M V V Q A C G C H
    PATTERN: X - - P T p L r A a S c L Y f D m r z r r V a L n r Y p I M X V p j C G C r
GDF SUBGROUP--+---------------+---------------+---------------+-----+-+
      GDF-1: V - - P E R L S P I S V L F F D N S - D N V V L R H Y E D M V V D E C G C R
      GDF-3: V - - P T K L S P I S M L Y Q D S D - K N V I L R H Y E D M V V D E C G C G
      GDF-9: V - - P G K Y S P L S V L T I E P D - G S I A Y K E Y E D M I A T R C T C R
    PATTERN: V - - P X n f S P c S c L X X k X r - X r a X f n r Y E D M a X r p C j C X
INHIBIN SUBGROUP------+---------------+---------------+---------------+-----+-+
   INHIBIN α: A A L P G T M R P L H V R T T S D G G Y S F K Y E T V P N L L T Q H C A C I
  INHIBIN ßA: V - - P T K L R P M S M L Y Y D D G - Q N I I K K D I Q N M I V E E C G C S
  INHIBIN ßB: I - - P T K L S T M S M L Y F D D E - Y N I V K R D V P N M I V E E C G C A
    PATTERN: X z z P j r b r j b r c X X X r D X z X r f X X p r a X N b c X o r C h C X
+---------------+---------------+---------------+-----+-+
|      80       |      90       |      100      | 110 | |
|     BETA      |     LOOP      |     BETA      |RING | |
|           FINGER_2                             |KNOT2|C|
+---------------+---------------+---------------+-----+-+
```

*FIG. 5C*

```
TGF-ß SUBGROUP  +---------------+----------+--------------+----------+--------+
       PATTERN: |C|C V R P L Y I D|F R n D L|G W K - W I H E P K|G Y X A N F|C X G j C|
Vg/dpp SUBGROUP +---------------+----------+--------------+----------+--------+
       PATTERN: |C|n n r r L Y V r|F r - D c|G W r D W I I A P p|G Y X A d Y|C r G k C|
GDF SUBGROUP    +---------------+----------+--------------+----------+--------+
       PATTERN: |C|r X r r f X c r|F r - r c|X W r r W a a A P r|X d X j r d|C r G r C|
INHIBIN SUBGROUP+---------------+----------+--------------+----------+--------+
       PATTERN: |C|X n X X f X a r|F p - X c|G W m r W I a X P j|j d X X r Y|C r G X C|
                +---------------+----------+--------------+----------+--------+
                |1|       10     |          |      20      |    30    |        |
                | |   BETA       |  HELIX   |    LOOP      |   BETA   |  RING  |
                |K|_____FINGER 1_____|KNOT_A |

TGF-ß SUBGROUP  --------------------+--------------------+------------+--+--+
       PATTERN: |P Y c W S - - - - - - - X D T|Q e S n V L j L Y N r X N|P - - X A S A j P|C|C|
Vg/dpp SUBGROUP --------------------+--------------------+------------+--+--+
       PATTERN: |X F P L X X X b - - - - N j T|N H A I a Q T L V r X c r|z z - r X a P K j|C|C|
GDF SUBGROUP    --------------------+--------------------+------------+--+--+
       PATTERN: |j X j X r X X X z z z z X j X|X e j f c p X c c e X X X|z z - P X X j r j|X|C|
INHIBIN SUBGROUP--------------------+--------------------+------------+--+--+
       PATTERN: |j X e c j j X X j X - - j X j|X X j j X X X r X X X X z|z z z X j X X r j|C|C|
                +--------------------+--------------------+------------+--+--+
                |      40     50|         60          |    70      |  | |/|
                |               |        HELIX        |            |  | | |
                |_____HEEL_____|I| pH2521  FB LEADER, AND 15 RESIDUES UPSTREAM FROM FIRST CYSTEINE

```
         10         20         30         40         50         60         70         80         90        100        110        120
ATGATCGAATTCATGGCTGACAACAAATTCAACAAGGAACAGCAGAACGCGTTCTACGAGATCTTGCACCTGCCGAACCTGAACGAAGAGCAGGTAACGGCTTCATCCAAAGCCTGAAA
 M  I  E  F  M  A  D  N  K  F  N  K  E  Q  Q  N  A  F  Y  E  I  L  H  L  P  N  L  N  E  E  Q  R  N  G  F  I  Q  S  L  K
 EcoRI:1                                            MluI:1              BglII:1
                                                    XmnI:b
```

```
        130        140        150        160        170        180        190
GAAGAGCCGTCTCAGTCTGCGAATCTGCTAGCGGGATGCCAAGAAACTGAACGATGCCGCAGGCACCGAAATCGGCC
 E  E  P  S  Q  S  A  N  L  L  A  K  K  L  N  D  A  Q  A  P  K  S  A
                            NheI:1                        FspI:b
```

```
        300        310        320        330        340
ATGGCCAACGTGGCAGAGAACAGCAGCAGCGACCAGAGGCAGGCCT
 M  A  N  V  A  E  N  S  S  S  D  Q  R  Q  A
                  BglI:7      op-1-exon5----        StuI
 NcoI:1
 XcmI:8
 MscIdcm:b
```

FIG. 7C pH2525   FB- AND His6-LEADER, RETAINING 35 RESIDUES UPSTREAM FROM FIRST CYSTEINE; GOOD REFOLDING

```
ATGATCGAATTCATGGCTGACAACAAATTCAACAAGGAACAGAGAACGCGTTCTACGAGATCTTGCACCTGCCGAACCTGAACGAAGAGCAGCGTAACGGCTTCATCCAAAGCCTGAAA
 M  I  E  F  M  A  D  N  K  F  N  K  E  Q  N  A  F  Y  E  I  L  H  L  P  N  L  N  E  E  Q  R  N  G  F  I  Q  S  L  K
EcoRI:1                                              MluI:1          BglII:1
                                                     XmnI:b

GAAGAGCCGTCTCAGTCTGCGAATCTGCTAGCGGATGCCAAGAAACTGAACGATGCCAGGACCGGAAATCGGCCATGGCTGACAACCATCACCATCATCACCATATG
 E  E  P  S  Q  S  A  N  L  L  A  D  A  K  K  L  N  D  A  Q  A  P  K  S  S  A  M  A  D  N  H  H  H  H  H  H  M
              NheI:1                            FspI:b                 NcoI:1                                NdeI:2

GGGAGCAAACAGCGCAGCCAGAACCGCTCCAAGACGCCCAAGAACCAGGAAGCCCTGCGACGTATGGCCAACGTGGCAGAGAACAGCAGCAGCGACCAGAGGCAGGCCT
 G  S  K  Q  R  S  Q  N  R  S  K  T  P  K  N  Q  E  A  L  R  M  A  N  V  A  E  N  S  S  S  D  Q  R  Q  A
                                                                        MscI                                 StuI
```

FIG. 7D

H2528
FB-His6-CHMP-3

```
         10         20         30         40         50         60         70         80         90        100        110        120
-CCATGATCGAATTCATGGCTGACAACAAATTCAACAAGGAACAGCAGAACGCGTTCTACGAGATCTTGCACCTGCCGAACCTGAACGAAGAGCAGCGTAACGGCTTCATCCAAAGCCTG
... M  I  E  F  M  A  D  N  K  F  N  K  E  Q  Q  N  A  F  Y  E  I  L  H  L  P  N  L  N  E  E  Q  R  N  G  F  I  Q  S  L
        130        140        150        160        170        180        190        200        210        220        230        240
AAAGAAGAGCCGTCTCAGTCTGCGAATCTGCTAGCGGATGCCAAGAAGCTGAACGATGCCCAGGCACCGAAATCGGATCATCATCACCATCACCATTCGGATCCCATGGCGTTGGCCGGG
 K  E  E  P  S  Q  S  A  N  L  L  A  D  A  K  K  L  N  D  A  Q  A  P  K  S  D  H  H  H  H  H  H  S  D  P  M  A  L  A  G
        250        260        270        280        290        300        310        320        330        340        350        360
ACGCGTACAGCCAGGGCCAGGGCGCGGAGGTGCCGGCAGGGCATGGTCGACGTGGTAGATCTCGCTGCAGCCGCAAGCGTTCAAGGAGCTCGGTGGGACGACTGG
 T  R  T  A  Q  G  S  G  G  A  G  R  G  H  G  R  R  R  G  R  S  R  C  S  R  K  P  L  H  V  D  F  K  E  L  G  W  D  D  W
        370        380        390        400        410        420        430        440        450        460        470        480
ATCATCGCGCCGCTCGACTACGAGGCCTACCACTGCGAGGGCCTTTGCGACTTCCCTTTGCTTCGTTCGCAGCCATCGAGACGCTGCTCAACTCCATGGCA
 I  I  A  P  L  D  Y  E  A  Y  H  C  E  G  L  C  D  F  P  L  R  S  H  L  E  P  T  N  H  A  I  I  Q  T  L  L  N  S  M  A
        490        500        510        520        530        540        550        560        570        580        590        600
CCAGACGCGGGCCCGGCCTCCTGCTGTGTGCCAGCGCCCTCAGCCGCCCATCAGCATCCTCTACATCGACGCCAACAACGTTGTCTACAAGCAATACGAGGACGACATGGTGGTGGAGGCC
 P  D  A  A  P  A  S  C  C  V  P  A  R  L  S  P  I  S  I  L  Y  I  D  A  A  N  N  V  V  Y  K  Q  Y  E  D  M  V  V  E  A
        610        620        630        640        650
TGCGGGCTGTAGGTAAGCTTGTGGCTGCAGATAGCTCCTCCGAGAATTC
 C  G  C  R  *
```

FIG. 7F pH2469  TRUNCATED, GOOD ROS ACTIVITY; 14 ORIGINAL RESIDUES UPSTREAM OF FIRST CYSTEINE
```
              10        20        30        40
-CCATGGCCAACGTGGCAGAGAACAGCAGCGACCAGAGAGGCAGGCC
   M  A  N  V  A  E  N  S  S  D  Q  R  Q  A
  NcoI BglI:7         OP-1-exon5-----         StuI
  MscIdcm:b
```

FIG. 7G pH2510   COLLAGEN SITE INSERTED 7 RESIDUES UPSTREAM OF CYSTEINE; GOOD EXPRESSION, REFOLDING

```
         10         20         30         40         50         60         70         80         90        100       110
ATGTCCACGGGGAGCAAAACAGCGCAGCAGAACCGCTCCAAGACGCCAAGACGCCCAGAACCAGGAAGCCCTGCGAGATGGCCAGCTGGAGAGAGCCAAGCTTCATGGCCTTAAGCAGC
 M  S  T  G  S  K  Q  R  S  Q  N  R  S  K  T  P  K  N  Q  E  A  L  R  M  A  S  W  R  E  P  S  F  M  A  L  S
                              BsaHI:2                                            BpmI+         HindIII:1   AflII:1
                                                                                 MscIdcm:b                 BfrI:1
                                                                                 PvuII
        120        130
AGCGACCAGAGGCAGGCC
 S  D  Q  R  Q  A
          StuI
```

FIG. 7H pH2523   COLLAGEN PEPTIDE, AND SPACER ADDED AT 13 RESIDUES UPSTREAM FROM 1ST CYSTEINE

```
         10         20         30         40         50         60         70         80         90        100       110
ATGTCCACGGGGAGCAAAACAGCGCAGCAGAACCGCTCCAAGACGCCAAGACGCCCAGAACCAGGAAGCCCTGCGAGATGGCCAGCTGGAGAGAGCCAAGCTTCATGGCCTTAAGCAGC
 M  S  T  G  S  K  Q  R  S  Q  N  R  S  K  T  P  K  N  Q  E  A  L  R  M  A  S  W  R  E  P  S  F  M  A  L  S  S  S  D
                              BsaHI:2                                            BpmI+         HindIII:1   AflII:1
                                                                                 MscIdcm:b                 BfrI:1   DUPLICATION
                                                                                 PvuII:b
        120        130        140        150        160
CAGAGGCAGGCCAACGTGGCAGAGAACAGCAGCAGCGACCAGCAGAGGCAGGCC
 Q  R  Q  A  N  V  A  E  N  S  S  S  D  Q  R  Q  A
       BglI                OP-1-exon5 ----          StuId
```

FIG. 7I pH2524   Hexa-His, COLLAGEN PEPTIDE, SPACER ADDED AT 13 RESIDUES UPSTREAM FROM 1ST CYSTEINE

```
         10         20         30
-CCATGGCTGACAACCATCACCATCACCATATG
 .. M  A  D  N  H  H  H  H  H  M
 NcoI:1

40         50         60         70         80         90        100       110       120       130       140
GGGAGCAAAACAGCGCAGCAGAACCGCTCCAAGACGCCAAGACGCCCAGAACCAGGAAGCCCTGCGAGATGGCCAGCTGGAGAGAGCCAAGCTTCATGGCCTTAAGCAGCAGCGACCAG
 G  S  K  Q  R  S  Q  N  R  S  K  T  P  K  N  Q  E  A  L  R  M  A  S  W  R  E  P  S  F  M  A  L  S  S  S  D  Q
         BsaHI:2                                            BpmI+         HindIII:1   AflII:1
                                                            MscIdcm:b                 BfrI:1   DUPLICATION
                                                            PvuII:b
        150        160        170        180
AGGCAGGCCAACGTGGCAGAGAACAGCAGCAGCGACCAGAGGCAGGCC
 R  Q  A  N  V  A  E  N  S  S  S  D  Q  R  Q  A
    BglI               OP-1-exon5 ----      StuId
```

FIG. 7J

7-CYSTEINE DOMAIN OF OP-1

FINGER-1

TGTAAGAAGCACGAGCTGTATGTCAGCTTCCGAGACCTGGGCTGGCAGGACTGGATCATCGCCCCTGAAGGCTACGCCGCCTACTACTGTGAGGGG
 C  K  K  H  E  L  Y  V  S  F  R  D  L  G  W  Q  D  W  I  I  A  P  E  G  Y  A  A  Y  Y  C  E  G

HEEL

GAGTGTGCCTTCCCTCTGAACTCCTACATGAACGCCACCAACCACGCCATCGTGCAGACGCTGGTCCACTTCATCAACCCGGAAACGGTGCCAAGCCCTGC
 E  C  A  F  P  L  N  S  Y  M  N  A  T  N  H  A  I  V  Q  T  L  V  H  F  I  N  P  E  T  V  P  K  P  C

FINGER-2

TGTGCGCCCACGCAGCTCAATGCCATCTCCGTCCTCTACTTCGATGACAGCTCCAACGTCATCCTGAAGAAATACAGAAACATGGTGGTCCGGGCCTGTGGCTGCCAC
 C  A  P  T  Q  L  N  A  I  S  V  L  Y  F  D  D  S  S  N  V  I  L  K  K  Y  R  N  M  V  V  R  A  C  G  C  H

FIG. 8

OP-1 CHIMERICS WITH CDMP-2 OR WITH BMP-2

REFOLDING ACTIVITY (CELL BASED)

PARENTAL MOLECULES:

| | FINGER1 | HEEL | FINGER2 | | | |
|---|---|---|---|---|---|---|
| OP-1 | | | | h | (-) | +++ (*) |
| BMP-2 | | | | r | +++ | +++ |
| CDMP-2 | | | | r | ++++ | +/- |

REPLACING FINGER-1 OR HEEL:

| H2383 | | r | +/- | N/A |
|---|---|---|---|---|
| H2362 | | r | + | N/A |
| H2360 | | r | + | N/A |
| H2331 | | r | + | N/A |

REPLACING FINGER-2 OR HEEL:

| H2389 | | r | +++ | +++ |
|---|---|---|---|---|
| H2471 | | r | +++ | +++ |
| H2388 | | r | +++ | +/- |
| H2410 | | r | +++ | +++ |
| H2429 | | r | +/- | N/A |

CHANGING PATCHES OF RESIDUES:

| H2381 | | r | +++ | N/A |
|---|---|---|---|---|
| H2390 | | r | + | N/A |
| H2396 | | r | + | N/A |
| H2421 | | r | +/- | N/A |

PAIRED CHANGES IN FINGER-2:

| H2418 | | r | +++ | ++ |
|---|---|---|---|---|
| H2420 | | r | ++++ | +/- |

FIG. 9A

OP-1 MUTANTS WITH C-TERMINAL ARGININE INSTEAD OF HISTIDINE:

H2247 ▬▬▬▬▬▬▬▬▬▬ r     +     +++

H2233 ▬▬▬▬▬▬ 25,26,30
              ed▬e▬ r     +     +++

BALANCING OF CHARGED RESIDUES IN FINGER-2 OF OP-1 MUTANTS:

H2406    1,4,6,7
        vktp▬▬▬ r     +/-     N/A
        ↑

H2443    1,4,6,7   25,26
        vktp▬▬ed▬ r     +++     ++
        ↑      ↑↑

H2447    1,4,6   25,26,30
        ves▬▬ede▬ r     +++     ++
        ↑      ↑↑↑

H2433    4
        k▬▬▬▬▬ r     +/-     N/A
        ↑

H2456    4,6   25,26,30
        ▬es▬▬ede▬ r     +++     +++
        ↑↑    ↑↑↑

*FIG. 9B*

CORRELATION OF REFOLDING EFFICIENCY AND CHARGED AMINO ACIDS
IN THE TGF-β (SEVEN CYSTEINE) DOMAIN

| PROTEIN | FINGER-1 | CXGXC | HEEL | FINGER-2 | CXCX C-TERM | TOTAL OF CHARGED RESIDUES (+), (-) = TOTAL | NEGATIVE CHARGES, FINGER-2 | NET CHARGES, FINGER-2 | REFOLDING EFFICIENCY |
|---|---|---|---|---|---|---|---|---|---|
| OP-1 | 3+, 4- | 2- | 1+, 1- | 4+, 2- | 0 | 8+, 9- = 17 | 2- | 2+ | +/- |
| H2247 | 3+, 4- | 2- | 1+, 1- | 4+, 2- | 1+ | 9+, 9- = 18 | 2- | 2+ | + |
| H2447 | 3+, 4- | 2- | 1+, 1- | 2+, 6- | 1+ | 7+, 12- = 19 | 6- | 4- | +++ |
| BMP-3 | 4+, 4- | 0 | 3+, 1- | 3+, 4- | 1+ | 11+, 9- = 20 | 4- | 1- | +++ |
| BMP-2 | 2+, 3- | 1- | 2+, 1- | 2+, 6- | 1+ | 7+, 11- = 18 | 6- | 4- | +++ |
| GDF-5 | 3+, 5- | 1- | 1+, 4- | 2+, 4- | 1+ | 6+, 14- = 20 | 4- | 2- | +++ |
| CDMP-2 | 3+, 5- | 1- | 1+, 3- | 2+, 4- | 1+ | 6+, 13- = 19 | 4- | 2- | +++ |
| GDNF | 2+, 4- | 0 | 6+, 4- | 5+, 5- | 0 | 13+, 13- = 26 | 5- | 0 | +++ |
| TGF-β1 | 5+, 3- | 0 | 1+, 1- | 5+, 2- | 1+ | 11+, 6- = 17 | 2- | 3+ | +/- |
| TGF-β2 | 5+, 3- | 0 | 1+, 2- | 4+, 3- | 1+ | 10+, 8- = 18 | 3- | 1+ | +/- |

| | Sequence | Folding | ROS | Changes |
|---|---|---|---|---|
| OP-1 | K P CC A P T Q L N A I S V L Y F D D S S N V I L K K Y R N M V V R A CGC | H | 5 | [-] |
| 2421 | P T CC V P T R L S P I S I L F I D A S N V L K K Y R R N M V V R A CGC | R | (+) | [8] |
| 2406 | N S CC V P T K L T P I S I L Y F D D S N N I L K K Y N M V V R A CGC | R | (+) | [18] |
| 2410 | N S CC V P T E L S A I S M L Y L D E N E K V V L K K Y R N M V V E G CGC | 3+ | 4 | |
| 2247 | K P CC A P T Q L N A I S V L Y F D D S S N V I L K K Y E D M V V R A CGC | R | (+) | 3 [1] |
| 2234 | K P CC A P T Q L N A I S V L Y F D D S S N V I L K K Y E D M V V R A CGC | R | (+) | [3] |
| 2233 | K P CC A P T Q L N A I S V L Y F D D S S N V I L K K Y E D M V V E A CGC | R | 1+ | 3 [4] |
| 2418 | N S CC V P T K L T P I S V L Y F D D S S N V I L K K Y E D M V V E A CGC | R | 3+ | 2 [10] |
| 2443 | N S CC V P T K L T P I S V L Y F D D S S N V I L K K Y E D M V V R S CGC | R | 3+ | [9] |
| 2447 | N S CC V P T E L S A I S V L Y F D D S S N V I L K K Y E D M V V E A CGC | R | 3+ | 2 [9] |
| 2457 | N S CC V P T E L N A I S V L Y F D D S S N V I L K K Y E D M V V E A CGC | R | 2+ | 3 [8] |
| 2456 | K P CC A P T E L S A I S V L Y F D D S S N V I L K K Y E D M V V E A CGC | R | 3+ | 3 [6] |
| 2460 | K P CC A P T E L Q L S A I S V L Y F D D S S N V I L K K Y E D M V V E A CGC | R | 3+ | [5] |
| 2457 | N S CC V P T E L N A I S V L Y F D D S S N V I L K K Y E D M V V E A CGC | R | 2+ | 3 [8] |
| 2449 | K P CC A P T E L N A I S V L Y F D D S S N V I L K K Y R N M V V R A CGC | R | 2+ | 3 [2] |
| 2467 | K P CC A P T E L S A I S V L Y F D D S S N V I L K K Y R N M V V R A CGC | R | (+) | [3] |
| 2464 | K P CC A P T Q L S A I S V L Y F D D S S N V I L K K Y R N M V V R A CGC | R | (+) | [2] |

FINGER-2 SEQUENCES OF OP-1 MUTANTS AND THEIR FOLDING EFFICIENCIES AND BIOLOGICAL ACTIVITIES IN THE ROS CELL BASED ALKALINE PHOSPHATASE ASSAY.

MODIFIED TGF-β SUPERFAMILY PROTEIN

The instant application is a continuation of U.S. application Ser. No. 10/816,768, filed Apr. 2, 2004, now abandoned which is a continuation of U.S. application Ser. No.09/375,333, filed Aug. 16, 1999, now abandoned, which claims priority to U.S. provisional patent application No. 60/103,418, filed on Oct. 7, 1998, the entire contents of which is incorporated herein by reference.

RELATED APPLICATION INFORMATION

The instant application is related to utility applications U.S. Ser. No. 09/374,958, now U.S. Pat. Nos. 6,677,432 and 09/374,936, now U.S. Pat. No. 6,846,906, both filed on Aug. 16, 1999 and also based on the aforementioned provisional application (60/103,418, filed on Oct. 7, 1998), the disclosures of which are incorporated herein by reference.

FIELD OF THE INVENTION

The invention relates to recombinant proteins having improved refolding properties, improved physical properties (such as solubility and stability), improved biological activity, including altered receptor binding, improved targeting capabilities, latent forms of proteins, and methods for producing such proteins. More particularly, the invention relates to biosynthetic members of the TGF-β super-family of structurally-related proteins. Such modified protein constructs include TGF-β family member proteins that have N-terminal truncations, "latent" proteins, fusion proteins and heterodimers.

BACKGROUND OF THE INVENTION

The TGF-β superfamily includes five distinct forms of TGF-β (Sporn and Roberts (1990) in *Peptide Growth Factors and Their Receptors*, Sporn and Roberts, eds., Springer-Verlag: Berlin pp. 419-472), as well as the differentiation factors vg-1 (Weeks and Melton (1987) *Cell* 51: 861-867), DPP-C polypeptide (Padgett et al. (1987) *Nature* 325: 81-84), the hormones activin and inhibin (Mason et al. (1985) *Nature* 318: 659-663; Mason et al. (1987) *Growth Factors* 1: 77-88), the Mullerian-inhibiting substance, MIS (Cate et al. (1986) *Cell* 45:685-698), osteogenic and morphogenic proteins OP-1 (PCT/US90/05903), OP-2 (PCT/US91/07654), OP-3 (PCT/WO94/10202), the BMPs, (see U.S. Pat. Nos. 4,877,864; 5,141,905; 5,013,649; 5,116,738; 5,108,922; 5,106,748; and 5,155,058), the developmentally regulated protein VGR-1 (Lyons et al. (1989) *Proc. Natl. Acad. Sci. USA* 86: 4554-4558), cartilage-derived growth factors CDMP-1, CDMP-2 and CDMP-3 (or GDF-5, GDF-6 and GDF-7), and the growth/differentiation factors GDF-1, GDF-3, GDF-9 and dorsalin-1 (McPherron et al. (1993) *J. Biol. Chem.* 268: 3444-3449; Basler et al. (1993) *Cell* 73: 687-702).

The proteins of the TGF-β superfamily are disulfide-linked homo- or heterodimers that are expressed as large precursor polypeptide chains containing a hydrophobic signal sequence, a long and relatively poorly conserved N-terminal pro region sequence of several hundred amino acids, a cleavage site, and a mature domain comprising an N-terminal region that varies among the family members and a more highly conserved C-terminal region. This C-terminal region, present in the processed mature proteins of all known family members, contains approximately 100 amino acids with a characteristic cysteine motif having a conserved six or seven cysteine skeleton. Although the position of the cleavage site between the mature and pro regions varies among the family members, the cysteine pattern of the C-terminus of all of the proteins is in the identical format, ending in the sequence Cys-X-Cys-X (Sporn and Roberts (1990), supra).

Recombinant TGF-β1 has been cloned (Derynck et al. (1985) *Nature* 316: 701-705), and expressed in Chinese hamster ovary cells (Gentry et al. (1987) *Mol. Cell. Biol.* 7: 3418-3427). Additionally, recombinant human TGF-β2 (deMartin et al. (1987) *EMBO J.* 6: 3673), as well as human and porcine TGF-β3 (Derynck et al. (1988) *EMBO J.* 7: 3737-3743; Dijke et al. (1988) *Proc. Natl. Acad. Sci. USA* 85: 4715), have been cloned. Expression levels of the mature TGF-β1 protein in COS cells have been increased by substituting cysteine residues located in the pro region of the TGF-β1 precursor with serine residues (Brunner et al. (1989) *J. Biol. Chem.* 264: 13660-13664).

A unifying feature of the biology of the proteins of the TGF-β superfamily is their ability to regulate developmental processes. These structurally related proteins have been identified as being involved in a variety of developmental events. For example, TGF-β and the polypeptides of the inhibin/activin group appear to play a role in the regulation of cell growth and differentiation. MIS causes regression of the Mullerian duct in development of the mammalian male embryo, and dpp, the gene product of the *Drosophila* decapentaplegic complex, is required for appropriate dorsal-ventral specification. Similarly, Vg-1 is involved in mesoderm induction in *Xenopus*, and Vgr-1 has been identified in a variety of developing murine tissues. Regarding bone formation, many of the proteins in the TGF-β supergene family, namely OP-1 and a subset of the BMPs, apparently play the major role. OP-1 (BMP-7) and other osteogenic proteins have been produced using recombinant techniques (U.S. Pat. No. 5,011,691 and PCT Application No. US 90/05903) and shown to be able to induce formation of true endochondral bone in vivo. BMP-2 has been recombinantly produced in monkey COS-1 cells and Chinese hamster ovary cells (Wang et al. (1990) *Proc. Natl. Acad. Sci. USA* 87: 2220-2224).

Recently the family of proteins taught as having osteogenic activity as judged by the Sampath and Reddi bone formation assay have been shown to be morphogenic, i.e., capable of inducing the developmental cascade of tissue morphogenesis in a mature mammal (See PCT Application No. US 92/01968). In particular, these proteins are capable of inducing the proliferation of uncommitted progenitor cells, and inducing the differentiation of these stimulated progenitor cells in a tissue-specific manner under appropriate environmental conditions. In addition, the morphogens are capable of supporting the growth and maintenance of these differentiated cells. These morphogenic activities allow the proteins to initiate and maintain the developmental cascade of tissue morphogenesis in an appropriate, morphogenically permissive environment, stimulating stem cells to proliferate and differentiate in a tissue-specific manner, and inducing the progression of events that culminate in new tissue formation. These morphogenic activities also allow the proteins to induce the "redifferentiation" of cells previously stimulated to stray from their differentiation path. Under appropriate environmental conditions it is anticipated that these morphogens also may stimulate the "redifferentiation" of committed cells.

The osteogenic proteins generally are classified in the art as a subgroup of the TGF-β superfamily of growth factors (Hogan (1996), Genes & Development, 10:1580-1594), and are variously termed "osteogenic proteins", "morphogenic proteins", "morphogens", "bone morphogenic proteins" or "BMPs" are identified by their ability to induce ectopic, endochondral bone morphogenesis. Members of the morphogen family of proteins include the mammalian osteogenic protein-1 (OP-1, also known as BMP-7, and the *Drosophila* homolog 60A), osteogenic protein-2 (OP-2, also known as BMP-8), osteogenic protein-3 (OP-3), BMP-2 (also known as BMP-2A or CBMP-2A, and the *Drosophila* homolog DPP), BMP-3, BMP-4 (also known as BMP-2B or CBMP-2B), BMP-5, BMP-6 and its murine homolog Vgr-1, BMP-9, BMP-10, BMP-11, BMP-12, GDF3 (also known as Vgr2), GDF-8, GDF-9, GDF-10, GDF-11, GDF-12, BMP-13, BMP-14, BMP-15, GDF-5 (also known as CDMP-1 or MP52), GDF-6 (also known as CDMP-2 or BMP-13), GDF-7 (also known as CDMP-3 or BMP-12), the *Xenopus* homolog Vgl and NODAL, UNIVIN, SCREW, ADMP, and NEURAL.

Whether naturally-occurring or synthetically prepared, osteogenic proteins, can induce recruitment and/or stimulation of progenitor cells, thereby inducing their differentiation into chondrocytes and osteoblasts, and further inducing differentiation of intermediate cartilage, vascularization, bone formation, remodeling, and, finally, marrow differentiation. Furthermore, numerous practitioners have demonstrated the ability of these osteogenic proteins, when admixed with either naturally-sourced matrix materials such as collagen or synthetically-prepared polymeric matrix materials, to induce bone formation, including membraneous and endochondral bone formation, under conditions where true replacement bone would not otherwise occur. For example, when combined with a matrix material, these osteogenic proteins induce formation of new bone in large segmental bone defects, spinal fusions, clavarial defects, and fractures.

Bacterial and other prokaryotic expression systems are relied on in the art as preferred means for generating recombinant proteins. Prokaryotic systems such as *E. coli* are useful for producing commercial quantities of proteins, as well as for evaluating biological properties of naturally occurring or biosynthetic mutants and analogs. Typically, an over-expressed eukaryotic protein aggregates as an insoluble intracellular precipitate ("inclusion body") in the prokaryote host cell. The aggregated protein is then collected from the inclusion bodies, solubilized using one or more standard denaturing agents, and then allowed, or induced, to refold into a functional state. Proper refolding to form a biologically active protein structure requires proper formation of any disulfide bonds.

Chemical synthesis may also be employed to produce protein constructs. Technology is widely available to permit routine, automated assembly of peptide chains. Techniques are known in the art which utilize enzymatic and chemical methods for coupling peptide fragments into synthetic protein molecules. See, e.g., Hilvert, *Chem. Biol.* (1994) 1(4): 201-03; Muir et al., *Proc. Nat'l Acad. Sci. USA* (1998) 95(12): 6705-10; Wallace, *Curr. Opin. Biotechnol.* (1995) 6(4): 403-10; Miranda et al., *Proc. Nat'l Acad. Sci. USA* (1999) 96(4): 1181-6; and Liu et al., *Proc. Nat'l Acad. Sci. USA* (1994) 91(14): 6584-8.

For example, the tertiary and quaternary structure of both TGF-β2 and OP-1 have been determined. Although TGF-β2 and OP-1 exhibit only about 35% amino acid identity in their respective amino acid sequences the tertiary and quaternary structures of both molecules are strikingly similar. Both TGF-β2 and OP-1 are dimeric in nature and have a unique folding pattern involving six of the seven C-terminal cysteine residues, as illustrated in FIG. 1A. FIG. 1A shows that in each subunit four cysteines bond to generate an eight residue ring, and two additional cysteine residues form a disulfide bond that passes through the ring to form a knot-like structure. With a numbering scheme beginning with the most N-terminal cysteine of the 7 conserved cysteine residues assigned number 1, the 2nd and 6th conserved cysteine residues bond to close one side of the eight residue ring while the 3rd and 7th cysteine residues close the other side. The 1st and 5th conserved cysteine residues bond through the center of the ring to form the core of the knot. The 4th conserved cysteine forms an interchain disulfide bond with the corresponding residue in the other subunit.

The TGF-β2 and OP-1 monomer subunits comprise three major structural elements and an N-terminal region. The structural elements are made up of regions of contiguous polypeptide chain that possess over 50% secondary structure of the following types: (1) loop, (2) α-helix and (3) β-sheet. Furthermore, in these regions the N-terminal and C-terminal strands are not more than 7 A° apart. The residues between the 1st and 2nd conserved cysteines (FIG. 1A) form a structural region characterized by an anti-parallel β-sheet finger, referred to herein as the finger 1 region (F1). A ribbon trace of the finger 1 peptide backbone is shown in FIG. 1B. Similarly the residues between the 5th and 6th conserved cysteines in FIG. 1A also form an anti-parallel β-sheet finger, referred to herein as the finger 2 region (F2). A ribbon trace of the finger 2 peptide backbone is shown in FIG. 1D. A β-sheet finger is a single amino acid chain, comprising a β-strand that folds back on itself by means of a β-turn or some larger loop so that the entering and exiting strands form one or more anti-parallel β-sheet structures. The third major structural region, involving the residues between the 3rd and 4th conserved cysteines in FIG. 1A, is characterized by a three turn α-helix referred to herein as the heel region (H). A ribbon trace of the heel peptide backbone is shown in FIG. 1C.

The organization of the monomer structure is similar to that of a left hand where the knot region is located at the position equivalent to the palm, finger 1 is equivalent to the index and middle fingers, the α-helix is equivalent to the heel of the hand, and finger 2 is equivalent to the ring and small fingers. The N-terminal region (not well defined in the published structures) is predicted to be located at a position roughly equivalent to the thumb.

In the dimeric forms of both TGF-β2 and OP-1, the subunits are oriented such that the heel region of one subunit contacts the finger regions of the other subunit with the knot regions of the connected subunits forming the core of the molecule. The 4th cysteine forms a disulfide bridge with its counterpart on the second chain thereby equivalently linking the chains at the center of the palms. The dimer thus formed is an ellipsoidal (cigar shaped) molecule when viewed from the top looking down the two-fold axis of symmetry between the subunits (FIG. 2A). Viewed from the side, the molecule resembles a bent "cigar" since the two subunits are oriented at a slight angle relative to each other (FIG. 2B).

However, not all solubilized heterologous proteins readily refold. Despite careful manipulation of refolding, the yields of properly folded, biologically active protein remain low. Many TBF-β family members, including BMPs, fall into the category of poor refolder proteins. While some members of the TBF-β protein family can be folded efficiently in vitro as, for example, when produced in *E. coli* or other prokaryotic hosts, many others, including BMP5, BMP6, and BMP7, cannot. See, e.g., EP 0433225, U.S. Pat. Nos. 5,399,677, 5,756,308 and 5,804,416.

A need remains for improved means for producing in vitro recombinant BMPs and other TGF-β family proteins using prokaryotic as well as eukaryotic host cells.

SUMMARY OF THE INVENTION

The present invention provides modified TGF-β family proteins which comprise N-terminal extensions, truncations and other modifications at the N-terminal end of C-terminal active domains. Modified proteins of the invention have altered refolding properties and altered solubility with respect to naturally occurring proteins when expressed recombinantly. Modified proteins of the invention also have altered activity profiles, including enhanced specific activity, and are amenable to tissue-specific targeting or specific surface binding.

As a result of these discoveries, means are available for predicting and designing de novo BMPs and other TGF-β family member analogs having altered biological properties, including improved folding capabilities in vitro, improved solubility, altered stability, altered isoelectric points, and/or altered biological activities, as desired. These discoveries also lend themselves to creating proteins whose activity can be directed towards specific sites within a mammal and/or whose activity can be regulated, inhibited and/or induced. The invention also provides means for easily and quickly evaluating biological and/or biochemical properties of candidate constructs, including mapping epitopes of folded proteins.

The invention provides "mutant" forms of proteins that improve the refolding properties of "poor refolder" TGF-β family members. As used herein, a "poor refolder" protein means any protein that, when induced to refold under suitable refolding conditions, yields less than about 1% properly refolded material, as measured using a standard protocol (see below). As contemplated herein, "suitable refolding conditions" are conditions under which proteins can be refolded to the extent required to confer functionality. One skilled in the art will recognize that at least Section IC and Example 3 of the "Detailed Description of the Preferred Embodiment" are non-limiting examples of such refolding conditions. Structural parameters relevant to the compositions and methods of the instant invention include one or more disulfide bridges properly distributed throughout the dimeric protein's structure and which require a reduction-oxidation ("redox") reaction step to yield a folded structure. Redox reactions typically occur at neutral pH, i.e., in the range of about pH 7.0-8.5, typically in the range of about pH 7.5-8.5, and preferably under physiologically-compatible conditions. The skilled artisan will appreciate and recognize optimal conditions for success.

The proteins preferably are manufactured in accordance with the principles disclosed herein by assembly of nucleotides and/or joining DNA restriction fragments to produce synthetic DNAs. The DNAs are transfected into an appropriate protein expression vehicle, the encoded protein expressed, folded if necessary, and purified. Particular constructs can be tested for activity in vitro. The tertiary structure of the candidate protein constructs may be iteratively refined and binding modulated by site-directed or nucleotide sequence directed mutagenesis aided by the principles disclosed herein, computer-based protein structure modeling, and recently developed rational drug design techniques to improve or modulate specific properties of a molecule of interest. Known phage display or other nucleotide expression systems may be exploited to produce simultaneously a large number of candidate constructs. The pool of candidate constructs subsequently may be screened for binding specificity using, for example, a chromatography column comprising surface immobilized receptors, salt gradient elution to select for, and to concentrate high binding candidates, and in vitro assays. Identification of a useful recombinant protein is followed by production of cell lines expressing commercially useful quantities of the protein for laboratory use and ultimately for producing therapeutically useful drugs. It has now been discovered how to design, make, test and use chimeric proteins comprising an amino acid sequence which, when properly folded, assume a tertiary structure defining a finger 1 region, a finger 2 region, and a heel region.

All of the constructs of the invention comprise regions of amino acid sequences defining the regions required for utility, namely, finger 1, finger 2, and heel regions, and an additional region that can modify activity, namely the N-terminal peptide sequence. Sequences for the finger and heel regions may be copied from the respective finger and heel region sequences of any known TGF-β superfamily member identified herein. Alternatively, the finger and heel regions may be selected from the amino acid sequence of a new member of this superfamily discovered hereafter using the principles disclosed hereinbelow.

The finger and heel sequences also may be altered by amino acid substitution, for example by exploiting substitute amino acid residues selected in accordance with the principles disclosed in Smith et al. (1990) *Proc. Natl. Acad. Sci. USA* 87: 118-122, the disclosure of which is incorporated herein by reference. Smith et al. disclose an amino acid class hierarchy, similar to the amino acid hierarchy table set forth in FIG. 3, which may be used to rationally substitute one amino acid for another while minimizing gross conformational distortions of the type which otherwise may inactivate the protein. In any event, it is contemplated that many synthetic finger 1, finger 2, and heel region sequences, having only 70% homology with natural regions, preferably 80%, and most preferably at least 90%, may be used to produce active morphon constructs. It is contemplated also, as disclosed herein, that the size of the constructs may be reduced significantly by truncating the natural finger and heel regions of the template TGF-β superfamily member.

As used herein, "acidic" or "negatively charged residues" are understood to include any amino acid residue, naturally-occurring or synthetic, that typically carries a negative charge on its R group under physiological conditions. Examples include, without limitation, aspartic acid ("Asp") and glutamic acid ("Glu"). Similarly, basic or positively charged residues include any amino acid residue, naturally-occurring or synthetically created, that typically carries a positive charge on its R group under physiological conditions. Examples include, without limitation, arginine ("Arg"), lysine ("Lys") and histidine ("His"). As used herein, "hydrophilic" residues include both acidic and basic amino acid residues, as well as uncharged residues carrying amide groups on their R groups, including, without limitation, glutamine ("Gln") and asparagine ("Asn"), and polar residues carrying hydroxyl groups on their R groups, including, without limitation, serine ("Ser"), tyrosine ("Tyr") and threonine ("Thr"). A skilled artisan will appreciate that the actual physiological pK will vary, and that the charge will vary in different physiological environments.

As used herein, "biosynthesis" or "biosynthetic" means occurring as a result of, or originating from a ligation of naturally- or synthetically-derived fragments. For example, but not limited to, ligating peptide or nucleic acid fragments corresponding to one or more subdomains (or fragments thereof) disclosed herein. "Chemosynthesis" or "chemosynthetic" means occurring as a result of, or originating from, a chemical means of production. For example, but not limited to, synthesis of a peptide or nucleic acid sequence using a standard automated synthesizer/sequencer from a commercially-available source. It is contemplated that both natural and non-natural amino acids can be used to obtain the desired attributes, as taught herein. "Recombinant" production or technology means occurring as a result of, or originating from, a genetically engineered means of production. For example, but not limited to, expression of a genetically-engineered DNA sequence or gene encoding a chimeric protein (or fragment thereof) of the present invention. Also included within the meaning of the foregoing are the teachings set forth below in at least Sections I.B.; Section II; and at least Examples 1 and 2. "Synthetic" means occurring or originating non-naturally, i.e., not naturally occurring.

As used herein, "corresponding residue position" refers to a residue position in a protein sequence that corresponds to a given position in an OP-1 or other reference TGF-β family member amino acid sequence, when the two sequences are aligned. As will be appreciated by those skilled in the art and as illustrated in FIG. 1, the sequences of BMP family members are highly conserved in the C-terminal active domain, and particularly in the finger 2 sub-domain. Amino acid sequence alignment methods and programs are well developed in the art. See, e.g., the method of Needleman, et al. (1970) *J. Mol. Biol.* 48:443-453, implemented conveniently by computer programs such as the Align program (DNAstar, Inc.). Internal gaps and amino acid insertions in the second sequence are ignored for purposes of calculating the alignment. For ease of description, hOP-1 (human OP-1, also referred to in the art as "BMP-7") is provided below as a representative osteogenic protein. It will be appreciated however, that OP-1 is merely representative of the TGF-β family of proteins.

As used herein, "TGF-β family member" or "TGF-β family protein," means a protein known to those of ordinary skill in the art as a member of the TGF-β superfamily. Structurally, such proteins are disulfide-linked homo or heterodimers that are expressed as large precursor polypeptide chains containing a hydrophobic signal sequence, an N-terminal pro region of several hundred amino acids, and a mature domain comprising a variable N-terminal region and a more highly conserved C-terminal region containing approximately 100 amino acids with a characteristic cysteine motif having a conserved six or seven cysteine skeleton. These structurally-related proteins have been identified as being involved in a variety of developmental events. TGF-β family members are typified by TGFβ1 and OP-1. Other TGF-β family proteins useful in the practice of the present invention include osteogenic proteins (as defined below), vg-1, DPP-C polypeptide, the hormones activin and inhibin, MIS, VGR-1 and growth/differentiation factors GDF-1, GDF-3, GDF-9 and dorsalin-1.

It has been found that various members of the TGF-β protein superfamily mediate their activity by interaction with two different cell surface receptors, referred to as Type I and Type II receptors, to form a hetero-complex. The Type I and Type II receptors are both serine/threonine kinases and share similar structures: an intracellular domain that consists essentially of the kinase, and a short, extended hydrophobic sequence sufficient to span the membrane one time, and an extracellular ligand-binding domain characterized by a high concentration of conserved cysteines. The various Type I and Type II receptors have specific binding affinity with OP-1 and other morphogenic proteins, and their analogs, including the modified morphogens of the present invention.

"Osteogenic protein", or "bone morphogenic protein," means a TGF-β superfamily protein which can induce the full cascade of morphogenic events culminating in skeletal tissue formation, including but not limited to cartilage and/or endochondral bone formation. Osteogenic proteins useful herein include any known naturally-occurring native proteins including allelic, phylogenetic counterpart and other variants thereof, whether naturally-occurring or biosynthetically produced (e.g., including "muteins" or "mutant proteins"), as well as new, osteogenically active members of the general morphogenic family of proteins. As described herein, this class of proteins is generally typified by human osteogenic protein 1 (hOP-1). Other osteogenic proteins useful in the practice of the invention include osteogenically active forms of proteins included within the list of: OP-1, OP-2, OP-3, BMP-2, BMP-3, BMP-4, BMP-5, BMP-6, BMP-9, DPP, Vg-1, Vgr, 60A protein, CDMP-1, CDMP-2, CDMP-3, GDF-1, GDF-3, GDF-5,6,7, MP-52, BMP-10, BMP-11, BMP-12, BMP-13, BMP-15, UNIVIN, NODAL, SCREW, ADMP or NEURAL, including amino acid sequence variants thereof, and/or heterodimers thereof. In one currently preferred embodiment, osteogenic protein useful in the practice of the invention includes any one of: OP-1, BMP-2, BMP-4, BMP-12, BMP-13, GDF-5, GDF-6, GDF-7, CDMP-1, CDMP-2, CDMP-3, MP-52 and amino acid sequence variants and homologs thereof, including species homologs thereof. In still another preferred embodiment, useful osteogenically active proteins have polypeptide chains with amino acid sequences comprising a sequence encoded by a nucleic acid that hybridizes, under low, medium or high stringency hybridization conditions, to DNA or RNA encoding reference osteogenic sequences, e.g., C-terminal sequences defining the conserved seven cysteine domains of OP-1, OP-2, BMP-2, BMP-4, BMP-5, BMP-6, 60A, GDF-5, GDF-6, GDF-7 and the like. As used herein, high stringent hybridization conditions are defined as hybridization according to known techniques in 40% formamide, 5×SSPE, 5×Denhardt's Solution, and 0.1% SDS at 37° C. overnight, and washing in 0.1×SSPE, 0.1% SDS at 50° C. Standard stringency conditions are well characterized in commercially available, standard molecular cloning texts. See, for example, *Molecular Cloning A Laboratory Manual,* 2nd Ed., ed. by Sambrook, Fritsch and Maniatis (Cold Spring Harbor Laboratory Press: 1989); *DNA Cloning,* Volumes I and II (D. N. Glover ed., 1985); *Oligonucleotide Synthesis* (M. J. Gait ed., 1984): *Nucleic Acid Hybridization* (B. D. Hames & S. J. Higgins eds. 1984); and B. Perbal, *A Practical Guide To Molecular Cloning* (1984); the disclosures of the foregoing are incorporated by reference herein. See also, U.S. Pat. Nos. 5,750,651 and 5,863,758, the disclosures of which are incorporated by reference herein.

Other members of the TGF-β superfamily of related proteins having utility in the practice of the instant invention include native poor refolder proteins among the list: TGF-β1, TGF-β2, TGF-β3, TGF-β4 and TGF-β5, various inhibins, activins, BMP-11, and MIS, to name a few. FIG. 4 lists the C-terminal 35 residues defining the finger 2 subdomain of various known members of the TGF-β superfamily. Any one of the proteins on the list that is a poor refolder can be improved by the methods of the invention, as can other known or discoverable family members. As further described herein, the biologically active osteogenic proteins suitable for use with the present invention can be identified by means of routine experimentation using the art-recognized bioassay described by Reddi and Sampath. A detailed description of useful proteins follows. Equivalents can be identified by the artisan using no more than routine experimentation and ordinary skill.

"Morphogens" or "morphogenic proteins" as contemplated herein includes members of the TGF-β superfamily which have been recognized to be morphogenic, i.e., capable of inducing the developmental cascade of tissue morphogenesis in a mature mammal (See PCT Application No. US 92/01968). In particular, these morphogens are capable of inducing the proliferation of uncommitted progenitor cells, and inducing the differentiation of these stimulated progenitor cells in a tissue-specific manner under appropriate environmental conditions. In addition, the morphogens are capable of supporting the growth and maintenance of these differentiated cells. These morphogenic activities allow the proteins to initiate and maintain the developmental cascade of tissue morphogenesis in an appropriate, morphogenically permissive environment, stimulating stem cells to proliferate and differentiate in a tissue-specific manner, and inducing the progression of events that culminate in new tissue formation. These morphogenic activities also allow the proteins to induce the "redifferentiation" of cells previously stimulated to stray from their differentiation path. Under appropriate environmental conditions it is anticipated that these morphogens also may stimulate the "redifferentiation" of committed cells. To guide the skilled artisan, described herein are numerous means for testing morphogenic proteins in a variety of tissues and for a variety of attributes typical of morphogenic proteins. It will be understood that these teachings can be used to assess morphogenic attributes of native proteins as well as modified proteins of the present invention.

Useful native or parent proteins of the present invention also include those sharing at least 70% amino acid sequence homology within the C-terminal seven-cysteine domain of human OP-1. To determine the percent homology of a candidate amino acid sequence to the conserved seven-cysteine domain, the candidate sequence and the seven cysteine domain are aligned. The first step for performing an alignment is to use an alignment tool, such as the dynamic programming algorithm described in Needleman et al., J. MOL. BIOL. 48: 443 (1970), the teachings of which are incorporated by reference herein and the Align Program, a commercial software package produced by DNAstar, Inc. After the initial alignment is made, it is then refined by comparison to a multiple sequence alignment of a family of related proteins. Once the alignment between the candidate sequence and the seven-cysteine domain is made and refined, a percent homology score is calculated. The individual amino acids of each sequence are compared sequentially according to their similarity to each other. Similarity factors include similar size, shape and electrical charge. One particularly preferred method of determining amino acid similarities is the PAM250 matrix described in Dayhoff et al., 5 ATLAS OF PROTEIN SEQUENCE AND STRUCTURE 345-352 (1978 & Supp.), incorporated by reference herein. A similarity score is first calculated as the sum of the aligned pairwise amino acid similarity scores. Insertions and deletions are ignored for the purposes of percent homology and identity. Accordingly, gap penalties are not used in this calculation. The raw score is then normalized by dividing it by the geometric mean of the scores of the candidate compound and the seven cysteine domain. The geometric mean is the square root of the product of these scores. The normalized raw score is the percent homology.

As used herein, "conservative substitutions" are residues that are physically or functionally similar to the corresponding reference residues, e.g., that have similar size, shape, electric charge, chemical properties including the ability to form covalent or hydrogen bonds, or the like. Particularly preferred conservative substitutions are those fulfilling the criteria defined for an accepted point mutation in Dayhoff et al. Ibid. Examples of conservative substitutions include the substitution of one amino acid for another with similar characteristics, e.g., substitutions within the following groups are well-known: (a) glycine, alanine; (b) valine, isoleucine, leucine; (c) aspartic acid, glutamic acid; (d) asparagine, glutamine; (e) serine, threonine; (f) lysine, arginine, histidine; and (g) phenylalanine, tyrosine. The term "conservative variant" or "conservative variation" also includes the use of a substituted amino acid in place of an unsubstituted parent amino acid in a given polypeptide chain, provided that antibodies having binding specificity for the resulting substituted polypeptide chain also have binding specificity (i.e., "cross-react" or "immunoreact" with) the unsubstituted or parent polypeptide chain.

As used herein, a "conserved residue position" refers to a location in a reference amino acid sequence occupied by the same amino acid or a conservative variant thereof in at least one other member sequence. For example, in FIG. 4, comparing BMP-2, BMP-4, BMP-5, and BMP-6 with OP-1 as the reference sequence, positions 1, 5, 9, 12, 14, 15, 16, 17, 19, 22, etc. are conserved positions, and residues 2, 3, 4, 6, 7, 8, 10, 11, 13, 18, 20, 21, etc. are non-conserved positions.

As used herein, the "base" or "neck" region of the finger 2 sub-domain is defined by residues 1-10 and 22-35, as exemplified by OP-1, and counting from the first residue following the cysteine doublet in the C-terminal active domain. (See FIG. 4). As is readily apparent from a sequence alignment of other TGF-β protein family members with OP-1, the corresponding base or neck region for a longer protein, such as BMP-9 or Dorsalin, is defined by residues 1-10 and 23-36; for a shorter protein, such as NODAL, the corresponding region is defined by residues 1-10 and 22-34 (See FIG. 4). In SEQ ID NO: 39, (human OP-1), the residues corresponding to the base or neck region of the finger 2 subdomain are residues 397-406 (corresponding to residues 1-10 in FIG. 4) and residues 418-431 (corresponding to residues 22-35 in FIG. 4).

As used herein, "C-terminal active domain" refers to the conserved C-terminal region of mature TGF-β family proteins. The C-terminal active domain contains approximately 100 amino acids with a characteristic cysteine motif having a six or seven cysteine skeleton. The cysteine pattern of the C-terminus of all of the proteins is in the identical format ending in the sequence Cys-X-Cys-X (Sporn and Roberts (1990), supra.)

As used herein, "amino acid sequence homology" includes both amino acid sequence identity and similarity. Homologous sequences share identical and/or similar amino acid residues, where similar residues are conservative substitutions for, or "allowed point mutations" of, corresponding amino acid residues in an aligned reference sequence.

As used herein, the terms "chimeric protein", "chimera", "chimeric polypeptide chain", "chimeric construct" and "chimeric mutant" refer to any BMP or TGF-β family member synthetic construct wherein the amino acid sequence of at least one defined region, domain or sub-domain, such as the finger 1, finger 2 or heel sub-domain, has been replaced in whole or in part with an amino acid sequence from at least one other, different BMP or TGF-β family member protein, such that the resulting construct has an amino acid sequence recognizable as being derived from the different protein sources. Chimeric constructs also comprise recombinant fusion proteins in which the C-terminal active domain of one morphogen is fused to the N-terminal domain of another morphogen.

As used herein, a "leader sequence" is any sequence of amino acids corresponding to a sequence of nucleotides upstream, that is, positioned farther to the C-terminal end, of the C-terminal active domain region of a TGF-β family protein. Modifications in the leader sequence can alter refolding properties, activity levels, solubility, control activation, and promote tissue-targeting as well as affinity-binding ability.

As used herein, useful expression host cells include prokaryotes and eukaryotes, including any host cell capable of making an inclusion body. Particularly useful host cells include, without limitation, bacterial hosts such as *E. coli*, as well as *B. subtilis* and *Pseudomonas*. Other useful hosts include lower eukaryotes, such as *Saccharomyces cereviceae* or other yeast, and higher eukaryotes, such as *Drosophila*, CHO cells, and other mammalian cells, and the like. As discussed herein, chemical synthesis methods can also be utilized to generate the modified proteins of the present invention.

In one aspect, the invention provides construction of recombinant proteins not readily expressed in mammalian cells, such as, for example, fusion proteins and the like. For example, a recombinant gene encoding a fusion protein having bone targeting properties is constructed, wherein a single sequence encodes both a BMP and an antibody binding site having specificity for a bone matrix protein such as osteocalcin or fibronectin. Similarly, a fusion protein can also be constructed to bind to cell surface receptors such as those on osteoprogenitor cells or chondrocytes. Other recombinant genes may encode for fusion proteins that specifically bind metals or other proteins. The specificity of the binding would depend on the composition of the leader sequence that is added to the BMP. These genes can be expressed in *E. coli* and refolded in vitro.

In another embodiment, a cleavable fusion construct (cleavable by proteases—such as trypsin, V8, factor Xa and others, or chemically—with mild acid, hydroxylamine and other agents) is synthesized wherein the TGF-β protein is attached to a leader sequence that blocks activity. In still another embodiment the activity of a TGF-β family member is restored or enhanced by cleaving a portion or all of the leader sequence. By adding a cleavable leader sequence that inhibits activity, a latent form of the protein is created that can subsequently be cleaved to release a protein fragment comprising the active C-terminal domain.

In yet another embodiment, the leader sequence is also a tissue-targeting sequence, such that release can be controlled to occur at the target site in vivo. The construction of the cleavage site can also allow one to control the release of active protein. For example, in bone tissue a number of proteases involved in bone remodeling typically are present and can be used to advantage. A cleavable "hexa-his", FB leader, or collagen binding sequence described below may be a suitable leader sequence for a latent form of the protein. By way of example, the tissue-targeting domain can be separated from a BMP by a leader sequence that includes a run of at least three basic residues, which is known to be cleaved in vivo.

In still another embodiment, the leader sequence can be constructed so that the portion of the protein that is inhibiting specific activity is cleaved and activity restored, but the tissue-targeting portion of the protein is retained.

In yet another preferred embodiment, the leader sequence of the TGF-β family protein is replaced by a leader sequence of another TGF-β member. The resultant "chimeric" protein may have altered solubility, folding and/or tissue targeting activity, improved stability, and/or the ability to bind to specific surfaces.

In another aspect of the invention, the fusion proteins are combined with other TGF-β family proteins to form heterodimers, wherein one can exploit the properties of each protein. For example, a fusion protein with tissue-targeting properties but no activity forms a heterodimer with a different protein which has activity, but no tissue-targeting ability. The former protein delivers the heterodimer to a target site where the latter protein can perform its function.

In one aspect the invention provides biosynthetic BMPs and TGF-β family member proteins having improved refolding properties under neutral or physiological conditions. In one embodiment, the biosynthetic proteins of the invention have improved refolding properties at a pH in the range of about 5.0-10.0, preferably in the range of about 6.0-9.0, more preferably in the range of about 6.0-8.5, including in the range of about pH 7.0-7.5.

In another aspect the invention provides biosynthetic BMPs and TGF-β family member proteins having improved solubility properties under neutral or physiological conditions. In one embodiment, the biosynthetic proteins of the invention have improved solubility at a pH in the range of about 5.0-10.0, preferably in the range of about 6.0-9.0, more preferably in the range of about 6.0-8.5, including in the range of about pH 7.0-7.5.

In still another aspect the invention provides biologically active biosynthetic BMPs and TGF-β family member constructs competent to refold under physiological conditions and having altered isoelectric points as compared with the parent sequence.

In another aspect, the invention provides a method for folding homodimers and heterodimers, which are poor refolders, under physiological or neutral pH conditions. In one embodiment, the method comprises the steps of providing one or more solubilized TGF-β family protein constructs of the invention, exposing the solubilized protein to a redox reaction in a suitable refolding buffer, and allowing the protein subunits to refold into homodimers and/or heterodimers, as desired. In another embodiment, the modified TGF-β family proteins of the invention are not denatured prior to exposing them to the redox reaction. In another embodiment, the redox reaction system can utilize oxidized and reduced forms of glutathione, DTT, β-mercaptomethanol, cysteine and cystamine. In another embodiment, the redox reaction system relies on air oxidation, preferably in the presence of a metal catalyst, such as copper. In still another embodiment, these can be used as redox systems at ratios of reductant to oxidant of about 1:10 to about 10:1, preferably in the range of about 1:2 to 2:1. In another preferred embodiment, the protein is solubilized in the presence of a detergent, including an ionic detergent, a non-ionic detergent, e.g. digitonin, or zwitterionic detergents, such as 3-[(3-cholamidopropyl)dimethylammonio]-1-propanesulfate (CHAPS), or N-octyl glucoside. In still another embodiment, the refolding reaction occurs in a pH range of about 5.0-10.0, preferably in the range of about 6.0-9.0, more preferably in the range of about 7.0-8.5. In still another embodiment, the refolding reaction occurs at a temperature within the range of about 32-0° C., preferably in the range of about 25-4° C. Where heterodimers are being created, optimal ratios for adding the two different subunits readily can be determined empirically and without undue experimentation.

In another aspect, the invention provides methods for recombinantly producing poor refolder BMP and other TGF-β family member proteins in a host cell, including a bacterial host, or any other host cell where overexpressed protein aggregates in a form that requires solubilization and/or refolding in vitro. The method comprises the steps of providing a host cell transfected with nucleic acid molecules encoding one or more of the biosynthetic proteins of the invention, cultivating the host cells under conditions suitable for expressing the biosynthetic protein, collecting the aggregated protein, and solubilizing and refolding the protein using the steps outlined above. In another embodiment, the method comprises the additional step of transfecting the host cell with a nucleic acid encoding the biosynthetic protein of the invention.

Modified morphogens of the invention may be used to form bone and/or cartilage in conjunction with a biocompatible matrix such as (but not limited to) collagen, hydroxyapatite, ceramics, carboxymethylcellulose, and/or other carrier suitable or matrix material. Such combinations are particularly useful in methods for regenerating bone, cartilage and/or other non-mineralized skeletal or connective tissues such as (but not limited to) articular cartilage, fibrocartilage, ligament, tendon, joint capsule, menisci, intervertebral disks, synovial membrane tissue, muscle, and fascia, to name but a few. See e.g. U.S. Pat. Nos. 5,674,292, 5,840,325 and U.S. application Ser. No. 08/235,398, the disclosures of which are incorporated by reference herein. The present invention contemplates that the binding and/or adherence properties to such matrix materials can be altered using the techniques disclosed herein for generating protein constructs. The modified proteins of the invention may also be utilized to generate tendon, ligament and/or muscle tissue.

BRIEF DESCRIPTION OF THE DRAWINGS

FIG. 4 lists the aligned C-terminal residues defining the finger 2 sub-domain for various known members of the BMP family, and TGF-β superfamily of proteins, starting with the first residue following the cysteine doublet. OP-1 (amino acid residues 66-102 of SEQ ID NO: 55); BMP-5(amino acid residues 66-102 of SEQ ID NO: 52); BMP-6(amino acid residues 66-102 of SEQ ID NO: 53); OP-2 (amino acid residues 66-102 of SEQ ID NO: 56); OP-3(amino acid residues 66-102 of SEQ ID NO: 57); 60A (amino acid residues 82-118 of SEQ ID NO: 48); Vg-1 (amino acid residues 66-102 of SEQ ID NO: 46); Univin (amino acid residues 1-35 of SEQ ID NO: 34); BMP-2(amino acid residues 66-102 of SEQ ID NO: 49); BMP-4(amino acid residues 65-101 of SEQ ID NO: 51); GDF-5 (amino acid residues 66-102 of SEQ ID NO: 83); GDF-6(amino acid residues 66-102 of SEQ ID NO: 85); GDF-7(amino acid residues 66-102 of SEQ ID NO: 87); CDMP-2(amino acid residues 66-102 of SEQ ID NO: 86); DPP (amino acid residues 66-102 of SEQ ID NO: 45); BMP-9(amino acid residues 1-35 of SEQ ID NO: 7); Dorsalin (amino acid residues 66-103 of SEQ ID NO: 54); BMP-10 (amino acid residues 1-35 of SEQ ID NO: 8); GDF-3(amino acid residues 65-101 of SEQ ID NO: 59); GDF-1 (amino acid residues 71-107 of SEQ ID NO: 58); SCREW (amino acid residues 1-35 of SEQ ID NO: 28); BMP-3(amino acid residues 67-103 of SEQ ID NO: 50); NODAL (amino acid residues 1-34 of SEQ ID NO: 25); TGF-β1 (amino acid residues 63-98 of SEQ ID NO: 40); TGF-β2 (amino acid residues 63-98 of SEQ ID NO: 41); TGF-β3 (amino acid residues 63-98 of SEQ ID NO: 42; TGF-β4(amino acid residues 63-98 of SEQ ID NO: 43); TGF-β5(amino acid residues 63-98 of SEQ ID NO: 44); GDF-5(amino acid residues 63-98 of SEQ ID NO: 40); Inhibin α(amino acid residues 66-105 of SEQ ID NO: 61); Inhibin βA (amino acid residues 70-106 of SEQ ID NO: 62); Inhibin βB (amino acid residues 70-106 of SEQ ID NO: 63); Inhibin βC (amino acid residues 1-35 of SEQ ID NO: 23); MIS (amino acid residues 1-34 of SEQ ID NO: 24); GDNF (amino acid residues 1-32 of SEQ ID NO: 19); BMP-11(amino acid residues 1-35 of SEQ ID NO: 9); GDF-9 (amino acid residues 66-102 of SEQ ID NO: 60).

FIGS. 5A, 5B, and 5C are sequence alignments using single letter amino acid code, arranged to indicate alignments and homologies of the finger 1, heel, and finger 2 regions, respectively, of the currently known members of the TGF-β superfamily. Shown are the respective amino acids comprising each region of human TGF-β1 through TGF-β5(the TGF-β subgroup), the Vg/dpp subgroup consisting of dpp, Vg-1, Vgr-1, 60A (see copending U.S. Ser. No. 08/271,556, BMP-2A (also known in the literature as BMP-2), dorsalin, BMP-2B (also known in the literature as BMP-4), BMP-3, BMP-5, BMP-6, OP-1 (also known in the literature as BMP-7), OP-2 (see PCT/US91/07635 and U.S. Pat. No. 5,266,683) and OP-3(U.S. Ser. No. 07/971,091), the GDF subgroup consisting of GDF-1, GDF-3, and GDF-9, the Inhibin subgroup consisting of Inhibin α, Inhibin βA, and Inhibin βB. The dashes (–) indicate a peptide bond between adjacent amino acids. A consensus sequence pattern for each subgroup is shown at the bottom of each subgroup. In FIG. 5A the finger 1 sequences correspond to the following SEQ ID NOS: TGF-β1 (residues 1-34 of SEQ ID NO: 40); TGF-β2(residues 1-34 of SEQ ID NO: 41); TGF-β3(residues 1-34 of SEQ ID NO: 42); TGF-β4 (residues 1-34 of SEQ ID NO: 43); TGF-β5 (residues 1-34 of SEQ ID NO: 44); TGF-β pattern (1-34 of SEQ ID NO: 64); dpp (residues 1-34 of SEQ ID NO: 45); Vg-1 (residues 1-34 of SEQ ID NO: 46); Vgr-1 (residues 1-34 of SEQ ID NO: 47); 60A (residues 1-34 of SEQ ID NO: 48); BMP-2A (residues 1-34 of SEQ ID NO: 49); DORSALIN (residues 1-34 of SEQ ID NO: 54); BMP-2B/BMP-4 (residues 1-34 of SEQ ID NO: 51); BMP-3 (residues 1-34 of SEQ ID NO: 50); BMP-5 (residues 1-34 of SEQ ID NO: 52); BMP-6 (residues 1-34 of SEQ ID NO: 53); OP-1/BMP-7 (residues 1-34 of SEQ ID NO: 55); OP-2(residues 1-34 of SEQ ID NO: 56); OP-3 (residues 1-34 of SEQ ID NO: 57); Vg/dpp subgroup pattern (residues 1-34 of SEQ ID NO: 65); GDF-1 (residues 1-34 of SEQ ID NO: 58); GDF-3 (residues 1-34 of SEQ ID NO: 59); GDF-9 (residues 1-34 of SEQ ID NO: 60); GDF subgroup pattern (residues 1-34 of SEQ ID NO: 66); Inhibin α(residues 1-34 of SEQ ID NO: 61); Inhibin βA (residues 1-34 of SEQ ID NO: 62); Inhibin βB (residues 1-34 of SEQ ID NO: 63); Inhibin subgroup pattern (residues 1-34 of SEQ ID NO: 67).

In FIG. 5B the heel sequences correspond to the following SEQ ID NOS: TGF-β1(residues 35-64 of SEQ ID NO: 40); TGF-β2(residues 35-64 of SEQ ID NO: 41); TGF-β3 (residues 35-64 of SEQ ID NO: 42); TGF-β4 (residues 35-64 of SEQ ID NO: 43); TGF-β5(residues 35-64 of SEQ ID NO: 44); TGF-β pattern (residues 35-64 of SEQ ID NO: 64); dpp (residues 35-67 of SEQ ID NO: 45); Vg-1 (residues 35-67 of SEQ ID NO: 46); Vgr-1 (residues 35-67 of SEQ ID NO: 47); 60A (residues 35-67 of SEQ ID NO: 48); BMP-2A (residues 35-66 of SEQ ID NO: 49); DORSALIN (residues 35-67 of SEQ ID NO: 54); BMP-2B/BMP-4 (residues 35-66 of SEQ ID NO: 51); BMP-3 (residues 35-68 of SEQ ID NO: 50); BMP-5 (residues 35-67 of SEQ ID NO: 52); BMP-6 (residues 35-67 of SEQ ID NO: 53); OP-1/BMP-7 (residues 35-67 of SEQ ID 35-67 of SEQ ID NO: 57); Vg/dpp subgroup pattern (residues 35-68 of SEQ ID NO: 65); GDF-1 (residues 35-72 of SEQ ID NO: 58); GDF-3 (residues 35-66 of SEQ ID NO: 59); GDF-9 (residues 35-67 of SEQ ID NO: 60); GDF subgroup pattern (residues 35-72 of SEQ ID NO: 66); Inhibin α(residues 35-67 of SEQ ID NO: 61); Inhibin βA (residues 35-71 of SEQ ID NO: 62); Inhibin βB (residues 35-71 of SEQ ID NO: 63); Inhibin subgroup pattern (residues 35-71 of SEQ ID NO: 67).

In FIG. 5C the finger 2 sequences correspond to the following SEQ ID NOS: TGF-β1 (residues 65-98 of SEQ ID NO: 40); TGF-β2 (residues 65-98 of SEQ ID NO: 41); TGF-β3 (residues 65-98 of SEQ ID NO: 42); TGF-β4 (residues 65-98 of SEQ ID NO: 43); TGF-β5 (residues 65-98 of SEQ ID NO: 44); TGF-β pattern (residues 65-98 of SEQ ID NO: 64); dpp (residues 68-102 of SEQ ID NO: 45); Vg-1 (residues 68-102 of SEQ ID NO: 46); Vgr-1 (residues 68-102 of SEQ ID NO: 47); 60A (residues 68-102 of SEQ ID NO: 48); BMP-2A (residues 68-102 of SEQ ID NO: 49); DORSALIN (residues 68-103 of SEQ ID NO: 54); BMP-2B/BMP-4 (residues 68-102 of SEQ ID NO: 51); BMP-3 (residues 68-102 of SEQ ID NO: 50); BMP-5 (residues 68-102 of SEQ ID NO: 52); BMP-6 (residues 68-102 of SEQ ID NO: 53); OP-1/BMP-7 (residues 68-102 of SEQ ID NO: 55); OP-2 (residues 68-102 of SEQ ID NO: 56); OP-3 (residues 68-102 of SEQ ID NO: 57); Vg/dpp subgroup pattern (residues 68-103 of SEQ ID NO: 65); GDF-1 (residues 73-107 of SEQ ID NO: 58); GDF-3 (residues 67-101 of SEQ ID NO: 59); GDF-9 (residues 68-102 of SEQ ID NO: 60); GDF subgroup pattern (residues 73-107 of SEQ ID NO: 66); Inhibin α(residues 68-105 of SEQ ID NO: 61); Inhibin βA (residues 72-106 of SEQ ID NO: 62); Inhibin βB (residues 72-106 of SEQ ID NO: 63); Inhibin subgroup pattern (residues 72-109 of SEQ ID NO: 67).

FIG. 6 is a single letter code listing of amino acid sequences, identified in capital letter in standard single letter amino acid code, and in lower case letters to identify groups of amino acids useful in that location, wherein the lower case letters stand for the amino acids indicated in accordance with the pattern definition key table set forth in FIG. 3. FIG. 6 identifies preferred pattern sequences for constituting the finger 1, heel, and finger 2 regions of biosynthetic constructs of the invention. The dashes (-) indicate a peptide bond between adjacent amino acids. The SEQ ID NOs for the subgroup patterns are as follows: TGF-β subgroup pattern finger 1 (residues 1-34 of SEQ ID NO: 64); TGF-β subgroup pattern heel (residues 35-64 of SEQ ID NO: 64); TGF-β subgroup pattern finger 2 (residues 65-98 of SEQ ID NO: 64); Vg/dpp subgroup pattern finger 1 (residues 1-34 of SEQ ID NO: 65); Vg/dpp subgroup pattern heel (residues 35-68 of SEQ ID NO: 65); Vg/dpp subgroup pattern finger 2 (residues 69-104 of SEQ ID NO: 65); GDF subgroup pattern finger 1 (residues 1-34 of SEQ ID NO: 66); GDF subgroup pattern heel (residues 35-72 of SEQ ID NO: 66); GDF subgroup pattern finger 2 (residues 73-107 of SEQ ID NO: 66); Inhibin subgroup pattern finger 1 (residues 1-34 of SEQ ID NO: 67); Inhibin subgroup pattern heel (residues 35-71 of SEQ ID NO: 67); Inhibin subgroup pattern finger 2 (residues 72-109 of SEQ ID NO: 67).

FIG. 7(C) shows the nucleotide (SEQ ID NO: 93) and amino acid (SEQ. ID NO: 94) sequences of H2521, a modified OP-1 comprising an FB leader domain of protein A attached 15 residues upstream of the first cysteine in the seven-cysteine domain.

FIG. 7(D) shows the nucleotide (SEQ ID NO: 95) and amino acid (SEQ. ID NO: 96) sequences of H2525, a modified OP-1 comprising both an FB leader domain of protein A and a hexa-histidine domain.

FIG. 7(F) shows the nucleotide (SEQ ID NO: 99) and amino acid (SEQ. ID NO: 100) sequences of H2528, a modified CDMP-3 comprising an FB leader domain and a hexa-histidine domain.

FIG. 7(G) shows the nucleotide (SEQ ID NO: 101) and amino acid (SEQ. ID NO: 102) sequences of H2469, a modified OP-1 (truncated) comprising 14 original residues upstream of the first cysteine in the conserved seven-cysteine domain.

FIG. 7(H) shows the nucleotide (SEQ ID NO: 103) and amino acid (SEQ. ID NO: 104) sequences of H2510, a modified OP-1 comprising a collagen binding site inserted 7 residues upstream of the first cysteine in the conserved seven-cysteine domain.

FIG. 7(I) shows the nucleotide (SEQ ID NO: 105) and amino acid (SEQ. ID NO: 106) sequences of H2523, a modified OP-1 comprising a collagen peptide and a spacer added 13 residues upstream from the first cysteine in the conserved seven-cysteine domain.

FIG. 7(J) shows the nucleotide (SEQ ID NO: 107) and amino acid (SEQ. ID NO: 108) sequences of H2524, a modified OP-1 comprising a hexa-histidine domain, a collagen peptide and a spacer added 13 residues upstream from the first cysteine in the conserved seven-cysteine domain.

FIG. 8 is a restriction map encoding the OP-1 C-terminal seven cysteine active domain. The DNA sequence corresponds to nucleotides 1036-1341 of SEQ ID NO: 38. The protein sequence corresponds to amino acid residues 330-431 of SEQ ID NO: 39.

FIG. 9(A) is a schematic representation of various biosynthetic chimeric BMP constructs;

FIG. 9(B) is a schematic representation of biosynthetic BMP mutants and their refolding and ROS activity;

FIG. 10 shows the number of charged residues in the C-terminal sub-domains for various BMPs.

FIG. 15 shows the amino acid sequences for the finger 2 subdomain of various OP-1 mutants and their folding efficiencies and biological activities in the ROS cell based alkaline phosphatase assay. OP-1 (residues 393-431 of SEQ ID NO: 39); 2421 (SEQ ID NO: 109); 2406 (SEQ ID NO: 110); 2410 (SEQ ID NO: 111); 2247 (SEQ ID NO: 112); 2234 (SEQ ID NO: 113); 2233 (SEQ ID NO: 114); 2418 (SEQ ID NO: 115); 2443 (SEQ ID NO: 116); 2447 (SEQ ID NO: 117); 2457 (SEQ ID NO: 118); 2456 (SEQ ID NO: 119); 2460 (SEQ ID NO: 120); 2449 (SEQ ID NO: 121); 2467 (SEQ ID NO: 122) and 2464 (SEQ ID NO: 123).

DETAILED DESCRIPTION OF PREFERRED EMBODIMENTS

Figure 1A:
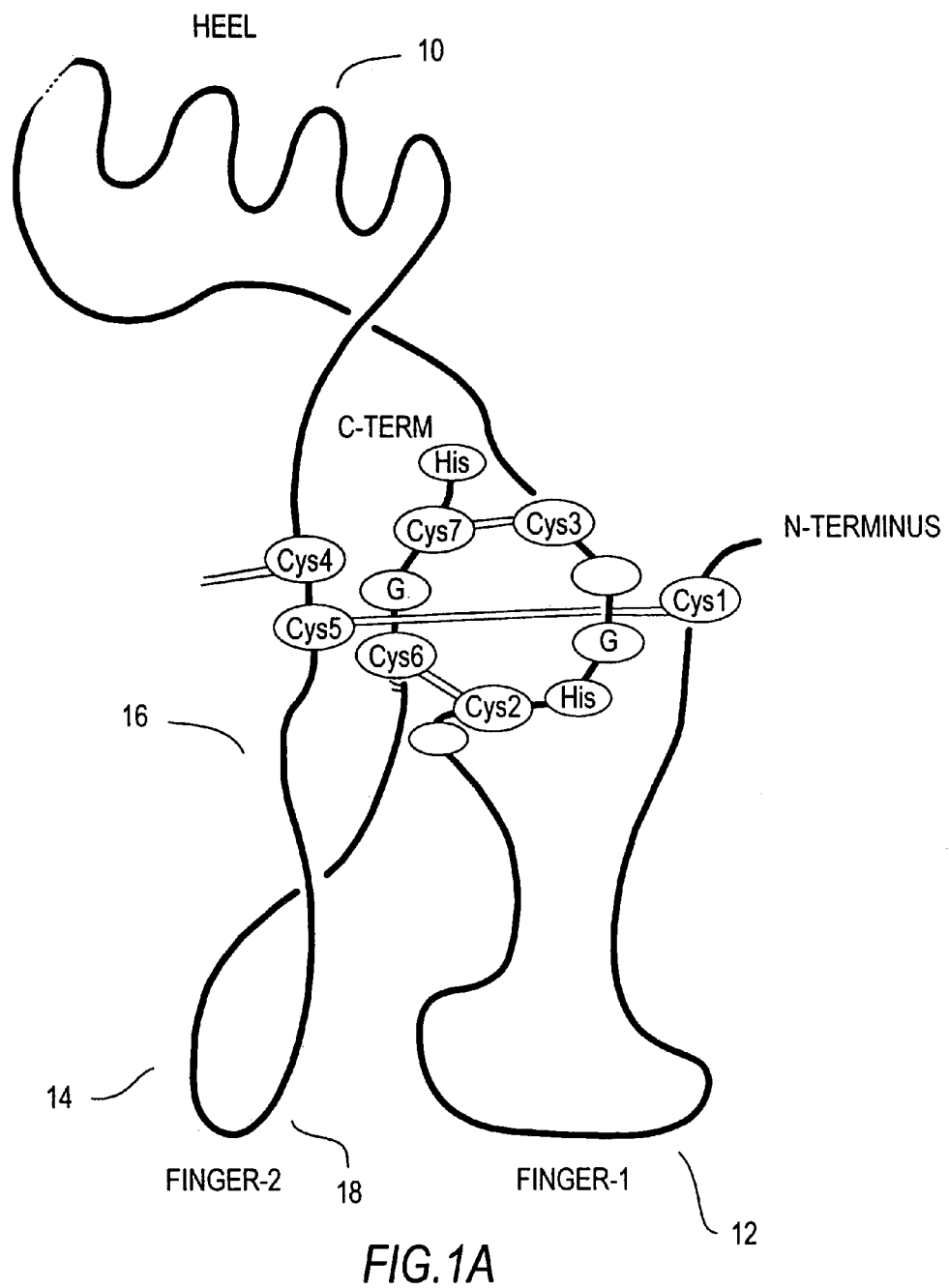
FIG. 1A is a simplified line drawing useful in describing the structure of a monomeric subunit of a TGF-β superfamily member. See the Background of the Invention, supra, for explanation.

The present invention provides modified forms of TGF-β family proteins which have altered refolding properties, and altered activity profiles compared to natural forms. Modified proteins of the invention comprise N-terminal modifications of naturally-occurring TGF-β family members, especially morphogenic proteins. These modifications include extension, truncation, and/or activation by protease or chemical cleavage at specific sites (e.g., by acid or CNBr), attachment (fusion) of distinct protein domains and production of heterodimers with subunits from other TGF-β family members. The detailed description provided below describes an exemplary array of substitutions, fusions, and extensions that result in improved activity and pharmaceutical properties. Methods of producing modified proteins are also taught.

According to one aspect of the invention, the folding capabilities of poor refolder BMPs and other members of the TGF-β superfamily of proteins, including heterodimers and chimeras thereof, are improved by fusing specific targeting and receptor-binding regions to the existing N-terminal domain of BMP or TGF-β family members, which can then be cleaved at sites within the fusion protein. As a result of this discovery, it is possible to design BMP and other TGF-β family proteins that (1) are expressed recombinantly in prokaryotic or eukaryotic cells or synthesized using polypeptide synthesizers; (2) have altered folding capabilities; (3) have altered solubility under neutral pHs, including but not limited to physiological conditions; (4) have altered isoelectric points; (5) have altered stability; (6) have altered binding or adherence properties to solid surfaces (e.g., biocompatible matrices or metals); and/or (7) have a desired, altered biological activity, such as tissue and/or receptor specificity. In addition, the invention provides means for testing new candidate constructs rapidly, particularly a biological or biochemical property of the candidate. The invention also provides means for rapidly mapping epitopes of antibodies, for example by making chimeric proteins with different combinations of domains. Specifically, making use of the discoveries disclosed herein, morphogen sequences which otherwise could not be expressed in a prokaryotic host such as *E. coli* now can be modified to allow expression in *E. coli* and refolding in vitro.

Thus, the present invention can provide mechanisms for designing quick-release, slow-release and/or timed-release formulations containing a preferred chimeric protein. In addition, the present invention provides mechanisms for designing formulations engineered for environmentally-triggered release of a protein construct. That is, modified proteins can be designed to modulate delivery and facilitate release and activity under particular environmental conditions in situ, such as changes in pH, presence of a specific protease, etc. Other advantages and features will be evident from the teachings below. Moreover, making use of the discoveries disclosed herein, modified proteins having altered surface-binding/surface-adherent properties can be designed and selected. Surfaces of particular significance include, but are not limited to, solid surfaces which can be naturally-occurring such as bone; or porous particulate surfaces such as collagen or other biocompatible matrices; or the fabricated surfaces of prosthetic implants, including metals. As contemplated herein, virtually any surface can be assayed for differential binding of constructs. Thus, the present invention embraces a diversity of functional molecules having alterations in their surface-binding/surface-adherent properties, thereby rendering such constructs useful for altered in vivo applications, including slow-release, fast-release and/or timed-release formulations.

The skilled artisan will appreciate that mixing-and-matching any one or more the above-recited attributes provides specific opportunities to manipulate the uses of customized modified proteins (and DNAs encoding the same). For example, the attribute of altered stability can be exploited to manipulate the turnover of a protein in vivo. Moreover, in the case of modified proteins also having attributes such as altered re-folding and/or function, there is likely an interconnection between folding, function and stability. See, for example, Lipscomb et al., 7 *Protein Sci.* 765-73 (1998); and Nikolova et al., 95 *Proc. Natl. Acad. Sci. USA* 14675-80 (1998). For purposes of the present invention, stability alterations can be routinely monitored using well-known techniques of circular dichroism and other indices of stability as a function of denaturant concentration or temperature. One can also use routine scanning calorimetry. Similarly, there is likely an interconnection between any of the foregoing attributes and the attribute of solubility. In the case of solubility, it is possible to manipulate this attribute so that a modified protein is either more or less soluble under physiologically-compatible conditions and it consequently diffuses readily or remains localized, respectively, when administered in vivo.

Provided below are detailed descriptions of suitable biosynthetic proteins and methods useful in the practice of the invention, as well as methods for using and testing these proteins; and numerous, nonlimiting examples which 1) illustrate the suitability of the biosynthetic proteins and methods described herein; and 2) provide assays with which to test and use these proteins.

I. Protein Considerations

A. Structural Features TGF-β and OP-1.

Each of the subunits in either TGF β2 or OP-1 have a characteristic folding pattern, illustrated schematically in FIG. 1A, that involves six of the seven C-terminal cysteine residues. Briefly, four of the cysteine residues in each subunit form two disulfide bonds which together create an eight residue ring, while two additional cysteine residues form a disulfide bond that passes through the ring to form a knot-like structure. With a numbering scheme beginning with the most N-terminal cysteine of the 7 conserved cysteine residues assigned number 1, the 2nd and 6th cysteine residues are disulfide bonded to close one side of the eight residue ring while the 3rd and 7th cysteine residues are disulfide bonded to close the other side of the ring. The 1st and 5th conserved cysteine residues are disulfide bonded through the center of the ring to form the core of the knot. Amino acid sequence alignment patterns suggest this structural motif is conserved between members of the TGF-β superfamily. The 4th cysteine is semi-conserved and when present typically forms an interchain disulfide bond (ICDB) with the corresponding cysteine residue in the other subunit.

The structure of each subunit in TGF-β2 and OP-1 comprise three major tertiary structural elements and an N-terminal region. The structural elements are made up of regions of contiguous polypeptide chain that possess over 50% secondary structure of the following types: (1) loop, (2) α-helix and (3) β-sheet. Another defining criterion for each structural region is that the entering (N-terminal) and exiting (C-terminal) peptide strands are fairly close together, being about 7 A apart.

The amino acid sequence between the 1st and 2nd conserved cysteines, as shown in FIG. 1A, forms a structural region characterized by an anti-parallel β-sheet finger referred to herein as the finger 1 region. Similarly the residues between the 5th and 6th conserved cysteines, as shown in FIG. 1A, also form an anti-parallel β-sheet finger, referred to herein as the finger 2 region. A β2-sheet finger is a single amino acid chain, comprising a β-strand that folds back on itself by means of a β-turn or some larger loop so that the polypeptide chain entering and exiting the region form one or more anti-parallel β-sheet structures. The third major structural region, involving the residues between the 3rd and 5th conserved cysteines, as shown in FIG. 1A, is characterized by a three turn α-helix, referred to herein as the heel region. The organization of the monomer structure is similar to that of a left hand where the knot region is located at the position equivalent to the palm, the finger 1 region is equivalent to the index and middle fingers, the α-helix, or heel region, is equivalent to the heel of the hand, and the finger 2 region is equivalent to the ring and small fingers. The N-terminal region, whose sequence is not conserved across the TGF-β superfamily, is predicted to be located at a position roughly equivalent to the thumb.

Figure 1B:
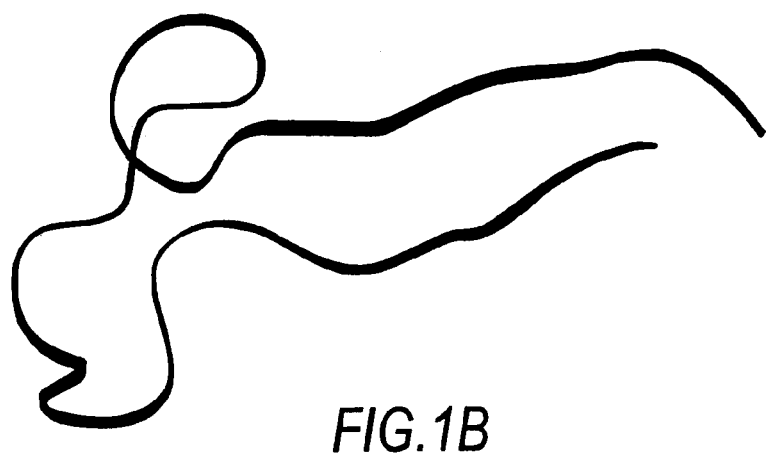
FIGS. 1B, 1C, and 1D are monovision ribbon tracings of the respective peptide backbones of typical secondary structures of the finger 1, heel, and finger 2 regions.
Figure 1C:
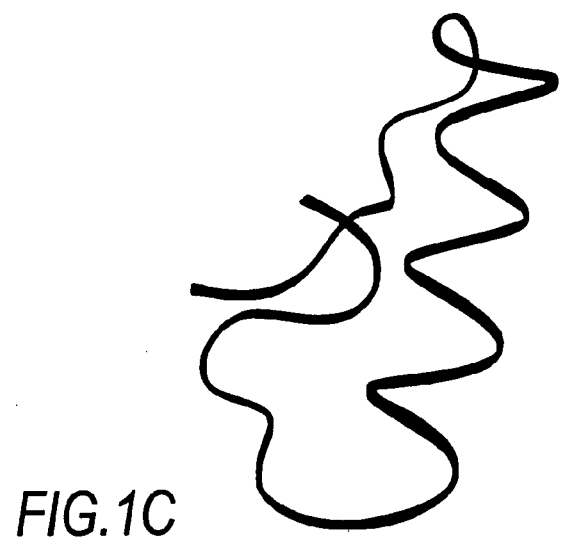
Figure 1D:
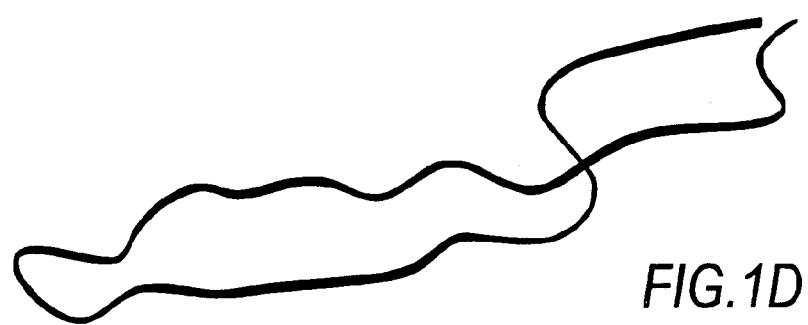

Monovision ribbon tracings of the alpha carbon backbones of each of the three major independent structural elements of the TGF-β2 monomer are illustrated in FIGS. 1B-1D. Specifically, an exemplary finger 1 region comprising the first anti-parallel β-sheet segment is shown in FIG. 1B, an exemplary heel region comprising the three turn α-helical segment is shown in FIG. 1C, and an exemplary finger 2 region comprising second and third anti-parallel β-sheet segments is shown in FIG. 1D.

Figure 2A:
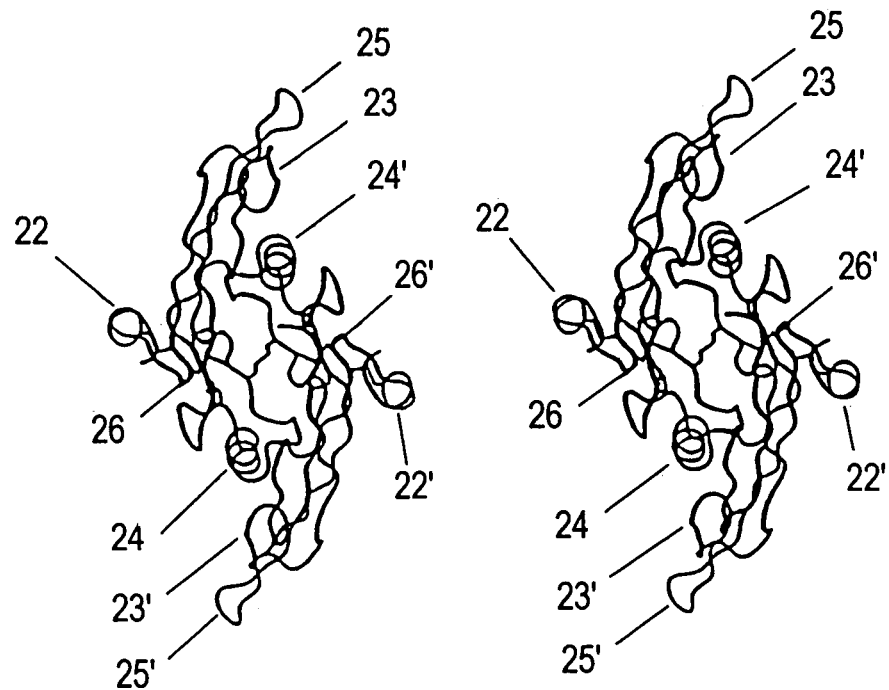
FIGS. 2A and 2B are stereo peptide backbone ribbon trace drawings illustrating the generic three-dimensional shape of TGF-β superfamily member protein dimer: A) from the "top" (down the two-fold axis of symmetry between the subunits) with the axes of the helical heel regions generally normal to the paper and the axes of each of the finger 1 and finger 2 regions generally vertical, and B) from the "side" with the two-fold axis between the subunits in the plane of the paper, with the axes of the heels generally horizontal, and the axes of the fingers generally vertical. The reader is encouraged to view the stereo alpha carbon trace drawings in wall eyed stereo to understand better the spatial relationships in the morphon design.
Figure 2B:
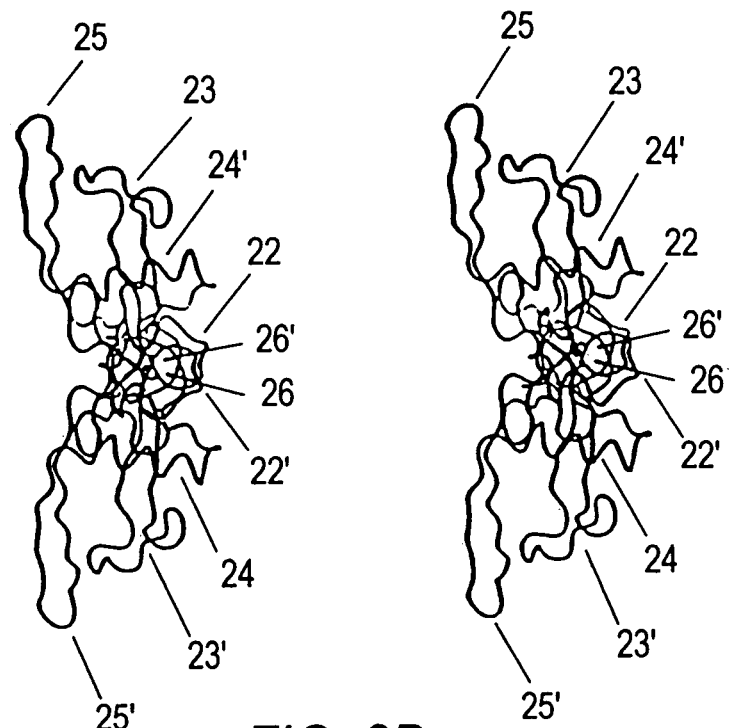

FIG. 2 shows stereo ribbon trace drawings of the peptide backbone of the conformationally active TGF-β2 dimer complex. The two monomer subunits in the dimer complex are oriented with two-fold rotational symmetry such that the heel region of one subunit contacts the finger regions of the other subunit with the knot regions of the connected subunits forming the core of the molecule. The 4th cysteine forms an interchain disulfide bond with its counterpart on the second chain thereby equivalently linking the chains at the center of the palms. The dimer thus formed is an ellipsoidal (cigar shaped) molecule when viewed from the top looking down the two-fold axis of symmetry between the subunits (FIG. 2A). Viewed from the side, the molecule resembles a bent "cigar" since the two subunits are oriented at a slight angle relative to each other (FIG. 2B).

As shown in FIG. 2, each of the structural elements which together define the native monomer subunits of the dimer are labeled 22, 22', 23, 23', 24, 24', 25, 25', 26, and 26', wherein, elements 22, 23, 24, 25, and 26 are defined by one subunit and elements 22', 23', 24', 25', and 26' belong to the other subunit. Specifically, 22 and 22' denote N-terminal domains; 23 and 23' denote the finger 1 regions; 24 and 24' denote heel regions; 25 and 25' denote the finger 2 regions; and 26 and 26' denote disulfide bonds which connect the 1st and 5th conserved cysteines of each subunit to form the knot-like structure. From FIG. 2, it can be seen that the heel region from one subunit, e.g., 24, and the finger 1 and finger 2 regions, e.g., 23' and 25', respectively from the other subunit, interact with one another. These three elements co-operate with one other to define a structure interactive with, and complimentary to the ligand binding interactive surface of the cognate receptor.

(1) Selection of Finger and Heel Regions

It is contemplated that the amino acid sequences defining the finger and heel regions may be utilized from the respective finger and heel region sequences of any known member of the TGF-β superfamily, identified herein, or from amino acid sequences of a new superfamily member discovered hereafter.

FIG. 5 summarizes the amino acid sequences of currently identified TGF-β superfamily members aligned into finger 1 (FIG. 5A), heel (FIG. 5B) and finger 2 (FIG. 5C) regions. The sequences were aligned by a computer algorithm which in order to optimally align the sequences inserted gaps into regions of amino acid sequence known to define loop structures rather than regions of amino acid sequence known to have conserved amino acid sequence or secondary structure. For example, if possible, no gaps were introduced into amino acid sequences of finger 1 and finger 2 regions defined by β sheet or heel regions defined by α helix. The dashes (-) indicate a peptide bond between adjacent amino acids. A consensus sequence pattern for each subgroup is shown at the bottom of each subgroup.

After the amino acid sequences of each of the TGF-β superfamily members were aligned, the aligned sequences were used to produce amino acid sequence alignment patterns which identify amino acid residues that may be substituted by another amino acid or group of amino acids without altering the overall tertiary structure of the resulting construct. The amino acids or groups of amino acids that may be useful at a particular position in the finger and heel regions were identified by a computer algorithm implementing the amino acid hierarchy pattern structure shown in FIG. 3.

Briefly, the algorithm performs four levels of analysis. In level I, the algorithm determines whether a particular amino acid residue occurs with a frequency greater than 75% at a specific position within the amino acid sequence. For example, if a glycine residue occurs 8 out of 10 times at a particular position in an amino acid sequence, then a glycine is designated at that position. If the position to be tested consists of all gaps then a gap character (-) is assigned to the position, otherwise, if at least one gap exists then a "z" (standing for any residue or a gap) is assigned to the position. If, no amino acid occurs in 75% of the candidate sequences at a particular position the algorithm implements the Level II analysis.

Level II defines pattern sets a, b, d, l , k, o, n, i, and h, wherein l , k, and o share a common amino acid residue. The algorithm then determines whether 75% or more of the amino acid residues at a particular position in the amino acid sequence satisfy one of the aforementioned patterns. If so, then the pattern is assigned to that position. It is possible, however, that both patterns l and k may be simultaneously satisfied because they share the same amino acid, specifically aspartic acid. If simultaneous assignment of l and k occurs then pattern m (Level III) is assigned to that position. Likewise, it is possible that both patterns k and o may be simultaneously assigned because they share the same amino acid, specifically glutamic acid. If simultaneous assignment of k and o occurs, then pattern q (Level III) is assigned to that position. If neither a Level II pattern nor the Level III patterns, m and q, satisfy a particular position in the amino acid sequence then the algorithm implements a Level III analysis.

Level III defines pattern sets c, e, m, q, p, and j, wherein m, q, and p share a common amino residue. Pattern q, however, is not tested in the Level III analysis. It is possible that both patterns m and p may be simultaneously satisfied because they share the same amino acid, specifically, glutamic acid. If simultaneous assignment of m and p occurs then pattern r (Level IV) is assigned to that position. If 75% of the amino acids at a pre-selected position in the aligned amino acid sequences satisfy a Level III pattern, then the Level III pattern is assigned to that position. If a Level III pattern cannot be assigned to that position then the algorithm implements a Level IV analysis.

Level IV comprises two non-overlapping patterns f and r. If 75% of the amino acids at a particular position in the amino acid sequence satisfy a Level IV pattern then the pattern is assigned to the position. If no Level IV pattern is assigned the algorithm assigns an X representing any amino acid (Level V) to that position.

Figure 3:
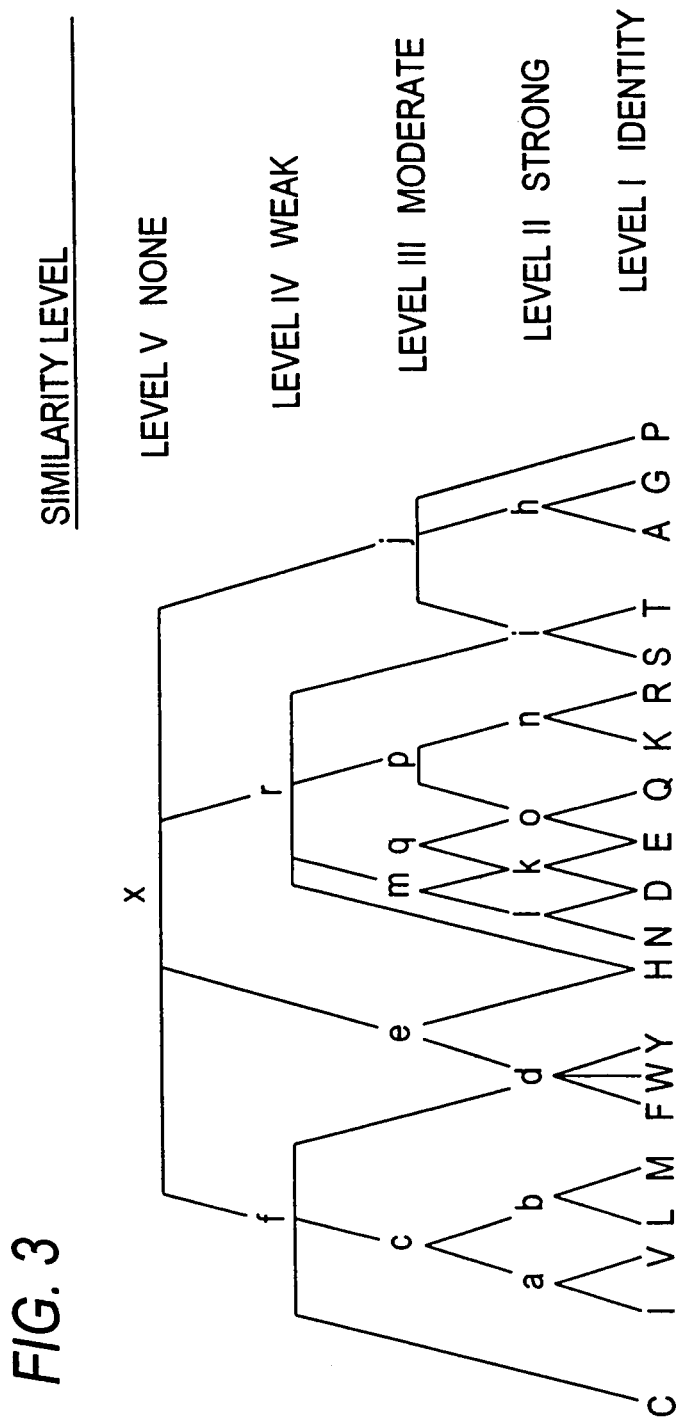
FIG. 3 is a pattern definition table prepared in accordance with the teaching of *Smith and Smith* (1990) *Proc. Natl. Acad. Sci. USA* 87:118-122.

In FIG. 3, Level I lists in upper case letters in single amino acid code the 20 naturally occurring amino acids. Levels II-V define, in lower case letters, groups of amino acids based upon the amino acid hierarchy set forth in Smith et A, supra. The amino acid sequences set forth in FIGS. 5 and 6 were aligned using the aforementioned computer algorithms.

It is contemplated that if the artisan wishes to produce a morphon construct based upon currently identified members of the TGF-β superfamily, then the artisan may use the amino acid sequences shown in FIG. 5 to provide the finger 1, finger 2 and heel regions useful in the production of the morphon constructs of the invention. In the case of members of the TGF-β superfamily discovered hereafter, the amino acid sequence of the new member may be aligned, either manually or by means of a computer algorithm, with the sequences set forth in FIG. 5 to define heel and finger regions useful in the practice of the invention.

Table 1 below summarizes publications which describe the amino acid sequences of each TGF-β superfamily member that were used to produce the sequence alignment patterns set forth in FIGS. 5 and 6.

TABLE 1

| TGF-β Superfamily Member | SEQ. ID. No. | Publication |
|---|---|---|
| TGF-β1 | 40 | Derynck et al. (1987) *Nucl. Acids. Res.* 15: 3187 |
| TGF-β2 | 41 | Burt et al. (1991) *DNA Cell Biol.* 10: 723-734 |
| TGF-β3 | 42 | Ten Dijke et al. (1988) *Proc. Natl. Acad. Sci.* USA 85: 4715-4719; Derynck et al. (1988) *EMBO J.* 7: 3737-3743. |
| TGF-β4 | 43 | Burt et al. (1992) *Mol. Endcrinol.* 6: 989-922. |
| TGF-β5 | 44 | Kondaiah et al. (1990) *J. Biol. Chem* 265: 1089-1093 |
| dpp | 45 | Padgett et al. (1987) *Nature* 325: 81-84; Paganiban et al. (1990) *Mol. Cell Biol.* 10: 2669-2677. |
| vg-1 | 46 | Weeks et al. (1987) *Cell* 51: 861-867 |
| vgr-1 | 47 | Lyons et al. (1989) *Proc. Natl. Acad. Sci* USA 86: 4554-4558 |
| 60A | 48 | Wharton et al. (1991) *Proc. Natl. Acad. Sci.* USA 88: 9214-9218; Doctor et al. (1992) *Dev. Biol.* 151: 491-505 |
| BMP-2A | 49 | Wozney et al. (1988) *Science* 242: 1528-1534 |
| BMP-3 | 50 | Wozney et al. (1988) *Science* 242: 1528-1534 |
| BMP-4 | 51 | Wozney et al. (1988) *Science* 242: 1528-1534 |
| BMP-5 | 52 | Celeste et al. (1990) *Proc. Natl. Acad. Sci.* USA 87: 9843-9847 |
| BMP-6 | 53 | Celeste et al. (1990) *Proc. Natl. Acad. Sci.* USA 87: 9843-9847 |
| Dorsalin | 54 | Basler et al. (1993) *Cell* 73: 687-702 |
| OP-1 | 55 | Celeste et al. (1990) *Proc. Natl. Acad. Sci.* USA 87: 9843-9847; Ozkaynak et al. (1990) EMBO J. 9: 2085-2093 |
| OP-2 | 56 | Ozkaynak et al. (1992) *J. Biol. Chem.* 267: 25220-25227 |
| OP-3 | 57 | Ozkaynak et al. PCT/WO94/10203 Seq. I.D. No. 1. |
| GDF-1 | 58 | Lee (1990) *Mol. Endocrinol.* 4: 1034-1040 |
| GDF-3 | 59 | McPherron et al. (1993) *J. Biol. Chem.* 268: 3444-3449 |
| GDF-9 | 60 | McPherron et al. (1993) *J. Biol. Chem.* 268: 3444-3449 |
| Inhibin α | 61 | Mayo et al. (1986) *Proc. Natl. Acad. Sci.* USA 83: 5849-5853; Stewart et al. (1986) *FEBS Lett* 206: 329-334; Mason et al. (1986) *Biochem. Biophys. Res. Commun.* 135: 957-964 |
| Inhibin βA | 62 | Forage et al. (1986) *Proc. Natl. Acad. Sci.* USA 83: 3091-3095; Chertov et al. (1990) *Biomed. Sci.* 1: 499-506 |
| Inhibin βB | 63 | Mason et al. (1986) *Biochem. Biophys. Res. Commun.* 135: 957-964 |

The invention further contemplates the use of corresponding finger 1 subdomain sequences from the well-known proteins: GDF-5, GDF-7 (as disclosed in U.S. Pat. No. 5,801,014, the entire disclosure of which is incorporated herein by reference); GDF-6 (as disclosed in U.S. Pat. No. 5,770,444, the entire disclosure of which is incorporated herein by reference); and BMP-12 and BMP-13 (as disclosed in U.S. Pat. No. 5,658,882, the entire disclosure of which is incorporated herein by reference).

In particular, it is contemplated that amino acid sequences defining finger 1 regions useful in the practice of the instant invention correspond to the amino acid sequence defining a finger 1 region for any TGF-β superfamily member identified herein. The finger 1 subdomain can confer at least biological and/or functional attribute(s) which are characteristic of the native protein. Useful intact finger 1 regions include, but are not limited to

| | |
|---|---|
| TGF-β1 | SEQ. ID. No. 40, residues 2 through 29, |
| TGF-β2 | SEQ. ID. No. 41, residues 2 through 29, |
| TGF-β3 | SEQ. ID. No. 42, residues 2 through 29, |
| TGF-β4 | SEQ. ID. No. 43, residues 2 through 29, |
| TGF-β5 | SEQ. ID. No. 44, residues 2 through 29, |
| dpp | SEQ. ID. No. 45, residues 2 through 29, |

| | |
|---|---|
| Vg-1 | SEQ. ID. No. 46, residues 2 through 29, |
| Vgr-1 | SEQ. ID. No. 47, residues 2 through 29, |
| 60A | SEQ. ID. No. 48, residues 2 through 29, |
| BMP-2A | SEQ. ID. No. 49, residues 2 through 29, |
| BMP-3 | SEQ. ID. No. 50, residues 2 through 29, |
| BMP-4 | SEQ. ID. No. 51, residues 2 through 29, |
| BMP-5 | SEQ. ID. No. 52, residues 2 through 29, |
| BMP-6 | SEQ. ID. No. 53, residues 2 through 29, |
| Dorsalin | SEQ. ID. No. 54, residues 2 through 29, |
| OP-1 | SEQ. ID. No. 55, residues 2 through 29, |
| OP-2 | SEQ. ID. No. 56, residues 2 through 29, |
| OP-3 | SEQ. ID. No. 57, residues 2 through 29, |
| GDF-1 | SEQ. ID. No. 58, residues 2 through 29, |
| GDF-3 | SEQ. ID. No. 59, residues 2 through 29, |
| GDF-9 | SEQ. ID. No. 60, residues 2 through 29, |
| Inhibin α | SEQ. ID. No. 61, residues 2 through 29, |
| Inhibin βA | SEQ. ID. No. 62, residues 2 through 29, |
| Inhibin βB | SEQ. ID. No. 63, residues 2 through 29, |
| CDMP-1/GDF-5 | SEQ. ID. No. 83, residues 2 through 29, |
| CDMP-2/GDF-6 | SEQ. ID. No. 84, residues 2 through 29, |
| GDF-6 (murine) | SEQ. ID. No. 85, residues 2 through 29, |
| CDMP-2 (bovine) | SEQ. ID. No. 86, residues 2 through 29, and |
| GDF-7 (murine) | SEQ. ID. No. 87, residues 2 through 29. |

The invention further contemplates the use of corresponding heel subdomain sequences from the well-known proteins BMP-12 and BMP-13 (as disclosed in U.S. Pat. No. 5,658,882, the entire disclosure of which is incorporated herein by reference).

It is contemplated also that amino acid sequences defining heel regions useful in the practice of the instant invention correspond to the amino acid sequence defining an intact heel region for any TGF-β superfamily member identified herein. The heel region can at least influence attributes of the native protein, including functional and/or folding attributes. Useful intact heel regions may include, but are not limited to

| | |
|---|---|
| TGF-β1 | SEQ. ID. No. 40, residues 35 through 62, |
| TGF-β2 | SEQ. ID. No. 41, residues 35 through 62, |
| TGF-β3 | SEQ. ID. No. 42, residues 35 through 62, |
| TGF-β4 | SEQ. ID. No. 43, residues 35 through 62, |
| TGF-β5 | SEQ. ID. No. 44, residues 35 through 62, |
| dpp | SEQ. ID. No. 45, residues 35 through 65, |
| Vg-1 | SEQ. ID. No. 46, residues 35 through 65, |
| Vgr-1 | SEQ. ID. No. 47, residues 35 through 65, |
| 60A | SEQ. ID. No. 48, residues 35 through 65, |
| BMP-2 | SEQ. ID. No. 49, residues 35 through 64, |
| BMP3 | SEQ. ID. No. 50, residues 35 through 66, |
| BMP-4 | SEQ. ID. No. 51, residues 35 through 64, |
| BMP-5 | SEQ. ID. No. 52, residues 35 through 65, |
| BMP-6 | SEQ. ID. No. 53, residues 35 through 65, |
| Dorsalin | SEQ. ID. No. 54, residues 35 through 65, |
| OP-1 | SEQ. ID. No. 55, residues 35 through 65, |
| OP-2 | SEQ. ID. No. 56, residues 35 through 65, |
| OP-3 | SEQ. ID. No. 57, residues 35 through 65, |
| GDF-1 | SEQ. ID. No. 58, residues 35 through 70, |
| GDF-3 | SEQ. ID. No. 59, residues 35 through 64, |
| GDF-9 | SEQ. ID. No. 60, residues 35 through 65, |
| Inhibin α | SEQ. ID. No. 61, residues 35 through 65, |
| Inhibin βA | SEQ. ID. No. 62, residues 35 through 69, |
| Inhibin βB | SEQ. ID. No. 63, residues 35 through 68, |
| CDMP-1/GDF-5 | SEQ. ID. No. 83, residues 35 through 65, |
| CDMP-2/GDF-6 | SEQ. ID. No. 84, residues 35 through 65, |
| GDF-6 (murine) | SEQ. ID. No. 85, residues 35 through 65, |
| CDMP-2 (bovine) | SEQ. ID. No. 86, residues 35 through 65, and |
| GDF-7 (murine) | SEQ. ID. No. 87, residues 35 through 65. |

The invention further contemplates the use of corresponding finger 2 subdomain sequences from the well-known proteins BMP-12 and BMP-13 (as disclosed in U.S. Pat. No. 5,658,882, the entire disclosure of which is incorporated herein by reference).

It is contemplated also that amino acid sequences defining finger 2 regions useful in the practice of the instant invention correspond to the amino acid sequence defining an intact finger 2 region for any TGF-β superfamily member identified herein. The finger 2 subdomain can confer at least folding attribute(s) which are characteristic of the native protein. Useful intact finger 2 regions may include, but are not limited to

| | |
|---|---|
| TGF-β1 | SEQ. ID. No. 40, residues 65 through 94, |
| TGF-β2 | SEQ. ID. No. 41, residues 65 through 94, |
| TGF-β3 | SEQ. ID. No. 42, residues 65 through 94, |
| TGF-β4 | SEQ. ID. No. 43, residues 65 through 94, |
| TGF-β5 | SEQ. ID. No. 44, residues 65 through 94, |
| dpp | SEQ. ID. No. 45, residues 68 through 98, |
| Vg-1 | SEQ. ID. No. 46, residues 68 through 98, |
| Vgr-1 | SEQ. ID. No. 47, residues 68 through 98, |
| 60A | SEQ. ID. No. 48, residues 68 through 98, |
| BMP-2A | SEQ. ID. No. 49, residues 67 through 97, |
| BMP-3 | SEQ. ID. No. 50, residues 69 through 99, |
| BMP-4 | SEQ. ID. No. 51, residues 67 through 97, |
| BMP-5 | SEQ. ID. No. 52, residues 68 through 98, |
| BMP-6 | SEQ. ID. No. 53, residues 68 through 98, |
| Dorsalin | SEQ. ID. No. 54, residues 68 through 99, |
| OP-1 | SEQ. ID. No. 55, residues 68 through 98, |
| OP-2 | SEQ. ID. No. 56, residues 68 through 98, |
| OP-3 | SEQ. ID. No. 57, residues 68 through 98, |
| GDF-1 | SEQ. ID. No. 58, residues 73 through 103, |
| GDF-3 | SEQ. ID. No. 59, residues 67 through 97, |
| GDF-9 | SEQ. ID. No. 60, residues 68 through 98, |
| Inhibin α | SEQ. ID. No. 61, residues 68 through 101, |
| Inhibin βA | SEQ. ID. No. 62, residues 72 through 102, |
| Inhibin βB | SEQ. ID. No. 63, residues 71 through 101, |
| CDMP-1/GDF-5 | SEQ. ID. No. 83, residues 68 through 98, |
| CDMP-2/GDF-6 | SEQ. ID. No. 84, residues 68 through 98, |
| GDF-6 (murine) | SEQ. ID. No. 85, residues 68 through 98, |
| CDMP-2 (bovine) | SEQ. ID. No. 86, residues 68 through 98, and |
| GDF-7 (murine) | SEQ. ID. No. 87, residues 68 through 98. |

In addition, it is contemplated that the amino acid sequences of the respective finger and heel regions can be altered by amino acid substitution, for example by exploiting substitute residues as disclosed herein or selected in accordance with the principles disclosed in Smith et al. (1990), supra. Briefly, Smith et al. disclose an amino acid class hierarchy similar to the one summarized in FIG. 3, which can be used to rationally substitute one amino acid for another while minimizing gross conformational distortions of the type which could compromise protein function. In any event, it is contemplated that many synthetic first finger, second finger, and heel region sequences, having only 70% homology with natural regions, preferably 80%, and most preferably at least 90%, can be used to produce the constructs of the present invention. Amino acid sequence patterns showing amino acids preferred at each location in the finger and heel regions, deduced in accordance with the principles described in Smith et al. (1990) supra, also are show in FIGS. 5 and 6, and are referred to as the: TGF-β; Vg/dpp; GDF; and Inhibin subgroup patterns. The amino acid sequences defining the finger 1, heel and finger 2 sequence patterns of each subgroup are set forth in FIGS. 5A, 5B, and 5C, respectively. In addition, the amino acid sequences defining the entire TGF-β, Vg/dpp, GDF and Inhibin subgroup patterns are set forth in the Sequence Listing as SEQ. ID. Nos. 64, 65, 66, and 67, respectively.

The preferred amino acid sequence patterns for each subgroup, disclosed in FIGS. 5A, 5B, and 5C, and summarized in FIG. 6, enable one skilled in the art to identify alternative amino acids that may be incorporated at specific positions in the finger 1, heel, and finger 2 elements. The amino acids identified in upper case letters in a single letter amino acid code identify conserved amino acids that together are believed to define structural and functional elements of the finger and heel regions. The upper case letter "X" in FIGS. 5 and 6 indicates that any naturally occurring amino acid is acceptable at that position. The lower case letter "z" in FIGS. 5 and 6 indicates that either a gap or any of the naturally occurring amino acids is acceptable at that position. The lower case letters stand for the amino acids indicated in accordance with the pattern definition table set forth in FIG. 5 and identify groups of amino acids which are useful in that location.

In accordance the amino acid sequence subgroup patterns set forth in FIGS. 5 and 6, it is contemplated, for example, that the skilled artisan may be able to predict that where applicable, one amino acid may be substituted by another without inducing disruptive stereochemical changes within the resulting protein construct. For example, in FIG. 5A, in the TGF-β subgroup pattern at residue number 12 it is contemplated that either a lysine residue (K) or a glutamine residue (Q) may be present at this position without affecting the structure of the resulting construct. Accordingly, the sequence pattern at position 12 contains an "n" which in accordance with FIG. 10 defines an amino acid residue selected from the group consisting of lysine or glutamine. It is contemplated, therefore, that many synthetic finger 1, finger 2 and heel region amino acid sequences, having 70% homology, preferably 80%, and most preferably at least 90% with the natural regions, may be used to produce conformationally active proteins of the invention.

In accordance with these principles, it is contemplated that one may design a synthetic construct by starting with the amino acid sequence patterns belonging to the TGF-β, Vg/dpp, GDF, or Inhibin subgroup patterns shown in FIGS. 5 and 6. Thereafter, by using conventional recombinant or synthetic methodologies a preselected amino acid may be substituted by another as guided by the principles herein and the resulting protein construct tested for binding activity in combination with either agonist or antagonist activity.

The TGF-β subgroup pattern, SEQ. ID. No. 64, accommodates the homologies shared among members of the TGF-β subgroup identified to date including TGF-β1, TGF-β2, TGF-β3, TGF-β4, and TGF-β5. The generic sequence, shown below, includes both the conserved amino acids (standard three letter code) as well as alternative amino acids (Xaa) present at the variable positions within the sequence and defined by the rules set forth in FIG. 3.

TGF-β Subgroup Pattern

```
Cys Cys Val Arg Pro Leu Tyr Ile Asp Phe Arg Xaa Asp Leu Gly Trp
 1           5                   10                  15

Lys Trp Ile His Glu Pro Lys Gly Tyr Xaa Ala Asn Phe Cys Xaa Gly
            20                  25                  30

Xaa Cys Pro Tyr Xaa Trp Ser Xaa Asp Thr Gln Xaa Ser Xaa Val Leu
        35                  40                  45

Xaa Leu Tyr Asn Xaa Xaa Asn Pro Xaa Ala Ser Ala Xaa Pro Cys Cys
        50                  55                  60

Val Pro Gln Xaa Leu Glu Pro Leu Xaa Ile Xaa Tyr Tyr Val Gly Arg
 65                 70                  75                  80

Xaa Xaa Lys Val Glu Gln Leu Ser Asn Met Xaa Val Xaa Ser Cys Lys
                85                  90                  95

Cys Ser.
```

Each Xaa can be independently selected from a group of one or more specified amino acids defined as follows, wherein: Xaa12 is Arg or Lys; Xaa26 is Ala, Arg, Asn, Asp, Cys, Glu, Gln, Gly, His, Ile, Leu, Lys, Met, Phe, Pro, Ser, Thr, Trp, Tyr or Val; Xaa31 is Ala, Arg, Asn, Asp, Cys, Glu, Gln, Gly, His, Ile, Leu, Lys, Met, Phe, Pro, Ser, Thr, Trp, Tyr or Val; Xaa33 is Ala, Gly, Pro, Ser, or Thr; Xaa37 is Ile, Leu, Met or Val; Xaa40 is Ala, Arg, Asn, Asp, Cys, Glu, Gln, Gly, His, Ile, Leu, Lys, Met, Phe, Pro, Ser, Thr, Trp, Tyr or Val; Xaa44 is His, Phe, Trp or Tyr; Xaa46 is Arg or Lys; Xaa49 is Ala, Gly, Pro, Ser, or Thr; Xaa53 is Arg, Asn, Asp, Gln, Glu, His, Lys, Ser or Thr; Xaa54 is Ala, Arg, Asn, Asp, Cys, Glu, Gln, Gly, His, Ile, Leu, Lys, Met, Phe, Pro, Ser, Thr, Trp, Tyr or Val; Xaa57 is Ala, Arg, Asn, Asp, Cys, Glu, Gln, Gly, His, Ile, Leu, Lys, Met, Phe, Pro, Ser, Thr, Trp, Tyr or Val; Xaa61 is Ala, Gly, Pro, Ser, or Thr; Xaa68 is Ala, Arg, Asn, Asp, Cys, Glu, Gln, Gly, His, Ile, Leu, Lys, Met, Phe, Pro, Ser, Thr, Trp, Tyr or Val; Xaa73 is Ala, Gly, Pro, Ser, or Thr; Xaa75 is Ile, Leu, Met or Val; Xaa81 is Arg, Asn, Asp, Gln, Glu, His, Lys, Ser or Thr; Xaa82 is Ala, Gly, Pro, Ser, or Thr; Xaa91 is Ile or Val; Xaa93 is Arg or Lys.

The Vg/dpp subgroup pattern, SEQ. ID. No. 65, accommodates the homologies shared among members of the Vg/dpp subgroup identified to date including dpp, vg-1, vgr-1, 60A, BMP-2A (BMP-2), Dorsalin, BMP-2B (BMP-4), BMP-3, BMP-5, BMP-6, OP-1 (BMP-7), OP-2 and OP-3. The generic sequence, below, includes both the conserved amino acids (standard three letter code) as well as alternative amino acids (Xaa) present at the variable positions within the sequence and defined by the rules set forth in FIG. 3.

Vg/dpp Subgroup Pattern

```
Cys Xaa Xaa Xaa Xaa Leu Tyr Val Xaa Phe Xaa Asp Xaa Gly Trp Xaa
1               5                   10                  15

Asp Trp Ile Ile Ala Pro Xaa Gly Tyr Xaa Ala Xaa Tyr Cys Xaa Gly
            20                  25                  30

Xaa Cys Xaa Phe Pro Leu Xaa Xaa Xaa Xaa Asn Xaa Thr Asn His Ala
        35                  40                  45

Ile Xaa Gln Thr Leu Val Xaa Xaa Xaa Xaa Xaa Xaa Xaa Xaa Xaa Pro
    50                  55                  60

Lys Xaa Cys Cys Xaa Pro Thr Xaa Leu Xaa Ala Xaa Ser Xaa Leu Tyr
65              70                  75                  80

Xaa Asp Xaa Xaa Xaa Xaa Xaa Val Xaa Leu Xaa Xaa Tyr Xaa Xaa Met
            85                  90                  95

Xaa Val Xaa Xaa Cys Gly Cys Xaa.
                100
```

Each Xaa can be independently selected from a group of one or more specified amino acids defined as follows, wherein: Xaa2 is Arg or Lys; Xaa3 is Arg or Lys; Xaa4 is Arg, Asn, Asp, Gln, Glu, His, Lys, Ser or Thr; Xaa5 is Arg, Asn, Asp, Gln, Glu, His, Lys, Ser or Thr; Xaa9 is Arg, Asn, Asp, Gln, Glu, His, Lys, Ser or Thr; Xaa11 is Arg, Asn, Asp, Gln, Glu, His, Lys, Ser or Thr; Xaa13 is Ile, Leu, Met or Val; Xaa16 is Arg, Asn, Asp, Gln, Glu, His, Lys, Ser or Thr; Xaa23 is Arg, Gln, Glu, or Lys; Xaa26 is Ala, Arg, Asn, Asp, Cys, Glu, Gln, Gly, His, Ile, Leu, Lys, Met, Phe, Pro, Ser, Thr, Trp, Tyr or Val; Xaa28 is Phe, Trp or Tyr; Xaa31 is Arg, Asn, Asp, Gln, Glu, His, Lys, Ser or Thr; Xaa33 is Asp or Glu; Xaa35 is Ala, Arg, Asn, Asp, Cys, Glu, Gln, Gly, His, Ile, Leu, Lys, Met, Phe, Pro, Ser, Thr, Trp, Tyr or Val; Xaa39 is Ala, Arg, Asn, Asp, Cys, Glu, Gln, Gly, His, Ile, Leu, Lys, Met, Phe, Pro, Ser, Thr, Trp, Tyr or Val; Xaa40 is Ala, Arg, Asn, Asp, Cys, Glu, Gln, Gly, His, Ile, Leu, Lys, Met, Phe, Pro, Ser, Thr, Trp, Tyr or Val; Xaa41 is Ala, Arg, Asn, Asp, Cys, Glu, Gln, Gly, His, Ile, Leu, Lys, Met, Phe, Pro, Ser, Thr, Trp, Tyr or Val; Xaa42 is Leu or Met; Xaa44 is Ala, Gly, Pro, Ser, or Thr; Xaa50 is Ile or Val; Xaa55 is Arg, Asn, Asp, Gln, Glu, His, Lys, Ser or Thr; Xaa56 is Ala, Arg, Asn, Asp, Cys, Glu, Gln, Gly, His, Ile, Leu, Lys, Met, Phe, Pro, Ser, Thr, Trp, Tyr or Val; Xaa57 is Ile, Leu, Met or Val; Xaa58 is Arg, Asn, Asp, Gln, Glu, His, Lys, Ser or Thr; Xaa59 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa60 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa61 is Arg, Asn, Asp, Gln, Glu, His, Lys, Ser or Thr; Xaa62 is Ala, Arg, Asn, Asp, Cys, Glu, Gln, Gly, His, Ile, Leu, Lys, Met, Phe, Pro, Ser, Thr, Trp, Tyr or Val; Xaa63 is Ile or Val; Xaa66 is Ala, Gly, Pro, Ser, or Thr; Xaa69 is Ala, Arg, Asn, Asp, Cys, Glu, Gln, Gly, His, Ile, Leu, Lys, Met, Phe, Pro, Ser, Thr, Trp, Tyr or Val; Xaa72 is Arg, Gln, Glu, or Lys; Xaa74 is Arg, Asn, Asp, Gln, Glu, His, Lys, Ser or Thr; Xaa76 is Ile or Val; Xaa78 is Ile, Leu, Met or Val; Xaa81 is Cys, Ile, Leu, Met, Phe, Trp, Tyr or Val; Xaa83 is Asn, Asp or Glu; Xaa84 is Arg, Asn, Asp, Gln, Glu, His, Lys, Ser or Thr; Xaa85 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa86 is Arg, Asn, Asp, Gln, Glu, His, Lys, Ser or Thr; Xaa87 is Arg, Asn, Asp, Gln, Glu, His, Lys, Ser or Thr; Xaa89 is Ile or Val; Xaa91 is Arg or Lys; Xaa92 is Arg, Asn, Asp, Gln, Glu, His, Lys, Ser or Thr; Xaa94 is Arg, Gln, Glu, or Lys; Xaa95 is Asn or Asp; Xaa97 is Ala, Arg, Asn, Asp, Cys, Glu, Gln, Gly, His, Ile, Leu, Lys, Met, Phe, Pro, Ser, Thr, Trp, Tyr or Val; Xaa99 is Arg, Gln, Glu, or Lys; Xaa100 is Ala, Gly, Pro, Ser, or Thr; Xaa104 is Arg, Asn, Asp, Gln, Glu, His, Lys, Ser or Thr.

The GDF subgroup pattern, SEQ. ID. No. 66, accommodates the homologies shared among members of the GDF subgroup identified to date including GDF-1, GDF-3, and GDF-9. The generic sequence, shown below, includes both the conserved amino acids (standard three letter code) as well as alternative amino acids (Xaa) present at the variable positions within the sequence and defined by the rules set forth in FIG. 3.

GDF Subgroup Pattern

```
Cys Xaa Xaa Xaa Xaa Xaa Xaa Xaa Xaa Phe Xaa Xaa Xaa Xaa Trp Xaa
1               5                   10                  15

Xaa Trp Xaa Xaa Ala Pro Xaa Xaa Xaa Xaa Xaa Xaa Xaa Cys Xaa Gly
            20                  25                  30

Xaa Cys Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Pro Xaa Xaa Xaa Xaa Xaa Xaa Cys Val Pro Xaa Xaa Xaa Ser Pro Xaa
65                  70                  75                  80

Ser Xaa Leu Xaa Xaa Xaa Xaa Xaa Xaa Xaa Xaa Xaa Xaa Xaa Xaa Tyr
                85                  90                  95
```

```
Glu Asp Met Xaa Xaa Xaa Xaa Cys Xaa Cys Xaa.
        100                 105
```

Each Xaa can be independently selected from a group of one or more specified amino acids defined as follows, wherein: Xaa2 is Arg, Asn, Asp, Gln, Glu, His, Lys, Ser or Thr; Xaa3 is Ala, Arg, Asn, Asp, Cys, Glu, Gln, Gly, His, Ile, Leu, Lys, Met, Phe, Pro, Ser, Thr, Trp, Tyr or Val; Xaa4 is Arg, Asn, Asp, Gln, Glu, His, Lys, Ser or Thr; Xaa5 is Arg, Asn, Asp, Gln, Glu, His, Lys, Ser or Thr; Xaa6 is Cys, Ile, Leu, Met, Phe, Trp, Tyr or Val; Xaa7 is Ala, Arg, Asn, Asp, Cys, Glu, Gln, Gly, His, Ile, Leu, Lys, Met, Phe, Pro, Ser, Thr, Trp, Tyr or Val; Xaa8 is Ile, Leu, Met or Val; Xaa9 is Arg, Asn, Asp, Gln, Glu, His, Lys, Ser or Thr; Xaa11 is Arg, Asn, Asp, Gln, Glu, His, Lys, Ser or Thr; Xaa12 is Arg, Asn, Asp, Gln, Glu, His, Lys, Ser or Thr; Xaa13 is Ile, Leu, Met or Val; Xaa14 is Ala, Arg, Asn, Asp, Cys, Glu, Gln, Gly, His, Ile, Leu, Lys, Met, Phe, Pro, Ser, Thr, Trp, Tyr or Val; Xaa16 is Arg, Asn, Asp, Gln, Glu, His, Lys, Ser or Thr; Xaa17 is Arg, Asn, Asp, Gln, Glu, His, Lys, Ser or Thr; Xaa19 is Ile or Val; Xaa20 is Ile or Val; Xaa23 is Arg, Asn, Asp, Gln, Glu, Gln, Lys, Ser or Thr; Xaa24 is Ala, Arg, Asn, Asp, Cys, Glu, Gln, Gly, His, Ile, Leu, Lys, Met, Phe, Pro, Ser, Thr, Trp, Tyr or Val; Xaa25 is Phe, Trp or Tyr; Xaa26 is Ala, Arg, Asn, Asp, Cys, Glu, Gln, Gly, His, Ile, Leu, Lys, Met, Phe, Pro, Ser, Thr, Trp, Tyr or Val; Xaa27 is Ala, Gly, Pro, Ser, or Thr; Xaa28 is Arg, Asn, Asp, Gln, Glu, His, Lys, Ser or Thr; Xaa29 is Phe, Trp or Tyr; Xaa31 is Arg, Asn, Asp, Gln, Glu, His, Lys, Ser or Thr; Xaa33 is Arg, Asn, Asp, Gln, Glu, His, Lys, Ser or Thr; Xaa35 is Ala, Gly, Pro, Ser, or Thr; Xaa36 is Ala, Arg, Asn, Asp, Cys, Glu, Gln, Gly, His, Ile, Leu, Lys, Met, Phe, Pro, Ser, Thr, Trp, Tyr or Val; Xaa37 is Ala, Gly, Pro, Ser, or Thr; Xaa38 is Ala, Arg, Asn, Asp, Cys, Glu, Gln, Gly, His, Ile, Leu, Lys, Met, Phe, Pro, Ser, Thr, Trp, Tyr or Val; Xaa39 is Arg, Asn, Asp, Gln, Glu, His, Lys, Ser or Thr; Xaa40 is Ala, Arg, Asn, Asp, Cys, Glu, Gln, Gly, His, Ile, Leu, Lys, Met, Phe, Pro, Ser, Thr, Trp, Tyr or Val; Xaa41 is Ala, Arg, Asn, Asp, Cys, Glu, Gln, Gly, His, Ile, Leu, Lys, Met, Phe, Pro, Ser, Thr, Trp, Tyr or Val; Xaa42 is Ala, Arg, Asn, Asp, Cys, Glu, Gln, Gly, His, Ile, Leu, Lys, Met, Phe, Pro, Ser, Thr, Trp, Tyr or Val; Xaa43 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa44 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa45 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa46 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa47 is Ala, Arg, Asn, Asp, Cys, Glu, Gln, Gly, His, Ile, Leu, Lys, Met, Phe, Pro, Ser, Thr, Trp, Tyr or Val; Xaa48 is Ala, Gly, Pro, Ser, or Thr; Xaa49 is Ala, Arg, Asn, Asp, Cys, Glu, Gln, Gly, His, Ile, Leu, Lys, Met, Phe, Pro, Ser, Thr, Trp, Tyr or Val; Xaa50 is Ala, Arg, Asn, Asp, Cys, Glu, Gln, Gly, His, Ile, Leu, Lys, Met, Phe, Pro, Ser, Thr, Trp, Tyr or Val; Xaa51 is His, Phe, Trp or Tyr; Xaa52 is Ala, Gly, Pro, Ser, or Thr; Xaa53 is Cys, Ile, Leu, Met, Phe, Trp, Tyr or Val; Xaa54 is Ile, Leu, Met or Val; Xaa55 is Arg, Gln, Glu, or Lys; Xaa56 is Ala, Arg, Asn, Asp, Cys, Glu, Gln, Gly, His, Ile, Leu, Lys, Met, Phe, Pro, Ser, Thr, Trp, Tyr or Val; Xaa57 is Ile, Leu, Met or Val; Xaa58 is Ile, Leu, Met or Val; Xaa59 is His, Phe, Trp or Tyr; Xaa60 is Ala, Arg, Asn, Asp, Cys, Glu, Gln, Gly, His, Ile, Leu, Lys, Met, Phe, Pro, Ser, Thr, Trp, Tyr or Val; Xaa61 is Ala, Arg, Asn, Asp, Cys, Glu, Gln, Gly, His, Ile, Leu, Lys, Met, Phe, Pro, Ser, Thr, Trp, Tyr or Val; Xaa62 is Ala, Arg, Asn, Asp, Cys, Glu, Gln, Gly, His, Ile, Leu, Lys, Met, Phe, Pro, Ser, Thr, Trp, Tyr or Val; Xaa63 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa64 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa66 is Ala, Arg, Asn, Asp, Cys, Glu, Gln, Gly, His, Ile, Leu, Lys, Met, Phe, Pro, Ser, Thr, Trp, Tyr or Val; Xaa67 is Ala, Arg, Asn, Asp, Cys, Glu, Gln, Gly, His, Ile, Leu, Lys, Met, Phe, Pro, Ser, Thr, Trp, Tyr or Val; Xaa68 is Ala, Gly, Pro, Ser, or Thr; Xaa69 is Arg, Asn, Asp, Gln, Glu, His, Lys, Ser or Thr; Xaa70 is Ala, Gly, Pro, Ser, or Thr; Xaa71 is Ala, Arg, Asn, Asp, Cys, Glu, Gln, Gly, His, Ile, Leu, Lys, Met, Phe, Pro, Ser, Thr, Trp, Tyr or Val; Xaa75 is Ala, Arg, Asn, Asp, Cys, Glu, Gln, Gly, His, Ile, Leu, Lys, Met, Phe, Pro, Ser, Thr, Trp, Tyr or Val; Xaa76 is Arg or Lys; Xaa77 is Cys, Ile, Leu, Met, Phe, Trp, Tyr or Val; Xaa80 is Ile, Leu, Met or Val; Xaa82 is Ile, Leu, Met or Val; Xaa84 is Ala, Arg, Asn, Asp, Cys, Glu, Gln, Gly, His, Ile, Leu, Lys, Met, Phe, Pro, Ser, Thr, Trp, Tyr or Val; Xaa85 is Ala, Arg, Asn, Asp, Cys, Glu, Gln, Gly, His, Ile, Leu, Lys, Met, Phe, Pro, Ser, Thr, Trp, Tyr or Val; Xaa86 is Asp or Glu; Xaa87 is Ala, Arg, Asn, Asp, Cys, Glu, Gln, Gly, His, Ile, Leu, Lys, Met, Phe, Pro, Ser, Thr, Trp, Tyr or Val; Xaa88 is Arg, Asn, Asp, Gln, Glu, His, Lys, Ser or Thr; Xaa89 is Ala, Arg, Asn, Asp, Cys, Glu, Gln, Gly, His, Ile, Leu, Lys, Met, Phe, Pro, Ser, Thr, Trp, Tyr or Val; Xaa90 is Arg, Asn, Asp, Gln, Glu, His, Lys, Ser or Thr; Xaa91 is Ile or Val; Xaa92 is Ala, Arg, Asn, Asp, Cys, Glu, Gln, Gly, His, Ile, Leu, Lys, Met, Phe, Pro, Ser, Thr, Trp, Tyr or Val; Xaa93 is Cys, Ile, Leu, Met, Phe, Trp, Tyr or Val; Xaa94 is Arg or Lys; Xaa95 is Arg, Asn, Asp, Gln, Glu, His, Lys, Ser or Thr; Xaa100 is Ile or Val; Xaa101 is Ala, Arg, Asn, Asp, Cys, Glu, Gln, Gly, His, Ile, Leu, Lys, Met, Phe, Pro, Ser, Thr, Trp, Tyr or Val; Xaa102 is Arg, Asn, Asp, Gln, Glu, His, Lys, Ser or Thr; Xaa103 is Arg, Gln, Glu, or Lys; Xaa105 is Ala, Gly, Pro, Ser, or Thr; Xaa107 is Ala, Arg, Asn, Asp, Cys, Glu, Gln, Gly, His, Ile, Leu, Lys, Met, Phe, Pro, Ser, Thr, Trp, Tyr or Val.

The Inhibin subgroup pattern, SEQ. ID. No. 67, accommodates the homologies shared among members of the Inhibin subgroup identified to date including Inhibin α, Inhibin βA and Inhibin βB. The generic sequence, shown below, includes both the conserved amino acids (standard three letter code) as well as alternative amino acids (Xaa) present at the variable positions within the sequence and defined by the rules set forth in FIG. 3.

Inhibin Subgroup Pattern

```
Cys Xaa Xaa Xaa Xaa Xaa Xaa Xaa Xaa Phe Xaa Xaa Xaa Gly Trp Xaa
1               5                   10                  15

Xaa Trp Ile Xaa Xaa Pro Xaa Xaa Xaa Xaa Xaa Xaa Tyr Cys Xaa Gly
            20              25                  30
```

```
                                    -continued
Xaa Cys Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
 50                  55                  60

Xaa Xaa Xaa Xaa Xaa Cys Cys Xaa Xaa Xaa Pro Xaa Xaa Xaa Xaa Xaa
 65                  70                  75                  80

Xaa Xaa Xaa Xaa Xaa Xaa Xaa Asp Xaa Xaa Xaa Xaa Xaa Xaa Xaa
            85                  90                  95

Xaa Xaa Xaa Asn Xaa Xaa Xaa Xaa Xaa Cys Xaa Cys Xaa.
            100                 105
```

Each Xaa can be independently selected from a group of one or more specified amino acids defined as follows, wherein: Xaa2 is Ala, Arg, Asn, Asp, Cys, Glu, Gln, Gly, His, Ile, Leu, Lys, Met, Phe, Pro, Ser, Thr, Trp, Tyr or Val; Xaa3 is Arg or Lys; Xaa4 is Ala, Arg, Asn, Asp, Cys, Glu, Gln, Gly, His, Ile, Leu, Lys, Met, Phe, Pro, Ser, Thr, Trp, Tyr or Val; Xaa5 is Ala, Arg, Asn, Asp, Cys, Glu, Gln, Gly, His, Ile, Leu, Lys, Met, Phe, Pro, Ser, Thr, Trp, Tyr or Val; Xaa6 is Cys, Ile, Leu, Met, Phe, Trp, Tyr or Val; Xaa7 is Ala, Arg, Asn, Asp, Cys, Glu, Gln, Gly, His, Ile, Leu, Lys, Met, Phe, Pro, Ser, Thr, Trp, Tyr or Val; Xaa8 is Ile or Val; Xaa9 is Arg, Asn, Asp, Gln, Glu, His, Lys, Ser or Thr; Xaa11 is Arg, Gln, Glu, or Lys; Xaa12 is Ala, Arg, Asn, Asp, Cys, Glu, Gln, Gly, His, Ile, Leu, Lys, Met, Phe, Pro, Ser, Thr, Trp, Tyr or Val; Xaa13 is Ile, Leu, Met or Val; Xaa16 is Asn, Asp or Glu; Xaa17 is Arg, Asn, Asp, Gln, Glu, His, Lys, Ser or Thr; Xaa20 is Ile or Val; Xaa21 is Ala, Arg, Asn, Asp, Cys, Glu, Gln, Gly, His, Ile, Leu, Lys, Met, Phe, Pro, Ser, Thr, Trp, Tyr or Val; Xaa23 is Ala, Gly, Pro, Ser, or Thr; Xaa24 is Ala, Gly, Pro, Ser, or Thr; Xaa25 is Phe, Trp or Tyr; Xaa26 is Ala, Arg, Asn, Asp, Cys, Glu, Gln, Gly, His, Ile, Leu, Lys, Met, Phe, Pro, Ser, Thr, Trp, Tyr or Val; Xaa27 is Ala, Arg, Asn, Asp, Cys, Glu, Gln, Gly, His, Ile, Leu, Lys, Met, Phe, Pro, Ser, Thr, Trp, Tyr or Val; Xaa28 is Arg, Asn, Asp, Gln, Glu, His, Lys, Ser or Thr; Xaa31 is Arg, Asn, Asp, Gln, Glu, His, Lys, Ser or Thr; Xaa33 is Ala, Arg, Asn, Asp, Cys, Glu, Gln, Gly, His, Ile, Leu, Lys, Met, Phe, Pro, Ser, Thr, Trp, Tyr or Val; Xaa35 is Ala, Gly, Pro, Ser, or Thr; Xaa36 is Ala, Arg, Asn, Asp, Cys, Glu, Gln, Gly, His, Ile, Leu, Lys, Met, Phe, Pro, Ser, Thr, Trp, Tyr or Val; Xaa37 is His, Phe, Trp or Tyr; Xaa38 is Ile, Leu, Met or Val; Xaa39 is Ala, Gly, Pro, Ser, or Thr; Xaa40 is Ala, Gly, Pro, Ser, or Thr; Xaa41 is Ala, Arg, Asn, Asp, Cys, Glu, Gln, Gly, His, Ile, Leu, Lys, Met, Phe, Pro, Ser, Thr, Trp, Tyr or Val; Xaa42 is Ala, Arg, Asn, Asp, Cys, Glu, Gln, Gly, His, Ile, Leu, Lys, Met, Phe, Pro, Ser, Thr, Trp, Tyr or Val; Xaa43 is Ala, Gly, Pro, Ser, or Thr; Xaa44 is Ala, Arg, Asn, Asp, Cys, Glu, Gln, Gly, His, Ile, Leu, Lys, Met, Phe, Pro, Ser, Thr, Trp, Tyr or Val; Xaa45 is Ala, Gly, Pro, Ser, or Thr; Xaa46 is Ala, Arg, Asn, Asp, Cys, Glu, Gln, Gly, His, Ile, Leu, Lys, Met, Phe, Pro, Ser, Thr, Trp, Tyr or Val; Xaa47 is Ala, Gly, Pro, Ser, or Thr; Xaa48 is Ala, Arg, Asn, Asp, Cys, Glu, Gln, Gly, His, Ile, Leu, Lys, Met, Phe, Pro, Ser, Thr, Trp, Tyr or Val; Xaa49 is Ala, Arg, Asn, Asp, Cys, Glu, Gln, Gly, His, Ile, Leu, Lys, Met, Phe, Pro, Ser, Thr, Trp, Tyr or Val; Xaa50 is Ala, Gly, Pro, Ser, or Thr; Xaa51 is Ala, Gly, Pro, Ser, or Thr; Xaa52 is Ala, Arg, Asn, Asp, Cys, Glu, Gln, Gly, His, Ile, Leu, Lys, Met, Phe, Pro, Ser, Thr, Trp, Tyr or Val; Xaa53 is Ala, Arg, Asn, Asp, Cys, Glu, Gln, Gly, His, Ile, Leu, Lys, Met, Phe, Pro, Ser, Thr, Trp, Tyr or Val; Xaa54 is Ala, Arg, Asn, Asp, Cys, Glu, Gln, Gly, His, Ile, Leu, Lys, Met, Phe, Pro, Ser, Thr, Trp, Tyr or Val; Xaa55 is Arg, Asn, Asp, Gln, Glu, His, Lys, Ser or Thr; Xaa56 is Ala, Arg, Asn, Asp, Cys, Glu, Gln, Gly, His, Ile, Leu, Lys, Met, Phe, Pro, Ser, Thr, Trp, Tyr or Val; Xaa57 is Ala, Arg, Asn, Asp, Cys, Glu, Gln, Gly, His, Ile, Leu, Lys, Met, Phe, Pro, Ser, Thr, Trp, Tyr or Val; Xaa58 is Ala, Arg, Asn, Asp, Cys, Glu, Gln, Gly, His, Ile, Leu, Lys, Met, Phe, Pro, Ser, Thr, Trp, Tyr or Val; Xaa59 is Ala, Arg, Asn, Asp, Cys, Glu, Gln, Gly, His, Ile, Leu, Lys, Met, Phe, Pro, Ser, Thr, Trp, Tyr or Val; Xaa60 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa61 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa62 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa63 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa64 is Ala, Arg, Asn, Asp, Cys, Glu, Gln, Gly, His, Ile, Leu, Lys, Met, Phe, Pro, Ser, Thr, Trp, Tyr or Val; Xaa65 is Ala, Gly, Pro, Ser, or Thr; Xaa66 is Ala, Arg, Asn, Asp, Cys, Glu, Gln, Gly, His, Ile, Leu, Lys, Met, Phe, Pro, Ser, Thr, Trp, Tyr or Val; Xaa67 is Ala, Arg, Asn, Asp, Cys, Glu, Gln, Gly, His, Ile, Leu, Lys, Met, Phe, Pro, Ser, Thr, Trp, Tyr or Val; Xaa68 is Arg, Asn, Asp, Gln, Glu, His, Lys, Ser or Thr; Xaa69 is Ala, Gly, Pro, Ser, or Thr; Xaa72 is Ala, Arg, Asn, Asp, Cys, Glu, Gln, Gly, His, Ile, Leu, Lys, Met, Phe, Pro, Ser, Thr, Trp, Tyr or Val; Xaa73 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa74 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa76 is Ala, Gly, Pro, Ser, or Thr; Xaa77 is Arg, Asn, Asp, Gln, Glu, His, Lys, Ser or Thr; Xaa78 is Leu or Met; Xaa79 is Arg, Asn, Asp, Gln, Glu, His, Lys, Ser or Thr; Xaa80 is Ala, Gly, Pro, Ser, or Thr; Xaa81 is Leu or Met; Xaa82 is Arg, Asn, Asp, Gln, Glu, His, Lys, Ser or Thr; Xaa83 is Ile, Leu, Met or Val; Xaa84 is Ala, Arg, Asn, Asp, Cys, Glu, Gln, Gly, His, Ile, Leu, Lys, Met, Phe, Pro, Ser, Thr, Trp, Tyr or Val; Xaa85 is Ala, Arg, Asn, Asp, Cys, Glu, Gln, Gly, His, Ile, Leu, Lys, Met, Phe, Pro, Ser, Thr, Trp, Tyr or Val; Xaa86 is Ala, Arg, Asn, Asp, Cys, Glu, Gln, Gly, His, Ile, Leu, Lys, Met, Phe, Pro, Ser, Thr, Trp, Tyr or Val; Xaa87 is Arg, Asn, Asp, Gln, Glu, His, Lys, Ser or Thr; Xaa89 is Ala, Arg, Asn, Asp, Cys, Glu, Gln, Gly, His, Ile, Leu, Lys, Met, Phe, Pro, Ser, Thr, Trp, Tyr or Val; Xaa90 is Ala, Arg, Asn, Asp, Cys, Glu, Gln, Gly, His, Ile, Leu, Lys, Met, Phe, Pro, Ser, Thr, Trp, Tyr, Val or a peptide bond; Xaa91 is Ala, Arg, Asn, Asp, Cys, Glu, Gln, Gly, His, Ile, Leu, Lys, Met, Phe, Pro, Ser, Thr, Trp, Tyr or Val; Xaa92 is Arg, Asn, Asp, Gln, Glu, His, Lys, Ser or Thr; Xaa93 is Cys, Ile, Leu, Met, Phe, Trp, Tyr or Val; Xaa94 is Ala, Arg, Asn, Asp, Cys, Glu, Gln, Gly, His, Ile, Leu, Lys, Met, Phe, Pro, Ser, Thr, Trp, Tyr or Val; Xaa95 is Ala, Arg, Asn, Asp, Cys, Glu, Gln, Gly, His, Ile, Leu, Lys, Met, Phe, Pro, Ser, Thr, Trp, Tyr or Val; Xaa96 is Arg, Gln, Glu, or Lys; Xaa97 is Arg, Asn, Asp, Gln, Glu, His, Lys, Ser or Thr; Xaa98 is Ile or Val; Xaa99 is Ala, Arg, Asn, Asp, Cys, Glu, Gln, Gly, His, Ile, Leu, Lys, Met, Phe, Pro, Ser, Thr, Trp, Tyr or Val; Xaa101 is Leu or Met; Xaa102 is Ile, Leu, Met or Val; Xaa103 is Ala, Arg, Asn, Asp, Cys, Glu, Gln, Gly, His, Ile, Leu, Lys, Met, Phe, Pro, Ser, Thr, Trp, Tyr or Val; Xaa104 is Gln or Glu; Xaa105 is Arg, Asn, Asp, Gln, Glu, His, Lys, Ser or Thr; Xaa107 is Ala or Gly; Xaa109 is Ala, Arg, Asn, Asp, Cys, Glu, Gln, Gly, His, Ile, Leu, Lys, Met, Phe, Pro, Ser, Thr, Trp, Tyr or Val.

(2) Biochemical, Structural and Functional Properties of Bone Morphogenic Proteins In its mature, native form, natural-sourced osteogenic protein is a glycosylated dimer, typically having an apparent molecular weight of about 30-36 kDa as determined by SDS-PAGE. When reduced, the 30 kDa protein gives rise to two glycosylated peptide subunits having apparent molecular weights of about 16 kDa and 18 kDa. In the reduced state, the protein has no detectable osteogenic activity. The unglycosylated protein, which also has osteogenic activity, has an apparent molecular weight of about 27 kDa. When reduced, the 27 kDa protein gives rise to two unglycosylated polypeptide chains, having molecular weights of about 14 kDa to 16 kDa. Typically, the naturally occurring osteogenic proteins are translated as a precursor, having an N-terminal signal peptide sequence typically less than about 30 residues, followed by a "pro" domain that is cleaved to yield the mature C-terminal domain. The signal peptide is cleaved rapidly upon translation, at a cleavage site that can be predicted in a given sequence using the method of Von Heijne (1986) *Nucleic Acids Research* 14:4683-4691. Osteogenic proteins useful herein include any known naturally-occurring native proteins including allelic, phylogenetic counterpart and other variants thereof, whether naturally-occurring or biosynthetically produced (e.g., including "muteins" or "mutant proteins"), as well as new, osteogenically active members of the general morphogenic family of proteins.

In still another preferred embodiment, useful osteogenically active proteins have polypeptide chains with amino acid sequences comprising a sequence encoded by a nucleic acid that hybridizes, under low, medium or high stringency hybridization conditions, to DNA or RNA encoding reference osteogenic sequences, e.g., C-terminal sequences defining the conserved seven cysteine domains of OP-1, OP-2, BMP2, 4, 5, 6, 60A, GDF5, GDF6, GDF7 and the like. As used herein, high stringent hybridization conditions are defined as hybridization according to known techniques in 40% formamide, 5×SSPE, 5×Denhardt's Solution, and 0.1% SDS at 37° C. overnight, and washing in 0.1×SSPE, 0.1% SDS at 50° C. Standard stringency conditions are well characterized in commercially available, standard molecular cloning texts. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984): *Nucleic Acid Hybridization* (B. D. Hames & S. J. Higgins eds. 1984); and B. Perbal, *A Practical Guide To Molecular Cloning* (1984).

Other members of the TGF-β superfamily of related proteins having utility in the practice of the instant invention include poor refolder proteins among the list: TGF-β1, TGF-β2, TGF-β3, TGF-β4 and TGF-β5, various inhibins, activins, BMP-11, and MIS, to name a few. FIG. 5C lists the C-terminal residues defining the finger 2 subdomain of various known members of the TGF-β superfamily. Any one of the proteins on the list that is a poor refolder can be improved by the methods of the invention, as can other known or discoverable family members.

B. Production of Recombinant Proteins

As mentioned above, the constructs of the invention can be manufactured by using conventional recombinant DNA methodologies well known and thoroughly documented in the art, as well as by using well-known biosynthetic and chemosynthetic methodologies using routine peptide or nucleotide chemistries and automated peptide or nucleotide synthesizers. Such routine methodologies are described for example in the following publications, the teachings of which are incorporated by reference herein: Hilvert, 1 *Chem. Biol.* 201-3 (1994); Muir et al., 95 *Proc. Natl. Acad. Sci. USA* 6705-10 (1998); Wallace, 6 *Curr. Opin. Biotechnol.* 403-10 (1995); Miranda et al., 96 *Proc. Natl. Acad. Sci. USA* 1181-86 (1999); Liu et al., 91 *Proc. Natl. Acad. Sci. USA* 6584-88 (1994). Suitable for use in the present invention are naturally-occurring amino acids and nucleotides; non-naturally occurring amino acids and nucleotides; modified or unusual amino acids; modified bases; amino acid sequences that contain post-translaterially modified amino acids and/or modified linkages, cross-links and end caps, non-peptidyl bonds, etc.; and, further including without limitation, those moieties disclosed in the *World Intellectual Property Organization (WIPO) Handbook on Industrial Property Information and Documentation, Standard St.* 25 (1998) including Tables 1 through 6 in Appendix 2, herein incorporated by reference. Equivalents of the foregoing will be appreciated by the skilled artisan relying only on routine experimentation together with the knowledge of the art.

For example, the contemplated DNA constructs may be manufactured by the assembly of synthetic nucleotide sequences and/or joining DNA restriction fragments to produce a synthetic DNA molecule. The DNA molecules then are ligated into an expression vehicle, for example an expression plasmid, and transfected into an appropriate host cell, for example *E. coli*. The contemplated protein construct encoded by the DNA molecule then is expressed, purified, refolded, tested in vitro for certain attributes, e.g., binding activity with a receptor having binding affinity for the template TGF-β superfamily member, and subsequently tested to assess whether the biosynthetic construct mimics other preferred attributes of the template superfamily member.

Alternatively, a library of synthetic DNA constructs can be prepared simultaneously for example, by the assembly of synthetic nucleotide sequences that differ in nucleotide composition in a preselected region. For example, it is contemplated that during production of a construct based upon a specific TGF-β superfamily member, the artisan can choose appropriate finger and heel regions for such a superfamily member (for example from FIGS. 5-6). Once the appropriate finger and heel regions have been selected, the artisan then can produce synthetic DNA encoding these regions. For example, if a plurality of DNA molecules encoding different linker sequences are included into a ligation reaction containing DNA molecules encoding finger and heel sequences, by judicious choice of appropriate restriction sites and reaction conditions, the artisan may produce a library of DNA constructs wherein each of the DNA constructs encode finger and heel regions but connected by different linker sequences. The resulting DNAs then are ligated into a suitable expression vehicle, i.e., a plasmid useful in the preparation of a phage display library, transfected into a host cell, and the polypeptides encoded by the synthetic DNAs expressed to generate a pool of candidate proteins. The pool of candidate proteins subsequently can be screened to identify specific proteins having binding affinity and/or selectivity for a pre-selected receptor.

Screening can be performed by passing a solution comprising the candidate proteins through a chromatography column containing surface immobilized receptor. Then proteins with the desired binding specificity are eluted, for example by means of a salt gradient and/or a concentration gradient of the template TGF-β superfamily member. Nucleotide sequences encoding such proteins subsequently can be isolated and characterized. Once the appropriate nucleotide sequences have been identified, the lead proteins subsequently can be produced, either by conventional recombinant DNA or peptide synthesis methodologies, in quantities sufficient to test whether the particular construct mimics the activity of the template TGF-β superfamily member.

It is contemplated that, which ever approach is adopted to produce DNA molecules encoding constructs of the invention, the tertiary structure of the preferred proteins can subsequently be modulated in order to optimize binding and/or biological activity by, for example, by a combination of nucleotide mutagenesis methodologies aided by the principles described herein and phage display methodologies. Accordingly, an artisan can produce and test simultaneously large numbers of such proteins.

(1) Gene Synthesis.

The processes for manipulating, amplifying, and recombining DNA which encode amino acid sequences of interest generally are well known in the art, and therefore, are not described in detail herein. Methods of identifying and isolating genes encoding members of the TGF-β superfamily and their cognate receptors also are well understood, and are described in the patent and other literature.

Briefly, the construction of DNAs encoding the biosynthetic constructs disclosed herein is performed using known techniques involving the use of various restriction enzymes which make sequence specific cuts in DNA to produce blunt ends or cohesive ends, DNA ligases, techniques enabling enzymatic addition of sticky ends to blunt-ended DNA, construction of synthetic DNAs by assembly of short or medium length oligonucleotides, cDNA synthesis techniques, polymerase chain reaction (PCR) techniques for amplifying appropriate nucleic acid sequences from libraries, and synthetic probes for isolating genes of members of the TGF-b superfamily and their cognate receptors. Various promoter sequences from bacteria, mammals, or insects to name a few, and other regulatory DNA sequences used in achieving expression, and various types of host cells are also known and available. Conventional transfection techniques, and equally conventional techniques for cloning and subcloning DNA are useful in the practice of this invention and known to those skilled in the art. Various types of vectors may be used such as plasmids and viruses including animal viruses and bacteriophages. The vectors may exploit various marker genes which impart to a successfully transfected cell a detectable phenotypic property that can be used to identify which of a family of clones has successfully incorporated the recombinant DNA of the vector.

One method for obtaining DNA encoding the biosynthetic constructs disclosed herein is by assembly of synthetic oligonucleotides produced in a conventional, automated, oligonucleotide synthesizer followed by ligation with appropriate ligases. For example, overlapping, complementary DNA fragments may be synthesized using phosphoramidite chemistry, with end segments left unphosphorylated to prevent polymerization during ligation. One end of the synthetic DNA is left with a "sticky end" corresponding to the site of action of a particular restriction endonuclease, and the other end is left with an end corresponding to the site of action of another restriction endonuclease. The complimentary DNA fragments are ligated together to produce a synthetic DNA construct.

Alternatively nucleic acid strands encoding finger 1, finger 2 and heel regions may be isolated from libraries of nucleic acids, for example, by colony hybridization procedures such as those described in Sambrook et al. eds. (1989) "*Molecular Cloning*", Coldspring Harbor Laboratories Press, NY, and/or by PCR amplification methodologies, such as those disclosed in Innis et al. (1990) "*PCR Protocols, A guide to methods and applications*", Academic Press. The nucleic acids encoding the finger and heel regions then are joined together to produce a synthetic DNA encoding the biosynthetic single-chain morphon construct of interest.

It is appreciated, however, that a library of DNA constructs encoding a plurality of morphons may be produced simultaneously by standard recombinant DNA methodologies, such as the ones, described above, For example, the skilled artisan by the use of cassette mutagenesis or oligonucleotide directed mutagenesis may produce, for example, a series of DNA constructs each of which contain different DNA sequences within a predefined location, e.g., within a DNA cassette encoding a linker sequence. The resulting library of DNA constructs subsequently may be expressed, for example, in a phage display library and any protein constructs that binds to a specific receptor may be isolated by affinity purification, e.g., using a chromatographic column comprising surface immobilized receptor (see section V below). Once molecules that bind the preselected receptor have been isolated, their binding and agonist properties may be modulated using the empirical refinement techniques also discussed in section V, below.

Methods of mutagenesis of proteins and nucleic acids are well known and well described in the art. See, e.g., Sambrook et al., (1990) *Molecular Cloning: A Laboratory Manual.*, 2d ed. (Cold Spring Harbor, N.Y.: Cold Spring Harbor Laboratory Press). Useful methods include PCR (overlap extension, see, e.g., *PCR Primer* (Dieffenbach and Dveksler, eds., Cold Spring Harbor Press, Cold Spring Harbor, N.Y., 1995, pp. 603-611); cassette mutagenesis and single-stranded mutagenesis following the method of Kunkel. It will be appreciated by the artisan that any suitable method of mutagenesis can be utilized and the mutagenesis method is not considered a material aspect of the invention. The nucleotide codons competent to encode amino acids, including arginine (Arg), glutamic acid (Glu) and aspartic acid (Asp) also are well known and described in the art. See, for example, Lehninger, *Biochemistry*, (Worth Publishers, N.Y., N.Y.) Standard codons encoding arginine, glutamic acid and aspartic acid are: Arg: CGU, CGC, CGA, CGG, AGA, AGG; Glu: GAA, GAG; and Asp: GAU, GAC. Chimeric constructs of the invention can readily be constructed by aligning the nucleic acid sequences of protein regions, or domains to be switched, and identifying compatible splice sites and/or constructing suitable crossover sequences using PCR overlap extension.

The mutant forms of TGF-β family members of the present invention can be produced in bacteria using standard, well-known methods. Full-length mature forms or shorter sequences defining only the C-terminal seven cysteine domain can be provided to the host cell. It may be preferred to modify the N-terminal sequences of the mutant forms of the protein in order to optimize bacterial expression. For example, the preferred form of native OP-1 for bacterial expression is the sequence encoding the mature, active sequence (residues 293-431 of SEQ No. 39 or a fragment thereof encoding the C-terminal seven cysteine domain (e.g., residues 330-431 of SEQ ID NO: 39). A methionine can be introduced at position 293, replacing the native serine residue, or it can precede this serine residue. Alternatively, a methionine can be introduced anywhere within the first thirty-six residues of the natural sequence (residues 293-329), up to the first cysteine of the TGF-β domain. The DNA sequence further can be modified at its N-terminus to improve purification, for example, by adding a "hexa-his" tail to assist purification on an IMAC column; or by using a FB leader sequence, which facilitates purification on an IgG/column. These and other methods are well described and well known in the art. Other bacterial species and/or proteins may require or benefit from analogous modifications to optimize the yield of the mutant BMP obtained therefrom. Such modifications are well within the level of ordinary skill in the art and are not considered material aspects of the invention.

The synthetic nucleic acids preferably are inserted into a vector suitable for overexpression in the host cell of choice. Any expression vector can be used, so long as it is capable of directing the expression of a heterologous protein such as a BMP in the host cell of choice. Useful vectors include plasmids, phagemids, mini chromosomes and YACs, to name a few. Other vector systems are well known and characterized in the art. The vector typically includes a replicon, one or more selectable marker gene sequences, and means for maintaining a high copy number of the vector in the host cell. Well known selectable marker genes include antibiotics like ampicillin, tetracycline and the like, as well as resistance to heavy metals. Useful selectable marker genes for use in yeast cells include the URA3, LEU2, HIS3 or TRP1 gene for use with an auxotrophic yeast mutant host. In addition, the vector also includes a suitable promoter sequence for expressing the gene of interest and which may or may not be inducible, as desired, as well as useful transcription and translation initiation sites, terminators, and other sequences that can maximize transcription and translation of the gene of interest. Well characterized promotors particularly useful in bacterial cells include the lac, tac, trp, and tpp promoters, to name a few. Promoters useful in yeast include ADHI, ADHII, or PHO5 promoter, for example.

Suitable host cells include microbial cells such as *Bacillus subtilis* (*B. subtilis*), species of *Pseudomonas, Escherichia coli* (*E. coli*), and yeast cells, e.g., *Saccharomyces cereviceae*. Other hosts cells, for example mammalian cells such as CHO, can be used.

The gene of interest can be transformed into the host cell of choice using standard microbiology techniques (electroporation or calcium chloride, for example) and the cells induced to grow under suitable conditions. Cell culturing media are well described in the art, including numerous well known texts, including Sambrook, et al. Useful media include LB (Luria's Broth) and Dulbecco's DMEM. The overexpressed protein can be collected from insoluble, refractile inclusion bodies by standard techniques, including cell lysis or mechanical disruption of the cell (Frenchpress, SLM Instruments, Inc, for example) followed by centrifugation and resolubilization (see below).

For example, if the gene is to be expressed in *E. coli*, it is cloned into an appropriate expression vector. This can be accomplished by positioning the engineered gene downstream of a promoter sequence such as Trp or Tac, and/or a gene coding for a leader peptide such as fragment B of protein A (FB). During expression, the resulting fusion proteins accumulate in refractile bodies in the cytoplasm of the cells, and may be harvested after disruption of the cells by French press or sonication. The isolated refractile bodies then are solubilized, and the expressed proteins folded and the leader sequence cleaved, if necessary, by methods already established with many other recombinant proteins.

Expression of the engineered genes in eukaryotic cells requires cells and cell lines that are easy to transfect, are capable of stably maintaining foreign DNA with an unrearranged sequence, and which have the necessary cellular components for efficient transcription, translation, post-translation modification, and secretion of the protein. In addition, a suitable vector carrying the gene of interest also is necessary. DNA vector design for transfection into mammalian cells should include appropriate sequences to promote expression of the gene of interest as described herein, including appropriate transcription initiation, termination, and enhancer sequences, as well as sequences that enhance translation efficiency, such as the Kozak consensus sequence. Preferred DNA vectors also include a marker gene and means for amplifying the copy number of the gene of interest. A detailed review of the state of the art of the production of foreign proteins in mammalian cells, including useful cells, protein expression-promoting sequences, marker genes, and gene amplification methods, is disclosed in Bendig (1988) *Genetic Engineering* 7:91-127.

The best characterized transcription promoters useful for expressing a foreign gene in a particular mammalian cell are the SV40 early promoter, the adenovirus promoter (AdMLP), the mouse metallothionein-I promoter (mMT-I), the Rous sarcoma virus (RSV) long terminal repeat (LTR), the mouse mammary tumor virus long terminal repeat (MMTV-LTR), and the human cytomegalovirus major intermediate-early promoter (hCMV). The DNA sequences for all of these promoters are known in the art and are available commercially.

The use of a selectable DHFR gene in a dhfr$^-$ cell line is a well characterized method useful in the amplification of genes in mammalian cell systems. Briefly, the DHFR gene is provided on the vector carrying the gene of interest, and addition of increasing concentrations of the cytotoxic drug methotrexate, which is metabolized by DHFR, leads to amplification of the DHFR gene copy number, as well as that of the associated gene of interest. DHFR as a selectable, amplifiable marker gene in transfected chinese hamster ovary cell lines (CHO cells) is particularly well characterized in the art. Other useful amplifiable marker genes include the adenosine deaminase (ADA) and glutamine synthetase (GS) genes.

The choice of cells/cell lines is also important and depends on the needs of the experimenter. COS cells provide high levels of transient gene expression, providing a useful means for rapidly screening the biosynthetic constructs of the invention. COS cells typically are transfected with a simian virus 40 (SV40) vector carrying the gene of interest. The transfected COS cells eventually die, thus preventing the long term production of the desired protein product. However, transient expression does not require the time consuming process required for the development of a stable cell line, and thus provides a useful technique for testing preliminary constructs for binding activity.

The various cells, cell lines and DNA sequences that can be used for mammalian cell expression of the single-chain constructs of the invention are well characterized in the art and are readily available. Other promoters, selectable markers, gene amplification methods and cells also may be used to express the proteins of this invention. Particular details of the transfection, expression, and purification of recombinant proteins are well documented in the art and are understood by those having ordinary skill in the art. Further details on the various technical aspects of each of the steps used in recombinant production of foreign genes in mammalian cell expression systems can be found in a number of texts and laboratory manuals in the art, such as, for example, F. M. Ausubel et al., ed., *Current Protocols in Molecular Biology*, John Wiley & Sons, New York, (1989).

C. Refolding Considerations

The protein, once isolated from inclusion bodies, is solubilized using a denaturant or chaotropic agent such as guanidine HCl or urea, preferably in the range of about 4-9 M and at an elevated temperature (e.g., 25-37° C.) and/or basic pH (8-10). Alternatively, the proteins can be solubilized by acidification, e.g., with acetic acid or trifluoroacetic acid, generally at a pH in the range of 1-4. Preferably, a reducing agent such as β-mercaptoethanol or dithiothreitol (DTT) is used in conjunction with the solubilizing agent. The solubilized heterologous protein can be purified further from solubilizing chaotropes by dialysis and/or by known chromatographic methods such as size exclusion chromatography, ion exchange chromatography, or reverse phase high performance liquid chromatography (RP-HPLC), for example.

The solubilized protein can be refolded as follows. The dissolved protein is diluted in a refolding medium, typically a Tris-buffered medium having a pH in the range of about pH 5.0-10.0, preferably in the range of about pH 6-9 and one which includes a detergent and/or chaotropic agent. Useful commercially available detergents can be ionic, nonionic or zwitterionic, such as NP40 (Nonidet 40), CHAPS (such as 3-[(3-cholamido-propyl)dimethylammonio]-1-propane-sulfate, digitonin, deoxycholate, or N-octyl glucoside. Useful chaotropic agents include guanidine, urea, or arginine. Preferably the detergent or chaotropic agent is present at a concentration in the range of about 0.1-10M, preferably in the range of about 0.5-4M. When CHAPS is the detergent, it preferably comprises about 0.5-5% of the solution, more preferably about 1-3% of the solution. Preferably the solution also includes a suitable redox system such as the oxidized and reduced forms of glutathione, DTT, β-mercaptoethanol, β-mercaptomethanol, cysteine or cystamine, to name a few. Preferably, the redox systems are present at ratios of reductant to oxidant in the range of about 1:1 to about 5:1. When the glutathione redox system is used, the ratio of reduced glutathione to oxidized glutathione is preferably is in the range of about 0.5 to 5; more preferably 1 to 1; and most preferably 2 to 1 of reduced form to oxidized form. Preferably the buffer also contains a salt, typically NaCl, present in the range of about 0.25M-2.5 M, preferably in the range of about 0.5-1.5M, most preferably in the range of about 1M. One skilled in the art will recognize that the above conditions and media may be varied using no more than ordinary experimentation. Such variations and modifications are within the scope of the present invention.

Preferably the protein concentration for a given refolding reaction is in the range of about 0.001-1.0 mg/ml, more preferably it is in the range of about 0.05-0.25 mg/ml, most preferably in the range of about 0.075-0.125 mg/ml. As will be appreciated by the skilled artisan, higher concentrations tend to produce more aggregates. Where heterodimers are to be produced (for example an OP1/BMP2 or BMP2/BMP6 heterodimer) preferably the individual proteins are provided to the refolding buffer in equal amounts.

Typically, the refolding reaction takes place at a temperature range from about 4° C. to about 25° C. More preferably, the refolding reaction is performed at 4° C., and allowed to go to completion. Refolding typically is complete in about one to seven days, generally within 16-72 hours or 24-48 hours, depending on the protein. As will be appreciated by the skilled artisan, rates of refolding can vary by protein, and longer and shorter refolding times are contemplated and within the scope of the present invention. As used herein, a "good refolder" protein is one where at least 20% of the protein is present in dimeric form following a folding reaction when compared to the total protein in the refolding reaction, as measured by any of the refolding assays described herein and without requiring further purification. Native BMPs that are considered in the art to be "good refolder" proteins include BMP2, CDMP1, CDMP2 and CDMP3. BMP-3 also refolds reasonably well. In contrast, a "poor refolder" protein yields less than 1% of properly-folded protein.

Properly refolded dimeric proteins readily can be assessed using any of a number of well known and well characterized assays. In particular, any one or more of three assays, all well known and well described in the art, and further described below can be used to advantage. Useful refolding assays include one or more of the following. First, the presence of dimers can be detected visually either by standard SDS-PAGE in the absence of a reducing agent such as DTT or by HPLC (e.g., C18 reverse phase HPLC). BMP dimeric proteins have an apparent molecular weight in the range about 28-36 kDa, as compared to monomeric subunits, which have an apparent molecular weight of about 14-18 kDa. The dimeric protein can readily be visualized on an electrophoresis gel by comparison to commercially available molecular weight standards. The dimeric protein also elutes from a C18 RP HPLC (45-50% acetonitrile: 0.1% TFA) at about 19 minutes (mammalian produced hOP-1 elutes at 18.95 minutes).

A second assay evaluates the presence of dimer by its ability to bind to hydroxyapatite. Properly-folded dimer binds a hydroxyapatite column well in the presence of 0.1-0.2M NaCl (dimer elutes at 0.25 M NaCl) as compared to monomer, which does not bind substantially at those concentrations (monomer elutes at 0.1M NaCl).

A third assay evaluates the presence of dimer by the protein's resistant to trypsin or pepsin digestion. The folded dimeric species is substantially resistant to both enzymes, particularly trypsin, which cleaves only a small portion of the N-terminus of the mature protein, leaving a biologically active dimeric species only slightly smaller in size than the untreated dimer. By contrast, the monomer is substantially degraded. In the assay, the protein is subjected to an enzyme digest using standard conditions, e.g., digestion in a standard buffer such as 50 mM Tris buffer, pH 8, containing 4 M urea, 100 mM NaCl, 0.3% Tween-80 and 20 mM methylamine. Digestion is allowed to occur at 37° C. for on the order of 16 hours, and the product visualized by any suitable means, preferably SDS-PAGE.

The biological activity of the refolded TGF-β family protein readily can be assessed by any of a number of means. A BMP's ability to induce endochondral bone formation can be evaluated using the well characterized rat subcutaneous bone assay, described in the art and in detail below. In the assay bone formation is measured by histology, as well as by alkaline phosphatase and/or osteoclacin production. In addition, osteogenic proteins having high specific bone forming activity, such as OP-1, BMP-2, BMP-4, BMP5 and BMP6, also induce alkaline phosphatase activity in an in vitro rat osteoblast or osteosarcoma cell-based assay. Such assays are well described in the art and are detailed herein below. See, for example, Sabokdar et al. (1994) *Bone and Mineral* 27:57-67.; Knutsen et al. (1993) *Biochem. Biophys. Res. Commun.* 194: 1352-1358; and Maliakal et al. (1994) *Growth Factors* 1:227-234). By contrast, osteogenic proteins having low specific bone forming activity, such as CDMP-1 and CDMP-2, for example, do not induce similar levels of alkaline phosphatase activity in the cell based osteoblast assay. The assay thus provides a ready method for evaluating biological activity mutants of BMPs. For example, CDMP 1, CDMP2 and CMDP3 all are competent to induce bone formation, although with a lower specific activity than BMP2, BMP4, BMP5, BMP6 or OP-1. Conversely, BMP2, BMP4, BMP5, BMP6 and OP-1 all can induce articular cartilage formation, albeit with a lower specific activity than CDMP1, CDMP2 or CDMP3. Accordingly, a CDMP mutant competent to induce alkaline phosphatase activity in the cell-based assay of Example 5 is expected to demonstrate a higher specific bone forming activity in the rat animal bioassay. Similarly, an OP-1 mutant containing a substitution present in a corresponding position of a CDMP1, CDMP2 or CDMP3 protein, and competent to induce bone in the rat assay but not to induce alkaline phosphatase activity in the cell based assay, is expected to have a higher specific articular cartilage inducing activity in an in vivo articular cartilage assay. As described herein below, a suitable in vitro assay for CDMP activity utilizes mouse embyronic osteoprogenitor or carcinoma cells, such as ATDC5 cells. See Example 6, below.

TGF-β activity can be readily evaluated by the protein's ability to inhibit epithelial cell growth. A useful, well characterized in vitro assay utilizes mink lung cells or melanoma cells. See Example 7. Other assays for other members of the TGF-β superfamily are well described in the literature and can be performed without undue experimentation.

D. Formulation and Bioactivity

The resulting chimeric proteins can be provided to an individual as part of a therapy to enhance, inhibit, or otherwise modulate in vivo events, such as but not limited to, the binding interaction between a TGF-β superfamily member and one or more of its cognate receptors. The constructs may be formulated in a pharmaceutical composition, as described below, and may be administered in morphogenic effective amounts by any suitable means, preferably directly or systematically, e.g., parenterally or orally. Resulting DNA constructs encoding preferred chimeric proteins can also be administered directly to a recipient for gene therapeutic purposes; such DNAs can be administered with or without carrier components, or with or without matrix components. Alternatively, cells transferred with such DNA constructs can be implanted in a recipient. Such materials and methods are well-known in the art.

Where any of the constructs disclosed here are to be provided directly (e.g., locally, as by injection, to a desired tissue site), or parentally, such as by intravenous, subcutaneous, intramuscular, intraorbital, ophthalmic, intraventricular, intracranial, intracapsular, intraspinal, intracisternal, intraperitoneal, buccal, rectal, vaginal, intranasal or by aerosol administration, the therapeutic composition preferably comprises part of an aqueous solution. The solution preferably is physiologically acceptable so that in addition to delivery of the desired construct to the patient, the solution does not otherwise adversely affect the patient's electrolyte and volume balance. The aqueous medium for the therapeutic molecule thus may comprise, for example, normal physiological saline (0.9% NaCl, 0.15M), pH 7-7.4 or other pharmaceutically acceptable salts thereof.

Useful solutions for oral or parenteral administration may be prepared by any of the methods well known in the pharmaceutical art, described, for example, in *Remington's Pharmaceutical Sciences*, (Gennaro, A., ed.), Mack Pub., 1990. Formulations may include, for example, polyalkylene glycols such as polyethylene glycol, oils of vegetable origin, hydrogenated naphthalenes, and the like. Formulations for direct administration, in particular, may include glycerol and other compositions of high viscosity. Biocompatible, preferably bioresorbable polymers, including, for example, hyaluronic acid, collagen, tricalcium phosphate, polybutyrate, polylactide, polyglycolide and lactide/glycolide copolymers, may be useful excipients to control the release of the morphogen in vivo.

Other potentially useful parenteral delivery systems for these therapeutic molecules include ethylene-vinyl acetate copolymer particles, osmotic pumps, implantable infusion systems, and liposomes. Formulations for inhalation administration may contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally.

Finally, therapeutic molecules may be administered alone or in combination with other molecules known to effect tissue morphogenesis, i.e., molecules capable of tissue repair and regeneration and/or inhibiting inflammation. Examples of useful cofactors for stimulating bone tissue growth in osteoporotic individuals, for example, include but are not limited to, vitamin $D_3$, calcitonin, prostaglandins, parathyroid hormone, dexamethasone, estrogen and IGF-I or IGF-II. Useful cofactors for nerve tissue repair and regeneration may include nerve growth factors. Other useful cofactors include symptom-alleviating cofactors, including antiseptics, antibiotics, antiviral and antifungal agents and analgesics and anesthetics.

Therapeutic molecules further can be formulated into pharmaceutical compositions by admixture with pharmaceutically acceptable nontoxic excipients and carriers. As noted above, such compositions may be prepared for parenteral administration, particularly in the form of liquid solutions or suspensions; for oral administration, particularly in the form of tablets or capsules; or intranasally, particularly in the form of powders, nasal drops or aerosols. Where adhesion to a tissue surface is desired the composition may include the biosynthetic construct dispersed in a fibrinogen-thrombin composition or other bioadhesive such as is disclosed, for example in PCT US91/09275, the disclosure of which is incorporated herein by reference. The composition then may be painted, sprayed or otherwise applied to the desired tissue surface. The compositions can be formulated for parenteral or oral administration to humans or other mammals in therapeutically effective amounts, e.g., amounts which provide appropriate concentrations of the morphon to target tissue for a time sufficient to induce the desired effect.

Where the therapeutic molecule comprises part of a tissue or organ preservation solution, any commercially available preservation solution may be used to advantage. For example, useful solutions known in the art include Collins solution, Wisconsin solution, Belzer solution, Eurocollins solution and lactated Ringer's solution. A detailed description of preservation solutions and useful components may be found, for example, in U.S. Pat. No. 5,002,965, the disclosure of which is incorporated herein by reference.

It is contemplated that some of the protein constructs, for example those based upon members of the Vg/dpp subgroup, will also exhibit high levels of activity in vivo when combined with a matrix. See for example, U.S. Pat. No. 5,266,683 the disclosure of which is incorporated by reference herein. The currently preferred matrices are xenogenic, allogenic or autogenic in nature. It is contemplated, however, that synthetic materials comprising polylactic acid, polyglycolic acid, polybutyric acid, derivatives and copolymers thereof can also be used to generate suitable matrices. Preferred synthetic and naturally derived matrix materials, their preparation, methods for formulating them with the morphogenic proteins of the invention, and methods of administration are well known in the art and so are not discussed in detailed herein. See for example, U.S. Pat. No. 5,266,683, the disclosure of which is herein incorporated by reference. It is further contemplated that binding to, adherence to or association with a matrix or the metal surface of a prosthetic device is an attribute that can be altered using the materials and methods disclosed herein. For example, devices comprising a matrix and an osteoactive construct of the present invention having enhanced matrix-adherent properties can be used as a slow-release device. The skilled artisan will appreciate the variation and manipulations now possible in light of the teachings herein.

As will be appreciated by those skilled in the art, the concentration of the compounds described in a therapeutic composition will vary depending upon a number of factors, including the morphogenic effective amount to be administered, the chemical characteristics (e.g., hydrophobicity) of the compounds employed, and the route of administration. The preferred dosage of drug to be administered also is likely to depend on such variables as the type and extent of a disease, tissue loss or defect, the overall health status of the particular patient, the relative biological efficacy of the compound selected, the formulation of the compound, the presence and types of excipients in the formulation, and the route of administration. In general terms, the therapeutic molecules of this invention may be provided to and individual where typical doses range from about 10 ng/kg to about 1 g/kg of body weight per day; with a preferred dose range being from about 0.1 mg/kg to 100 mg/kg of body weight.

II. Specific Modified Protein Constructs

Generally, the present invention relates to four types of modified TGF-β family protein constructs: (1) TGF-β family proteins which are truncated at the N-terminal region, (2) "latent" proteins that can be activated upon cleavage, including, but not limited to, release of an N-terminal sequence (e.g., by acid cleavage or protease treatment), (3) fusion proteins with specific binding capabilities and (4) heterodimers consisting of naturally-occurring or modified subunits of TGF-β family members. Particular species of these morphogen constructs are described in detail below. The species exemplified below generally relate to modified morphogen or osteogenic protein constructs, but the skilled practitioner will appreciate that these constructs are representative of similar constructs that can be generated with other members of the TGF-β super family.

According to the present invention, the attributes of native BMPs or other members of the TGF-β superfamily of proteins, including heterodimers and homodimers thereof, are altered by modifying the N-terminus of a native protein to alter one or more biological properties of a BMP or TGF-β superfamily member. As a result of this discovery, it is possible to design, TGF-β superfamily proteins that (1) are expressed recombinantly in prokaryotic or eukaryotic cells or synthesized using polypeptide synthesizers; (2) have altered folding attributes; (3) have altered solubility under neutral pHs, including but not limited to physiologically compatible conditions; (4) have altered isoelectric points; (5) have altered stability; (6) have an altered tissue or receptor specificity; (7) have a re-designed, altered biological activity; and/or (8) have altered binding or adherence properties to solid surfaces, such as but not limited to, biocompatible matrices or metals. Thus, the present invention can provide mechanisms for designing quick-release, slow-release and/or timed-release formulations containing a preferred protein construct. Other advantages and features will be evident from the teachings below. Moreover, making use of the discoveries disclosed herein, modified proteins having altered surface-binding/surface-adherent properties can be designed and selected. Surfaces of particular significance include, but are not limited to, solid surfaces which can be naturally-occurring such as bone; or porous particulate surfaces such as collagen or other biocompatible matrices; or the fabricated surfaces of prosthetic implants, including metals. As contemplated herein, virtually any surface can be assayed for differential binding of constructs. Thus, the present invention embraces a diversity of functional molecules having alterations in their surface-binding/surface-adherent properties, thereby rendering such constructs useful for altered in vivo applications, including slow-release, fast-release and/or timed-release formulations.

The skilled artisan will appreciate that mixing-and-matching any one or more the above-recited attributes provides specific opportunities to manipulate the uses of customized proteins (and DNAs encoding the same). For example, the attribute of altered stability can be exploited to manipulate the turnover of a protein in vivo. Moreover, in the case of proteins also having attributes such as altered re-folding and/or function, there is likely an interconnection between folding, function and stability. See, for example, Lipscomb et al., 7 *Protein Sci.* 765-73 (1998); and Nikolova et al., 95 *Proc. Natl. Acad. Sci. USA* 14675-80 (1998). For purposes of the present invention, stability alterations can be routinely monitored using well-known techniques of circular dichroism other indices of stability as a function of denaturant concentration or temperature. One can also use routine scanning calorimetry. Similarly, there is likely an interconnection between any of the foregoing attributes and the attribute of solubility. In the case of solubility, it is possible to manipulate this attribute so that a protein construct is either more or less soluble under physiologically-compatible conditions and it consequently diffuses readily or remains localized, respectively, when administered in vivo.

In addition to the aforementioned uses of protein constructs with altered attributes, those with altered stability can also be used to practical advantage for shelf-life, storage and/or shipping considerations. Furthermore, on a related matter, altered stability can also directly affect dosage considerations thereby, for example, reducing the cost of treatment.

A particularly significant class of constructs are those having altered binding to solubilized carriers or excipients. By way of non-limiting example, an altered BMP having enhanced binding to a solubilized carrier such as hyaluronic acid permits the skilled artisan to administer an injectable formulation at a defect site without loss or dilution of the BMP by either diffusion or body fluids. Thus localization is maximized. The skilled artisan will appreciate the variations made possible by the instant teachings. Similarly, another class of constructs having altered binding to body/tissue components can be exploited. By way of non-limiting example, an altered BMP having diminished binding to an in-situ inhibitor can be used to enhance repair of certain tissues in vivo. It is well known in the art, for example, that cartilage tissue is associated with certain proteins found in body fluids and/or within cartilage per se that can inhibit the activity of native BMPs. Chimeric constructs with altered binding properties, however, can overcome the effects of these in-situ inhibitors thereby enhancing repair, etc. The skilled artisan will appreciate the variations made possible by the instant teachings.

A. Truncation

There are different forms of OP-1, such as 23k, 17k, and variable amounts of 15k, whereby the typical OP-1 preparation contains all these species. N-terminal sequencing of purified mature OP-1 has revealed heterogeneity showing that the N-terminus can be more or less truncated. Through experiments with the species retrieved by elution from RP-HPLC and by trypsin cleavage, ROS activity is greatest among the 15k species. For example, truncated mutant H2469 has relatively high activity by comparison with the CHO-derived OP-1 standard. Whereas initial maturation occurs in pro-OP-1 at the RXXR site resulting in the 17k species, a secondary maturation by a different protease produces the most active 15k species. Trypsin cleavage can mimic this secondary activation.

Trypsin treatment of mammalian OP-1 or E-coli refolded OP-1 results in increased ROS activity. Removal of the N-terminus of the constructs described herein (e.g., hexa-his, collagen binding site, and BMP-2 N-terminus) also resulted in increased activity in a ROS assay. Truncation of OP-1 can increase solubility of the morphogen, which can affect ROS activity. Thus, constructs can be created having specific cleavage activity, that is, they are selective for the type of cleavage and the timing of the cleavage. One skilled in the art will appreciate that cleavage activity may differ based on the system used (mammalian or prokaryote). For example, a mammalian system may require that the morphogen construct include a pro region, which in the context of the construct, could disrupt folding and consequently will result (in the mammalian system), in complete intracellular degradation with no protein at the end. It may also be desirable to produce other constructs that include the pro-protein form. In such constructs, the pro-domain can be considered as another N-terminal element which can be cleaved to obtain increased activity. The skilled practitioner will appreciate that the uncleaved pro-protein can be utilized to take advantage of its attributes (relating to solubility and activity).

The mutant proteins of the present invention exhibit improved biological activity as well as extended half- life. Further, increased activity observed with the truncated proteins of the present invention may be due to elimination of basic residues and/or the lowering of the protein's isoelectric point. Biological activity and improved refolding can be enhanced when the modified proteins of the present invention are combined with the modifications described in copending applications, U.S. Ser. No. 09/374,958, filed on Aug. 16, 1999 and, U.S. Ser. No. 09/374,936, filed on Aug. 16, 1999, the disclosures of which are incorporated herein by reference.

B. N-terminal Regions with Specific Properties

Figure 7A:
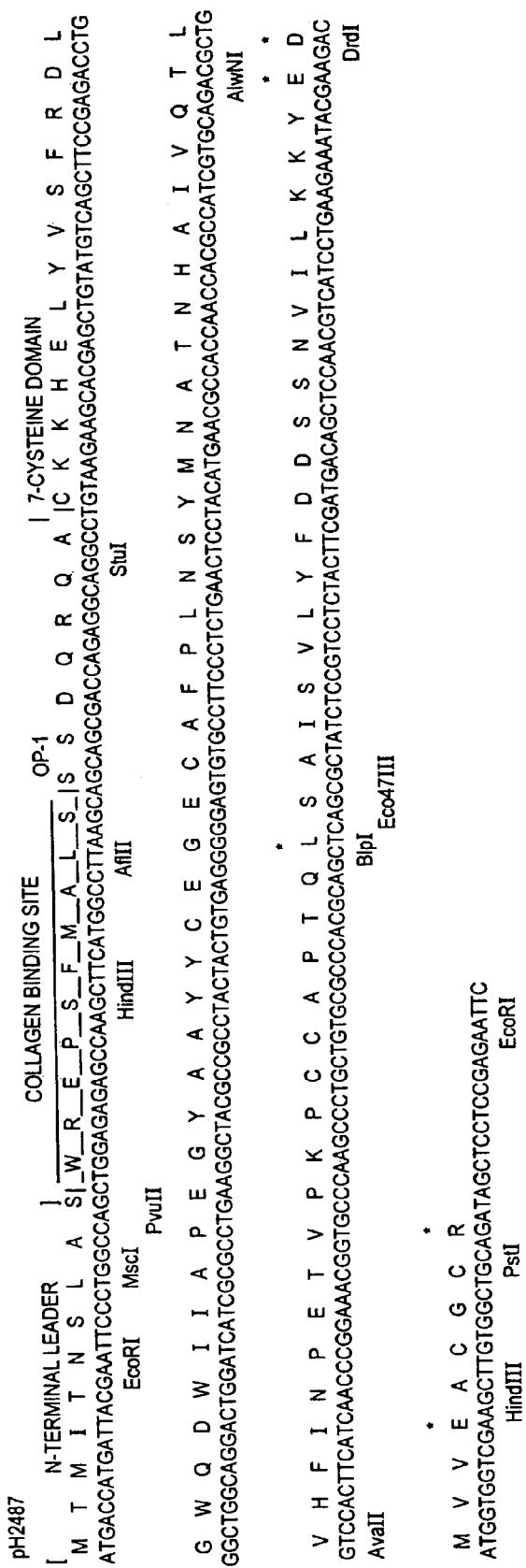
FIG. 7(A) shows the nucleotide (SEQ. ID NO: 90) and corresponding amino acid (SEQ. ID NO: 89) sequences of H2487, a modified OP-1 comprising N-terminal decapeptide collagen binding site inserted upstream of the seven-cysteine domain.
Figure 7B:
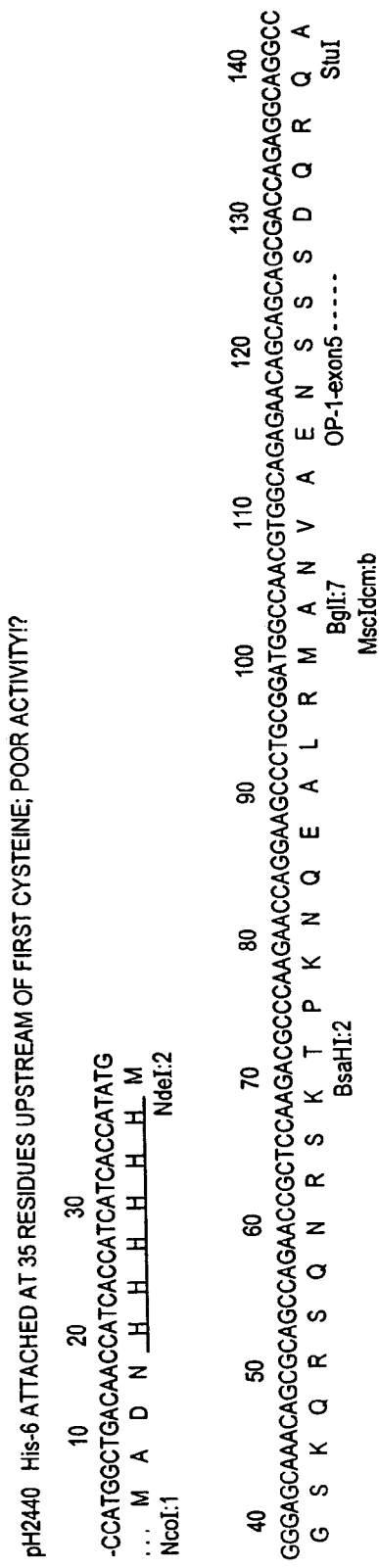
FIG. 7(B) shows the nucleotide (SEQ ID NO: 92) and corresponding amino acid (SEQ ID NO: 91) sequences of H2440, a modified OP-1 comprising a hexa-histidine domain attached 35 residues upstream of the first cysteine in the seven-cysteine domain.
Figure 7E:
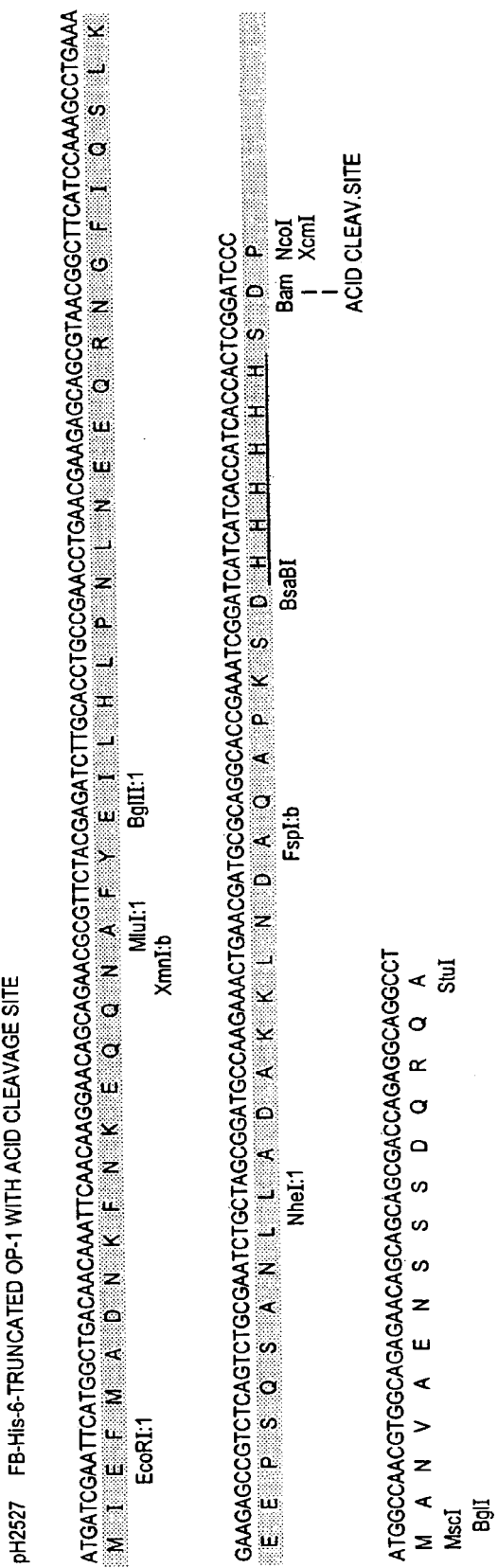
FIG. 7(E) shows the nucleotide (SEQ ID NO: 97) and amino acid (SEQ. ID NO: 98) sequences of H2527, a modified OP-1 comprising an FB leader domain, a hexa-histidine domain, and an ASP-PRO acid cleavage site.

Additional modified proteins of the invention comprise peptides of non-morphogen origin fused to the N-terminus of a morphogen 7-cysteine domain. See e.g., FIGS. 7A-7E. The resulting N-terminal fusion proteins have additional biological or biochemical properties not present in the unmodified morphogen from which the fusion is derived. Fusions of this type comprise a morphogen 7-cysteine domain fused at its N-terminus to a protein, or protein fragment, such as a collagen binding domain, an FB domain of protein A, or a hexa-histidine region. For example, H2440 is OP-1 with a hexa-his tag attached to its N-terminus as a binding domain for IMAC (immobilized metal affinity chromatography) resin. (FIG. 7B). This protein has been purified over copper IMAC resin, initially in its unfolded state, in the presence of urea. After the purification of the unfolded protein on IMAC, followed by refolding, the successfully refolded fraction is purified by RP-HPLC. Such N-terminal fusion proteins display little or no activity in a ROS assay, but are activated upon cleavage of the N-terminal non-morphogen peptide to yield an active C-terminal morphogen domain.

Particularly preferred are those engineered OP-1 constructs that can target specific sites. For example, an OP-1 with a N-terminal decapeptide collagen binding domain was constructed, H2487, in which the decapeptide was placed 7 residues upstream from the first cysteine (see FIG. 7A) to obtain specific and tight binding of OP-1 to bone matrix. This new construct was successfully refolded and active in the ROS assay, thereby indicating specific bone forming activity. Other binding domains can be used similarly to direct activity. For example, in the context of cartilage repair, OP-1 can also be engineered to specifically adhere to prosthetic devices. Other peptides, such as a peptide derived from *Clostridium* collagenase, can also be explored for collagen binding properties.

One of ordinary skill in the art will appreciate that the techniques of the present invention can be used to generate specific modified protein formulations that are capable of environmentally-triggered release of active protein at specific sites under particular conditions. For example, changes in pH or presence of a particular protease can modulate delivery and trigger release of active protein.

Modifications of the leader sequence of a BMP or other TGF-β family members can also affect solubility, activity, and expression of the protein. For example, construct H2528, which utilizes CDMP-3 (thought to be useful for tendon repair) engineered with a leader sequence as the FB subdomain of *staphylococcus aureus* protein A, has improved expression of the osteogenic protein.

The skilled artisan will appreciate that the constructs of the present invention can be engineered to contain a variety of specialized, functional domains that can be attached to the N-terminus of the TGF-β family protein, provided that steric interference and the consequent reduction in biological activity are taken into account. Such constructs may require at least a minimum spacing of the N-terminal addition from the 7-cysteine domain to avoid inhibition of activity or folding. The skilled artisan will appreciate that minimum spacing requirements will depend upon the steric properties of the added moiety and the ultimate intended activity of the modified construct, so that both the specialized domain and the TGF-β family protein will retain their intended activities.

C. Latent BMPs

The present invention also takes advantage of the surprising discovery of the extent to which the N-terminus can effect the solubility and activity of the fusion proteins, since truncations of the OP-1 N-terminus had no negative effects on the protein. In addition, the crystal structure of OP-1 had not revealed any topological information regarding the N-terminus.

The N-terminal fusion proteins described herein are useful for providing latent (i.e. inactive) forms of a protein that can be cleaved to produce an active protein at a desired time and location. For example, a modified morphogen containing a collagen binding domain (e.g. H2487, shown in FIG. 7A) can be delivered in an inactive form to a desired tissue locus (e.g. a locus containing an implanted collagen matrix) and cleaved at that locus to produce an active morphogen. Cleavage can result from conditions endogenous to the target locus (e.g., naturally-occurring proteases) or can be the result of administration of specific proteases or other factors (e.g., acidification of a locus). In addition, a very specific protease cleavage site may be engineered, e.g., for a protease found in a fracture site, allowing selective, delayed, and/or gradual activation of OP-1 at the site of implant.

D. Domain Swapping

Additional constructs to alter refolding, solubility, activity and expression can be designed by replacing the native leader sequence of one TGF-β superfamily protein with the native leader sequence of another TGF-β family member. For example, the construct H2549 has the N-terminus of BMP-2 transposed onto OP-1.

E. Heterodimers

Although some N-terminal fusion protein monomers as described above do not form active homodimers without cleavage of the leader sequence, active heterodimers are formed between those proteins and unmodified monomers of TGF-β family proteins. Accordingly, such heterodimers can be used to provide proteins to a target site by virtue of the N-terminal non-TGF-β family protein domain attached to the fusion protein, such as a collagen binding domain. Alternatively, design features can be used to enhance purification of heterodimers. Purification can be facilitated by accentuating purification differences between two kinds of subunits, for instance, by adding a hexa-histidine. A mixed refolding would provide a mixture of two homodimers and the heterodimer, which provides three separable species. For example, an N-terminal fusion protein containing a hexa-histidine domain (e.g. H2440, shown in FIG. 7B) which binds an IMAC column, is useful to aid in purification of the fusion protein, which can subsequently be activated by cleavage of the N-terminal domain.

*E.coli* expression for construction of heterodimers of the present invention is preferred, because the practitioner can adjust the ratio of each monomer for optimal yields of heterodimer. In addition, this method is very rapid. For example, in an in vitro heterodimer formation experiment between the hexa-histidine tagged OP-1, modified with the preferred modifications of charged amino acids, E, D, E, and R, (H2440) (U.S. Ser. No. 09/374,958, filed on Aug. 16, 1999, the entire disclosure of which is incorporated by reference herein) and BMP-2, the yield of heterodimers were excellent. There is an exceptionally high yield of heterodimer, more than the theoretically expected 50% heterodimer and 25% of each homodimer. This may occur because BMP-2 associates more readily with OP-1 than with itself, or faster than OP-1 reassociates with itself. Alternatively, the BMP-2 may act as chaperone for folding. Another experiment also showed heterodimer formation between BMP-2 and the H2447 mutant, OP-1 (no hexa-his tag), which also associated readily, generating good yields of heterodimer. Heterodimers were also made between FB-OP-1 (H2521) and BMP-2. Heterodimers of truncated OP-1, H2469 (retaining 15 residues upstream of the first cysteine), and BMP-5 (H2475); and H2469 and CDMP-2 (H2471) have also been constructed.

As well as being efficient in refolding, heterodimers of hexa-his-OP-1 (H2440) and BMP-2 (H2142) have much greater activity in a ROS assay than the homodimers. The hexa-his-OP-1 homodimer had very low activity. The homodimer of BMP-2 had better activity. However, OP-1/BMP-2 heterodimer was far more active than either parent homodimer. In this assay the heterodimer had only about 3-fold less activity than the CHO derived OP-1 standard. The heterodimer of OP-1 without the hexa-his tag, (H2447) with BMP-2 had similar activity. H2447 is a refolding mutant with modifications in finger-2 and had relatively lower activity as a homodimer. Heterodimers of OP-1 (H2469)/BMP-5 (H2475) and OP-1 (H2469)/CDMP-2 (H2471) provided a good result on a ROS assay (2.5-3+).

Using this same protocol and methodology, an OP-1/BMP-2 heterodimer was constructed, expressed in *E. coli*, and refolded in vitro. Specifically, H2447/BMP-2 heterodimers and H2440/BMP-2 heterodimers were created by *E. coli* expression and refolded in vitro under physiological conditions. Based on SDS-PAGE analysis, most of the material readily combined to form a heterodimeric species. Additional species are formed using heterodimers comprising a non-morphogen domain. Examples of such species are N-terminal fused to morphogens, such as collagen binding domain fused to OP-1 (H2487), hexa-histidine fused to OP-1 (H2440), and FB domain of Protein A fused to OP1 (H2521), and FB-domain fused to the hexa-histidine/OP-1 construct H2440 (H2525).

Active heterodimers can also be constructed from two BMPs or other TGF-β family proteins that were expressed in different systems. Some constructs are expressed better and are more active when expressed in certain systems over others. One can express each construct in the environment best suited for its expression and then form active heterodimers with them. For example, H2223, a mutant OP-1, is expressed in CHO cells, a mammalian expression system, while H2525 (FIG. 7D), FB-domain OP-1, is best expressed in *E. coli*, a bacterial expression system.

Further, the activity of the heterodimers can be manipulated by changing the two proteins used. For example, a heterodimer of H2487, OP-1 with a decapeptide collagen binding site, and CDMP3 can be formed. This heterodimer will have an activity different from a H2487 and BMP-2 heterodimer.

F. Choice and Optimization of Constructs

As taught herein, the present invention provides the skilled artisan with the know-how to craft customized chimeric proteins and DNAs encoding the same. Further taught and exemplified herein are the means to design chimeric proteins having certain desired attribute(s) making them suitable for specific in vivo applications (see at least Sections I.B., II., and III. Examples 1-4, 8 and 11 for exemplary embodiments of the foregoing chimeric proteins). For example, chimeric proteins having altered solubility attributes can be used in vivo to manipulate morphogenic effective amounts provided to a recipient. That is, increased solubility can result in increased availability; diminished solubility can result in decreased availability. Thus, such systemically administered chimeric proteins can be immediately available/have immediate morphogenic effects, whereas locally administered chimeric proteins can be available more slowly/have prolonged morphogenic effects. The skilled artisan will appreciate when increased versus diminished solubility attributes are preferred given the facts and circumstances at hand. Optimization of such parameters requires routine experimentation and ordinary skill.

Similarly, chimeric proteins having altered stability attributes can be used in vivo to manipulate morphogenic effective amounts provided to a recipient. That is, increased stability can result in increased half-life because turnover in vivo is less; diminished stability can result in decreased half-life and availability because turnover in vivo is more. Thus, such systemically administered chimeric proteins can either be immediately available/have immediate morphogenic effects achieving a bolus-type dosage or can be available in vivo for prolonged periods/have prolonged morphogenic effects achieving a sustained release type dosage. The skilled artisan will appreciate when increased versus diminished stability attributes are preferred given the facts and circumstances at hand. Optimization of such parameters requires routine experimentation and ordinary skill.

In addition, those protein constructs with altered stability can also be used to practical advantage for improving shelf-life, storage and/or shipping considerations. Furthermore, on a related matter, altered stability can also directly affect dosage considerations thereby, for example, reducing the cost of treatment.

Additionally, chimeric proteins having a combination of altered attributes, such as but not limited to solubility and stability attributes, can be used in vivo to manipulate morphogenic effective amounts provided to a recipient. That is, by designing a chimeric protein with a combination of specific altered attributes, morphogenic effective amounts can be administered in a timed-release fashion; dosages can be regulated both in terms of amount and duration; treatment regimens can be initiated at low doses systemically or locally followed by a transition to high doses, or vice versa; to name but a few paradigms. The skilled artisan will appreciate when low versus high morphogenic effective amounts are suitable under the facts and circumstances at hand. Optimization of such parameters requires routine experimentation and ordinary skill.

Furthermore, chimeric proteins having one or more altered attributes are useful to overcome inherent deficiencies in development. Chimeric proteins having one or more altered attributes can be designed to circumvent an inherent defect in a host's native morphogenic signaling system. As a non-limiting example, a chimeric protein of the present invention can be used to bypass a defect in a native receptor in a target tissue, a defect in an intracellular signaling pathway, and/or a defect in other events which are reliant on the attributes of a subdomain(s) associated with recognition of a moiety per se as opposed to the attributes associated with function/biological activity which are embodied in a different subdomain(s). The skilled artisan will appreciate when such chimeric proteins are suitable given the facts and circumstances at hand. Optimization requires routine experimentation and ordinary skill.

Practice of the invention will be still more fully understood from the following examples, which are presented herein for illustration only and should not be construed as limiting the invention in any way.

EXAMPLE 1

Synthesis of a BMP Mutant

FIG. 8 shows the nucleotide and corresponding amino acid sequence for the OP-1 C-terminal seven cysteine domain. Knowing these sequences permits identification of useful restriction sites for engineering in mutations by, for example, cassette mutagenesis or the well-known method of Kunkel (mutagenesis by primer extension using m13-derived single-stranded templates) or by the well-known PCR methods, including overlap extension. An exemplary mutant of OP-1 is H2460, with 4 amino acid changes in the finger 2 sub-domain and an amino acid change in the last C-terminal amino acid, constructed as described below. It is understood by the skilled artisan that the mutagenesis protocol described is exemplary only, and that other means for creating the constructs of the invention are well-known and well described in the art.

Four amino acid changes were introduced into the OP-1 finger 2 sub-domain sequence by means of standard polymerase chain reactions using overlap extension technique, resulting in OP-1 mutant H2460. The four changes in the finger 2 region were N6>S, R25>E, N26>D and R30>E. This mutant also contained a further change, H35>R, of the C-terminal residue. The template for these reactions was the mature domain of a wild type OP-1 cDNA clone, which had been inserted into an E. coli expression vector engineered with an ATG start codon at the beginning of the mature region. The ATG had been introduced by PCR using as a forward primer a synthetic oligonucleotide of the following sequence: ATG TCC ACG GGG AGC AAA CAG (SEQ ID NO: 36), encoding M S T G S K Q (SEQ ID NO: 37). The PCR reaction was done in combination with an appropriate back-primer complementary to the 3' coding region of the cDNA.

In order to construct the finger 2 mutant H2460, a PCR fragment encoding the modified finger-2 was made in a standard PCR reaction, using a commercially available PCR kit and following the manufacturer's instructions using as primers synthetic oligonucleotides.

To obtain the N6>S change, a forward primer (primer #1) of the sequence GCG CCC ACG CAG CTC AGC GCT ATC TCC GTC CTC (SEQ ID NO: 70) was used, encoding the amino acid sequence: A P T Q L S A I S V L (SEQ ID NO: 71).

For the changes near the C-terminus, a back-primer, 43 nucleotides long, (primer #2) was used which introduced the R25>E and N26>D and R30>E and C-terminal H35>R changes. This primer #2 had the sequence: CTA TCT GCA GCC ACA AGC TTC GAC CAC CAT GTC TTC GTA TTT C (SEQ ID NO: 72) which is the complement of the coding sequence, G AAA TAC GAA GAC ATG GTG GTC GAA GCT TGT GGC TGC AGA TAG (SEQ ID NO: 73) encoding the amino acids: K Y E D M V V E A C G C R stop (SEQ ID NO: 74).

The fragment with finger 2 and C-terminus mutations was then combined with another PCR fragment encoding the upstream part of mature OP-1, with N-terminus, finger-1 and heel sub-domains. The latter PCR fragment, encoding the N-terminus, finger 1 and heel sub-domains was constructed again using an OP-1 expression vector for E. coli as template. The vector contained an OP-1 cDNA fragment, encoding the mature OP-1 protein attached to a T7 promoter and ribosome binding site for expression under control of either a T7 promoter in an appropriate host or under control of a trp promoter. In this T7 expression vector, Pet 3d (Novagen Inc., Madison Wis.) the sequence between the T7 promoter, at the XbaI site, and the ATG codon of mature OP-1 is as follows: TCTAGAATAATTTTGTTTAACCTTTAA-GAAGGAGATATACGATG (SEQ ID NO: 75).

This second PCR reaction was primed with a forward primer (primer #3) TAA TAC GAC TCA CTA TAG G (SEQ ID NO: 76) which primes in the T7 promoter region and a back-primer (primer #4) that overlaps with primer #1 and has the nucleotide sequence GCT GAG CTG CGT GGG CGC (SEQ ID NO: 77), which is the complement of the coding sequence GCG CCC ACG CAG CTC AGC (SEQ ID NO: 78), encoding A P T Q L S (SEQ ID NO: 79).

In a third PCR reaction, the actual overlap extension reaction, portions of the above two PCR fragments were combined and amplified by PCR, resulting in a single fragment containing the complete mature OP-1 region. For this reaction, primer #3 was used as forward primer and a new primer (primer #5) was used as a back-primer with the following sequence GG ATC CTA TCT GCA GCC ACA AGC (SEQ ID NO: 80), which is the complement to coding sequence GCT TGT GGC TGC AGA TAG GAT CC (SEQ ID NO: 81), encoding A C G C R stop (SEQ ID NO: 82). This primer also adds a convenient 3' BamHI site for of inserting the gene into the expression vector.

The resulting fragment bearing the complete mutant gene, resulting from the overlap extension PCR, was cloned into a commercial cloning vector designed for cloning of PCR fragments, such as pCR2.1-topo-TA (Invitrogen Inc., Carlsbad Calif.). The cloned PCR fragment was recovered by restriction digest with XbaI and BamHI and inserted into the XbaI and BamHI sites of a commercially available T7 expression vector such as Pet3d (Novagen Inc., Madison Wis.).

EXAMPLE 2

E. coli Expression of a BMP

Transformed cells were grown in standard SPYE 2YT media, 1:1 ratio, (see, Sambrook et al., for example) at 37° C., under standard culturing conditions. Heterologous protein overexpression typically produced inclusion bodies within 8-48 hours. Inclusion bodies were isolated and solubilized as follows. One liter of culture fluid was centrifuged to collect the cells. The cells in the resulting pellet then were resuspended in 60 ml 25 mM Tris, 10 mM EDTA, pH 8.0 (TE Buffer)+100 µg/ml lysozyme and incubated at 37° C. for 2 hours. The cell suspension was then chilled on ice and sonicated to lyse the cells. Cell lysis was ascertained by microscopic examination. The volume of the lysate was adjusted to approximately 300 ml with TE Buffer, then centrifuged to obtain an inclusion body pellet. The pellet was washed by 2-4 successive resuspensions in TE Buffer and centrifugation. The washed inclusion body pellet was solubilized by denaturation and reduction in 40 ml 100 mM Tris, 10 mM EDTA, 6M GuHCl (guanidinium hydrochloride), 250 mM DTT, pH 8.8. Proteins then were pre-purified using a standard, commercially available C2 or C8 cartridge (SPICE cartridges, 400 mg, Ananitech, Inc.). Protein solutions were acidified with 2% TFA (trifluoroacetic acid), applied to the cartridge, washed with 0.1% TFA/10% acetonitrile, and eluted with 0.1% TFA/70% acetonitrile. The eluted material then was dried down or diluted and fractionated by C4 RP-HPLC.

EXAMPLE 3

Refolding of a BMP Dimer

Proteins prepared as described above were dried down prior to refolding, or diluted directly into refolding buffer. The preferred refolding buffer used was: 100 mM Tris, 10 mM EDTA, 1 M NaCl, 2% CHAPS, 5 mM GSH (reduced glutathione), 2.5 mM GSSG (oxidized glutathione), pH 8.5. Refoldings (12.5-200 µg protein/ml) were carried out at 4° C. for 24-90 hours, typically 36-48 hours, although longer than this (up to weeks) are expected to provide good refolding in some mutants, followed by dialysis against 0.1% TFA, then 0.01% TFA, 50% ethanol. Aliquots of the dialyzed material then was dried down in preparation for the various assays.

EXAMPLE 4

Purification and Testing of a Refolded BMP Dimer

4A. SDS-PAGE, HPLC—Samples were dried down and resuspended in Laemmli gel sample buffer and then electrophoresed in a 15% SDS-polyacrylamide gel. All assays included molecular weight standards and/or purified mammalian cell produced OP-1 for comparison. Analysis of OP-1 dimers was performed in the absence of added reducing agents, while OP-1 monomers were produced by the addition of 100 mM DTT to the gel samples. Folded dimer has an apparent molecular weight in the range of about 30-36 kDa, while monomeric species have an apparent molecular weight of about 14-16 kDa.

Alternatively, samples were chromatographed on a commercially available RP-HPLC, as follows. Samples were dried down and resuspended in 0.1% TFA/30% acetonitrile. The protein then was applied to a C18 column in 0.1% TFA, 30% acetonitrile and fractionated using a 30-60% acetonitrile gradient in TFA. Properly folded dimers elute as a discrete peak at 45-50% acetonitrile; monomers elute at 50-60% acetonitrile.

4B. Hydroxyapatite Chromatography—Samples were loaded onto hydroxyapatite in 10 mM phosphate, 6 M urea, pH 7.0 (Column Buffer). Unbound material was removed by washing with column buffer, followed by elution of monomer with Column Buffer+100 mM NaCl. Dimers were eluted with Column Buffer+250 mM NaCl.

4C. Trypsin Digest—Tryptic digests were performed in a digestion buffer of 50 mM Tris, 4 M urea, 100 mM NaCl, 0.3% Tween 80, 20 mM methylamine, pH 8.0. The ratio of enzyme to substrate was 1:50 (weight to weight). After incubation at 37° C. for 16 hours, 15 µl of digestion mixture was combined with 5 µl 4× gel sample buffer without DTT and analyzed by SDS-PAGE. Purified mammalian OP-1 and undigested BMP dimer were included for comparison. Under these conditions, properly folded dimers are cleaved to produce a species with slightly faster migration than uncleaved standards, while monomers and mis-folded dimers are completely digested and do not appear as bands in the stained gel.

EXAMPLE 5

In vitro Cell-Based Bioassay of Osteogenic Activity

This example demonstrates the bioactivity of morphogen constructs which have acquired osteogenic or bone-forming capabilities in accordance with the present invention. Osteogenic proteins having either an inuate ability or an acquired ability for high specific bone forming activity can induce alkaline phosphatase activity in rat osteoblasts, including rat osteosarcoma cells and rat calveria cells. In the assay rat osteosarcoma or calveria cells were plated onto a multi-well plate (e.g., a 48 well plate) at a concentration of 50,000 osteoblasts per well, in aMEM (modified Eagle's medium, Gibco, Inc. Long Island) containing 10% FBS (fetal bovine serum), L-glutamine and penicillin/streptomycin. The cells were incubated for 24 hours at 37° C., at which time the growth medium was replaced with α MEM containing 1% FBS and the cells incubated for an additional 24 hours so that cells were in serum-deprived growth medium at the time of the experiment.

Cultured cells then were divided into three groups: (1) wells receiving various concentrations of biosynthetic osteogenic protein; (2) a positive control, such as mammalian expressed hOP-1; and a negative control (no protein or TGF-β). The protein concentrations tested were in the range of 50-500 ng/ml. Cells were incubated for 72 hours. After the incubation period the cell layer was extracted with 0.5 ml of 1% TritonX-100. The resultant cell extract was centrifuged, 100 µl of the extract was added to 90 µl of PNPP (paranitrosophenylphosphate)/glycerine mixture and incubated for 30 minutes in a 37° C. water bath and the reaction stopped with 100 µl A 0.2N NaOH. The samples then were run through a plate reader (e.g., Dynatech MR700) and absorbance measured at 400 nm, using p-nitrophenol as a standard, to determine the presence and amount of alkaline phosphatase activity. Protein concentrations were determined by standard means, e.g., the Biorad method, UV scan or HPLC area at 214 nm. Alkaline phosphatase activity was calculated in units/µg protein, where 1 unit equals 1 nmol p-nitrophenol liberated/ 30 minutes at 37° C.

HOP-1 and BMP2 generate approximately 1.0-1.4 units at between 100-200 ng/ml. Other results are provided in Table 1 for the various protein constructs.

EXAMPLE 6

In Vitro Cell-Based Bioassay of CDMP Activity

This example demonstrates the bioactivity of constructs which have acquired enhanced tissue morphogenic capabilities in accordance with the present invention. Native CDMPs fail to induce alkaline phosphatase activity in rat osteosarcoma cells as used in Example 5, but they do induce alkaline phosphatase activity in the mouse teratocarcinoma cell line ATDC-5, a chondroprogenitor cell line (Atsumi, et al., 1990, *Cell Differentiation and Development* 30: 109). Folded mutants that are negative in the rat osteocarcinoma cell assay but positive in the ATDC-5 assay are described as having acquired CDMP-like activity. In the ATDC-5 assay, cells were plated at density of $4 \times 10^4$ in serum-free basal medium (BM: Ham's F-12/DMEM [1:1] with ITS™+culture supplement [Collaborative Biomedical Products, Bedford, Mass.], alpha-ketoglutarate ($1 \times 10^{-4}$ M), ceruloplasmin (0.25 U/ml), cholesterol (5 µg/ml), phosphatidylethanolamine (2 µg/ml), alpha-tocopherol acid succinate ($9 \times 10^{-7}$ M), reduced glutathione (10 µg/ml), taurine (1.25 µg/ml), triiodothyronin ($1.6 \times 10^{-9}$ M), parathyroid hormone ($5 \times 10^{-10}$M), β-glycerophosphate (10 mM), and L-ascorbic acid 2-sulphate (50 µg/ml)). CDMP or other biosynthetic osteogenic protein (0-300 ng/ml) was added the next day and the culture medium, including CDMP or biosynthetic osteogenic protein, replaced every other day. Alkaline phosphatase activity was determined in sonicated cell homogenates after 4, 6 and/ or 12 days of treatment. After extensive washing with PBS, cell layers were sonicated in 500 µl of PBS containing 0.05% Triton-X100. 50-100 µl aliquots were assayed for enzyme activity in assay buffer (0.1M sodium barbital buffer, pH 9.3) and p-nitrophenyl phosphate as substrate. Absorbance was measured at 400 nm, and activity normalized to protein content measured by Bradford protein assay (bovine serum albumin standard).

CDMP-1 and CDMP-2 generated approximately 2-3 units of activity at day 10 at 100 ng/ml. OP-1 generated approximately 6-7 units of activity at day 10 at 100 ng/ml.

EXAMPLE 7

In Vitro Cell-Based Bioassay of TGF-β-Like Activity

This example demonstrates the bioactivity of biosynthetic mutant TGF-β proteins having altered biological capabilities in accordance with the invention. TGF-β proteins can inhibit epithelial cell proliferation. Numerous cell inhibition assays are well described in the art. See, for example, Brown, et. al. (1987) *J. Immunol.* 139:2977, describing a colorimetric assay using human melanoma A375 fibroblast cells, and described herein below. Another assay uses epithelial cells, e.g., mink lung epithelial cells, and proliferative effects are determined by $^3$H-thymidine uptake.

Briefly, in the assay the TGF-β biosynthetic construct is serially diluted in a multi-well tissue plate containing RPMI-1640 medium (Gibco) and 5% fetal calf serum. Control wells receive medium only. Melanoma cells then are added to the well ($1.5 \times 10^4$). The plates then are incubated at 37° C. for about 72 hours in 5% $CO_2$, and the cell monolayers washed once, fixed and stained with crystalviolet for 15 minutes. Unbound stain is washed out and the stained cells then lysed with 33% acetic acid to release the stain (confined to the cell nuclei), and the OD measured at 590 nm with a standard, commercially available photometer to calculate the activity of the test molecules. The intensity of staining in each well is directly related to the number of nuclei. Accordingly, active TGF-β molecules are expected to stain lighter than inactive compounds or the negative control well.

In another assay, mink lung cells are used. These cells grow and proliferate under standard culturing conditions, but are arrested following exposure to TGF-β, as determined by $^3$H-thymidine uptake using culture cells from a mink lung epithelial cell line (ATTC No. CCL 64, Rockville, Md.). Briefly cells are grown to confluency in EMEM, supplemented with 10% FBS, 200 units/ml penicillin, and 200 µg/ml streptomycin. These cells are cultured to a cell density of about 200,000 cells per well. At confluency the media is replaced with 0.5 ml of EMEM containing 1% FBS and penicillin/streptomycin and the culture incubated for 24 hours at 37° C. Candidate proteins then are added to each well and the cells incubated for 18 hours at 37° C. After incubation, 1.0 µCi of $^3$H-thymidine in 10 µl was added to each well, and the cells incubated for four hours at 37° C. The media then is removed from each well and the cells washed once with ice-cold phosphate buffered saline and DNA precipitated by adding 0.5 ml of 10% TCA to each well and incubated at room temperature for 15 minutes. The cells are washed three times with ice-cold distilled water, lysed with 0.5 ml 0.4 M NaOH, and the lysate from each well then transferred to a scintillation vial and the radioactivity recorded using a scintillation counter (Smith-Kline Beckman). Biologically active molecules will inhibit cell proliferation resulting in less thymidine uptake and fewer counts as compared to inactive proteins and/or the negative control well (no added growth factor).

EXAMPLE 8

In Vivo Bioassay of Osteogenic Activity:
Endochondral Bone Formation and Related
Properties The art-recognized bioassay for bone induction as described by Sampath and Reddi (Proc. Natl. Acad. Sci. USA (1983) 80:6591-6595) and U.S. Pat. Nos. 4,968,590, 5,266, 683, the disclosures of which is herein incorporated by reference, can be used to establish the efficacy of a given protein, device or formulation. Briefly, the assay consists of depositing test samples in subcutaneous sites in recipient rats under ether anesthesia. A vertical incision (1 cm) is made under sterile conditions in the skin over the thoracic region, and a pocket is prepared by blunt dissection. In certain cases, the desired amount of osteogenic protein (10 ng-10 µg) is mixed with approximately 25 mg of matrix material, prepared using standard procedures such as lyophilization, and the test sample is implanted deep into the pocket and the incision is closed with a metallic skin clip. The heterotropic site allows for the study of bone induction without the possible ambiguities resulting from the use of orthotopic sites. The implants also can be provided intramuscularly which places the devices in closer contact with accessable progenitor cells. Typically intramuscular implants are made in the skeletal muscle of both legs.

The sequential cellular reactions occurring at the heterotropic site are complex. The multistep cascade of endochondral bone formation includes: binding of fibrin and fibronectin to implanted matrix, chemotaxis of cells, proliferation of fibroblasts, differentiation into chondroblasts, cartilage formation, vascular invasion, bone formation, remodeling, and bone marrow differentiation.

Successful implants exhibit a controlled progression through the stages of protein-induced endochondral bone development including: (1) transient infiltration by polymorphonuclear leukocytes on day one; (2) mesenchymal cell migration and proliferation on days two and three; (3) chondrocyte appearance on days five and six; (4) cartilage matrix formation on day seven; (5) cartilage calcification on day eight; (6) vascular invasion, appearance of osteoblasts, and formation of new bone on days nine and ten; (7) appearance of osteoblastic and bone remodeling on days twelve to eighteen; and (8) hematopoietic bone marrow differentiation in the ossicle on day twenty-one.

Histological sectioning and staining is preferred to determine the extent of osteogenesis in the implants. Staining with toluidine blue or hemotoxylin/eosin clearly demonstrates the ultimate development of endochondral bone. Twelve day bioassays are sufficient to determine whether bone inducing activity is associated with the test sample.

Additionally, alkaline phosphatase activity and/or total calcium content can be used as biochemical markers for osteogenesis. The alkaline phosphatase enzyme activity can be determined spectrophotometrically after homogenization of the excised test material. The activity peaks at 9-10 days in vivo and thereafter slowly declines. Samples showing no bone development by histology should have no alkaline phosphatase activity under these assay conditions. The assay is useful for quantitation and obtaining an estimate of bone formation very quickly after the test samples are removed from the rat. The results as measured by alkaline phosphatase activity level and histological evaluation can be represented as "bone forming units". One bone forming unit represents the amount of protein that is needed for half maximal bone forming activity on day 12. Additionally, dose curves can be constructed for bone inducing activity in vivo at each step of a purification scheme by assaying various concentrations of protein. Accordingly, the skilled artisan can construct representative dose curves using only routine experimentation.

Total calcium content can be determined after homogenization in, for example, cold 0.15M NaCl, 3 mM NaHCO$_3$, pH 9.0, and measuring the calcium content of the acid soluble fraction of sediment.

EXAMPLE 9

Activity of "Domain Swapping" Mutant

Domain swapping occurs, for example, when one takes the N-terminal region of one type of TGF-β family member protein and attaches it to the seven cysteine domain of another type of TGF-β family member protein. A mutant construct was created by splicing the sequence of the BMP-2 terminus onto the seven cysteine active domain of OP-1 using routine techniques generally known to those of ordinary skill in the art. The resulting mutant, H2549, has an N-terminal region consisting of MQAKHKQRKRLKSS-C. The last amino acid, cysteine, is the first cysteine of the seven cysteine active domain of OP-1. A ROS assay, as described above in Example 5, was used to test activity of H2549.

Figure 11:
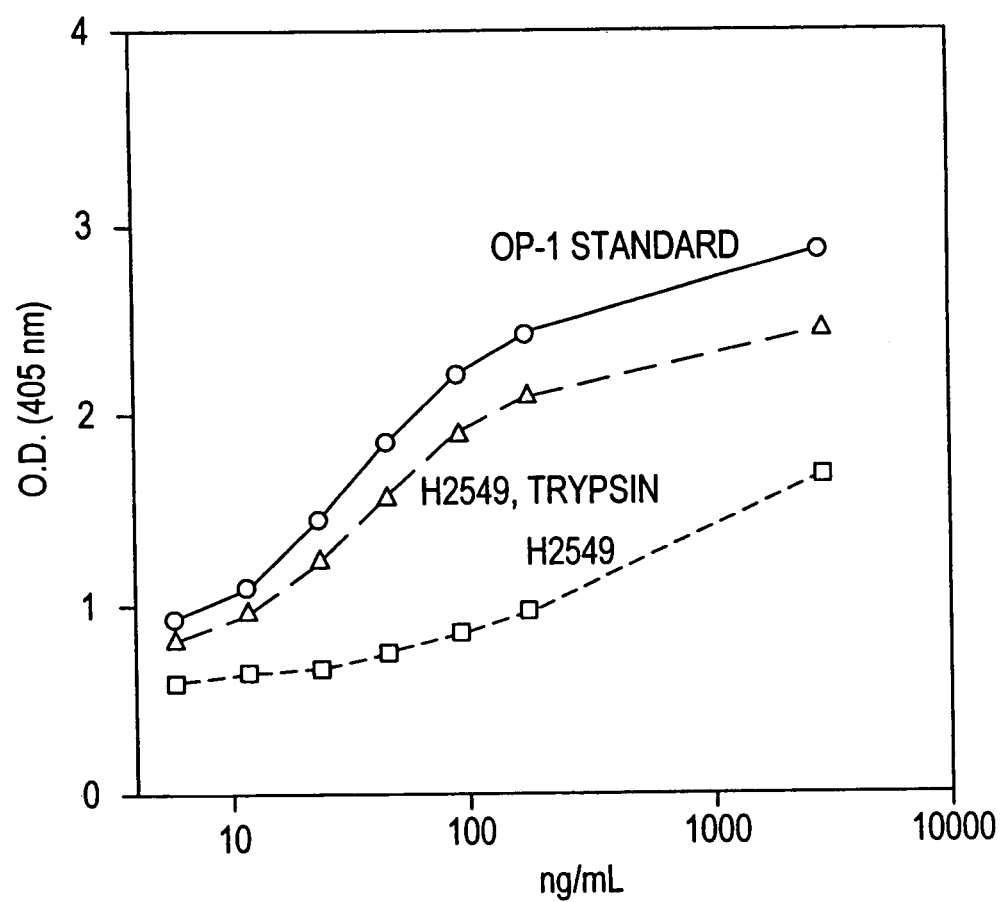
FIG. 11 is a graph of ROS activity for OP-1 (standard), the mutant H2549 protein and H2549 treated with trypsin, plotted as concentration (ng/mL) vs. optical density (at 405 nm).

As illustrated in FIG. 11, the results show that H2549 has very low activity as compared to the level of activity of OP-1. However, upon trypsin cleavage of H2549, using a method similar to trypsin cleavage of dimers described in Example 4, ROS activity is significantly increased. In this manner, the activity of TGF-β family member proteins can be selectively controlled by attaching non-native N-terminal sequences to inactivate it and cleaving the non-native sequences to activate it.

EXAMPLE 10

N-Terminal Truncations Increase Activity

Truncations at the N-terminal regions of modified morphogen proteins, for example by trypsin cleavage, increase ROS activity. Construct H2223 is a modified OP-1 mutant expressed in CHO cells. Two HPLC fractions of H2223 were collected, fractions 13 and 14. An amount of each fraction was truncated by trypsin cleavage, in a manner similar to that used upon dimers in Example 4. The four resulting samples, i.e., fractions 13 and 14 untreated with trypsin and fractions 13 and 14 treated with trypsin, were then subjected to a ROS assay, as described in Example 5 above, using OP-1 activity as the standard.

Figure 12:
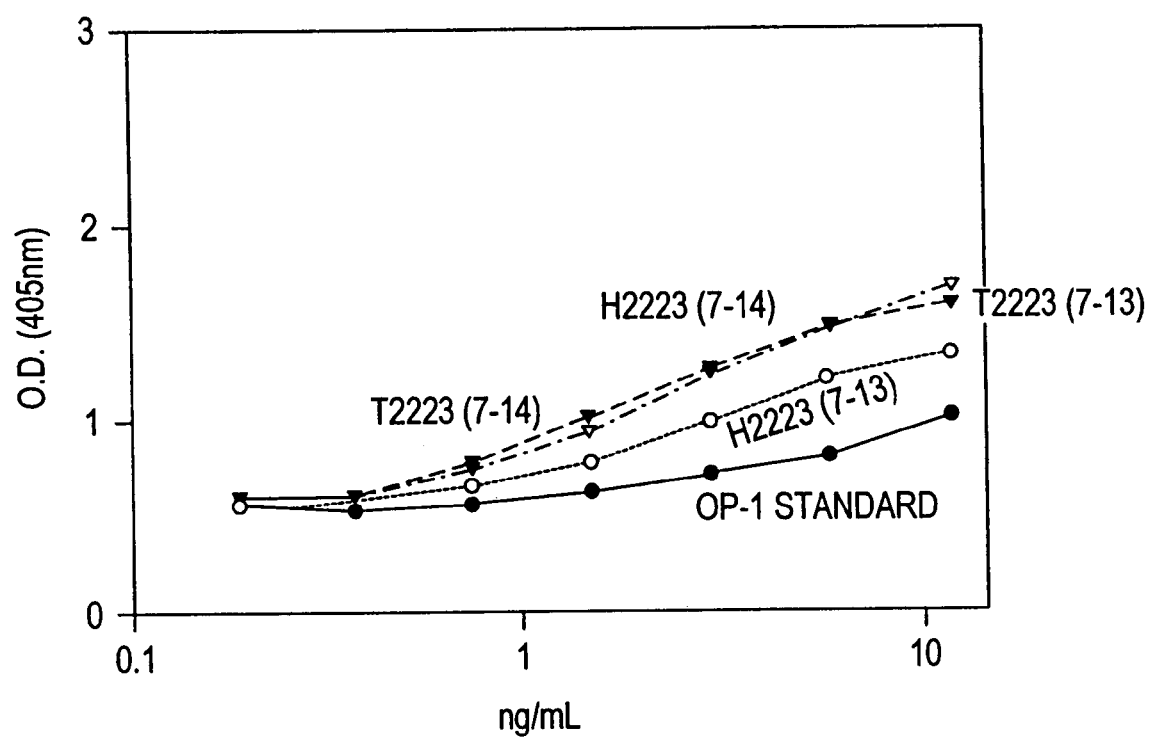
FIG. 12 is a graph of ROS activity for OP-1 (standard) and various fractions of the mutant H2223 protein and the trypsin truncated form of this protein, plotted as concentration (ng/mL) vs. optical density (at 405 nm).

As illustrated in FIG. 12, the activity level of fractions 14 treated and untreated with trypsin are relatively the same. This is explained by fraction 14 being composed of partially truncated H2223 and, thus, further truncation with trypsin does not alter activity. In contrast, untreated fraction 13 is composed of mainly full length H2223 (i.e., the entire N-terminus of 39 amino acids) and truncation of the N-terminus of fraction 13 does increase ROS activity to levels comparable to those of fraction 14. These activity levels are well above the ROS activity level of the OP-1 standard, and demonstrate that improvements in activity obtained with the modified proteins of the present invention.

EXAMPLE 11

Heterodimer Activity

Activity levels of heterodimers are higher than those of the homodimers formed from each of the respective subunits of the heterodimer. Construct H2440, OP-1 with a hexa-his N-terminus, and H2142, BMP-2, were allowed to form heterodimers and homodimers using the method as described in Example 3 above. Heterodimers of H2440/2142, and homodimers of H2440/2440 and H2142/2142 were then subjected to a ROS assay, as described in Examples 4 and 5 above.

Figure 13A:
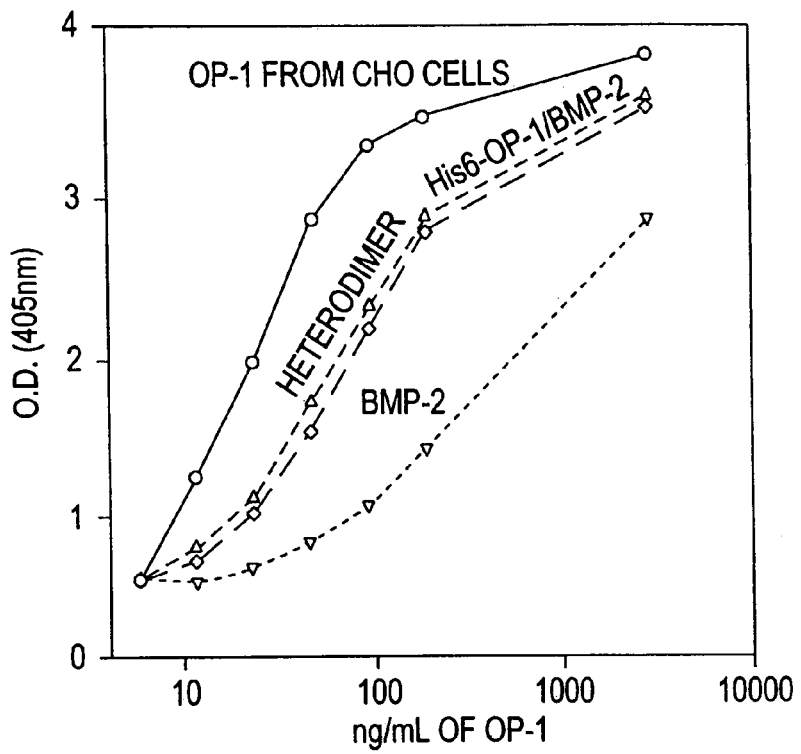
FIG. 13(A) is a graph of ROS activity for OP-1 homodimer (from CHO cells), BMP-2 homodimer and hexa-his OP-1 heterodimer, plotted as concentration (ng/mL) vs. optical density (405 nm).
Figure 13B:
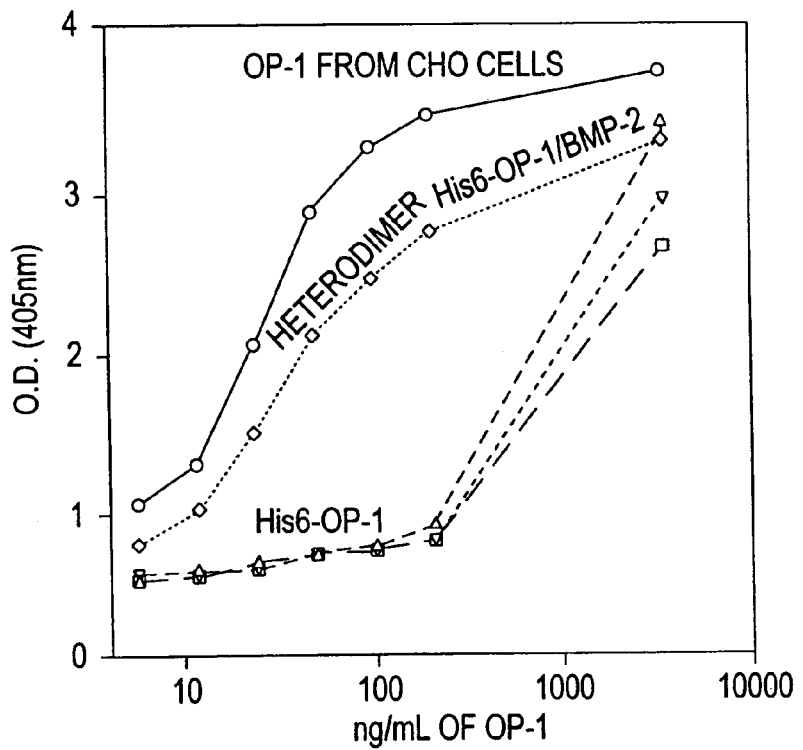
FIG. 13(B) is a graph of ROS activity for OP-1 homodimer (from CHO cells), hexa-his OP-1/BMP-2 heterodimer and hexa-his OP-1, plotted as concentration (ng/mL) vs. optical density (405 nm).

As shown in FIGS. 13A and 13B, the homodimers of H2440, OP-1 with a hexa-his at the N-terminal have very low activity. The homodimers of H2142, BMP-2, have better activity, but activity is still relatively low. However, the heterodimer, OP-1 hexa-his and BMP-2, have far greater activity than either of the homodimers. The heterodimers have only 3-fold less activity than the CHO derived OP-1.

Figure 14:
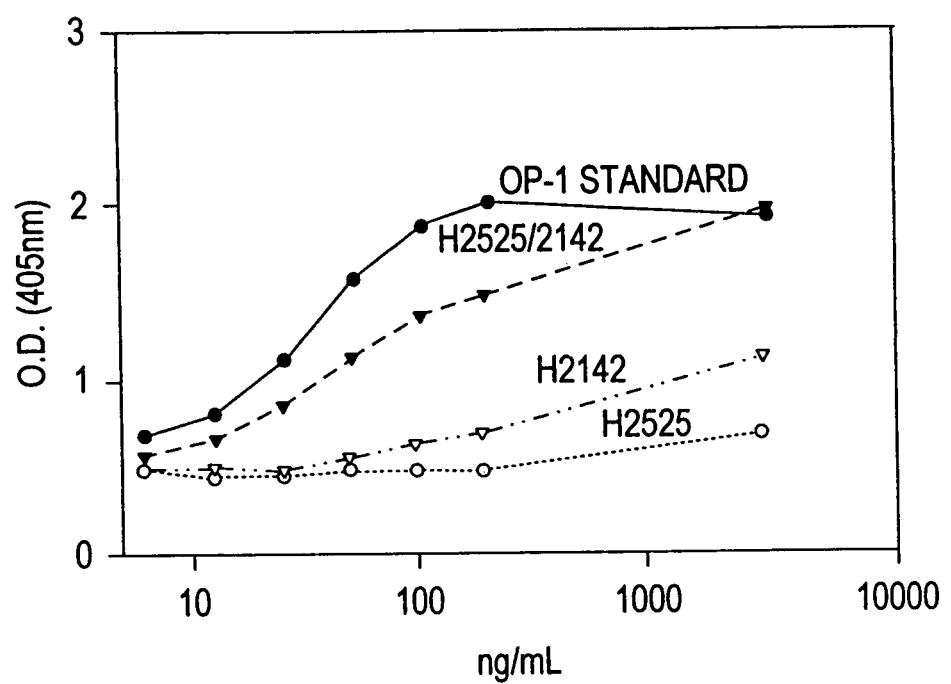
FIG. 14 is a graph of ROS activity for OP-1(standard), BMP-2mutant H2142 protein homodimer, mutant H2525 protein homodimer and H2525/2142 heterodimer, plotted as concentration (ng/mL) vs. optical density (405 nm).

In a similar experiment, homodimers and heterodimers were created between H2525, OP-1 with FB leader sequence, and H2142, BMP-2. These were also subjected to a ROS assay with the level of OP-1 activity as the standard. As illustrated in FIG. 14, homodimers of H2525, OP-1 with FB, have virtually no activity and homodimers of H2142, BMP-2, have very low activity. In contrast, heterodimers of the two, H2525/2142, have unexpectedly high activity levels.

SEQUENCE LISTING

```
<160> NUMBER OF SEQ ID NOS: 124

<210> SEQ ID NO 1
<211> LENGTH: 35
<212> TYPE: PRT
<213> ORGANISM: Drosophila melanogaster
<220> FEATURE:
<223> OTHER INFORMATION: 60-A
```

```
<400> SEQUENCE: 1

Ala Pro Thr Arg Leu Gly Ala Leu Pro Val Leu Tyr His Leu Asn Asp
1               5                   10                  15

Glu Asn Val Asn Leu Lys Lys Tyr Arg Asn Met Ile Val Lys Ser Cys
            20                  25                  30

Gly Cys His
        35

<210> SEQ ID NO 2
<211> LENGTH: 35
<212> TYPE: PRT
<213> ORGANISM: Homo sapiens
<220> FEATURE:
<223> OTHER INFORMATION: BMP-2

<400> SEQUENCE: 2

Val Pro Thr Glu Leu Ser Ala Ile Ser Met Leu Tyr Leu Asp Glu Asn
1               5                   10                  15

Glu Lys Val Val Leu Lys Asn Tyr Gln Asp Met Val Val Glu Gly Cys
            20                  25                  30

Gly Cys Arg
        35

<210> SEQ ID NO 3
<211> LENGTH: 35
<212> TYPE: PRT
<213> ORGANISM: Homo sapiens
<220> FEATURE:
<223> OTHER INFORMATION: BMP-3

<400> SEQUENCE: 3

Val Pro Glu Lys Met Ser Ser Leu Ser Ile Leu Phe Phe Asp Glu Asn
1               5                   10                  15

Lys Asn Val Val Leu Lys Val Tyr Pro Asn Met Thr Val Glu Ser Cys
            20                  25                  30

Ala Cys Arg
        35

<210> SEQ ID NO 4
<211> LENGTH: 35
<212> TYPE: PRT
<213> ORGANISM: Homo sapiens
<220> FEATURE:
<223> OTHER INFORMATION: BMP-4

<400> SEQUENCE: 4

Val Pro Thr Glu Leu Ser Ala Ile Ser Met Leu Tyr Leu Asp Glu Tyr
1               5                   10                  15

Asp Lys Val Val Leu Lys Asn Tyr Gln Glu Met Val Val Glu Gly Cys
            20                  25                  30

Gly Cys Arg
        35

<210> SEQ ID NO 5
<211> LENGTH: 35
<212> TYPE: PRT
<213> ORGANISM: Homo sapiens
<220> FEATURE:
<223> OTHER INFORMATION: BMP-5

<400> SEQUENCE: 5

Ala Pro Thr Lys Leu Asn Ala Ile Ser Val Leu Tyr Phe Asp Asp Ser
```

```
                 1               5                  10                 15
Ser Asn Val Ile Leu Lys Lys Tyr Arg Asn Met Val Val Arg Ser Cys
                20                 25                 30

Gly Cys His
        35

<210> SEQ ID NO 6
<211> LENGTH: 35
<212> TYPE: PRT
<213> ORGANISM: Homo sapiens
<220> FEATURE:
<223> OTHER INFORMATION: BMP-6

<400> SEQUENCE: 6

Ala Pro Thr Lys Leu Asn Ala Ile Ser Val Leu Tyr Phe Asp Asp Asn
1               5                  10                 15

Ser Asn Val Ile Leu Lys Lys Tyr Arg Asn Met Val Val Arg Ala Cys
                20                 25                 30

Gly Cys His
        35

<210> SEQ ID NO 7
<211> LENGTH: 36
<212> TYPE: PRT
<213> ORGANISM: Homo sapiens
<220> FEATURE:
<223> OTHER INFORMATION: BMP-9

<400> SEQUENCE: 7

Val Pro Thr Lys Leu Ser Pro Ile Ser Val Leu Tyr Lys Asp Asp Met
1               5                  10                 15

Gly Val Pro Thr Leu Lys Tyr His Tyr Glu Gly Met Ser Val Ala Glu
                20                 25                 30

Cys Gly Cys Arg
        35

<210> SEQ ID NO 8
<211> LENGTH: 35
<212> TYPE: PRT
<213> ORGANISM: Homo sapiens
<220> FEATURE:
<223> OTHER INFORMATION: BMP-10

<400> SEQUENCE: 8

Val Pro Thr Lys Leu Glu Pro Ile Ser Ile Leu Tyr Leu Asp Lys Gly
1               5                  10                 15

Val Val Thr Tyr Lys Phe Lys Tyr Glu Gly Met Ala Val Ser Glu Cys
                20                 25                 30

Gly Cys Arg
        35

<210> SEQ ID NO 9
<211> LENGTH: 35
<212> TYPE: PRT
<213> ORGANISM: Homo sapiens
<220> FEATURE:
<223> OTHER INFORMATION: BMP-11

<400> SEQUENCE: 9

Thr Pro Thr Lys Met Ser Pro Ile Asn Met Leu Tyr Phe Asn Asp Lys
1               5                  10                 15

Gln Gln Ile Ile Tyr Gly Lys Ile Pro Gly Met Val Val Asp Arg Cys
                20                 25                 30
```

```
Gly Cys Ser
        35

<210> SEQ ID NO 10
<211> LENGTH: 35
<212> TYPE: PRT
<213> ORGANISM: Bos taurus
<220> FEATURE:
<223> OTHER INFORMATION: CDMP-2

<400> SEQUENCE: 10

Val Pro Thr Lys Leu Thr Pro Ile Ser Ile Leu Tyr Ile Asp Ala Gly
1               5                   10                  15

Asn Asn Val Val Tyr Asn Glu Tyr Glu Glu Met Val Val Glu Ser Cys
            20                  25                  30

Gly Cys Arg
        35

<210> SEQ ID NO 11
<211> LENGTH: 36
<212> TYPE: PRT
<213> ORGANISM: Gallus gallus
<220> FEATURE:
<223> OTHER INFORMATION: Dorsalin

<400> SEQUENCE: 11

Val Pro Thr Lys Leu Asp Ala Ile Ser Ile Leu Tyr Lys Asp Asp Ala
1               5                   10                  15

Gly Val Pro Thr Leu Ile Tyr Asn Tyr Glu Gly Met Lys Val Ala Glu
            20                  25                  30

Cys Gly Cys Arg
        35

<210> SEQ ID NO 12
<211> LENGTH: 35
<212> TYPE: PRT
<213> ORGANISM: Drosophila melanogaster
<220> FEATURE:
<223> OTHER INFORMATION: DPP

<400> SEQUENCE: 12

Val Pro Thr Gln Leu Asp Ser Val Ala Met Leu Tyr Leu Asn Asp Gln
1               5                   10                  15

Ser Thr Val Val Leu Lys Asn Tyr Gln Glu Met Thr Val Val Gly Cys
            20                  25                  30

Gly Cys Arg
        35

<210> SEQ ID NO 13
<211> LENGTH: 35
<212> TYPE: PRT
<213> ORGANISM: Mus musculus
<220> FEATURE:
<223> OTHER INFORMATION: GDF-1

<400> SEQUENCE: 13

Val Pro Glu Arg Leu Ser Pro Ile Ser Val Leu Phe Phe Asp Asn Glu
1               5                   10                  15

Asp Asn Val Val Leu Arg His Tyr Glu Asp Met Val Val Asp Glu Cys
            20                  25                  30

Gly Cys Arg
        35
```

```
<210> SEQ ID NO 14
<211> LENGTH: 35
<212> TYPE: PRT
<213> ORGANISM: Mus musculus
<220> FEATURE:
<223> OTHER INFORMATION: GDF-3

<400> SEQUENCE: 14

Val Pro Thr Lys Leu Ser Pro Ile Ser Met Leu Tyr Gln Asp Ser Asp
1               5                   10                  15

Lys Asn Val Ile Leu Arg His Tyr Glu Asp Met Val Val Asp Glu Cys
            20                  25                  30

Gly Cys Gly
        35

<210> SEQ ID NO 15
<211> LENGTH: 35
<212> TYPE: PRT
<213> ORGANISM: Homo sapiens
<220> FEATURE:
<223> OTHER INFORMATION: GDF-5

<400> SEQUENCE: 15

Val Pro Thr Arg Leu Ser Pro Ile Ser Ile Leu Phe Ile Asp Ser Ala
1               5                   10                  15

Asn Asn Val Val Tyr Lys Gln Tyr Glu Asp Met Val Val Glu Ser Cys
            20                  25                  30

Gly Cys Arg
        35

<210> SEQ ID NO 16
<211> LENGTH: 35
<212> TYPE: PRT
<213> ORGANISM: Mus musculus
<220> FEATURE:
<223> OTHER INFORMATION: GDF-6

<400> SEQUENCE: 16

Val Pro Thr Lys Leu Thr Pro Ile Ser Ile Leu Tyr Ile Asp Ala Gly
1               5                   10                  15

Asn Asn Val Val Tyr Lys Gln Tyr Glu Asp Met Val Val Glu Ser Cys
            20                  25                  30

Gly Cys Arg
        35

<210> SEQ ID NO 17
<211> LENGTH: 35
<212> TYPE: PRT
<213> ORGANISM: Mus musculus
<220> FEATURE:
<223> OTHER INFORMATION: GDF-7

<400> SEQUENCE: 17

Val Pro Ala Arg Leu Ser Pro Ile Ser Ile Leu Tyr Ile Asp Ala Ala
1               5                   10                  15

Asn Asn Val Val Tyr Lys Gln Tyr Glu Asp Met Val Val Glu Ala Cys
            20                  25                  30

Gly Cys Arg
        35

<210> SEQ ID NO 18
<211> LENGTH: 35
<212> TYPE: PRT
```

```
<213> ORGANISM: Mus musculus
<220> FEATURE:
<223> OTHER INFORMATION: GDF-9

<400> SEQUENCE: 18

Val Pro Gly Lys Tyr Ser Pro Leu Ser Val Leu Thr Ile Glu Pro Asp
1               5                   10                  15

Gly Ser Ile Ala Tyr Lys Glu Tyr Glu Asp Met Ile Ala Thr Arg Cys
                20                  25                  30

Thr Cys Arg
        35

<210> SEQ ID NO 19
<211> LENGTH: 32
<212> TYPE: PRT
<213> ORGANISM: Homo sapiens
<220> FEATURE:
<223> OTHER INFORMATION: GDNF

<400> SEQUENCE: 19

Arg Pro Ile Ala Phe Asp Asp Leu Ser Phe Leu Asp Asp Asn Leu
1               5                   10                  15

Val Tyr His Ile Leu Arg Lys His Ser Ala Lys Arg Cys Gly Cys Ile
                20                  25                  30

<210> SEQ ID NO 20
<211> LENGTH: 38
<212> TYPE: PRT
<213> ORGANISM: Homo sapiens
<220> FEATURE:
<223> OTHER INFORMATION: Inhibin Alpha

<400> SEQUENCE: 20

Ala Ala Leu Pro Gly Thr Met Arg Pro Leu His Val Arg Thr Thr Ser
1               5                   10                  15

Asp Gly Gly Tyr Ser Phe Lys Tyr Glu Thr Val Pro Asn Leu Leu Thr
                20                  25                  30

Gln His Cys Ala Cys Ile
        35

<210> SEQ ID NO 21
<211> LENGTH: 35
<212> TYPE: PRT
<213> ORGANISM: Homo sapiens
<220> FEATURE:
<223> OTHER INFORMATION: Inhibin BetaA

<400> SEQUENCE: 21

Val Pro Thr Lys Leu Arg Pro Met Ser Met Leu Tyr Tyr Asp Asp Gly
1               5                   10                  15

Gln Asn Ile Ile Lys Lys Asp Ile Gln Asn Met Ile Val Glu Glu Cys
                20                  25                  30

Gly Cys Ser
        35

<210> SEQ ID NO 22
<211> LENGTH: 35
<212> TYPE: PRT
<213> ORGANISM: Homo sapiens
<220> FEATURE:
<223> OTHER INFORMATION: Inhibin BetaB

<400> SEQUENCE: 22

Ile Pro Thr Lys Leu Ser Thr Met Ser Met Leu Tyr Phe Asp Asp Glu
```

```
                 1               5                  10                 15
Tyr Asn Ile Val Lys Arg Asp Val Pro Asn Met Ile Val Glu Glu Cys
                20                 25                 30

Gly Cys Ala
        35

<210> SEQ ID NO 23
<211> LENGTH: 35
<212> TYPE: PRT
<213> ORGANISM: Homo sapiens
<220> FEATURE:
<223> OTHER INFORMATION: Inhibin BetaC

<400> SEQUENCE: 23

Val Pro Thr Ala Arg Arg Pro Leu Ser Leu Leu Tyr Tyr Asp Arg Asp
1               5                  10                 15

Ser Asn Ile Val Lys Thr Asp Ile Pro Asp Met Val Val Glu Ala Cys
                20                 25                 30

Gly Cys Ser
        35

<210> SEQ ID NO 24
<211> LENGTH: 34
<212> TYPE: PRT
<213> ORGANISM: Homo sapiens
<220> FEATURE:
<223> OTHER INFORMATION: MIS

<400> SEQUENCE: 24

Val Pro Thr Ala Tyr Ala Gly Lys Leu Leu Ile Ser Leu Ser Glu Glu
1               5                  10                 15

Arg Ile Ser Ala His His Val Pro Asn Met Val Ala Thr Glu Cys Gly
                20                 25                 30

Cys Arg

<210> SEQ ID NO 25
<211> LENGTH: 34
<212> TYPE: PRT
<213> ORGANISM: Mus musculus
<220> FEATURE:
<223> OTHER INFORMATION: Nodal

<400> SEQUENCE: 25

Ala Pro Val Lys Thr Lys Pro Leu Ser Met Leu Tyr Val Asp Asn Gly
1               5                  10                 15

Arg Val Leu Leu Glu His His Lys Asp Met Ile Val Glu Glu Cys Gly
                20                 25                 30

Cys Leu

<210> SEQ ID NO 26
<211> LENGTH: 35
<212> TYPE: PRT
<213> ORGANISM: Homo sapiens
<220> FEATURE:
<223> OTHER INFORMATION: OP-2

<400> SEQUENCE: 26

Ala Pro Thr Lys Leu Ser Ala Thr Ser Val Leu Tyr Tyr Asp Ser Ser
1               5                  10                 15

Asn Asn Val Ile Leu Arg Lys His Arg Asn Met Val Val Lys Ala Cys
                20                 25                 30

Gly Cys His
```

-continued

```
<210> SEQ ID NO 27
<211> LENGTH: 35
<212> TYPE: PRT
<213> ORGANISM: Mus musculus
<220> FEATURE:
<223> OTHER INFORMATION: OP-3

<400> SEQUENCE: 27

Val Pro Thr Glu Leu Ser Ala Ile Ser Leu Leu Tyr Tyr Asp Arg Asn
1               5                   10                  15

Asn Asn Val Ile Leu Arg Arg Glu Arg Asn Met Val Val Gln Ala Cys
            20                  25                  30

Gly Cys His
        35

<210> SEQ ID NO 28
<211> LENGTH: 35
<212> TYPE: PRT
<213> ORGANISM: Drosophila melanogaster
<220> FEATURE:
<223> OTHER INFORMATION: Screw

<400> SEQUENCE: 28

Val Pro Thr Val Leu Gly Ala Ile Thr Ile Leu Arg Tyr Leu Asn Glu
1               5                   10                  15

Asp Ile Ile Asp Leu Thr Lys Tyr Gln Lys Ala Val Ala Lys Glu Cys
            20                  25                  30

Gly Cys His
        35

<210> SEQ ID NO 29
<211> LENGTH: 34
<212> TYPE: PRT
<213> ORGANISM: Homo sapiens
<220> FEATURE:
<223> OTHER INFORMATION: TGF-Beta1

<400> SEQUENCE: 29

Val Pro Gln Ala Leu Glu Pro Leu Pro Ile Val Tyr Tyr Val Gly Arg
1               5                   10                  15

Lys Pro Lys Val Glu Gln Leu Ser Asn Met Ile Val Arg Ser Cys Lys
            20                  25                  30

Cys Ser

<210> SEQ ID NO 30
<211> LENGTH: 34
<212> TYPE: PRT
<213> ORGANISM: Homo sapiens
<220> FEATURE:
<223> OTHER INFORMATION: TGF-Beta2

<400> SEQUENCE: 30

Val Ser Gln Asp Leu Glu Pro Leu Thr Ile Leu Tyr Tyr Ile Gly Lys
1               5                   10                  15

Thr Pro Lys Ile Glu Gln Leu Ser Asn Met Ile Val Lys Ser Cys Lys
            20                  25                  30

Cys Ser

<210> SEQ ID NO 31
<211> LENGTH: 34
<212> TYPE: PRT
```

```
<213> ORGANISM: Homo sapiens
<220> FEATURE:
<223> OTHER INFORMATION: TGF-Beta3

<400> SEQUENCE: 31

Val Pro Gln Asp Leu Glu Pro Leu Thr Ile Leu Tyr Tyr Val Gly Arg
1               5                   10                  15

Thr Pro Lys Val Glu Gln Leu Ser Asn Met Val Val Lys Ser Cys Lys
            20                  25                  30

Cys Ser

<210> SEQ ID NO 32
<211> LENGTH: 34
<212> TYPE: PRT
<213> ORGANISM: Gallus gallus
<220> FEATURE:
<223> OTHER INFORMATION: TGF-Beta4

<400> SEQUENCE: 32

Val Pro Gln Thr Leu Asp Pro Leu Pro Ile Ile Tyr Tyr Val Gly Arg
1               5                   10                  15

Asn Val Arg Val Glu Gln Leu Ser Asn Met Val Val Arg Ala Cys Lys
            20                  25                  30

Cys Ser

<210> SEQ ID NO 33
<211> LENGTH: 34
<212> TYPE: PRT
<213> ORGANISM: Xenopus laevis
<220> FEATURE:
<223> OTHER INFORMATION: TGF-Beta5

<400> SEQUENCE: 33

Val Pro Asp Val Leu Glu Pro Leu Pro Ile Ile Tyr Tyr Val Gly Arg
1               5                   10                  15

Thr Ala Lys Val Glu Gln Leu Ser Asn Met Val Val Arg Ser Cys Asn
            20                  25                  30

Cys Ser

<210> SEQ ID NO 34
<211> LENGTH: 35
<212> TYPE: PRT
<213> ORGANISM: Strongylocentrotus purpuratus
<220> FEATURE:
<223> OTHER INFORMATION: UNIVIN

<400> SEQUENCE: 34

Ala Pro Thr Lys Leu Ser Gly Ile Ser Met Leu Tyr Phe Asp Asn Asn
1               5                   10                  15

Glu Asn Val Val Leu Arg Gln Tyr Glu Asp Met Val Val Glu Ala Cys
            20                  25                  30

Gly Cys Arg
        35

<210> SEQ ID NO 35
<211> LENGTH: 35
<212> TYPE: PRT
<213> ORGANISM: Xenopus laevis
<220> FEATURE:
<223> OTHER INFORMATION: VG-1

<400> SEQUENCE: 35

Val Pro Thr Lys Met Ser Pro Ile Ser Met Leu Phe Tyr Asp Asn Asn
```

```
                1               5                  10                  15
Asp Asn Val Val Leu Arg His Tyr Glu Asn Met Ala Val Asp Glu Cys
            20                  25                  30

Gly Cys Arg
        35

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence:synthetic
      primer
<220> FEATURE:
<221> NAME/KEY: CDS
<222> LOCATION: (1)..(21)

<400> SEQUENCE: 36 atg tcc acg ggg agc aaa cag                                             21
Met Ser Thr Gly Ser Lys Gln
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: amino acids
      encoded by synthetic primer

<400> SEQUENCE: 37

Met Ser Thr Gly Ser Lys Gln
1               5

<210> SEQ ID NO 38
<211> LENGTH: 1822
<212> TYPE: DNA
<213> ORGANISM: Homo sapiens
<220> FEATURE:
<221> NAME/KEY: CDS
<222> LOCATION: (49)..(1341)
<223> OTHER INFORMATION: Morphogenic Protein OP1

<400> SEQUENCE: 38
ggtgcgggcc cggagcccgg agcccgggta gcgcgtagag ccggcgcg atg cac gtg       57
                                                    Met His Val
                                                    1 cgc tca ctg cga gct gcg gcg ccg cac agc ttc gtg gcg ctc tgg gca       105
Arg Ser Leu Arg Ala Ala Ala Pro His Ser Phe Val Ala Leu Trp Ala
    5                   10                  15 ccc ctg ttc ctg ctg cgc tcc gcc ctg gcc gac ttc agc ctg gac aac       153
Pro Leu Phe Leu Leu Arg Ser Ala Leu Ala Asp Phe Ser Leu Asp Asn
20                  25                  30                  35 gag gtg cac tcg agc ttc atc cac cgg cgc ctc cgc agc cag gag cgg       201
Glu Val His Ser Ser Phe Ile His Arg Arg Leu Arg Ser Gln Glu Arg
                40                  45                  50 cgg gag atg cag cgc gag atc ctc tcc att ttg ggc ttg ccc cac cgc       249
Arg Glu Met Gln Arg Glu Ile Leu Ser Ile Leu Gly Leu Pro His Arg
            55                  60                  65 ccg cgc ccg cac ctc cag ggc aag cac aac tcg gca ccc atg ttc atg       297
Pro Arg Pro His Leu Gln Gly Lys His Asn Ser Ala Pro Met Phe Met
        70                  75                  80 ctg gac ctg tac aac gcc atg gcg gtg gag gag ggc ggc ggg ccc ggc       345
Leu Asp Leu Tyr Asn Ala Met Ala Val Glu Glu Gly Gly Gly Pro Gly
    85                  90                  95
```

```
ggc cag ggc ttc tcc tac ccc tac aag gcc gtc ttc agt acc cag ggc      393
Gly Gln Gly Phe Ser Tyr Pro Tyr Lys Ala Val Phe Ser Thr Gln Gly
100                 105                 110                 115 ccc cct ctg gcc agc ctg caa gat agc cat ttc ctc acc gac gcc gac      441
Pro Pro Leu Ala Ser Leu Gln Asp Ser His Phe Leu Thr Asp Ala Asp
            120                 125                 130 atg gtc atg agc ttc gtc aac ctc gtg gaa cat gac aag gaa ttc ttc      489
Met Val Met Ser Phe Val Asn Leu Val Glu His Asp Lys Glu Phe Phe
                135                 140                 145 cac cca cgc tac cac cat cga gag ttc cgg ttt gat ctt tcc aag atc      537
His Pro Arg Tyr His His Arg Glu Phe Arg Phe Asp Leu Ser Lys Ile
        150                 155                 160 cca gaa ggg gaa gct gtc acg gca gcc gaa ttc cgg atc tac aag gac      585
Pro Glu Gly Glu Ala Val Thr Ala Ala Glu Phe Arg Ile Tyr Lys Asp
    165                 170                 175 tac atc cgg gaa cgc ttc gac aat gag acg ttc cgg atc agc gtt tat      633
Tyr Ile Arg Glu Arg Phe Asp Asn Glu Thr Phe Arg Ile Ser Val Tyr
180                 185                 190                 195 cag gtg ctc cag gag cac ttg ggc agg gaa tcg gat ctc ttc ctg ctc      681
Gln Val Leu Gln Glu His Leu Gly Arg Glu Ser Asp Leu Phe Leu Leu
                200                 205                 210 gac agc cgt acc ctc tgg gcc tcg gag gag ggc tgg ctg gtg ttt gac      729
Asp Ser Arg Thr Leu Trp Ala Ser Glu Glu Gly Trp Leu Val Phe Asp
            215                 220                 225 atc aca gcc acc agc aac cac tgg gtg gtc aat ccg cgg cac aac ctg      777
Ile Thr Ala Thr Ser Asn His Trp Val Val Asn Pro Arg His Asn Leu
                230                 235                 240 ggc ctg cag ctc tcg gtg gag acg ctg gat ggg cag agc atc aac ccc      825
Gly Leu Gln Leu Ser Val Glu Thr Leu Asp Gly Gln Ser Ile Asn Pro
    245                 250                 255 aag ttg gcg ggc ctg att ggg cgg cac ggg ccc cag aac aag cag ccc      873
Lys Leu Ala Gly Leu Ile Gly Arg His Gly Pro Gln Asn Lys Gln Pro
260                 265                 270                 275 ttc atg gtg gct ttc ttc aag gcc acg gag gtc cac ttc cgc agc atc      921
Phe Met Val Ala Phe Phe Lys Ala Thr Glu Val His Phe Arg Ser Ile
                280                 285                 290 cgg tcc acg ggg agc aaa cag cgc agc cag aac cgc tcc aag acg ccc      969
Arg Ser Thr Gly Ser Lys Gln Arg Ser Gln Asn Arg Ser Lys Thr Pro
            295                 300                 305 aag aac cag gaa gcc ctg cgg atg gcc aac gtg gca gag aac agc agc     1017
Lys Asn Gln Glu Ala Leu Arg Met Ala Asn Val Ala Glu Asn Ser Ser
                310                 315                 320 agc gac cag agg cag gcc tgt aag aag cac gag ctg tat gtc agc ttc     1065
Ser Asp Gln Arg Gln Ala Cys Lys Lys His Glu Leu Tyr Val Ser Phe
    325                 330                 335 cga gac ctg ggc tgg cag gac tgg atc atc gcg cct gaa ggc tac gcc     1113
Arg Asp Leu Gly Trp Gln Asp Trp Ile Ile Ala Pro Glu Gly Tyr Ala
340                 345                 350                 355 gcc tac tac tgt gag ggg gag tgt gcc ttc cct ctg aac tcc tac atg     1161
Ala Tyr Tyr Cys Glu Gly Glu Cys Ala Phe Pro Leu Asn Ser Tyr Met
                360                 365                 370 aac gcc acc aac cac gcc atc gtg cag acg ctg gtc cac ttc atc aac     1209
Asn Ala Thr Asn His Ala Ile Val Gln Thr Leu Val His Phe Ile Asn
            375                 380                 385 ccg gaa acg gtg ccc aag ccc tgc tgt gcg ccc acg cag ctc aat gcc     1257
Pro Glu Thr Val Pro Lys Pro Cys Cys Ala Pro Thr Gln Leu Asn Ala
                390                 395                 400 atc tcc gtc ctc tac ttc gat gac agc tcc aac gtc atc ctg aag aaa     1305
Ile Ser Val Leu Tyr Phe Asp Asp Ser Ser Asn Val Ile Leu Lys Lys
405                 410                 415
```

```
tac aga aac atg gtg gtc cgg gcc tgt ggc tgc cac tagctcctcc    1351
Tyr Arg Asn Met Val Val Arg Ala Cys Gly Cys His
420                 425                 430 gagaattcag acccctttggg gccaagttttt tctggatcct ccattgctcg ccttggccag   1411
gaaccagcag accaactgcc ttttgtgaga ccttccctc cctatcccca actttaaagg     1471
tgtgagagta ttaggaaaca tgagcagcat atggcttttg atcagttttt cagtggcagc   1531
atccaatgaa caagatccta caagctgtgc aggcaaaacc tagcaggaaa aaaaaacaac   1591
gcataaagaa aaatggccgg gccaggtcat tggctgggaa gtctcagcca tgcacggact   1651
cgtttccaga ggtaattatg agcgcctacc agccaggcca cccagccgtg ggaggaaggg   1711
ggcgtggcaa ggggtgggca cattggtgtc tgtgcgaaag gaaaattgac ccggaagttc   1771
ctgtaataaa tgtcacaata aaacgaatga atgaaaaaaa aaaaaaaaaa a             1822
```

<210> SEQ ID NO 39
<211> LENGTH: 431
<212> TYPE: PRT
<213> ORGANISM: Homo sapiens
<220> FEATURE:
<223> OTHER INFORMATION: Morphogenic protein OP1

<400> SEQUENCE: 39

```
Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
            35                  40                  45

Gln Glu Arg Arg Glu Met Gln Arg Glu Ile Leu Ser Ile Leu Gly Leu
        50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270
```

-continued

```
Lys Gln Pro Phe Met Val Ala Phe Lys Ala Thr Glu Val His Phe
            275                 280                 285
Arg Ser Ile Arg Ser Thr Gly Ser Lys Gln Arg Ser Gln Asn Arg Ser
        290                 295                 300
Lys Thr Pro Lys Asn Gln Glu Ala Leu Arg Met Ala Asn Val Ala Glu
305                 310                 315                 320
Asn Ser Ser Ser Asp Gln Arg Gln Ala Cys Lys Lys His Glu Leu Tyr
                325                 330                 335
Val Ser Phe Arg Asp Leu Gly Trp Gln Asp Trp Ile Ile Ala Pro Glu
            340                 345                 350
Gly Tyr Ala Ala Tyr Tyr Cys Glu Gly Glu Cys Ala Phe Pro Leu Asn
        355                 360                 365
Ser Tyr Met Asn Ala Thr Asn His Ala Ile Val Gln Thr Leu Val His
            370                 375                 380
Phe Ile Asn Pro Glu Thr Val Pro Lys Pro Cys Cys Ala Pro Thr Gln
385                 390                 395                 400
Leu Asn Ala Ile Ser Val Leu Tyr Phe Asp Asp Ser Ser Asn Val Ile
                405                 410                 415
Leu Lys Lys Tyr Arg Asn Met Val Val Arg Ala Cys Gly Cys His
            420                 425                 430

<210> SEQ ID NO 40
<211> LENGTH: 98
<212> TYPE: PRT
<213> ORGANISM: Homo sapiens
<220> FEATURE:
<223> OTHER INFORMATION: TGF-Beta1

<400> SEQUENCE: 40

Cys Cys Val Arg Gln Leu Tyr Ile Asp Phe Arg Lys Asp Leu Gly Trp
1               5                   10                  15
Lys Trp Ile His Glu Pro Lys Gly Tyr His Ala Asn Phe Cys Leu Gly
            20                  25                  30
Pro Cys Pro Tyr Ile Trp Ser Leu Asp Thr Gln Tyr Ser Lys Val Leu
        35                  40                  45
Ala Leu Tyr Asn Gln His Asn Pro Gly Ala Ser Ala Ala Pro Cys Cys
    50                  55                  60
Val Pro Gln Ala Leu Glu Pro Leu Pro Ile Val Tyr Tyr Val Gly Arg
65                  70                  75                  80
Lys Pro Lys Val Glu Gln Leu Ser Asn Met Ile Val Arg Ser Cys Lys
                85                  90                  95
Cys Ser

<210> SEQ ID NO 41
<211> LENGTH: 98
<212> TYPE: PRT
<213> ORGANISM: Homo sapiens
<220> FEATURE:
<223> OTHER INFORMATION: TGF-Beta2

<400> SEQUENCE: 41

Cys Cys Leu Arg Pro Leu Tyr Ile Asp Phe Lys Arg Asp Leu Gly Trp
1               5                   10                  15
Lys Trp Ile His Glu Pro Lys Gly Tyr Asn Ala Asn Phe Cys Ala Gly
            20                  25                  30
Ala Cys Pro Tyr Leu Trp Ser Ser Asp Thr Gln His Ser Arg Val Leu
        35                  40                  45
```

```
Ser Leu Tyr Asn Thr Ile Asn Pro Glu Ala Ser Ala Ser Pro Cys Cys
        50                  55                  60

Val Ser Gln Asp Leu Glu Pro Leu Thr Ile Leu Tyr Tyr Ile Gly Lys
 65                  70                  75                  80

Thr Pro Lys Ile Glu Gln Leu Ser Asn Met Ile Val Lys Ser Cys Lys
                 85                  90                  95

Cys Ser

<210> SEQ ID NO 42
<211> LENGTH: 98
<212> TYPE: PRT
<213> ORGANISM: Homo sapiens
<220> FEATURE:
<223> OTHER INFORMATION: TGF-Beta3

<400> SEQUENCE: 42

Cys Cys Val Arg Pro Leu Tyr Ile Asp Phe Arg Gln Asp Leu Gly Trp
 1               5                  10                  15

Lys Trp Val His Glu Pro Lys Gly Tyr Tyr Ala Asn Phe Cys Ser Gly
                20                  25                  30

Pro Cys Pro Tyr Leu Arg Ser Ala Asp Thr Thr His Ser Thr Val Leu
             35                  40                  45

Gly Leu Tyr Asn Thr Leu Asn Pro Glu Ala Ser Ala Ser Pro Cys Cys
        50                  55                  60

Val Pro Gln Asp Leu Glu Pro Leu Thr Ile Leu Tyr Tyr Val Gly Arg
 65                  70                  75                  80

Thr Pro Lys Val Glu Gln Leu Ser Asn Met Val Val Lys Ser Cys Lys
                 85                  90                  95

Cys Ser

<210> SEQ ID NO 43
<211> LENGTH: 98
<212> TYPE: PRT
<213> ORGANISM: Gallus gallus
<220> FEATURE:
<223> OTHER INFORMATION: TGF-Beta4

<400> SEQUENCE: 43

Cys Cys Val Arg Pro Leu Tyr Ile Asp Phe Arg Lys Asp Leu Gln Trp
 1               5                  10                  15

Lys Trp Ile His Glu Pro Lys Gly Tyr Met Ala Asn Phe Cys Met Gly
                20                  25                  30

Pro Cys Pro Tyr Ile Trp Ser Ala Asp Thr Gln Tyr Thr Lys Val Leu
             35                  40                  45

Ala Leu Tyr Asn Gln His Asn Pro Gly Ala Ser Ala Ala Pro Cys Cys
        50                  55                  60

Val Pro Gln Thr Leu Asp Pro Leu Pro Ile Ile Tyr Tyr Val Gly Arg
 65                  70                  75                  80

Asn Val Arg Val Glu Gln Leu Ser Asn Met Val Val Arg Ala Cys Lys
                 85                  90                  95

Cys Ser

<210> SEQ ID NO 44
<211> LENGTH: 98
<212> TYPE: PRT
<213> ORGANISM: Xenopus laevis
<220> FEATURE:
<223> OTHER INFORMATION: TGF-Beta5

<400> SEQUENCE: 44
```

```
Cys Cys Val Lys Pro Leu Tyr Ile Asn Phe Arg Lys Asp Leu Gly Trp
  1               5                   10                  15

Lys Trp Ile His Glu Pro Lys Gly Tyr Glu Ala Asn Tyr Cys Leu Gly
                 20                  25                  30

Asn Cys Pro Tyr Ile Trp Ser Met Asp Thr Gln Tyr Ser Lys Val Leu
             35                  40                  45

Ser Leu Tyr Asn Gln Asn Asn Pro Gly Ala Ser Ile Ser Pro Cys Cys
         50                  55                  60

Val Pro Asp Val Leu Glu Pro Leu Pro Ile Ile Tyr Tyr Val Gly Arg
 65                  70                  75                  80

Thr Ala Lys Val Glu Gln Leu Ser Asn Met Val Val Arg Ser Cys Asn
                 85                  90                  95

Cys Ser

<210> SEQ ID NO 45
<211> LENGTH: 102
<212> TYPE: PRT
<213> ORGANISM: Drosophila melanogaster
<220> FEATURE:
<223> OTHER INFORMATION: DPP

<400> SEQUENCE: 45

Cys Arg Arg His Ser Leu Tyr Val Asp Phe Ser Asp Val Gly Trp Asp
  1               5                   10                  15

Asp Trp Ile Val Ala Pro Leu Gly Tyr Asp Ala Tyr Tyr Cys His Gly
                 20                  25                  30

Lys Cys Pro Phe Pro Leu Ala Asp His Phe Asn Ser Thr Asn His Ala
             35                  40                  45

Val Val Gln Thr Leu Val Asn Asn Met Asn Pro Gly Lys Val Pro Lys
         50                  55                  60

Ala Cys Cys Val Pro Thr Gln Leu Asp Ser Val Ala Met Leu Tyr Leu
 65                  70                  75                  80

Asn Asp Gln Ser Thr Val Val Leu Lys Asn Tyr Gln Glu Met Thr Val
                 85                  90                  95

Val Gly Cys Gly Cys Arg
            100

<210> SEQ ID NO 46
<211> LENGTH: 102
<212> TYPE: PRT
<213> ORGANISM: Xenopus laevis
<220> FEATURE:
<223> OTHER INFORMATION: VG1

<400> SEQUENCE: 46

Cys Lys Lys Arg His Leu Tyr Val Glu Phe Lys Asp Val Gly Trp Gln
  1               5                   10                  15

Asn Trp Val Ile Ala Pro Gln Gly Tyr Met Ala Asn Tyr Cys Tyr Gly
                 20                  25                  30

Glu Cys Pro Tyr Pro Leu Thr Glu Ile Leu Asn Gly Ser Asn His Ala
             35                  40                  45

Ile Leu Gln Thr Leu Val His Ser Ile Glu Pro Glu Asp Ile Pro Leu
         50                  55                  60

Pro Cys Cys Val Pro Thr Lys Met Ser Pro Ile Ser Met Leu Phe Tyr
 65                  70                  75                  80

Asp Asn Asn Asp Asn Val Val Leu Arg His Tyr Glu Asn Met Ala Val
                 85                  90                  95
```

-continued

```
Asp Glu Cys Gly Cys Arg
            100

<210> SEQ ID NO 47
<211> LENGTH: 102
<212> TYPE: PRT
<213> ORGANISM: Mus musculus
<220> FEATURE:
<223> OTHER INFORMATION: VGR1

<400> SEQUENCE: 47

Cys Lys Lys His Glu Leu Tyr Val Ser Phe Gln Asp Leu Gly Trp Gln
1               5                   10                  15

Asp Trp Ile Ile Ala Pro Lys Gly Tyr Ala Ala Asn Tyr Cys Asp Gly
            20                  25                  30

Glu Cys Ser Phe Pro Leu Asn Ala His Met Asn Ala Thr Asn His Ala
        35                  40                  45

Ile Val Gln Thr Leu Val His Leu Met Asn Pro Glu Tyr Val Pro Lys
    50                  55                  60

Pro Cys Cys Ala Pro Thr Lys Leu Asn Ala Ile Ser Val Leu Tyr Phe
65                  70                  75                  80

Asp Asp Asn Ser Asn Val Ile Leu Lys Lys Tyr Arg Asn Met Val Val
                85                  90                  95

Arg Ala Cys Gly Cys His
            100

<210> SEQ ID NO 48
<211> LENGTH: 118
<212> TYPE: PRT
<213> ORGANISM: Drosophila melanogaster
<220> FEATURE:
<223> OTHER INFORMATION: 60A

<400> SEQUENCE: 48

Cys Gln Met Gln Thr Leu Tyr Ile Asp Phe Lys Asp Leu Gly Trp His
1               5                   10                  15

Asp Trp Ile Ile Ala Pro Glu Gly Tyr Gly Ala Phe Tyr Cys Ser Gly
            20                  25                  30

Glu Cys Asn Phe Pro Leu Asn Ala His Met Asn Ala Thr Asn His Ala
        35                  40                  45

Ile Val Gln Thr Leu Val His Leu Leu Glu Pro Lys Lys Val Pro Lys
    50                  55                  60

Pro Cys Cys Ala Pro Thr Arg Leu Gly Ala Leu Pro Val Leu Tyr His
65                  70                  75                  80

Pro Cys Cys Ala Pro Thr Arg Leu Gly Ala Leu Pro Val Leu Tyr His
                85                  90                  95

Leu Asn Asp Glu Asn Val Asn Leu Lys Lys Tyr Arg Asn Met Ile Val
            100                 105                 110

Lys Ser Cys Gly Cys His
        115

<210> SEQ ID NO 49
<211> LENGTH: 101
<212> TYPE: PRT
<213> ORGANISM: Homo sapiens
<220> FEATURE:
<223> OTHER INFORMATION: BMP-2A

<400> SEQUENCE: 49

Cys Lys Arg His Pro Leu Tyr Val Asp Phe Ser Asp Val Gly Trp Asn
1               5                   10                  15
```

Asp Trp Ile Val Ala Pro Pro Gly Tyr His Ala Phe Tyr Cys His Gly
            20                  25                  30

Glu Cys Pro Phe Pro Leu Ala Asp His Leu Asn Ser Thr Asn His Ala
            35                  40                  45

Ile Val Gln Thr Leu Val Asn Ser Val Asn Ser Lys Ile Pro Lys Ala
        50                  55                  60

Cys Cys Val Pro Thr Glu Leu Ser Ala Ile Ser Met Leu Tyr Leu Asp
65                  70                  75                  80

Glu Asn Glu Lys Val Val Leu Lys Asn Tyr Gln Asp Met Val Val Glu
                85                  90                  95

Gly Cys Gly Cys Arg
            100

<210> SEQ ID NO 50
<211> LENGTH: 103
<212> TYPE: PRT
<213> ORGANISM: Homo sapiens
<220> FEATURE:
<223> OTHER INFORMATION: BMP3

<400> SEQUENCE: 50

Cys Ala Arg Arg Tyr Leu Lys Val Asp Phe Ala Asp Ile Gly Trp Ser
1               5                   10                  15

Glu Trp Ile Ile Ser Pro Lys Ser Phe Asp Ala Tyr Tyr Cys Ser Gly
            20                  25                  30

Ala Cys Gln Phe Pro Met Pro Lys Ser Leu Lys Pro Ser Asn His Ala
            35                  40                  45

Thr Ile Gln Ser Ile Val Arg Ala Val Gly Val Val Pro Gly Ile Pro
        50                  55                  60

Glu Pro Cys Cys Val Pro Glu Lys Met Ser Ser Leu Ser Ile Leu Phe
65                  70                  75                  80

Phe Asp Glu Asn Lys Asn Val Val Leu Lys Val Tyr Pro Asn Met Thr
                85                  90                  95

Val Glu Ser Cys Ala Cys Arg
            100

<210> SEQ ID NO 51
<211> LENGTH: 101
<212> TYPE: PRT
<213> ORGANISM: Homo sapiens
<220> FEATURE:
<223> OTHER INFORMATION: BMP-4

<400> SEQUENCE: 51

Cys Arg Arg His Ser Leu Tyr Val Asp Phe Ser Asp Val Gly Trp Asn
1               5                   10                  15

Asp Trp Ile Val Ala Pro Pro Gly Tyr Gln Ala Phe Tyr Cys His Gly
            20                  25                  30

Asp Cys Pro Phe Pro Leu Ala Asp His Leu Asn Ser Thr Asn His Ala
            35                  40                  45

Ile Val Gln Thr Leu Val Asn Ser Val Asn Ser Ser Ile Pro Lys Ala
        50                  55                  60

Cys Cys Val Pro Thr Glu Leu Ser Ala Ile Ser Met Leu Tyr Leu Asp
65                  70                  75                  80

Glu Tyr Asp Lys Val Val Leu Lys Asn Tyr Gln Glu Met Val Val Glu
                85                  90                  95

Gly Cys Gly Cys Arg
            100

```
<210> SEQ ID NO 52
<211> LENGTH: 102
<212> TYPE: PRT
<213> ORGANISM: Homo sapiens
<220> FEATURE:
<223> OTHER INFORMATION: BMP-5

<400> SEQUENCE: 52

Cys Lys Lys His Glu Leu Tyr Val Ser Phe Arg Asp Leu Gly Trp Gln
  1               5                  10                  15

Asp Trp Ile Ile Ala Pro Glu Gly Tyr Ala Ala Phe Tyr Cys Asp Gly
             20                  25                  30

Glu Cys Ser Phe Pro Leu Asn Ala His Met Asn Ala Thr Asn His Ala
         35                  40                  45

Ile Val Gln Thr Leu Val His Leu Met Phe Pro Asp His Val Pro Lys
     50                  55                  60

Pro Cys Cys Ala Pro Thr Lys Leu Asn Ala Ile Ser Val Leu Tyr Phe
 65                  70                  75                  80

Asp Asp Ser Ser Asn Val Ile Leu Lys Lys Tyr Arg Asn Met Val Val
                 85                  90                  95

Arg Ser Cys Gly Cys His
            100

<210> SEQ ID NO 53
<211> LENGTH: 102
<212> TYPE: PRT
<213> ORGANISM: Homo sapiens
<220> FEATURE:
<223> OTHER INFORMATION: BMP-6

<400> SEQUENCE: 53

Cys Arg Lys His Glu Leu Tyr Val Ser Phe Gln Asp Leu Gly Trp Gln
  1               5                  10                  15

Asp Trp Ile Ile Ala Pro Lys Gly Tyr Ala Ala Asn Tyr Cys Asp Gly
             20                  25                  30

Glu Cys Ser Phe Pro Leu Asn Ala His Met Asn Ala Thr Asn His Ala
         35                  40                  45

Ile Val Gln Thr Leu Val His Leu Met Asn Pro Glu Tyr Val Pro Lys
     50                  55                  60

Pro Cys Cys Ala Pro Thr Lys Leu Asn Ala Ile Ser Val Leu Tyr Phe
 65                  70                  75                  80

Asp Asp Asn Ser Asn Val Glu Leu Lys Lys Tyr Arg Asn Met Val Val
                 85                  90                  95

Arg Ala Cys Gly Cys His
            100

<210> SEQ ID NO 54
<211> LENGTH: 103
<212> TYPE: PRT
<213> ORGANISM: Gallus gallus
<220> FEATURE:
<223> OTHER INFORMATION: DORSALIN

<400> SEQUENCE: 54

Cys Arg Arg Thr Ser Leu His Val Asn Phe Lys Glu Ile Gly Trp Asp
  1               5                  10                  15

Ser Trp Ile Ile Ala Pro Lys Asp Tyr Glu Ala Phe Glu Cys Lys Gly
             20                  25                  30

Gly Cys Phe Phe Pro Leu Thr Asp Asn Val Thr Pro Thr Lys His Ala
```

```
                35                  40                  45
Ile Val Gln Thr Leu Val His Leu Gln Asn Pro Lys Lys Ala Ser Lys
 50                  55                  60

Ala Cys Cys Val Pro Thr Lys Leu Asp Ala Ile Ser Ile Leu Tyr Lys
 65                  70                  75                  80

Asp Asp Ala Gly Val Pro Thr Leu Ile Tyr Asn Tyr Glu Gly Met Lys
                 85                  90                  95

Val Ala Glu Cys Gly Cys Arg
            100

<210> SEQ ID NO 55
<211> LENGTH: 102
<212> TYPE: PRT
<213> ORGANISM: Homo sapiens
<220> FEATURE:
<223> OTHER INFORMATION: OP-1

<400> SEQUENCE: 55

Cys Lys Lys His Glu Leu Tyr Val Ser Phe Arg Asp Leu Gly Trp Gln
 1               5                  10                  15

Asp Trp Ile Ile Ala Pro Glu Gly Tyr Ala Ala Tyr Tyr Cys Glu Gly
                 20                  25                  30

Glu Cys Ala Phe Pro Leu Asn Ser Tyr Met Asn Ala Thr Asn His Ala
             35                  40                  45

Ile Val Gln Thr Leu Val His Phe Ile Asn Pro Glu Thr Val Pro Lys
 50                  55                  60

Pro Cys Cys Ala Pro Thr Gln Leu Asn Ala Ile Ser Val Leu Tyr Phe
 65                  70                  75                  80

Asp Asp Ser Ser Asn Val Ile Leu Lys Lys Tyr Arg Asn Met Val Val
                 85                  90                  95

Arg Ala Cys Gly Cys His
            100

<210> SEQ ID NO 56
<211> LENGTH: 102
<212> TYPE: PRT
<213> ORGANISM: Homo sapiens
<220> FEATURE:
<223> OTHER INFORMATION: OP-2

<400> SEQUENCE: 56

Cys Arg Arg His Glu Leu Tyr Val Ser Phe Gln Asp Leu Gly Trp Leu
 1               5                  10                  15

Asp Trp Val Ile Ala Pro Gln Gly Tyr Ser Ala Tyr Tyr Cys Glu Gly
                 20                  25                  30

Glu Cys Ser Phe Pro Leu Asp Ser Cys Met Asn Ala Thr Asn His Ala
             35                  40                  45

Ile Leu Gln Ser Leu Val His Leu Met Lys Pro Asn Ala Val Pro Lys
 50                  55                  60

Ala Cys Cys Ala Pro Thr Lys Leu Ser Ala Thr Ser Val Leu Tyr Tyr
 65                  70                  75                  80

Asp Ser Ser Asn Asn Val Ile Leu Arg Lys His Arg Asn Met Val Val
                 85                  90                  95

Lys Ala Cys Gly Cys His
            100

<210> SEQ ID NO 57
<211> LENGTH: 102
<212> TYPE: PRT
```

-continued

```
<213> ORGANISM: Mus musculus
<220> FEATURE:
<223> OTHER INFORMATION: OP-3

<400> SEQUENCE: 57

Cys Arg Arg His Glu Leu Tyr Val Ser Phe Arg Asp Leu Gly Trp Leu
1               5                   10                  15

Asp Ser Val Ile Ala Pro Gln Gly Tyr Ser Ala Tyr Tyr Cys Ala Gly
            20                  25                  30

Glu Cys Ile Tyr Pro Leu Asn Ser Cys Met Asn Ser Thr Asn His Ala
        35                  40                  45

Thr Met Gln Ala Leu Val His Leu Met Lys Pro Asp Ile Ile Pro Lys
    50                  55                  60

Val Cys Cys Val Pro Thr Glu Leu Ser Ala Ile Ser Leu Leu Tyr Tyr
65                  70                  75                  80

Asp Arg Asn Asn Asn Val Ile Leu Arg Arg Glu Arg Asn Met Val Val
                85                  90                  95

Gln Ala Cys Gly Cys His
            100

<210> SEQ ID NO 58
<211> LENGTH: 107
<212> TYPE: PRT
<213> ORGANISM: Mus musculus
<220> FEATURE:
<223> OTHER INFORMATION: GDF-1

<400> SEQUENCE: 58

Cys Arg Thr Arg Arg Leu His Val Ser Phe Arg Glu Val Gly Trp His
1               5                   10                  15

Arg Trp Val Ile Ala Pro Arg Gly Phe Leu Ala Asn Phe Cys Gln Gly
            20                  25                  30

Thr Cys Ala Leu Pro Glu Thr Leu Arg Gly Pro Gly Gly Pro Pro Ala
        35                  40                  45

Leu Asn His Ala Val Leu Arg Ala Leu Met His Ala Ala Ala Pro Thr
    50                  55                  60

Pro Gly Ala Gly Ser Pro Cys Cys Val Pro Glu Arg Leu Ser Pro Ile
65                  70                  75                  80

Ser Val Leu Phe Phe Asp Asn Ser Asp Asn Val Val Leu Arg His Tyr
                85                  90                  95

Glu Asp Met Val Val Asp Glu Cys Gly Cys Arg
            100                 105

<210> SEQ ID NO 59
<211> LENGTH: 101
<212> TYPE: PRT
<213> ORGANISM: Mus musculus
<220> FEATURE:
<223> OTHER INFORMATION: GDF-3

<400> SEQUENCE: 59

Cys His Arg His Gln Leu Phe Ile Asn Phe Gln Asp Leu Gly Trp His
1               5                   10                  15

Lys Trp Val Ile Ala Pro Lys Gly Phe Met Ala Asn Tyr Cys His Gly
            20                  25                  30

Glu Cys Pro Phe Ser Met Thr Thr Tyr Leu Asn Ser Ser Asn Tyr Ala
        35                  40                  45

Phe Met Gln Ala Leu Met His Met Ala Asp Pro Lys Val Pro Lys Ala
    50                  55                  60
```

```
Val Cys Val Pro Thr Lys Leu Ser Pro Ile Ser Met Leu Tyr Gln Asp
 65                  70                  75                  80

Ser Asp Lys Asn Val Ile Leu Arg His Tyr Glu Asp Met Val Val Asp
                 85                  90                  95

Glu Cys Gly Cys Gly
            100

<210> SEQ ID NO 60
<211> LENGTH: 102
<212> TYPE: PRT
<213> ORGANISM: Mus musculus
<220> FEATURE:
<223> OTHER INFORMATION: GDF-9

<400> SEQUENCE: 60

Cys Glu Leu His Asp Phe Arg Leu Ser Phe Ser Gln Leu Lys Trp Asp
 1               5                  10                  15

Asn Trp Ile Val Ala Pro His Arg Tyr Asn Pro Arg Tyr Cys Lys Gly
                 20                  25                  30

Asp Cys Pro Arg Ala Val Arg His Arg Tyr Gly Ser Pro Val His Thr
             35                  40                  45

Met Val Gln Asn Ile Ile Tyr Glu Lys Leu Asp Pro Ser Val Pro Arg
 50                  55                  60

Pro Ser Cys Val Pro Gly Lys Tyr Ser Pro Leu Ser Val Leu Thr Ile
 65                  70                  75                  80

Glu Pro Asp Gly Ser Ile Ala Tyr Lys Glu Tyr Glu Asp Met Ile Ala
                 85                  90                  95

Thr Arg Cys Thr Cys Arg
            100

<210> SEQ ID NO 61
<211> LENGTH: 105
<212> TYPE: PRT
<213> ORGANISM: Homo sapiens
<220> FEATURE:
<223> OTHER INFORMATION: INHIBIN-Alpha

<400> SEQUENCE: 61

Cys His Arg Val Ala Leu Asn Ile Ser Phe Gln Glu Leu Gly Trp Glu
 1               5                  10                  15

Arg Trp Ile Val Tyr Pro Pro Ser Phe Ile Phe His Tyr Cys His Gly
                 20                  25                  30

Gly Cys Gly Leu His Ile Pro Pro Asn Leu Ser Leu Pro Val Pro Gly
             35                  40                  45

Ala Pro Pro Thr Pro Ala Gln Pro Tyr Ser Leu Leu Pro Gly Ala Gln
 50                  55                  60

Pro Cys Cys Ala Ala Leu Pro Gly Thr Met Arg Pro Leu His Val Arg
 65                  70                  75                  80

Thr Thr Ser Asp Gly Gly Tyr Ser Phe Lys Tyr Glu Thr Val Pro Asn
                 85                  90                  95

Leu Leu Thr Gln His Cys Ala Cys Ile
            100                 105

<210> SEQ ID NO 62
<211> LENGTH: 106
<212> TYPE: PRT
<213> ORGANISM: Bos taurus
<220> FEATURE:
<223> OTHER INFORMATION: INHIBIN-BetaA

<400> SEQUENCE: 62
```

-continued

```
Cys Cys Lys Lys Gln Phe Phe Val Ser Phe Lys Asp Ile Gly Trp Asn
1               5                   10                  15

Asp Trp Ile Ile Ala Pro Ser Gly Tyr His Ala Asn Tyr Cys Glu Gly
            20                  25                  30

Glu Cys Pro Ser His Ile Ala Gly Thr Ser Gly Ser Ser Leu Ser Phe
        35                  40                  45

His Ser Thr Val Ile Asn His Tyr Arg Met Arg Gly His Ser Pro Phe
    50                  55                  60

Ala Asn Leu Lys Ser Cys Cys Val Pro Thr Lys Leu Arg Pro Met Ser
65                  70                  75                  80

Met Leu Tyr Tyr Asp Asp Gly Gln Asn Ile Ile Lys Lys Asp Ile Gln
                85                  90                  95

Asn Met Ile Val Glu Glu Cys Gly Cys Ser
                100                 105
```

<210> SEQ ID NO 63
<211> LENGTH: 106
<212> TYPE: PRT
<213> ORGANISM: Homo sapiens
<220> FEATURE:
<223> OTHER INFORMATION: INHIBIN-Betab

<400> SEQUENCE: 63

```
Cys Cys Lys Lys Gln Phe Phe Val Ser Phe Lys Asp Ile Gly Trp Asn
1               5                   10                  15

Asp Trp Ile Ile Ala Pro Ser Gly Tyr His Ala Asn Tyr Cys Glu Gly
            20                  25                  30

Glu Cys Pro Ser His Ile Ala Gly Thr Ser Gly Ser Ser Leu Ser Phe
        35                  40                  45

His Ser Thr Val Ile Asn His Tyr Arg Met Arg Gly His Ser Pro Phe
    50                  55                  60

Ala Asn Leu Lys Ser Cys Cys Val Pro Thr Lys Leu Arg Pro Met Ser
65                  70                  75                  80

Met Leu Tyr Tyr Asp Asp Gly Gln Asn Ile Ile Lys Lys Asp Ile Gln
                85                  90                  95

Asn Met Ile Val Glu Glu Cys Gly Cys Ser
                100                 105
```

<210> SEQ ID NO 64
<211> LENGTH: 98
<212> TYPE: PRT
<213> ORGANISM: Artificial Sequence
<220> FEATURE:
<223> OTHER INFORMATION: Description of Artificial Sequence: TGF-B
      SUBGROUP SEQUENCE PATTERN
<220> FEATURE:
<221> NAME/KEY: misc_feature
<222> LOCATION: (12)..(12)
<223> OTHER INFORMATION: Xaa12 can be Arg or Lys
<220> FEATURE:
<221> NAME/KEY: misc_feature
<222> LOCATION: (26)..(26)
<223> OTHER INFORMATION: Xaa26 can be Ala, Arg, Asn, Asp, Cys, Glu, Gln,
      Gly, His, Ile, Leu, Lys, Met, Phe, Pro, Ser, Thr, Trp, Tyr or Val
<220> FEATURE:
<221> NAME/KEY: misc_feature
<222> LOCATION: (31)..(31)
<223> OTHER INFORMATION: Xaa31 can be Ala, Arg, Asn, Asp, Cys, Glu, Gln,
      Gly, His, Ile, Leu, Lys, Met, Phe, Pro, Ser, Thr, Trp, Tyr or Val
<220> FEATURE:
<221> NAME/KEY: misc_feature
<222> LOCATION: (33)..(33)
<223> OTHER INFORMATION: Xaa33 can be Ala, Gly, Pro, Ser or Thr
<220> FEATURE:

```
<221> NAME/KEY: misc_feature
<222> LOCATION: (37)..(37)
<223> OTHER INFORMATION: Xaa37 can be Ile, Leu lys, Met or Val
<220> FEATURE:
<221> NAME/KEY: misc_feature
<222> LOCATION: (40)..(40)
<223> OTHER INFORMATION: Xaa40 can be Ala, Arg, Asn, Asp, Cys, Glu, Gln,
      Gly, His, Ile, Leu, Lys, Met, Phe, Pro, Ser, Thr, Trp, Tyr or Val
<220> FEATURE:
<221> NAME/KEY: misc_feature
<222> LOCATION: (44)..(44)
<223> OTHER INFORMATION: Xaa44 can be His, Phe, Trp or Tyr
<220> FEATURE:
<221> NAME/KEY: misc_feature
<222> LOCATION: (46)..(46)
<223> OTHER INFORMATION: Xaa46 can be Arg or Lys
<220> FEATURE:
<221> NAME/KEY: misc_feature
<222> LOCATION: (49)..(49)
<223> OTHER INFORMATION: Xaa49 can be Ala, Gly, Pro, Ser or Thr
<220> FEATURE:
<221> NAME/KEY: misc_feature
<222> LOCATION: (53)..(54)
<223> OTHER INFORMATION: Xaa53 can be Arg, Asn, Asp, Gln, Glu, His, Lys,
      Ser or Thr; Xaa54 can be Ala, Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: misc_feature
<222> LOCATION: (57)..(57)
<223> OTHER INFORMATION: Xaa57 can be Ala, Arg, Asn, Asp, Cys, Glu, Gln,
      Gly, His, Ile, Leu, Lys, Met, Phe, Pro, Ser, Thr, Trp, Tyr or Val
<220> FEATURE:
<221> NAME/KEY: misc_feature
<222> LOCATION: (61)..(61)
<223> OTHER INFORMATION: Xaa61 can be Ala, Gly, Pro, Ser or Thr
<220> FEATURE:
<221> NAME/KEY: misc_feature
<222> LOCATION: (68)..(68)
<223> OTHER INFORMATION: Xaa68 can be Ala, Arg, Asn, Asp, Cys, Glu, Gln,
      Gly, His, Ile, Leu, Lys, Met, Phe, Pro, Ser, Thr, Trp, Tyr or Val
<220> FEATURE:
<221> NAME/KEY: misc_feature
<222> LOCATION: (73)..(73)
<223> OTHER INFORMATION: Xaa73 can be Ala, Gly, Pro, Ser or Thr
<220> FEATURE:
<221> NAME/KEY: misc_feature
<222> LOCATION: (75)..(75)
<223> OTHER INFORMATION: Xaa75 can be Ile, Leu, Met or Val
<220> FEATURE:
<221> NAME/KEY: misc_feature
<222> LOCATION: (81)..(82)
<223> OTHER INFORMATION: Xaa81 can be Arg, Asn, Asp, Gln, Glu, His, Lys,
      Ser or Thr; Xaa82 can be Ala, Gly, Pro, Ser, or Thr
<220> FEATURE:
<221> NAME/KEY: misc_feature
<222> LOCATION: (91)..(91)
<223> OTHER INFORMATION: Xaa91 can be any Ile or Val
<220> FEATURE:
<221> NAME/KEY: misc_feature
<222> LOCATION: (93)..(93)
<223> OTHER INFORMATION: Xaa93 can be Arg or Lys

<400> SEQUENCE: 64

Cys Cys Val Arg Pro Leu Tyr Ile Asp Phe Arg Xaa Asp Leu Gly Trp
1               5                   10                  15

Lys Trp Ile His Glu Pro Lys Gly Tyr Xaa Ala Asn Phe Cys Xaa Gly
            20                  25                  30

Xaa Cys Pro Tyr Xaa Trp Ser Xaa Asp Thr Gln Xaa Ser Xaa Val Leu
        35                  40                  45

Xaa Leu Tyr Asn Xaa Xaa Asn Pro Xaa Ala Ser Ala Xaa Pro Cys Cys
    50                  55                  60

Val Pro Gln Xaa Leu Glu Pro Leu Xaa Ile Xaa Tyr Tyr Val Gly Arg
65                  70                  75                  80

Xaa Xaa Lys Val Glu Gln Leu Ser Asn Met Xaa Val X

Cys Ser

<210> SEQ ID NO 65
<211> LENGTH: 104
<212> TYPE: PRT
<213> ORGANISM: Artificial Sequence
<220> FEATURE:
<223> OTHER INFORMATION: Description of Artificial Sequence: VG/DPP
     SUBGROUP SEQUENCE PATTERN
<220> FEATURE:
<221> NAME/KEY: misc_feature
<222> LOCATION: (2)..(5)
<223> OTHER INFORMATION: Xaa2 can be Arg or Lys; Xaa3 can be Arg or Lys;
     Xaa4 and Xaa5 independently can be Arg, Asn, Asp, Glu, Gln, His,
     Lys, Ser or Thr
<220> FEATURE:
<221> NAME/KEY: misc_feature
<222> LOCATION: (9)..(9)
<223> OTHER INFORMATION: Xaa9 can be Arg, Asn, Asp, Glu, Gln, His, Lys,
     Ser or Thr
<220> FEATURE:
<221> NAME/KEY: misc_feature
<222> LOCATION: (11)..(11)
<223> OTHER INFORMATION: Xaa11 can be Arg, Asn, Asp, Glu, Gln, His, Lys,
     Ser or Thr
<220> FEATURE:
<221> NAME/KEY: misc_feature
<222> LOCATION: (13)..(13)
<223> OTHER INFORMATION: Xaa13 can be Ile, Leu, Met, or Val
<220> FEATURE:
<221> NAME/KEY: misc_feature
<222> LOCATION: (16)..(16)
<223> OTHER INFORMATION: Xaa16 can be Arg, Asn, Asp, Glu, Gln, His, Lys,
     Ser or Thr
<220> FEATURE:
<221> NAME/KEY: misc_feature
<222> LOCATION: (23)..(23)
<223> OTHER INFORMATION: Xaa23 can be Arg, Gln, Glu or Lys
<220> FEATURE:
<221> NAME/KEY: misc_feature
<222> LOCATION: (26)..(26)
<223> OTHER INFORMATION: Xaa26 can be Ala, Arg, Asn, Asp, Cys, Glu, Gln,
     Gly, His,Ile, Leu, Lys, Met, Phe, Pro, Ser, Thr, Trp, Tyr or Val
<220> FEATURE:
<221> NAME/KEY: misc_feature
<222> LOCATION: (28)..(28)
<223> OTHER INFORMATION: Xaa28 can be Phe, Trp or Tyr
<220> FEATURE:
<221> NAME/KEY: misc_feature
<222> LOCATION: (31)..(31)
<223> OTHER INFORMATION: Xaa31 can be Arg, Asn, Asp, Glu, Gln, His, Lys,
     Ser or Thr
<220> FEATURE:
<221> NAME/KEY: misc_feature
<222> LOCATION: (33)..(33)
<223> OTHER INFORMATION: Xaa33 can be Asp or Glu
<220> FEATURE:
<221> NAME/KEY: misc_feature
<222> LOCATION: (35)..(35)
<223> OTHER INFORMATION: Xaa35 can be Ala, Arg, Asn, Asp, Cys, Glu, Gln,
     Gly, His, Ile,Leu, Lys, Met, Phe, Pro, Ser, Thr, Trp, Tyr or Val
<220> FEATURE:
<221> NAME/KEY: misc_feature
<222> LOCATION: (39)..(42)
<223> OTHER INFORMATION: Xaa39, Xaa40 and Xaa41 independently can be
     Ala, Arg, Asn, Asp, Cys, Glu, Gln, Gly, His, Ile, Leu, Lys, Met,
     Phe, Pro, Ser, Thr, Trp, Tyr or Val; Xaa42 can be Leu or Met
<220> FEATURE:
<221> NAME/KEY: misc_feature
<222> LOCATION: (44)..(44)
<223> OTHER INFORMATION: Xaa44 can be Ala, Gly, Pro, Ser or Thr
<220> FEATURE:
<221> NAME/KEY: misc_feature
<222> LOCATION: (50)..(50)
<223> OTHER INFORMATION: Xaa50 can be Ile or Val
<220> FEATURE:
<221> NAME/KEY: misc_feature

```
<222> LOCATION: (55)..(57)
<223> OTHER INFORMATION: Xaa55 can be Arg, Asn, Asp, Glu, Gln, His, Lys,
      Ser or Thr; Xaa56 can be Ala, Arg, Asn, Asp, Cys, Glu, Gln, Gly,
      His, Ile, Leu, Lys, Met, Phe, Pro, Ser, Thr, Trp, Tyr or Val;
      Xaa57 can be Ile, Leu, Met or Val
<220> FEATURE:
<221> NAME/KEY: misc_feature
<222> LOCATION: (58)..(60)
<223> OTHER INFORMATION: Xaa58 can be Arg, Asn, Asp, Glu, Gln, His, Lys,
      Ser or Thr; Xaa59 and Xaa60 independently can be Ala, Arg, Asn,
      Asp, Cys, Glu, Gln, Gly, His, Ile, Leu, Lys, Met, Phe, Pro, Ser,
      Thr, Trp, Tyr, Val or a peptide bond
<220> FEATURE:
<221> NAME/KEY: misc_feature
<222> LOCATION: (61)..(63)
<223> OTHER INFORMATION: Xaa61 can be Arg, Asn, Asp, Glu, Gln, His, Lys,
      Ser or Thr; Xaa62 can be Ala, Arg, Asn, Asp, Cys, Glu, Gln, Gly,
      His, Ile, Leu, Lys, Met, Phe, Pro, Ser, Thr, Trp, Tyr or Val;
      Xaa63 can be Ile or Val
<220> FEATURE:
<221> NAME/KEY: misc_feature
<222> LOCATION: (66)..(66)
<223> OTHER INFORMATION: Xaa66 can be Ala Gly, Pro, Ser or Thr
<220> FEATURE:
<221> NAME/KEY: misc_feature
<222> LOCATION: (69)..(69)
<223> OTHER INFORMATION: Xaa69 can be Ala, Arg, Asn, Asp, Cys, Glu, Gln,
      Gly, His, Ile, Leu, Lys, Met, Phe, Pro, Ser, Thr, Trp, Tyr or Val
<220> FEATURE:
<221> NAME/KEY: misc_feature
<222> LOCATION: (72)..(72)
<223> OTHER INFORMATION: Xaa72 can be Arg, Gln, Glu or Lys
<220> FEATURE:
<221> NAME/KEY: misc_feature
<222> LOCATION: (74)..(74)
<223> OTHER INFORMATION: Xaa74 can be Arg, Asn, Asp, Glu, Gln, His, Lys,
      Ser or Thr
<220> FEATURE:
<221> NAME/KEY: misc_feature
<222> LOCATION: (76)..(76)
<223> OTHER INFORMATION: Xaa76 can be Ile or Val
<220> FEATURE:
<221> NAME/KEY: misc_feature
<222> LOCATION: (78)..(78)
<223> OTHER INFORMATION: Xaa78 can be Ile, Leu, Met or Val
<220> FEATURE:
<221> NAME/KEY: misc_feature
<222> LOCATION: (81)..(81)
<223> OTHER INFORMATION: Xaa81 can be Cys, Ile, Leu, Met, Phe, Trp, Tyr
      or Val
<220> FEATURE:
<221> NAME/KEY: misc_feature
<222> LOCATION: (83)..(85)
<223> OTHER INFORMATION: Xaa83 can be Asn, Asp or Glu; Xaa84 can be Arg,
      Asn, Asp, Glu, Gln, His, Lys, Ser or Thr; Xaa85 can be Ala, Arg,
      Asn, Asp, Cys, Glu, Gln, Gly, His, Ile, Leu, Lys, Met, Phe,
      Pro, Ser, Thr, Trp, Tyr, Val or a peptide bond
<220> FEATURE:
<221> NAME/KEY: misc_feature
<222> LOCATION: (86)..(87)
<223> OTHER INFORMATION: Xaa86 and Xaa87 independently can be Arg, Asn,
      Asp, Glu, Gln, His, Lys, Ser or Thr
<220> FEATURE:
<221> NAME/KEY: misc_feature
<222> LOCATION: (89)..(89)
<223> OTHER INFORMATION: Xaa89 can be Ile or Val
<220> FEATURE:
<221> NAME/KEY: misc_feature
<222> LOCATION: (91)..(92)
<223> OTHER INFORMATION: Xaa91 can be Arg or Lys;  Xaa92 can be Arg,
      Asn, Asp, Glu, Gln, His, Lys, Ser or Thr
<220> FEATURE:
<221> NAME/KEY: misc_feature
<222> LOCATION: (94)..(95)
<223> OTHER INFORMATION: Xaa94 can be Arg, Gln, Glu or Lys; Xaa95 can be
      Asn or Asp
<220> FEATURE:
<221> NAME/KEY: misc_feature
<222> LOCATION: (97)..(97)
<223> OTHER INFORMATION: Xaa97 can be Ala, Arg, Asn, Asp, Cys, Glu, Gln,
```

```
      Gly, His, Ile, Leu, Lys, Met, Phe, Pro, Ser, Thr, Trp, Tyr or Val
<220> FEATURE:
<221> NAME/KEY: misc_feature
<222> LOCATION: (99)..(100)
<223> OTHER INFORMATION: Xaa99 can be Arg, Gln, Glu or Lys; Xaa100 can
      be Ala Gly, Pro, Ser or Thr
<220> FEATURE:
<221> NAME/KEY: misc_feature
<222> LOCATION: (104)..(104)
<223> OTHER INFORMATION: Xaa104 can be Arg, Asn, Asp, Glu, Gln, His,
      Lys, Ser or Thr

<400> SEQUENCE: 65

Cys Xaa Xaa Xaa Xaa Leu Tyr Val Xaa Phe Xaa Asp Xaa Gly Trp Xaa
1               5                   10                  15

Asp Trp Ile Ile Ala Pro Xaa Gly Tyr Xaa Ala Xaa Tyr Cys Xaa Gly
                20                  25                  30

Xaa Cys Xaa Phe Pro Leu Xaa Xaa Xaa Asn Xaa Thr Asn His Ala
            35                  40                  45

Ile Xaa Gln Thr Leu Val Xaa Xaa Xaa Xaa Xaa Xaa Xaa Pro
    50                  55                  60

Lys Xaa Cys Cys Xaa Pro Thr Xaa Leu Xaa Ala Xaa Ser Xaa Leu Tyr
65              70                  75                  80

Xaa Asp Xaa Xaa Xaa Xaa Xaa Val Xaa Leu Xaa Xaa Tyr Xaa Xaa Met
                85                  90                  95

Xaa Val Xaa Xaa Cys Gly Cys Xaa
                100

<210> SEQ ID NO 66
<211> LENGTH: 107
<212> TYPE: PRT
<213> ORGANISM: Artificial Sequence
<220> FEATURE:
<223> OTHER INFORMATION: Description of Artificial Sequence: GDF
      SUBGROUP PATTERN
<220> FEATURE:
<221> NAME/KEY: misc_feature
<222> LOCATION: (2)..(3)
<223> OTHER INFORMATION: Xaa2 can be Arg, Asn, Asp, Glu, Gln, His, Lys,
      Ser or Thr; Xaa3 can be Ala, Arg, Asn, Asp, Cys, Glu, Gln, Gly,
      His, Ile, Leu, Lys, Met, Phe, Pro, Ser, Thr, Trp, Tyr or Val
<220> FEATURE:
<221> NAME/KEY: misc_feature
<222> LOCATION: (4)..(5)
<223> OTHER INFORMATION: Xaa4 and Xaa5 independently can be Arg, Asn,
      Asp, Glu, Gln, His, Lys, Ser or Thr
<220> FEATURE:
<221> NAME/KEY: misc_feature
<222> LOCATION: (6)..(8)
<223> OTHER INFORMATION: Xaa6 can be Cys, Ile, Leu, Met, Phe, Trp, Tyr
      or Val; Xaa7 can be Ala, Arg, Asn, Asp, Cys, Glu, Gln, Gly, His,
      Ile, Leu, Lys, Met, Phe, Pro,Ser, Thr, Trp, Tyr or Val; Xaa8 can
      be Ile, Leu, Met or Val
<220> FEATURE:
<221> NAME/KEY: misc_feature
<222> LOCATION: (9)..(9)
<223> OTHER INFORMATION: Xaa9 can be Arg, Asn, Asp, Glu, Gln, His, Lys,
      Ser or Th
<220> FEATURE:
<221> NAME/KEY: misc_feature
<222> LOCATION: (11)..(14)
<223> OTHER INFORMATION: Xaa11 and Xaa12 independently can be Arg, Asn,
      Asp, Glu, Gln, His, Lys, Ser or Thr; Xaa13 can be Ile, Leu, Met or
      Val; Xaa14 can be Ala, Arg, Asn, Asp, Cys, Glu, Gln, Gly, His,
      Ile, Leu, Lys, Met, Phe, Pro, Ser, Thr, Trp, Tyr or Val
<220> FEATURE:
<221> NAME/KEY: misc_feature
<222> LOCATION: (16)..(17)
<223> OTHER INFORMATION: Xaa16 and Xaa17 independently can be Arg, Asn,
      Asp, Glu, Gln, His, Lys, Ser or Thr
<220> FEATURE:
<221> NAME/KEY: misc_feature
```

```
<222> LOCATION: (19)..(20)
<223> OTHER INFORMATION: Xaa19 and Xaa20 independently can be Ile or Val
<220> FEATURE:
<221> NAME/KEY: misc_feature
<222> LOCATION: (23)..(25)
<223> OTHER INFORMATION: Xaa23 can be Arg, Asn, Asp, Glu, Gln, His, Lys,
      Ser or Thr; Xaa24 can be Ala, Arg, Asn, Asp, Cys, Glu, Gln, Gly,
      His, Ile, Leu, Lys, Met, Phe, Pro, Ser, Thr, Trp, Tyr or Val;
      Xaa25 can be Phe, Trp or Tyr
<220> FEATURE:
<221> NAME/KEY: misc_feature
<222> LOCATION: (26)..(29)
<223> OTHER INFORMATION: Xaa26 can be Ala, Arg, Asn, Asp, Cys, Glu, Gln,
      Gly, His, Ile, Leu, Lys, Met, Phe, Pro, Ser, Thr, Trp, Tyr or Val;
      Xaa27 can be Ala Gly, Pro, Ser or Thr; Xaa28 can be Arg, Asn, Asp,
      Glu, Gln, His, Lys, Ser or Thr; Xaa29 can be Phe, Trp or Tyr
<220> FEATURE:
<221> NAME/KEY: misc_feature
<222> LOCATION: (31)..(31)
<223> OTHER INFORMATION: Xaa31 can be Arg, Asn, Asp, Glu, Gln, His, Lys,
      Ser or Thr
<220> FEATURE:
<221> NAME/KEY: misc_feature
<222> LOCATION: (33)..(33)
<223> OTHER INFORMATION: Xaa33 can be Arg, Asn, Asp, Glu, Gln, His, Lys,
      Ser or Thr
<220> FEATURE:
<221> NAME/KEY: misc_feature
<222> LOCATION: (35)..(37)
<223> OTHER INFORMATION: Xaa35 can be Ala, Gly, Pro, Ser or Thr; Xaa36
      can be Ala, Arg, Asn, Asp, Cys, Glu, Gln, Gly, His, Ile, Leu, Lys,
      Met, Phe, Pro, Ser, Thr, Trp, Tyr or Val; Xaa37 can be Ala, Gly,
      Pro, Ser or Thr
<220> FEATURE:
<221> NAME/KEY: misc_feature
<222> LOCATION: (38)..(39)
<223> OTHER INFORMATION: Xaa38 can be Ala, Arg, Asn, Asp, Cys, Glu, Gln,
      Gly, His, Ile, Leu, Lys, Met, Phe, Pro, Ser, Thr, Trp, Tyr or Val;
      Xaa39 can be Arg, Asn, Asp, Glu, Gln, His, Lys, Ser or Thr
<220> FEATURE:
<221> NAME/KEY: misc_feature
<222> LOCATION: (40)..(42)
<223> OTHER INFORMATION: Xaa40 to Xaa42 independently can be Ala, Arg,
      Asn, Asp, Cys, Glu, Gln, Gly, His, Ile, Leu, Lys, Met, Phe, Pro,
      Ser, Thr, Trp, Tyr or Val
<220> FEATURE:
<221> NAME/KEY: misc_feature
<222> LOCATION: (43)..(46)
<223> OTHER INFORMATION: Xaa43 to Xaa46 independently can be Ala, Arg,
      Asn, Asp, Cys, Glu, Gln, Gly, His, Ile, Leu, Lys, Met, Phe, Pro,
      Ser, Thr, Trp, Tyr, Val or a peptide bond
<220> FEATURE:
<221> NAME/KEY: misc_feature
<222> LOCATION: (47)..(48)
<223> OTHER INFORMATION: Xaa47 can be Ala, Arg, Asn, Asp, Cys, Glu, Gln,
      Gly, His, Ile, Leu, Lys, Met, Phe, Pro, Ser, Thr, Trp, Tyr or Val;
      Xaa48 can be Ala, Gly, Pro, Ser or Thr
<220> FEATURE:
<221> NAME/KEY: misc_feature
<222> LOCATION: (49)..(49)
<223> OTHER INFORMATION: Xaa49 can be Ala, Arg, Asn, Asp, Cys, Glu, Gln,
      Gly, His, Ile, Leu, Lys, Met, Phe, Pro, Ser, Thr, Trp, Tyr or Val
<220> FEATURE:
<221> NAME/KEY: misc_feature
<222> LOCATION: (50)..(53)
<223> OTHER INFORMATION: Xaa50 can be Ala, Arg, Asn, Asp, Cys, Glu, Gln,
      Gly, His, Ile, Leu, Lys, Met, Phe, Pro, Ser, Thr, Trp, Tyr or Val;
      Xaa51 can be His, Phe, Trp or Tyr; Xaa52 can be Ala, Gly, Pro, Ser
      or Thr; Xaa53 can be Cys, Ile, Leu, Met, Phe, Trp or Val
<220> FEATURE:
<221> NAME/KEY: misc_feature
<222> LOCATION: (54)..(55)
<223> OTHER INFORMATION: Xaa54 can be Ile, Leu, Met or Val; Xaa55 can be
      Arg, Gln, Glu or Lys; Xaa56 can be Ala, Arg, Asn, Asp, Cys, Glu,
      Gln, Gly, His, Ile, Leu, Lys, Met, Phe, Pro, Ser, Thr, Trp, Tyr or
      Val; Xaa57 and Xaa58 independently can be Ile, Leu, Met or Val
<220> FEATURE:
<221> NAME/KEY: misc_feature
<222> LOCATION: (59)..(62)
<223> OTHER INFORMATION: Xaa59 can be His, Phe, Trp or Tyr; Xaa60, Xaa61
```

```
        and Xaa62 independently can be Ala, Arg, Asn, Asp, Cys, Glu, Gln,
        Gly, His, Ile, Leu, Lys, Met, Phe, Pro, Ser, Thr, Trp, Tyr or Val
<220> FEATURE:
<221> NAME/KEY: misc_feature
<222> LOCATION: (63)..(64)
<223> OTHER INFORMATION: Xaa63 and Xaa64 independently can be Ala, Arg,
        Asn, Asp, Cys, Glu, Gln, Gly, His, Ile, Leu, Lys, Met, Phe, Pro,
        Ser, Thr, Trp, Tyr, Val or a peptide bond
<220> FEATURE:
<221> NAME/KEY: misc_feature
<222> LOCATION: (66)..(69)
<223> OTHER INFORMATION: Xaa66 and Xaa67 independently can be Ala, Arg,
        Asn, Asp, Cys, Glu, Gln, Gly, His, Ile, Leu, Lys, Met, Phe, Pro,
        Ser, Thr, Trp, Tyr or Val; Xaa68 can be Ala, Gly, Pro, Ser or Thr;
        Xaa69 can be Arg, Asn, Asp, Glu, Gln, His, Lys, Ser or Thr
<220> FEATURE:
<221> NAME/KEY: misc_feature
<222> LOCATION: (70)..(71)
<223> OTHER INFORMATION: Xaa70 can be Ala, Gly, Pro, Ser or Thr; Xaa71
        can be Ala, Arg, Asn, Asp, Cys, Glu, Gln, Gly, His, Ile, Leu, Lys,
        Met, Phe, Pro, Ser, Thr, Trp, Tyr or Val
<220> FEATURE:
<221> NAME/KEY: misc_feature
<222> LOCATION: (75)..(77)
<223> OTHER INFORMATION: Xaa75 can be Ala, Arg, Asn, Asp, Cys, Glu, Gln,
        Gly, His, Ile, Leu, Lys, Met, Phe, Pro, Ser, Thr, Trp, Tyr or Val;
        Xaa76 can be Arg, or Lys; Xaa77 can be Cys, Ile, Leu, Met,
        Phe, Trp, Tyr or Val
<220> FEATURE:
<221> NAME/KEY: misc_feature
<222> LOCATION: (80)..(80)
<223> OTHER INFORMATION: Xaa80 can be Ile, Leu, Met or Val
<220> FEATURE:
<221> NAME/KEY: misc_feature
<222> LOCATION: (82)..(82)
<223> OTHER INFORMATION: Xaa82 can be Ile, Leu, Met or Val
<220> FEATURE:
<221> NAME/KEY: misc_feature
<222> LOCATION: (84)..(86)
<223> OTHER INFORMATION: Xaa84 and Xaa85 independently can be Ala, Arg,
        Asn, Asp, Cys, Glu, Gln, Gly, His, Ile, Leu, Lys, Met, Phe, Pro,
        Ser, Thr, Trp, Tyr or Val; Xaa86 can be Asp or Glu
<220> FEATURE:
<221> NAME/KEY: misc_feature
<222> LOCATION: (87)..(88)
<223> OTHER INFORMATION: Xaa87 can be Ala, Arg, Asn, Asp, Cys, Glu, Gln,
        Gly, His, Ile, Leu, Lys, Met, Phe, Pro, Ser, Thr, Trp, Tyr or Val;
        Xaa88 can be Arg, Asn, Asp, Glu, Gln, His, Lys, Ser or Thr
<220> FEATURE:
<221> NAME/KEY: misc_feature
<222> LOCATION: (89)..(91)
<223> OTHER INFORMATION: Xaa89 can be Ala, Arg, Asn, Asp, Cys, Glu, Gln,
        Gly, His, Ile, Leu, Lys, Met, Phe, Pro, Ser, Thr, Trp, Tyr or Val;
        Xaa90 can be Arg, Asn, Asp, Glu, Gln, His, Lys, Ser or Thr;
        Xaa 91 is Ile or Val
<220> FEATURE:
<221> NAME/KEY: misc_feature
<222> LOCATION: (92)..(94)
<223> OTHER INFORMATION: Xaa92 can be Ala, Arg, Asn, Asp, Cys, Glu, Gln,
        Gly, His, Ile, Leu, Lys, Met, Phe, Pro, Ser, Thr, Trp, Tyr or Val;
        Xaa93 can be Cys, Ile, Leu, Met, Phe, Trp, Tyr or Val;
        Xaa94 can be Arg or Lys
<220> FEATURE:
<221> NAME/KEY: misc_feature
<222> LOCATION: (95)..(95)
<223> OTHER INFORMATION: Xaa95 can be Arg, Asn, Asp, Glu, Gln, His, Lys,
        Ser or Thr
<220> FEATURE:
<221> NAME/KEY: misc_feature
<222> LOCATION: (100)..(103)
<223> OTHER INFORMATION: Xaa100 can be Ile or Val; Xaa101 can be Ala,
        Arg, Asn, Asp, Cys, Glu, Gln, Gly, His, Ile, Leu, Lys, Met, Phe,
        Pro, Ser, Thr, Trp, Tyr or Val; Xaa102 can be Arg, Asn, Asp, Glu,
        Gln, His, Lys, Ser or Thr; Xaa103 can be Arg, Gln, Glu or Lys
<220> FEATURE:
<221> NAME/KEY: misc_feature
<222> LOCATION: (105)..(105)
<223> OTHER INFORMATION: Xaa105 can be Ala, Gly, Pro, Ser or Thr
<220> FEATURE:
<221> NAME/KEY: misc_feature
```

<222> LOCATION: (107)..(107)
<223> OTHER INFORMATION: Xaa107 can be Ala, Arg, Asn, Asp, Cys, Glu,
    Gln, Gly, His, Ile, Leu, Lys, Met, Phe, Pro, Ser, Thr, Trp, Tyr or
    Val

<400> SEQUENCE: 66

Cys Xaa Xaa Xaa Xaa Xaa Xaa Xaa Phe Xaa Xaa Xaa Xaa Trp Xaa
1               5                   10                  15

Xaa Trp Xaa Xaa Ala Pro Xaa Xaa Xaa Xaa Xaa Xaa Cys Xaa Gly
            20                  25                  30

Xaa Cys Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Pro Xaa Xaa Xaa Xaa Xaa Xaa Cys Val Pro Xaa Xaa Xaa Ser Pro Xaa
65                  70                  75                  80

Ser Xaa Leu Xaa Xaa Xaa Xaa Xaa Xaa Xaa Xaa Xaa Xaa Xaa Tyr
            85                  90                  95

Glu Asp Met Xaa Xaa Xaa Xaa Cys Xaa Cys Xaa
            100                 105

<210> SEQ ID NO 67
<211> LENGTH: 109
<212> TYPE: PRT
<213> ORGANISM: Artificial Sequence
<220> FEATURE:
<223> OTHER INFORMATION: Description of Artificial Sequence: INHIBIN
    SUBGROUP PATTERN
<220> FEATURE:
<221> NAME/KEY: misc_feature
<222> LOCATION: (2)..(3)
<223> OTHER INFORMATION: Xaa2 can be Ala, Arg, Asn, Asp, Cys, Glu, Gln,
    Gly, His, Ile, Leu, Lys, Met, Phe, Pro, Ser, Thr, Trp, Tyr or Val;
    Xaa3 is Arg or Lys
<220> FEATURE:
<221> NAME/KEY: misc_feature
<222> LOCATION: (4)..(6)
<223> OTHER INFORMATION: Xaa4 and Xaa5 independently can be Ala, Arg,
    Asn, Asp, Cys, Glu, Gln, Gly, His, Ile, Leu, Lys, Met, Phe, Pro,
    Ser, Thr, Trp, Tyr or Val; Xaa6 can be Cys, Ile, Leu,
    Met, Phe, Trp, Tyr or Val
<220> FEATURE:
<221> NAME/KEY: misc_feature
<222> LOCATION: (7)..(9)
<223> OTHER INFORMATION: Xaa7 can be Ala, Arg, Asn, Asp, Cys, Glu, Gln,
    Gly, His, Ile, Leu, Lys, Met, Phe, Pro, Ser, Thr, Trp, Tyr or Val;
    Xaa8  can be Ile or Val; Xaa9 can be Arg, Asn, Asp, Glu,
    Gln, His, Lys, Ser or Thr
<220> FEATURE:
<221> NAME/KEY: misc_feature
<222> LOCATION: (11)..(13)
<223> OTHER INFORMATION: Xaa11 can be Arg, Gln, Glu or Lys; Xaa12 can be
    Ala, Arg, Asn, Asp, Cys, Glu, Gln, Gly, His, Ile, Leu, Lys, Met,
    Phe, Pro, Ser, Thr, Trp, Tyr or Val; Xaa13 can be Ile,
    Leu, Met or Val
<220> FEATURE:
<221> NAME/KEY: misc_feature
<222> LOCATION: (16)..(17)
<223> OTHER INFORMATION: Xaa16 can be Asn, Asp or Glu; Xaa17 can be Arg,
    Asn, Asp, Glu, Gln, His, Lys, Ser or Thr
<220> FEATURE:
<221> NAME/KEY: misc_feature
<222> LOCATION: (20)..(21)
<223> OTHER INFORMATION: Xaa20 can be Ile or Val; Xaa21 can be Ala, Arg,
    Asn, Asp, Cys, Glu, Gln, Gly, His, Ile, Leu, Lys, Met, Phe, Pro,
    Ser, Thr, Trp, Tyr or Val
<220> FEATURE:
<221> NAME/KEY: misc_feature
<222> LOCATION: (23)..(27)
<223> OTHER INFORMATION: Xaa23 and Xaa24 independently can be Ala, Gly,
    Pro, Ser or Thr; Xaa25 can be Phe, Tr or Tyr; Xaa26 and Xaa27
    independently can beAla, Arg, Asn, Asp, Cys, Glu, Gln, Gly, -continued

```
    His, Ile, Leu, Lys, Met, Phe, Pro, Ser, Thr, Trp, Tyr or Val
<220> FEATURE:
<221> NAME/KEY: misc_feature
<222> LOCATION: (28)..(28)
<223> OTHER INFORMATION: Xaa28 can be Arg, Asn, Asp, Glu, Gln, His, Lys,
    Ser or Thr
<220> FEATURE:
<221> NAME/KEY: misc_feature
<222> LOCATION: (31)..(31)
<223> OTHER INFORMATION: Xaa31 can be Arg, Asn, Asp, Glu, Gln, His, Lys,
    Ser or Thr
<220> FEATURE:
<221> NAME/KEY: misc_feature
<222> LOCATION: (33)..(33)
<223> OTHER INFORMATION: Xaa33 can be Ala, Arg, Asn, Asp, Cys, Glu, Gln,
    Gly, His, Ile, Leu, Lys, Met, Phe, Pro, Ser, Thr, Trp, Tyr or Val
<220> FEATURE:
<221> NAME/KEY: misc_feature
<222> LOCATION: (35)..(38)
<223> OTHER INFORMATION: Xaa35 can be Ala, Gly, Pro, Ser or Thr; Xaa36
    can be Ala, Arg, Asn, Asp, Cys, Glu, Gln, Gly, His, Ile, Leu, Lys,
    Met, Phe, Pro, Ser, Thr, Trp, Tyr or Val; Xaa37 can be His, Phe,
    Trp or Tyr; Xaa38 can be Ile, Leu, Met or Val
<220> FEATURE:
<221> NAME/KEY: misc_feature
<222> LOCATION: (39)..(43)
<223> OTHER INFORMATION: Xaa39 and Xaa40 independently can be Ala, Gly,
    Pro, Ser or Thr; Xaa41 and Xaa42 independently can be Ala, Arg,
    Asn, Asp, Cys, Glu, Gln, Gly, His, Ile, Leu, Lys, Met, Phe, Pro,
    Ser, Thr, Trp, Tyr or Val; Xaa43 can be Ala, Gly, Pro, Ser or Thr
<220> FEATURE:
<221> NAME/KEY: misc_feature
<222> LOCATION: (44)..(45)
<223> OTHER INFORMATION: Xaa44 can be Ala, Arg, Asn, Asp, Cys, Glu, Gln,
    Gly, His, Ile, Leu, Lys, Met, Phe, Pro, Ser, Thr, Trp, Tyr or Val;
    Xaa45 can be Ala, Gly, Pro, Ser or Thr
<220> FEATURE:
<221> NAME/KEY: misc_feature
<222> LOCATION: (46)..(47)
<223> OTHER INFORMATION: Xaa46 can be Ala, Arg, Asn, Asp, Cys, Glu, Gln,
    Gly, His, Ile, Leu, Lys, Met, Phe, Pro, Ser, Thr, Trp, Tyr or Val;
    Xaa47 can be Ala, Gly, Pro, Ser or Thr
<220> FEATURE:
<221> NAME/KEY: misc_feature
<222> LOCATION: (48)..(51)
<223> OTHER INFORMATION: Xaa48 and Xaa49 independently can be Ala, Arg,
    Asn, Asp, Cys, Glu, Gln, Gly, His, Ile, Leu, Lys, Met, Phe, Pro,
    Ser, Thr, Trp, Tyr or Val; Xaa50 and Xaa51 independently can be
    Ala, Gly, Pro, Ser or Thr
<220> FEATURE:
<221> NAME/KEY: misc_feature
<222> LOCATION: (52)..(55)
<223> OTHER INFORMATION: Xaa52 to Xaa54 independently can be Ala, Arg,
    Asn, Asp, Cys, Glu, Gln, Gly, His, Ile, Leu, Lys, Met, Phe, Pro,
    Ser, Thr, Trp, Tyr or Val; Xaa55 can be Arg, Asn, Asp, Glu,
    Gln, His, Lys, Ser or Thr
<220> FEATURE:
<221> NAME/KEY: misc_feature
<222> LOCATION: (56)..(59)
<223> OTHER INFORMATION: Xaa56 to Xaa59 indepedently can be Ala, Arg,
    Asn, Asp, Cys, Glu, Gln, Gly, His, Ile, Leu, Lys, Met, Phe, Pro,
    Ser, Thr, Trp, Tyr or Val
<220> FEATURE:
<221> NAME/KEY: misc_feature
<222> LOCATION: (60)..(63)
<223> OTHER INFORMATION: Xaa60 to Xaa63 can be Ala, Arg, Asn, Asp, Cys,
    Glu, Gln, Gly, His, Ile, Leu, Lys, Met, Phe, Pro, Ser, Thr, Trp,
    Tyr, Val or a peptide bond
<220> FEATURE:
<221> NAME/KEY: misc_feature
<222> LOCATION: (64)..(65)
<223> OTHER INFORMATION: Xaa64 can be Ala, Arg, Asn, Asp, Cys, Glu, Gln,
    Gly, His, Ile, Leu, Lys, Met, Phe, Pro, Ser, Thr, Trp, Tyr or Val;
    Xaa65 can be Ala, Gly, Pro, Ser or Thr
<220> FEATURE:
<221> NAME/KEY: misc_feature
<222> LOCATION: (66)..(69)
<223> OTHER INFORMATION: Xaa66 to Xaa67 independently can be Ala, Arg,
    Asn, Asp, Cys, Glu, Gln, Gly, His, Ile, Leu, Lys, Met, Phe, Pro,
    Ser, Thr, Trp, Tyr or Val; Xaa68 can be Arg, Asn, Asp, Glu, Gln,
```

```
        His, Lys, Ser or Thr; Xaa69 can be Ala, Gly, Pro, Ser or Thr
<220> FEATURE:
<221> NAME/KEY: misc_feature
<222> LOCATION: (72)..(72)
<223> OTHER INFORMATION: Xaa72 can be Ala, Arg, Asn, Asp, Cys, Glu, Gln,
        Gly, His, Ile, Leu, Lys, Met, Phe, Pro, Ser, Thr, Trp, Tyr or Val
<220> FEATURE:
<221> NAME/KEY: misc_feature
<222> LOCATION: (73)..(74)
<223> OTHER INFORMATION: Xaa73 and Xaa74 independently can be Ala, Arg,
        Asn, Asp, Cys, Glu, Gln, Gly, His, Ile, Leu, Lys, Met, Phe, Pro,
        Ser, Thr, Trp, Tyr or Val
<220> FEATURE:
<221> NAME/KEY: misc_feature
<222> LOCATION: (76)..(80)
<223> OTHER INFORMATION: Xaa76 can be Ala, Gly, Pro, Ser or Thr; Xaa77
        can be Arg, Asn, Asp, Glu, Gln, His, Lys, Ser or Thr; Xaa78 can be
        Leu or Met; Xaa79 can be Arg, Asn, Asp, Glu, Gln, His, Lys, Ser
        or Thr; Xaa80 can be Ala, Gly, Pro, Ser or Thr
<220> FEATURE:
<221> NAME/KEY: misc_feature
<222> LOCATION: (81)..(83)
<223> OTHER INFORMATION: Xaa81 can be Leu or Met; Xaa82 can be Arg, Asn,
        Asp, Glu, Gln, His, Lys, Ser or Thr; Xaa83 can be Ile, Leu, Met or
        Val
<220> FEATURE:
<221> NAME/KEY: misc_feature
<222> LOCATION: (84)..(87)
<223> OTHER INFORMATION: Xaa84 to Xaa86 independently can be Ala, Arg,
        Asn, Asp, Cys, Glu, Gln, Gly, His, Ile, Leu, Lys, Met, Phe, Pro,
        Ser, Thr, Trp, Tyr or Val; Xaa87 can be Arg, Asn, Asp, Glu, Gln,
        His, Lys, Ser or Thr
<220> FEATURE:
<221> NAME/KEY: misc_feature
<222> LOCATION: (89)..(89)
<223> OTHER INFORMATION: Xaa89 can be Ala, Arg, Asn, Asp, Cys, Glu, Gln,
        Gly, His, Ile, Leu, Lys, Met, Phe, Pro, Ser, Thr, Trp, Tyr or Val
<220> FEATURE:
<221> NAME/KEY: misc_feature
<222> LOCATION: (90)..(90)
<223> OTHER INFORMATION: Xaa90 can be Ala, Arg, Asn, Asp, Cys, Glu, Gln,
        Gly, His, Ile, Leu, Lys, Met, Phe, Pro, Ser, Thr, Trp, Tyr, Val or
        a peptide bond
<220> FEATURE:
<221> NAME/KEY: misc_feature
<222> LOCATION: (91)..(93)
<223> OTHER INFORMATION: Xaa91 can be Ala, Arg, Asn, Asp, Cys, Glu, Gln,
        Gly, His, Ile, Leu, Lys, Met, Phe, Pro, Ser, Thr, Trp, Tyr or Val;
        Xaa92 can be Arg, Asn, Asp, Glu, Gln, His, Lys, Ser or Thr;
        Xaa93 can be Cys, Ile, Leu, Met, Phe, Trp, Tyr or Val
<220> FEATURE:
<221> NAME/KEY: misc_feature
<222> LOCATION: (94)..(97)
<223> OTHER INFORMATION: Xaa94 to Xaa95 independently can be Ala, Arg,
        Asn, Asp, Cys, Glu, Gln, Gly, His, Ile, Leu, Lys, Met, Phe, Pro,
        Ser, Thr, Trp, Tyr or Val; Xaa96 can be Arg, Gln, Glu or Lys;
        Xaa97 can be Arg, Asn, Asp, Glu, Gln, His, Lys, Ser or Thr
<220> FEATURE:
<221> NAME/KEY: misc_feature
<222> LOCATION: (98)..(99)
<223> OTHER INFORMATION: Xaa98 can be Ile or Val; Xaa99 can be Ala, Arg,
        Asn, Asp, Cys, Glu, Gln, Gly, His, Ile, Leu, Lys, Met, Phe, Pro,
        Ser, Thr, Trp, Tyr or Val
<220> FEATURE:
<221> NAME/KEY: misc_feature
<222> LOCATION: (101)..(104)
<223> OTHER INFORMATION: Xaa101 can be Leu or Met; Xaa102 can be Ile,
        Leu, Met or Val; Xaa103 can be Ala, Arg, Asn, Asp, Cys,Glu, Gln,
        Gly, His, Ile, Leu, Lys, Met, Phe, Pro, Ser, Thr, Trp,Tyr or
        Val; Xaa104 can be Gln or Glu
<220> FEATURE:
<221> NAME/KEY: misc_feature
<222> LOCATION: (105)..(105)
<223> OTHER INFORMATION: Xaa105 can be Arg, Asn, Asp, Glu, Gln, His,
        Lys, Ser or Thr
<220> FEATURE:
<221> NAME/KEY: misc_feature
<222> LOCATION: (107)..(107)
<223> OTHER INFORMATION: Xaa107 can be Ala or Gly
<220> FEATURE:
```

```
<221> NAME/KEY: misc_feature
<222> LOCATION: (109)..(109)
<223> OTHER INFORMATION: Xaa109 can be Ala, Arg, Asn, Asp, Cys, Glu,
      Gln, Gly, His, Ile, Leu, Lys, Met, Phe, Pro, Ser, Thr, Trp, Tyr or
      Val

<400> SEQUENCE: 67

Cys Xaa Xaa Xaa Xaa Xaa Xaa Xaa Phe Xaa Xaa Xaa Gly Trp Xaa
1               5                   10                  15

Xaa Trp Ile Xaa Xaa Pro Xaa Xaa Xaa Xaa Xaa Tyr Cys Xaa Gly
            20                  25                  30

Xaa Cys Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Cys Cys Xaa Xaa Xaa Pro Xaa Xaa Xaa Xaa
65                  70                  75                  80

Xaa Xaa Xaa Xaa Xaa Xaa Xaa Asp Xaa Xaa Xaa Xaa Xaa Xaa Xaa
                85                  90                  95

Xaa Xaa Xaa Asn Xaa Xaa Xaa Xaa Xaa Cys Xaa Cys Xaa
            100                 105

<210> SEQ ID NO 68
<211> LENGTH: 139
<212> TYPE: PRT
<213> ORGANISM: Homo sapiens
<220> FEATURE:
<223> OTHER INFORMATION: Mature H2223 mutant

<400> SEQUENCE: 68

Ser Thr Gly Ser Lys Gln Arg Ser Gln Asn Arg Ser Lys Thr Pro Lys
1               5                   10                  15

Asn Gln Glu Ala Leu Arg Met Ala Asn Val Ala Glu Asn Ser Ser Ser
                20                  25                  30

Asp Gln Arg Gln Ala Cys Lys Lys His Glu Leu Tyr Val Ser Phe Arg
            35                  40                  45

Asp Leu Gly Trp Gln Asp Trp Ile Ile Ala Pro Glu Gly Tyr Ala Ala
        50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Glu Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Glu Asp Met Val Val Glu Ala Cys Gly Cys Arg
    130                 135

<210> SEQ ID NO 69
<211> LENGTH: 117
<212> TYPE: PRT
<213> ORGANISM: Homo sapiens
<220> FEATURE:
<223> OTHER INFORMATION: Trypsin truncated H2223 mutant

<400> SEQUENCE: 69

Met Ala Asn Val Ala Glu Asn Ser Ser Ser Asp Gln Arg Gln Ala Cys
1               5                   10                  15

Lys Lys His Glu Leu Tyr Val Ser Phe Arg Asp Leu Gly Trp Gln Asp
```

```
            20                  25                  30
Trp Ile Ile Ala Pro Glu Gly Tyr Ala Ala Tyr Cys Glu Gly Glu
        35                  40                  45

Cys Ala Phe Pro Leu Asn Ser Tyr Met Asn Ala Thr Asn His Ala Ile
 50                  55                  60

Val Gln Thr Leu Val His Phe Ile Asn Pro Glu Thr Val Pro Lys Pro
 65                  70                  75                  80

Cys Cys Ala Pro Thr Gln Leu Asn Ala Ile Ser Val Leu Tyr Phe Asp
                85                  90                  95

Asp Ser Ser Asn Val Ile Leu Lys Lys Tyr Glu Asp Met Val Val Glu
                100                 105                 110

Ala Cys Gly Cys Arg
        115
```

```
<210> SEQ ID NO 70
<211> LENGTH: 33
<212> TYPE: DNA
<213> ORGANISM: Artificial Sequence
<220> FEATURE:
<223> OTHER INFORMATION: Description of Artificial Sequence: Primer #1
<220> FEATURE:
<221> NAME/KEY: CDS
<222> LOCATION: (1)..(33)

<400> SEQUENCE: 70 gcg ccc acg cag ctc agc gct atc tcc gtc ctc                         33
Ala Pro Thr Gln Leu Ser Ala Ile Ser Val Leu
 1               5                  10

<210> SEQ ID NO 71
<211> LENGTH: 11
<212> TYPE: PRT
<213> ORGANISM: Artificial Sequence
<220> FEATURE:
<223> OTHER INFORMATION: Amino acid sequence encoded by Primer #1

<400> SEQUENCE: 71

Ala Pro Thr Gln Leu Ser Ala Ile Ser Val Leu
 1               5                  10

<210> SEQ ID NO 72
<211> LENGTH: 43
<212> TYPE: DNA
<213> ORGANISM: Artificial Sequence
<220> FEATURE:
<223> OTHER INFORMATION: Description of Artificial Sequence: Primer #2

<400> SEQUENCE: 72
ctatctgcag ccacaagctt cgaccaccat gtcttcgtat ttc                     43

<210> SEQ ID NO 73
<211> LENGTH: 43
<212> TYPE: DNA
<213> ORGANISM: Artificial Sequence
<220> FEATURE:
<223> OTHER INFORMATION: Description of Artificial Sequence: Complement
      of Primer #2
<220> FEATURE:
<221> NAME/KEY: CDS
<222> LOCATION: (2)..(43)

<400> SEQUENCE: 73 g aaa tac gaa gac atg gtg gtc gaa gct tgt ggc tgc aga tag          43
  Lys Tyr Glu Asp Met Val Val Glu Ala Cys Gly Cys Arg
   1               5                  10
```

```
<210> SEQ ID NO 74
<211> LENGTH: 13
<212> TYPE: PRT
<213> ORGANISM: Artificial Sequence
<220> FEATURE:
<223> OTHER INFORMATION: Amino acid sequence encoded by complement of
      Primer #2

<400> SEQUENCE: 74

Lys Tyr Glu Asp Met Val Val Glu Ala Cys Gly Cys Arg
1               5                   10

<210> SEQ ID NO 75
<211> LENGTH: 44
<212> TYPE: DNA
<213> ORGANISM: Artificial Sequence
<220> FEATURE:
<223> OTHER INFORMATION: Description of Artificial Sequence: the
      sequence between the T7 promoter, at the XbaI site, and the
      ATG codon

<400> SEQUENCE: 75
tctagaataa ttttgtttaa cctttaagaa ggagatatac gatg                    44

<210> SEQ ID NO 76
<211> LENGTH: 19
<212> TYPE: DNA
<213> ORGANISM: Artificial Sequence
<220> FEATURE:
<223> OTHER INFORMATION: Description of Artificial Sequence: Primer #3

<400> SEQUENCE: 76
taatacgact cactatagg                                                19

<210> SEQ ID NO 77
<211> LENGTH: 18
<212> TYPE: DNA
<213> ORGANISM: Artificial Sequence
<220> FEATURE:
<223> OTHER INFORMATION: Description of Artificial Sequence: Primer #4

<400> SEQUENCE: 77
gctgagctgc gtgggcgc                                                 18

<210> SEQ ID NO 78
<211> LENGTH: 18
<212> TYPE: DNA
<213> ORGANISM: Artificial Sequence
<220> FEATURE:
<223> OTHER INFORMATION: Description of Artificial Sequence: complement
      of Primer #4
<220> FEATURE:
<221> NAME/KEY: CDS
<222> LOCATION: (1)..(18)

<400> SEQUENCE: 78 gcg ccc acg cag ctc agc                                             18
Ala Pro Thr Gln Leu Ser
1               5

<210> SEQ ID NO 79
<211> LENGTH: 6
<212> TYPE: PRT
<213> ORGANISM: Artificial Sequence
<220> FEATURE:
<223> OTHER INFORMATION: Amino acid sequence encoded by complement of
      Primer #4

<400> SEQUENCE: 79
```

```
Ala Pro Thr Gln Leu Ser
1               5
```

<210> SEQ ID NO 80
<211> LENGTH: 23
<212> TYPE: DNA
<213> ORGANISM: Artificial Sequence
<220> FEATURE:
<223> OTHER INFORMATION: Description of Artificial Sequence: Primer #5

<400> SEQUENCE: 80
ggatcctatc tgcagccaca agc                                    23

<210> SEQ ID NO 81
<211> LENGTH: 23
<212> TYPE: DNA
<213> ORGANISM: Artificial Sequence
<220> FEATURE:
<223> OTHER INFORMATION: Description of Artificial Sequence: complement
      of Primer #5
<220> FEATURE:
<221> NAME/KEY: CDS
<222> LOCATION: (1)..(18)

<400> SEQUENCE: 81

```
gct tgt ggc tgc aga tag gatcc                                23
Ala Cys Gly Cys Arg
1               5
```

<210> SEQ ID NO 82
<211> LENGTH: 5
<212> TYPE: PRT
<213> ORGANISM: Artificial Sequence
<220> FEATURE:
<223> OTHER INFORMATION: Amino acid sequence encoded by complement of
      Primer #5

<400> SEQUENCE: 82

```
Ala Cys Gly Cys Arg
1               5
```

<210> SEQ ID NO 83
<211> LENGTH: 102
<212> TYPE: PRT
<213> ORGANISM: Homo sapiens
<220> FEATURE:
<223> OTHER INFORMATION: CDMP-1/GDF-5

<400> SEQUENCE: 83

```
Cys Ser Arg Lys Ala Leu His Val Asn Phe Lys Asp Met Gly Trp Asp
1               5                   10                  15

Asp Trp Ile Ile Ala Pro Leu Glu Tyr Glu Ala Phe His Cys Glu Gly
            20                  25                  30

Leu Cys Glu Phe Pro Leu Arg Ser His Leu Glu Pro Thr Asn His Ala
        35                  40                  45

Val Ile Gln Thr Leu Met Asn Ser Met Asp Pro Glu Ser Thr Pro Pro
    50                  55                  60

Thr Cys Cys Val Pro Thr Arg Leu Ser Pro Ile Ser Ile Leu Phe Ile
65                  70                  75                  80

Asp Ser Ala Asn Asn Val Val Tyr Lys Gln Tyr Glu Asp Met Val Val
                85                  90                  95

Glu Ser Cys Gly Cys Arg
            100
```

```
<210> SEQ ID NO 84
<211> LENGTH: 102
<212> TYPE: PRT
<213> ORGANISM: Homo sapiens
<220> FEATURE:
<223> OTHER INFORMATION: CDMP-2/GDF-6

<400> SEQUENCE: 84

Cys Ser Lys Lys Pro Leu His Val Asn Phe Lys Glu Leu Gly Trp Asp
1               5                   10                  15

Asp Trp Ile Ile Ala Pro Leu Glu Tyr Glu Ala Tyr His Cys Glu Gly
            20                  25                  30

Val Cys Asp Phe Pro Leu Arg Ser His Leu Glu Pro Thr Asn His Ala
        35                  40                  45

Ile Ile Gln Thr Leu Met Asn Ser Met Asp Pro Gly Ser Thr Pro Pro
    50                  55                  60

Ser Cys Cys Val Pro Thr Lys Leu Thr Pro Ile Ser Ile Leu Tyr Ile
65                  70                  75                  80

Asp Ala Gly Asn Asn Val Val Tyr Lys Gln Tyr Glu Asp Met Val Val
                85                  90                  95

Glu Ser Cys Gly Cys Arg
            100

<210> SEQ ID NO 85
<211> LENGTH: 102
<212> TYPE: PRT
<213> ORGANISM: Mus musculus
<220> FEATURE:
<223> OTHER INFORMATION: GDF-6

<400> SEQUENCE: 85

Cys Ser Arg Lys Pro Leu His Val Asn Phe Lys Glu Leu Gly Trp Asp
1               5                   10                  15

Asp Trp Ile Ile Ala Pro Leu Glu Tyr Glu Ala Tyr His Cys Glu Gly
            20                  25                  30

Val Cys Asp Phe Pro Leu Arg Ser His Leu Glu Pro Thr Asn His Ala
        35                  40                  45

Ile Ile Gln Thr Leu Met Asn Ser Met Asp Pro Gly Ser Thr Pro Pro
    50                  55                  60

Ser Cys Cys Val Pro Thr Lys Leu Thr Pro Ile Ser Ile Leu Tyr Ile
65                  70                  75                  80

Asp Ala Gly Asn Asn Val Val Tyr Lys Gln Tyr Glu Asp Met Val Val
                85                  90                  95

Glu Ser Cys Gly Cys Arg
            100

<210> SEQ ID NO 86
<211> LENGTH: 102
<212> TYPE: PRT
<213> ORGANISM: Bos taurus
<220> FEATURE:
<223> OTHER INFORMATION: CDMP-2

<400> SEQUENCE: 86

Cys Ser Lys Lys Pro Leu His Val Asn Phe Lys Glu Leu Gly Trp Asp
1               5                   10                  15

Asp Trp Ile Ile Ala Pro Leu Glu Tyr Glu Ala Tyr His Cys Glu Gly
            20                  25                  30

Val Cys Asp Phe Pro Leu Arg Ser His Leu Glu Pro Thr Asn His Ala
        35                  40                  45
```

```
Ile Ile Gln Thr Leu Met Asn Ser Met Asp Pro Gly Ser Thr Pro Pro
        50                  55                  60

Ser Cys Cys Val Pro Thr Lys Leu Thr Pro Ile Ser Ile Leu Tyr Ile
65                  70                  75                  80

Asp Ala Gly Asn Asn Val Val Tyr Asn Glu Tyr Glu Glu Met Val Val
                85                  90                  95

Glu Ser Cys Gly Cys Arg
            100

<210> SEQ ID NO 87
<211> LENGTH: 102
<212> TYPE: PRT
<213> ORGANISM: Mus musculus
<220> FEATURE:
<223> OTHER INFORMATION: GDF-7

<400> SEQUENCE: 87

Cys Ser Arg Lys Ser Leu His Val Asp Phe Lys Glu Leu Gly Trp Asp
1               5                   10                  15

Asp Trp Ile Ile Ala Pro Leu Asp Tyr Glu Ala Tyr His Cys Glu Gly
                20                  25                  30

Val Cys Asp Phe Pro Leu Arg Ser His Leu Glu Pro Thr Asn His Ala
            35                  40                  45

Ile Ile Gln Thr Leu Leu Asn Ser Met Ala Pro Asp Ala Ala Pro Ala
        50                  55                  60

Ser Cys Cys Val Pro Ala Arg Leu Ser Pro Ile Ser Ile Leu Tyr Ile
65                  70                  75                  80

Asp Ala Ala Asn Asn Val Val Tyr Lys Gln Tyr Glu Asp Met Val Val
                85                  90                  95

Glu Ala Cys Gly Cys Arg
            100

<210> SEQ ID NO 88
<211> LENGTH: 102
<212> TYPE: PRT
<213> ORGANISM: Homo sapiens
<220> FEATURE:
<223> OTHER INFORMATION: CDMP-3 construct

<400> SEQUENCE: 88

Cys Ser Arg Lys Pro Leu His Val Asp Phe Lys Glu Leu Gly Trp Asp
1               5                   10                  15

Asp Trp Ile Ile Ala Pro Leu Asp Tyr Glu Ala Tyr His Cys Glu Gly
                20                  25                  30

Leu Cys Asp Phe Pro Leu Arg Ser His Leu Glu Pro Thr Asn His Ala
            35                  40                  45

Ile Ile Gln Thr Leu Leu Asn Ser Met Ala Pro Asp Ala Ala Pro Ala
        50                  55                  60

Ser Cys Cys Val Pro Ala Arg Leu Ser Pro Ile Ser Ile Leu Tyr Ile
65                  70                  75                  80

Asp Ala Ala Asn Asn Val Val Tyr Lys Gln Tyr Glu Asp Met Val Val
                85                  90                  95

Glu Ala Cys Gly Cys Arg
            100

<210> SEQ ID NO 89
<211> LENGTH: 129
<212> TYPE: PRT
<213> ORGANISM: Homo sapiens
<220> FEATURE:
```

-continued

<223> OTHER INFORMATION: H2487

<400> SEQUENCE: 89

| Met | Thr | Met | Ile | Thr | Asn | Ser | Leu | Ala | Ser | Trp | Arg | Glu | Pro | Ser | Phe |
| 1 | | | | 5 | | | | | 10 | | | | | 15 | |

| Met | Ala | Leu | Ser | Ser | Ser | Asp | Gln | Arg | Gln | Ala | Cys | Lys | Lys | His | Glu |
| | | | 20 | | | | | 25 | | | | | 30 | | |

| Leu | Tyr | Val | Ser | Phe | Arg | Asp | Leu | Gly | Trp | Gln | Asp | Trp | Ile | Ile | Ala |
| | | | 35 | | | | | 40 | | | | | 45 | | |

| Pro | Glu | Gly | Tyr | Ala | Ala | Tyr | Tyr | Cys | Glu | Gly | Glu | Cys | Ala | Phe | Pro |
| | | 50 | | | | | 55 | | | | | 60 | | | |

| Leu | Asn | Ser | Tyr | Met | Asn | Ala | Thr | Asn | His | Ala | Ile | Val | Gln | Thr | Leu |
| 65 | | | | | 70 | | | | | 75 | | | | | 80 |

| Val | His | Phe | Ile | Asn | Pro | Glu | Thr | Val | Pro | Lys | Pro | Cys | Cys | Ala | Pro |
| | | | | 85 | | | | | 90 | | | | | 95 | |

| Thr | Gln | Leu | Ser | Ala | Ile | Ser | Val | Leu | Tyr | Phe | Asp | Asp | Ser | Ser | Asn |
| | | | 100 | | | | | 105 | | | | | 110 | | |

| Val | Ile | Leu | Lys | Lys | Tyr | Glu | Asp | Met | Val | Val | Glu | Ala | Cys | Gly | Cys |
| | | | 115 | | | | | 120 | | | | | 125 | | |

Arg

<210> SEQ ID NO 90
<211> LENGTH: 405
<212> TYPE: DNA
<213> ORGANISM: Homo sapiens
<220> FEATURE:
<223> OTHER INFORMATION: H2487

<400> SEQUENCE: 90

```
atgaccatga ttacgaattc cctggccagc tggagagagc caagcttcat ggccttaagc      60
agcagcgacc agaggcaggc ctgtaagaag cacgagctgt atgtcagctt ccgagacctg     120
ggctggcagg actggatcat cgcgcctgaa ggctacgccg cctactactg tgaggggag      180
tgtgccttcc ctctgaactc ctacatgaac gccaccaacc acgccatcgt gcagacgctg     240
gtccacttca tcaacccgga aacggtgccc aagccctgct gtgcgcccac gcagctcagc     300
gctatctccg tcctctactt cgatgacagc tccaacgtca tcctgaagaa atacgaagac     360
atggtggtcg aagcttgtgg ctgcagatag ctcctccgag aattc                     405
```

<210> SEQ ID NO 91
<211> LENGTH: 46
<212> TYPE: PRT
<213> ORGANISM: Homo sapiens
<220> FEATURE:
<223> OTHER INFORMATION: H2440

<400> SEQUENCE: 91

| Met | Ala | Asp | Asn | His | His | His | His | His | His | Met | Gly | Ser | Lys | Gln | Arg |
| 1 | | | | 5 | | | | | 10 | | | | | 15 | |

| Ser | Gln | Asn | Arg | Ser | Lys | Thr | Pro | Lys | Asn | Gln | Glu | Ala | Leu | Arg | Met |
| | | | 20 | | | | | 25 | | | | | 30 | | |

| Ala | Asn | Val | Ala | Glu | Asn | Ser | Ser | Ser | Asp | Gln | Arg | Gln | Ala |
| | | | 35 | | | | | 40 | | | | | 45 |

<210> SEQ ID NO 92
<211> LENGTH: 143
<212> TYPE: DNA
<213> ORGANISM: Homo sapiens
<220> FEATURE:
<223> OTHER INFORMATION: H2440

<400> SEQUENCE: 92

```
ccatggctga caaccatcac catcatcatc accatatggg gagcaaacag cgcagccaga    60
accgctccaa gacgcccaag aaccaggaag ccctgcggat ggccaacgtg cagagaaca   120
gcagcagcga ccagaggcag gcc                                          143
```

<210> SEQ ID NO 93
<211> LENGTH: 241
<212> TYPE: DNA
<213> ORGANISM: Homo sapiens
<220> FEATURE:
<223> OTHER INFORMATION: H2521

<400> SEQUENCE: 93

```
atgatcgaat tcatggctga caacaaattc aacaaggaac agcagaacgc gttctacgag    60
atcttgcacc tgccgaacct gaacgaagag cagcgtaacg gcttcatcca aagcctgaaa   120
gaagagccgt ctcagtctgc gaatctgcta gcggatgcca agaaactgaa cgatgcgcag   180
gcaccgaaat cggccatggc caacgtggca gagaacagca gcgaccagag gcaggcc     240
t                                                                  241
```

<210> SEQ ID NO 94
<211> LENGTH: 80
<212> TYPE: PRT
<213> ORGANISM: Homo sapiens
<220> FEATURE:
<223> OTHER INFORMATION: H2521

<400> SEQUENCE: 94

Met Ile Glu Phe Met Ala Asp Asn Lys Phe Asn Lys Glu Gln Gln Asn
1               5                   10                  15

Ala Phe Tyr Glu Ile Leu His Leu Pro Asn Leu Asn Glu Glu Gln Arg
            20                  25                  30

Asn Gly Phe Ile Gln Ser Leu Lys Glu Glu Pro Ser Gln Ser Ala Asn
        35                  40                  45

Leu Leu Ala Asp Ala Lys Lys Leu Asn Asp Ala Gln Ala Pro Lys Ser
    50                  55                  60

Ala Met Ala Asn Val Ala Glu Asn Ser Ser Ser Asp Gln Arg Gln Ala
65                  70                  75                  80

<210> SEQ ID NO 95
<211> LENGTH: 334
<212> TYPE: DNA
<213> ORGANISM: Homo sapiens
<220> FEATURE:
<223> OTHER INFORMATION: H2525

<400> SEQUENCE: 95

```
atgatcgaat tcatggctga caacaaattc aacaaggaac agcagaacgc gttctacgag    60
atcttgcacc tgccgaacct gaacgaagag cagcgtaacg gcttcatcca aagcctgaaa   120
gaagagccgt ctcagtctgc gaatctgcta gcggatgcca agaaactgaa cgatgcgcag   180
gcaccgaaat cggccatggc tgacaaccat caccatcatc accatatggg gagcaaacag   240
cgcagccaga accgctccaa gacgcccaag aaccaggaag ccctgcggat ggccaacgtg   300
gcagagaaca gcagcagcga ccagaggcag gcct                              334
```

<210> SEQ ID NO 96
<211> LENGTH: 111
<212> TYPE: PRT

<213> ORGANISM: Homo sapiens
<220> FEATURE:
<223> OTHER INFORMATION: H2525

<400> SEQUENCE: 96

Met Ile Glu Phe Met Ala Asp Asn Lys Phe Asn Lys Glu Gln Gln Asn
1               5                   10                  15

Ala Phe Tyr Glu Ile Leu His Leu Pro Asn Leu Asn Glu Glu Gln Arg
            20                  25                  30

Asn Gly Phe Ile Gln Ser Leu Lys Glu Glu Pro Ser Gln Ser Ala Asn
        35                  40                  45

Leu Leu Ala Asp Ala Lys Lys Leu Asn Asp Ala Gln Ala Pro Lys Ser
    50                  55                  60

Ala Met Ala Asp Asn His His His His His His Met Gly Ser Lys Gln
65                  70                  75                  80

Arg Ser Gln Asn Arg Ser Lys Thr Pro Lys Asn Gln Glu Ala Leu Arg
                85                  90                  95

Met Ala Asn Val Ala Glu Asn Ser Ser Ser Asp Gln Arg Gln Ala
            100                 105                 110

<210> SEQ ID NO 97
<211> LENGTH: 268
<212> TYPE: DNA
<213> ORGANISM: Homo sapiens
<220> FEATURE:
<223> OTHER INFORMATION: H2527

<400> SEQUENCE: 97
atgatcgaat tcatggctga caacaaattc aacaaggaac agcagaacgc gttctacgag      60
atcttgcacc tgccgaacct gaacgaagag cagcgtaacg gcttcatcca aagcctgaaa     120
gaagagccgt ctcagtctgc gaatctgcta gcggatgcca agaaactgaa cgatgcgcag     180
gcaccgaaat cggatcatca tcaccatcac cactcggatc ccatggccaa cgtggcagag     240
aacagcagca gcgaccagag gcaggcct                                        268

<210> SEQ ID NO 98
<211> LENGTH: 89
<212> TYPE: PRT
<213> ORGANISM: Homo sapiens
<220> FEATURE:
<223> OTHER INFORMATION: H2527

<400> SEQUENCE: 98

Met Ile Glu Phe Met Ala Asp Asn Lys Phe Asn Lys Glu Gln Gln Asn
1               5                   10                  15

Ala Phe Tyr Glu Ile Leu His Leu Pro Asn Leu Asn Glu Glu Gln Arg
            20                  25                  30

Asn Gly Phe Ile Gln Ser Leu Lys Glu Glu Pro Ser Gln Ser Ala Asn
        35                  40                  45

Leu Leu Ala Asp Ala Lys Lys Leu Asn Asp Ala Gln Ala Pro Lys Ser
    50                  55                  60

Asp His His His His His His Ser Asp Pro Met Ala Asn Val Ala Glu
65                  70                  75                  80

Asn Ser Ser Ser Asp Gln Arg Gln Ala
                85

<210> SEQ ID NO 99
<211> LENGTH: 647
<212> TYPE: DNA
<213> ORGANISM: Homo sapiens

<220> FEATURE:
<223> OTHER INFORMATION: H2528

<400> SEQUENCE: 99

```
ccatgatcga attcatggct gacaacaaat tcaacaagga acagcagaac gcgttctacg     60
agatcttgca cctgccgaac ctgaacgaag agcagcgtaa cggcttcatc caaagcctga    120
aagaagagcc gtctcagtct gcgaatctgc tagcggatgc caagaaactg aacgatgcgc    180
aggcaccgaa atcggatcat catcaccatc accactcgga tcccatggcg ttggccggga   240
cgcgtacagc gcagggcagc ggcggaggtg ccggcagagg tcatggtcga cgtggtagat   300
ctcgctgcag ccgcaagccg ttgcacgtgg acttcaagga gctcggctgg gacgactgga   360
tcatcgcgcc gctggactac gaggcgtacc actgcgaggg cctttgcgac ttccctttgc   420
gttcgcacct cgagcccacc aaccatgcca tcattcagac gctgctcaac tccatggcac   480
cagacgcggc gccggcctcc tgctgtgtgc cagcgcgcct cagccccatc agcatcctct   540
acatcgacgc cgccaacaac gttgtctaca agcaatacga ggacatggtg gtggaggcct   600
gcggctgtag gtaagcttgt ggctgcagat agctcctccg agaattc                  647
```

<210> SEQ ID NO 100
<211> LENGTH: 203
<212> TYPE: PRT
<213> ORGANISM: Homo sapiens
<220> FEATURE:
<223> OTHER INFORMATION: H2528

<400> SEQUENCE: 100

```
Met Ile Glu Phe Met Ala Asp Asn Lys Phe Asn Lys Glu Gln Gln Asn
1               5                   10                  15

Ala Phe Tyr Glu Ile Leu His Leu Pro Asn Leu Asn Glu Glu Gln Arg
            20                  25                  30

Asn Gly Phe Ile Gln Ser Leu Lys Glu Glu Pro Ser Gln Ser Ala Asn
        35                  40                  45

Leu Leu Ala Asp Ala Lys Lys Leu Asn Asp Ala Gln Ala Pro Lys Ser
    50                  55                  60

Asp His His His His His Ser Asp Pro Met Ala Leu Ala Gly Thr
65                  70                  75                  80

Arg Thr Ala Gln Gly Ser Gly Gly Ala Gly Arg Gly His Gly Arg
                85                  90                  95

Arg Gly Arg Ser Arg Cys Ser Arg Lys Pro Leu His Val Asp Phe Lys
            100                 105                 110

Glu Leu Gly Trp Asp Asp Trp Ile Ile Ala Pro Leu Asp Tyr Glu Ala
        115                 120                 125

Tyr His Cys Glu Gly Leu Cys Asp Phe Pro Leu Arg Ser His Leu Glu
    130                 135                 140

Pro Thr Asn His Ala Ile Ile Gln Thr Leu Leu Asn Ser Met Ala Pro
145                 150                 155                 160

Asp Ala Ala Pro Ala Ser Cys Cys Val Pro Ala Arg Leu Ser Pro Ile
                165                 170                 175

Ser Ile Leu Tyr Ile Asp Ala Ala Asn Asn Val Val Tyr Lys Gln Tyr
            180                 185                 190

Glu Asp Met Val Val Glu Ala Cys Gly Cys Arg
        195                 200
```

<210> SEQ ID NO 101
<211> LENGTH: 47
<212> TYPE: DNA

```
<213> ORGANISM: Homo sapiens
<220> FEATURE:
<223> OTHER INFORMATION: H2469

<400> SEQUENCE: 101
ccatggccaa cgtggcagag aacagcagca gcgaccagag gcaggcc          47

<210> SEQ ID NO 102
<211> LENGTH: 15
<212> TYPE: PRT
<213> ORGANISM: Homo sapiens
<220> FEATURE:
<223> OTHER INFORMATION: H2469

<400> SEQUENCE: 102

Met Ala Asn Val Ala Glu Asn Ser Ser Ser Asp Gln Arg Gln Ala
1               5                   10                  15

<210> SEQ ID NO 103
<211> LENGTH: 129
<212> TYPE: DNA
<213> ORGANISM: Homo sapiens
<220> FEATURE:
<223> OTHER INFORMATION: H2510

<400> SEQUENCE: 103
atgtccacgg ggagcaaaca gcgcagccag aaccgctcca agacgcccaa gaaccaggaa     60
gccctgcgga tggccagctg gagagagcca agcttcatgg ccttaagcag cagcgaccag    120
aggcaggcc                                                            129

<210> SEQ ID NO 104
<211> LENGTH: 43
<212> TYPE: PRT
<213> ORGANISM: Homo sapiens
<220> FEATURE:
<223> OTHER INFORMATION: H2510

<400> SEQUENCE: 104

Met Ser Thr Gly Ser Lys Gln Arg Ser Gln Asn Arg Ser Lys Thr Pro
1               5                   10                  15

Lys Asn Gln Glu Ala Leu Arg Met Ala Ser Trp Arg Glu Pro Ser Phe
                20                  25                  30

Met Ala Leu Ser Ser Ser Asp Gln Arg Gln Ala
            35                  40

<210> SEQ ID NO 105
<211> LENGTH: 168
<212> TYPE: DNA
<213> ORGANISM: Homo sapiens
<220> FEATURE:
<223> OTHER INFORMATION: H2523

<400> SEQUENCE: 105
atgtccacgg ggagcaaaca gcgcagccag aaccgctcca agacgcccaa gaaccaggaa     60
gccctgcgga tggccagctg gagagagcca agcttcatgg ccttaagcag cagcgaccag    120
aggcaggcca acgtggcaga gaacagcagc agcgaccaga ggcaggcc                 168

<210> SEQ ID NO 106
<211> LENGTH: 56
<212> TYPE: PRT
<213> ORGANISM: Homo sapiens
<220> FEATURE:
<223> OTHER INFORMATION: H2523
```

<400> SEQUENCE: 106

Met Ser Thr Gly Ser Lys Gln Arg Ser Gln Asn Arg Ser Lys Thr Pro
1               5                   10                  15

Lys Asn Gln Glu Ala Leu Arg Met Ala Ser Trp Arg Glu Pro Ser Phe
            20                  25                  30

Met Ala Leu Ser Ser Ser Asp Gln Arg Gln Ala Asn Val Ala Glu Asn
        35                  40                  45

Ser Ser Ser Asp Gln Arg Gln Ala
    50                  55

<210> SEQ ID NO 107
<211> LENGTH: 194
<212> TYPE: DNA
<213> ORGANISM: Homo sapiens
<220> FEATURE:
<223> OTHER INFORMATION: H2524

<400> SEQUENCE: 107
ccatggctga caaccatcac catcatcacc atatggggag caaacagcgc agccagaacc      60
gctccaagac gcccaagaac caggaagccc tgcggatggc cagctggaga gagccaagct     120
tcatggcctt aagcagcagc gaccagaggc aggccaacgt ggcagagaac agcagcagcg     180
accagaggca ggcc                                                       194

<210> SEQ ID NO 108
<211> LENGTH: 64
<212> TYPE: PRT
<213> ORGANISM: Homo sapiens
<220> FEATURE:
<223> OTHER INFORMATION: H2524

<400> SEQUENCE: 108

Met Ala Asp Asn His His His His His His Met Gly Ser Lys Gln Arg
1               5                   10                  15

Ser Gln Asn Arg Ser Lys Thr Pro Lys Asn Gln Glu Ala Leu Arg Met
            20                  25                  30

Ala Ser Trp Arg Glu Pro Ser Phe Met Ala Leu Ser Ser Ser Asp Gln
        35                  40                  45

Arg Gln Ala Asn Val Ala Glu Asn Ser Ser Ser Asp Gln Arg Gln Ala
    50                  55                  60

<210> SEQ ID NO 109
<211> LENGTH: 39
<212> TYPE: PRT
<213> ORGANISM: Homo sapiens
<220> FEATURE:
<223> OTHER INFORMATION: 2421

<400> SEQUENCE: 109

Pro Thr Cys Cys Val Pro Thr Arg Leu Ser Pro Ile Ser Ile Leu Phe
1               5                   10                  15

Ile Asp Ala Ser Asn Asn Val Val Leu Lys Lys Tyr Arg Asn Met Val
            20                  25                  30

Val Arg Ala Cys Gly Cys Arg
        35

<210> SEQ ID NO 110
<211> LENGTH: 39
<212> TYPE: PRT
<213> ORGANISM: Homo sapiens
<220> FEATURE:
<223> OTHER INFORMATION: H2406

<400> SEQUENCE: 110

Asn Ser Cys Cys Val Pro Thr Lys Leu Thr Pro Ile Ser Ile Leu Tyr
1               5                   10                  15

Phe Asp Asp Ser Ser Asn Val Ile Leu Lys Lys Tyr Arg Asn Met Val
            20                  25                  30

Val Arg Ala Cys Gly Cys Arg
        35

<210> SEQ ID NO 111
<211> LENGTH: 39
<212> TYPE: PRT
<213> ORGANISM: Homo sapiens
<220> FEATURE:
<223> OTHER INFORMATION: 2410

<400> SEQUENCE: 111

Asn Ser Cys Cys Val Pro Thr Glu Leu Ser Ala Ile Ser Met Leu Tyr
1               5                   10                  15

Leu Asp Glu Asn Glu Lys Val Val Leu Lys Asn Tyr Gln Asp Met Val
            20                  25                  30

Val Glu Gly Cys Gly Cys Arg
        35

<210> SEQ ID NO 112
<211> LENGTH: 39
<212> TYPE: PRT
<213> ORGANISM: Homo sapiens
<220> FEATURE:
<223> OTHER INFORMATION: 2247

<400> SEQUENCE: 112

Lys Pro Cys Cys Ala Pro Thr Gln Leu Asn Ala Ile Ser Val Leu Tyr
1               5                   10                  15

Phe Asp Asp Ser Ser Asn Val Ile Leu Lys Lys Tyr Arg Asn Met Val
            20                  25                  30

Val Arg Ala Cys Gly Cys Arg
        35

<210> SEQ ID NO 113
<211> LENGTH: 39
<212> TYPE: PRT
<213> ORGANISM: Homo sapiens
<220> FEATURE:
<223> OTHER INFORMATION: 2234

<400> SEQUENCE: 113

Lys Pro Cys Cys Ala Pro Thr Gln Leu Asn Ala Ile Ser Val Leu Tyr
1               5                   10                  15

Phe Asp Asp Ser Ser Asn Val Ile Leu Lys Lys Tyr Glu Asp Met Val
            20                  25                  30

Val Arg Ala Cys Gly Cys Arg
        35

<210> SEQ ID NO 114
<211> LENGTH: 39
<212> TYPE: PRT
<213> ORGANISM: Homo sapiens
<220> FEATURE:
<223> OTHER INFORMATION: 2233

<400> SEQUENCE: 114

Lys Pro Cys Cys Ala Pro Thr Gln Leu Asn Ala Ile Ser Val Leu Tyr

```
                1               5                  10                  15
Phe Asp Asp Ser Ser Asn Val Ile Leu Lys Lys Tyr Glu Asp Met Val
 20                  25                  30

Val Glu Ala Cys Gly Cys Arg
 35

<210> SEQ ID NO 115
<211> LENGTH: 39
<212> TYPE: PRT
<213> ORGANISM: Homo sapiens
<220> FEATURE:
<223> OTHER INFORMATION: 2418

<400> SEQUENCE: 115

Asn Ser Cys Cys Val Pro Thr Lys Leu Thr Pro Ile Ser Val Leu Tyr
 1               5                  10                  15

Phe Asp Asp Ser Ser Asn Val Ile Leu Lys Lys Tyr Glu Asp Met Val
                 20                  25                  30

Val Glu Ser Cys Gly Cys Arg
             35

<210> SEQ ID NO 116
<211> LENGTH: 39
<212> TYPE: PRT
<213> ORGANISM: Homo sapiens
<220> FEATURE:
<223> OTHER INFORMATION: 2443

<400> SEQUENCE: 116

Asn Ser Cys Cys Val Pro Thr Lys Leu Thr Pro Ile Ser Val Leu Tyr
 1               5                  10                  15

Phe Asp Asp Ser Ser Asn Val Ile Leu Lys Lys Tyr Glu Asp Met Val
                 20                  25                  30

Val Arg Ser Cys Gly Cys Arg
             35

<210> SEQ ID NO 117
<211> LENGTH: 39
<212> TYPE: PRT
<213> ORGANISM: Homo sapiens
<220> FEATURE:
<223> OTHER INFORMATION: 2447

<400> SEQUENCE: 117

Asn Ser Cys Cys Val Pro Thr Glu Leu Ser Ala Ile Ser Val Leu Tyr
 1               5                  10                  15

Phe Asp Asp Ser Ser Asn Val Ile Leu Lys Lys Tyr Glu Asp Met Val
                 20                  25                  30

Val Glu Ala Cys Gly Cys Arg
             35

<210> SEQ ID NO 118
<211> LENGTH: 39
<212> TYPE: PRT
<213> ORGANISM: Homo sapiens
<220> FEATURE:
<223> OTHER INFORMATION: 2457

<400> SEQUENCE: 118

Asn Ser Cys Cys Val Pro Thr Glu Leu Asn Ala Ile Ser Val Leu Tyr
 1               5                  10                  15

Phe Asp Asp Ser Ser Asn Val Ile Leu Lys Lys Tyr Glu Asp Met Val
                 20                  25                  30
```

```
Val Glu Ala Cys Gly Cys Arg
        35

<210> SEQ ID NO 119
<211> LENGTH: 39
<212> TYPE: PRT
<213> ORGANISM: Homo sapiens
<220> FEATURE:
<223> OTHER INFORMATION: 2456

<400> SEQUENCE: 119

Lys Pro Cys Cys Ala Pro Thr Glu Leu Ser Ala Ile Ser Val Leu Tyr
1               5                   10                  15

Phe Asp Asp Ser Ser Asn Val Ile Leu Lys Lys Tyr Glu Asp Met Val
            20                  25                  30

Val Glu Ala Cys Gly Cys Arg
        35

<210> SEQ ID NO 120
<211> LENGTH: 39
<212> TYPE: PRT
<213> ORGANISM: Homo sapiens
<220> FEATURE:
<223> OTHER INFORMATION: 2460

<400> SEQUENCE: 120

Lys Pro Cys Cys Ala Pro Thr Gln Leu Ser Ala Ile Ser Val Leu Tyr
1               5                   10                  15

Phe Asp Asp Ser Ser Asn Val Ile Leu Lys Lys Tyr Glu Asp Met Val
            20                  25                  30

Val Glu Ala Cys Gly Cys Arg
        35

<210> SEQ ID NO 121
<211> LENGTH: 39
<212> TYPE: PRT
<213> ORGANISM: Homo sapiens
<220> FEATURE:
<223> OTHER INFORMATION: 2449

<400> SEQUENCE: 121

Lys Pro Cys Cys Ala Pro Thr Glu Leu Asn Ala Ile Ser Val Leu Tyr
1               5                   10                  15

Phe Asp Asp Ser Ser Asn Val Ile Leu Lys Lys Tyr Arg Asn Met Val
            20                  25                  30

Val Arg Ala Cys Gly Cys Arg
        35

<210> SEQ ID NO 122
<211> LENGTH: 39
<212> TYPE: PRT
<213> ORGANISM: Homo sapiens
<220> FEATURE:
<223> OTHER INFORMATION: 2467

<400> SEQUENCE: 122

Lys Pro Cys Cys Ala Pro Thr Glu Leu Ser Ala Ile Ser Val Leu Tyr
1               5                   10                  15

Phe Asp Asp Ser Ser Asn Val Ile Leu Lys Lys Tyr Arg Asn Met Val
            20                  25                  30

Val Arg Ala Cys Gly Cys Arg
        35
```

```
<210> SEQ ID NO 123
<211> LENGTH: 39
<212> TYPE: PRT
<213> ORGANISM: Homo sapiens
<220> FEATURE:
<223> OTHER INFORMATION: 2464

<400> SEQUENCE: 123

Lys Pro Cys Cys Ala Pro Thr Gln Leu Ser Ala Ile Ser Val Leu Tyr
1               5                  10                  15

Phe Asp Asp Ser Ser Asn Val Ile Leu Lys Lys Tyr Arg Asn Met Val
                20                  25                  30

Val Arg Ala Cys Gly Cys Arg
            35

<210> SEQ ID NO 124
<211> LENGTH: 15
<212> TYPE: PRT
<213> ORGANISM: Homo sapiens
<220> FEATURE:
<223> OTHER INFORMATION: BMP-2 N-Terminus

<400> SEQUENCE: 124

Met Gln Ala Lys His Lys Gln Arg Lys Arg Leu Lys Ser Ser Cys
1               5                  10                  15
```

What is claimed is:

1. A pharmaceutical composition comprising a therapeutically effective amount of an N-terminally truncated OP-1 or an N-terminally truncated mutant OP-1, wherein said N-terminally truncated OP-1 or N-terminally truncated mutant OP-1 is selected from the group consisting of:
   a) a polypeptide consisting of amino acid residues 323-431 of SEQ ID NO: 39;
   b) a polypeptide consisting essentially of amino acid residues 21-129 of SEQ ID NO: 89; and
   c) a polypeptide consisting essentially of the amino acid sequence of SEQ ID NO: 69.

2. The pharmaceutical composition of claim 1, wherein the N-terminally truncated mutant OP-1 is a polypeptide consisting essentially of the amino acid sequence of SEQ ID NO: 69.

3. The pharmaceutical composition of claim 1, wherein the composition is a liquid solution or a liquid suspension.

4. The pharmaceutical composition of claim 3, wherein the composition is an aqueous solution.

5. The pharmaceutical composition of claim 1, further comprising a biocompatible matrix.

6. The pharmaceutical composition of claim 5, wherein the biocompatible carrier is selected from the group consisting of hyaluronic acid, tricalcium phosphate, polybutyrate, polylactide, polyglycolide, lactide/glycolide copolymers, collagen, hydroxyapatite, ceramics and carboxymethylcellulose.

7. A method of regenerating bone in a patient, comprising the step of administering to the patient the pharmaceutical composition of any one of claims 1 to 6.

8. A method of regenerating a non-mineralized skeletal or connective tissue in a patient, comprising the step of administering to the patient the pharmaceutical composition of any one of claims 1 to 6.

9. The method of claim 8, wherein the non-mineralized skeletal or connective tissue is cartilage.

10. The method of claim 8, wherein the non-mineralized skeletal or connective tissue is selected from the group consisting of fibrocartilage, ligament, tendon, joint capsule, menisci, synovial membrane tissue, muscle and fascia.

11. The method of claim 8, wherein the non-mineralized skeletal or connective tissue is articular cartilage.

12. The method of claim 8, wherein the non-mineralized skeletal or connective tissue is an intervertebral disk.

13. The method of claim 7, wherein the pharmaceutical composition is administered locally.

14. The method of claim 8, wherein the pharmaceutical composition is administered locally.

* * * * *